United States Patent
Hecker et al.

(10) Patent No.: US 10,618,918 B2
(45) Date of Patent: Apr. 14, 2020

(54) SUBSTITUTED BORONIC ACIDS AS ANTIMICROBIALS

(71) Applicant: QPEX BIOPHARMA, INC., San Diego, CA (US)

(72) Inventors: Scott Hecker, Del Mar, CA (US); Raja K. Reddy, San Diego, CA (US)

(73) Assignee: QPEX BIOPHARMA, INC., San Diego, CA (US)

(*) Notice: Subject to any disclaimer, the term of this patent is extended or adjusted under 35 U.S.C. 154(b) by 0 days.

(21) Appl. No.: 16/353,693

(22) Filed: Mar. 14, 2019

(65) Prior Publication Data

US 2019/0211037 A1 Jul. 11, 2019

Related U.S. Application Data

(63) Continuation of application No. 15/558,544, filed as application No. PCT/US2016/022678 on Mar. 16, 2016, now abandoned.

(60) Provisional application No. 62/191,221, filed on Jul. 10, 2015, provisional application No. 62/134,329, filed on Mar. 17, 2015.

(51) Int. Cl.
| | |
|---|---|
| *A61K 31/69* | (2006.01) |
| *C07F 5/02* | (2006.01) |
| *A61K 45/06* | (2006.01) |

(52) U.S. Cl.
CPC ............. *C07F 5/025* (2013.01); *A61K 31/69* (2013.01); *A61K 45/06* (2013.01); *Y02A 50/401* (2018.01); *Y02A 50/47* (2018.01); *Y02A 50/471* (2018.01); *Y02A 50/473* (2018.01); *Y02A 50/475* (2018.01); *Y02A 50/478* (2018.01); *Y02A 50/483* (2018.01)

(58) Field of Classification Search
CPC .................................. A61K 31/69; C07F 5/02
USPC .................................................. 514/64; 568/6
See application file for complete search history.

(56) References Cited

U.S. PATENT DOCUMENTS

| | | | |
|---|---|---|---|
| 3,686,398 A | 8/1972 | Kohn et al. | |
| 4,194,047 A | 3/1980 | Christensen et al. | |
| 4,260,543 A | 4/1981 | Miller | |
| 4,353,807 A | 10/1982 | Braid | |
| 4,409,214 A | 10/1983 | Takaya et al. | |
| 4,822,786 A | 4/1989 | Zama et al. | |
| 5,442,100 A | 8/1995 | Bjorkquiest et al. | |
| 5,888,998 A | 3/1999 | Maiti et al. | |
| 6,184,363 B1 | 2/2001 | Shoichet et al. | |
| 6,586,615 B1 | 7/2003 | Kettner et al. | |
| 7,271,186 B1 | 9/2007 | Shoichet et al. | |
| 7,439,253 B2 | 10/2008 | Lampilas et al. | |
| 7,582,621 B2 | 9/2009 | Baker et al. | |
| 7,612,087 B2 | 11/2009 | Aszodi et al. | |
| 7,674,913 B2 | 3/2010 | Campbell et al. | |
| 7,825,139 B2 | 11/2010 | Campbell et al. | |
| 8,680,136 B2 | 3/2014 | Hirst et al. | |
| 9,012,491 B2 | 4/2015 | Reddy et al. | |
| 9,101,638 B2 | 8/2015 | Reddy et al. | |
| 9,132,140 B2 | 9/2015 | Reddy et al. | |
| 9,156,858 B2 | 10/2015 | Reddy et al. | |
| 9,241,947 B2 | 1/2016 | Reddy et al. | |
| 9,296,763 B2 | 3/2016 | Hirst et al. | |
| 9,511,142 B2 | 12/2016 | Burns et al. | |
| 9,642,869 B2 | 5/2017 | Reddy et al. | |
| 9,687,497 B1 | 6/2017 | Bis et al. | |
| 9,694,025 B2 | 7/2017 | Hirst et al. | |
| 10,004,758 B2 | 6/2018 | Hirst et al. | |
| 10,206,937 B2 | 2/2019 | Reddy et al. | |
| 2004/0019203 A1 | 1/2004 | Micetich et al. | |
| 2004/0157826 A1 | 8/2004 | Lampilas et al. | |
| 2005/0020572 A1 | 1/2005 | Aszodi et al. | |
| 2005/0070719 A1 | 3/2005 | Belyakov et al. | |
| 2006/0019116 A1 | 1/2006 | Conley et al. | |
| 2006/0178357 A1 | 8/2006 | Buynak et al. | |
| 2006/0210883 A1 | 9/2006 | Chen et al. | |
| 2010/0056478 A1 | 3/2010 | Desarbre et al. | |
| 2010/0120715 A1 | 5/2010 | Burns et al. | |
| 2010/0256092 A1 | 10/2010 | Xia et al. | |
| 2010/0292185 A1 | 11/2010 | Burns et al. | |

(Continued)

FOREIGN PATENT DOCUMENTS

| | | |
|---|---|---|
| EP | 1550657 A1 | 7/2005 |
| EP | 2508506 A1 | 10/2012 |

(Continued)

OTHER PUBLICATIONS

Abdel-Magid et al., "Reductive Amination of Aldehydes and Ketones with Sodium Triacetoxyborohydride: Studies on Direct and Indirect Reductive Amination Procedures", J Org Chem. (1996) 61(11):3849-3862.

(Continued)

*Primary Examiner* — Douglas M Willis
(74) *Attorney, Agent, or Firm* — Knobbe, Martens, Olson & Bear, LLP

(57) ABSTRACT

Disclosed herein are antimicrobial compounds having the structure of the formula III′

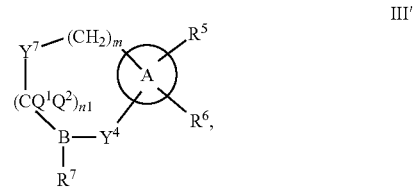

pharmaceutical compositions, the use and preparation thereof. The compounds are of the class of boronic acid derivatives, useful for antimicrobial treatment.

23 Claims, No Drawings

(56) References Cited

U.S. PATENT DOCUMENTS

| | | |
|---|---|---|
| 2011/0288063 A1 | 11/2011 | Maiti et al. |
| 2012/0040932 A1 | 2/2012 | Hirst et al. |
| 2013/0316978 A1 | 11/2013 | Reddy et al. |
| 2013/0331355 A1 | 12/2013 | Griffith et al. |
| 2013/0345172 A1 | 12/2013 | Hirst et al. |
| 2014/0194381 A1 | 7/2014 | Reddy et al. |
| 2014/0194382 A1 | 7/2014 | Reddy et al. |
| 2014/0194384 A1 | 7/2014 | Reddy et al. |
| 2014/0194385 A1 | 7/2014 | Reddy et al. |
| 2014/0194386 A1 | 7/2014 | Burns et al. |
| 2014/0206648 A1 | 7/2014 | Reddy et al. |
| 2014/0274954 A1 | 9/2014 | Chellappan et al. |
| 2015/0119363 A1 | 4/2015 | Dudley et al. |
| 2016/0220591 A1 | 8/2016 | Hirst et al. |
| 2016/0339045 A1 | 11/2016 | Griffith et al. |
| 2017/0057979 A1 | 3/2017 | Hecker et al. |
| 2017/0088561 A1 | 3/2017 | Reddy et al. |
| 2017/0136047 A1 | 5/2017 | Reddy et al. |
| 2017/0173055 A1 | 6/2017 | Bis et al. |
| 2018/0002351 A1 | 1/2018 | Hecker et al. |
| 2018/0051041 A1 | 2/2018 | Hecker et al. |
| 2018/0071325 A1 | 3/2018 | Hirst et al. |
| 2018/0207183 A1 | 7/2018 | Hirst et al. |
| 2018/0214465 A1 | 8/2018 | Hirst et al. |
| 2019/0084999 A1 | 3/2019 | Hecker et al. |

FOREIGN PATENT DOCUMENTS

| | | |
|---|---|---|
| FR | 2573070 A1 | 5/1986 |
| JP | 2003-229277 | 8/2003 |
| JP | 2004-291253 | 10/2004 |
| WO | WO 1987/05297 | 9/1987 |
| WO | WO 1989/10961 | 11/1989 |
| WO | WO 1998/56392 A1 | 12/1998 |
| WO | WO 2000/035904 A1 | 6/2000 |
| WO | WO 2000/035905 A1 | 6/2000 |
| WO | WO 2001/023374 A1 | 4/2001 |
| WO | WO 2001/030149 | 5/2001 |
| WO | WO 2002/022137 A1 | 3/2002 |
| WO | WO 2002/083884 | 10/2002 |
| WO | WO 2003/070714 | 8/2003 |
| WO | WO 2004/039859 | 5/2004 |
| WO | WO 2004/058679 A2 | 7/2004 |
| WO | WO 2004/064755 A2 | 8/2004 |
| WO | WO 2005/033090 | 4/2005 |
| WO | WO 2005/035532 A1 | 4/2005 |
| WO | WO 2005/087700 | 9/2005 |
| WO | WO 2006/052733 A1 | 5/2006 |
| WO | WO 2006/091771 | 8/2006 |
| WO | WO 2007/058602 A2 | 5/2007 |
| WO | WO 2007/065288 A2 | 6/2007 |
| WO | WO 2007/095638 | 8/2007 |
| WO | WO 2008/039420 A2 | 4/2008 |
| WO | WO 2008/116813 A1 | 10/2008 |
| WO | WO 2009/046098 A1 | 4/2009 |
| WO | WO 2009/064413 A1 | 5/2009 |
| WO | WO 2009/064414 A1 | 5/2009 |
| WO | WO 2009/091856 A1 | 7/2009 |
| WO | WO 2009/117540 A1 | 9/2009 |
| WO | WO 2009/139834 A1 | 11/2009 |
| WO | WO 2009/140309 A2 | 11/2009 |
| WO | WO 2010/056827 A1 | 5/2010 |
| WO | WO 2010/075286 A1 | 7/2010 |
| WO | WO 2010/097675 A1 | 9/2010 |
| WO | WO 2010/130708 A1 | 11/2010 |
| WO | WO 2010/144338 A1 | 12/2010 |
| WO | WO 2011/017125 A1 | 2/2011 |
| WO | WO 2011/103686 A1 | 9/2011 |
| WO | WO 2011/123502 A1 | 10/2011 |
| WO | WO 2011/154953 | 12/2011 |
| WO | WO 2012/021455 A1 | 2/2012 |
| WO | WO 2012/058065 A1 | 5/2012 |
| WO | WO 2012/067664 A1 | 5/2012 |
| WO | WO 2012/106995 A1 | 8/2012 |
| WO | WO 2012/136383 A1 | 10/2012 |
| WO | WO 2013/033461 A1 | 3/2013 |
| WO | WO 2013/053372 A1 | 4/2013 |
| WO | WO 2013/056163 A1 | 4/2013 |
| WO | WO 2013/092979 A1 | 6/2013 |
| WO | WO 2013/104774 A1 | 7/2013 |
| WO | WO 2013/104897 A1 | 7/2013 |
| WO | WO 2013/122888 A2 | 8/2013 |
| WO | WO 2013/184845 A1 | 12/2013 |
| WO | WO 2014/089365 A1 | 6/2014 |
| WO | WO 2014/107535 A1 | 7/2014 |
| WO | WO 2014/107536 A1 | 7/2014 |
| WO | WO 2014/110442 A1 | 7/2014 |
| WO | WO 2014/144380 A1 | 9/2014 |
| WO | WO 2014/151958 A1 | 9/2014 |
| WO | WO 2015/171398 A1 | 11/2015 |
| WO | WO 2015/171430 A1 | 11/2015 |
| WO | WO 2015/179308 A1 | 11/2015 |
| WO | WO 2015/191907 A1 | 12/2015 |
| WO | WO 2016/003929 A1 | 1/2016 |
| WO | WO 2016/065282 A1 | 4/2016 |

OTHER PUBLICATIONS

Adediran et al., "A 'cephalosporin-like' cyclic depsipeptide: Synthesis and reaction with beta-lactam-recognizing enzymes", Bioorg Med Chem Lett. (1999) 9(3):341-346.

Aizpurua et al., "Synthesis of benzyl halides from aldehydes promoted by halosilanes and 1,1,3,3-tetramethyldisiloxane (TMDS)", Tetrahedron Lett. (1984) 25(10):1103-1104.

Akiyama et al., "N-Hydroxy Amides. Part 6. Synthesis and Spectroscopic Properties of 1-Hydroxypiperazine-2,5-diones", J Chem Soc., Perkin Trans I, (1989) 2:235-239.

Allen et al., "Ansel's Pharmaceutical Dosage Forms and Drug Delivery Systems", 8th Edition (2004) TOC only.

Ambrose et al., Pharmacokinetics-pharmacodynamics of antimicrobial therapy: it's not just for mice anymore. Clin Infect Dis. (2007) 44: 79-86.

Ambrose et al., "Pharmacokinetics-pharmacodynamics of CB-618 in combination with cefepime, ceftazidime, ceftolozane and meropenem: the pharmacological basis for a standalone beta-lactamase inhibitor", Antimicrob Agents Chemother. (Nov. 2017) 61(12): e00630-17; 7 pages.

American Chemical Society. STN Chemical Database Registry RN: 1226917; Jun. 2010; 2 pages.

Arya et al., "Advances in asymmetric enolate methodology", Tetrahedron (2000) 56:917-947.

Austad et al. "Development of a multi kilogram-scale, tandem cyclopropanation ring-expansion reaction en route to hedgehog antagonist IPL-926", Org Process Res Dev., (2016) 20(4):786-798; Supporting Information, 70 pages.

Babic et al., "What's new in antibiotic resistance? Focus on beta-lactamases", Drug Res Updates (2006) 9:142-156.

Banker G.S. et al. [Eds.], Modern Pharmaceutics, 4th Edition; Marcel Dekker, Inc. (2002); Chapters 9 and 10, 98 pages.

Bassetti et al., "New antibiotics for bad bugs: where are we?", Ann Clin Microbiol Antimicrob. (2013) 12:22-36.

Becker, Daniel E., "Antimicrobial Drugs", Anesth Prog (2013) 60:111-123.

Beenen et al., "Asymmetric copper-catalyzed synthesis of alpha-amino boronate esters from N-tert-butanesulfinyl aldimines", J Am Chem Soc. (2008) 130(22):6910-6911.

Berkhout et al., "Pharmacodynamics of Ceftazidime and Avibactam in Neutropenic Mice with Thigh or Lung Infection", Antimicrob Agents Chemother. (2015) 60 (1): 368-375.

Bhavani et al., Pharmacokinetic-Pharmacodynamic (PK_PD) basis for CLSI carbapenem (CARB) susceptibility breakpoint changes. abstr Abstracts of Papers, 50th Interscience Conference on Antimicrobial Agents and Chemotherapy, Sep. 12-15, 2010; #A1-1382, Boston, MA; 3 pages.

Biedrzycki et al., "Derivatives of tetrahedral boronic acids", J. Organomet. Chem. (1992) 431:255-270.

Bilello et al., "Effect of 2',3'-8 didehydro-3'-deoxythymidine in an in vitro hollow-fiber pharmacodynamic model system correlates

(56) References Cited

OTHER PUBLICATIONS with results of dose-ranging clinical studies", Antimicrob Agents Chemother. (1994) 38(6): 1386-1391.
Bou et al., "Cloning, nucleotide sequencing, and analysis of the gene encoding an AmpC beta-lactamase in Acinetobacter baumannii", Antimicrob Agents Chemother (2000) 44(2):428-432.
Bou et al., "OXA-24, a novel class D beta-lactamase with carbapenemase activity in an Acinetobacter baumannii clinical strain", Antimicrob Agents Chemother (2000) 44(6):1556-1561 and Erratum: Antimicrob Agents Chemother. (2006) 50(6) 2280.
Bowker et al., Comparative pharmacodynamics of meropenem using an in-vitro model to simulate once, twice and three times daily dosing in humans. J Antimicrob Chemother (1998) 42: 461-467.
Brabez et al., "Design,synthesis, and biological studies of efficient multivalent melanotropin ligands: tools toward melanoma diagnosis and treatment", J Med Chem. (2011) 54(20):7375-7384.
Braisted et al., "Discovery of a potent small molecule IL-2 inhibitor through fragment assembly", J Am Chem Soc., (2003) 125(13): 3714-3715; Supporting Information, 42 pages.
Brosz et al., "Resolution of alpha-aminoboronic esters by diastereoselective crystallization with pinanediols. Confirmation by x-ray analysis", Tetrahedron: Asymmetry (1997) 8(9):1435-1440.
Buesking et al., "Asymmetric Synthesis of Protected alpha-Amino Boronic Acid Derivatives with an Air- and Moisture-stable Cu(II) Catalyst", J Org Chem. (Mar. 2014) 79(8): 3671-3677.
Bulik et al., "Comparison of the activity of a human simulated, high-dose, prolonged infusion of meropenem against Klebsiella pneumoniae producing the KPC carbapenemase versus that against Pseudomonas aeruginosa in an in vitro pharmacodynamic model", Antimicrob Agents Chemother (2010) 54(2): 804-810.
Bundgaard H. [Ed.], "Design of Prodrugs", Elsevier (1985); TOC, 2 pages.
Bush et al., "Minireview: Updated Functional Classification of beta-Lactamases," Antimicrob Agents Chemo. (2010) 54(3):969-976.
CAS Registry No. 2005:329437 CAPLUS; "Product subclass 28: Vinylboranes", Vaultier et al., (2004); XP-002764965; 1 page.
CAS Registry Nos. 69190-59/60 (2-(bis(phenylthio)methyl)-4,4,5,5-tetramethyl-1,3,2-dioxaborolane) and 69190-60-9 (2-(bis(phenylthio)methyl)-1,3,2-dioxaborinane) Scheme 18 (2015); 2 pages.
CAS Registry No. 105892-95-3 Boronic acid [1-(phenylsulfonyl)heptyl]-, dimethyl ester (2015); 2 pages.
CAS Registry No. 831209-98-4 6H-Dibenz[c,e][1,2]oxaborin, 6a,10a-dihydro-6-hydroxy; Entered STN: Feb. 15, 2005; 1 page.
CAS Registry No. 831210-03-8 6H-Dibenz[c,e][1,2]oxaborin, 2,4-dibromo-6a, 10a-dihydro-6-hydroxy; Feb. 15, 2005; 1 page.
Chandrasekhar et al., "The first Corey-Chaykovsky epoxidation and cyclopropanation in ionic liquids", Tetrahedron Letts. (2003) 44:3629-3630.
Charette et al., "Palladium-catalyzed Suzuki-type cross-couplings of iodocyclopropanes with boronic acids: Synthesis of trans-1,2-dicyclopropyl alkenes", J Org Chem. (1996) 61(25): 8718-8719; Supporting Information, 52 pages.
Cheng et al., "Synthesis of Aryl Thioethers through the N-Chlorosuccinimide-Promoted Cross-Coupling Reaction of Thiols with Grignard Reagents", J Org Chem. (2012) 77(22):10369-10374.
Chemicalland21.com. "Meglumine", Jun. 7, 2011. Downloaded from </www.chemicalland21.com/lifescience/phar/N-METHYL-D-GLUCAMINE.htm>; 2 pages.
Chinchilla et al., "Recent advances in Sonogashira reactions", Chem Soc Rev., (2011) 40: 5084-5121.
Clark et al., "Concise synthesis of the C-1—C-12 fragment of amphidinolides T1—T5", Org Biomol Chem. (2011) 9(13): 4823-4830.
Clinical and Laboratory Standards Institute (formerly NCCLS, National Committee for Clinical Laboratory Standards). "Methods for Dilution of Antimicrobial Susceptibility Tests for Bacteria That Grow Aerobically", CLSI (Jan. 2006) M7-A7 26(2), 64 pages.
Clinical and Laboratory Standards Institute (formerly NCCLS, National Committee for Clinical Laboratory Standards). "Methods for Dilution of Antimicrobial Susceptibility Tests for Bacteria That Grow Aerobically", CLSI (Jan. 2009) M07-A8 29(2), 88 pages.
Clinical and Laboratory Standards Institute (formerly NCCLS, National Committee for Clinical Laboratory Standards). "Methods for Dilution of Antimicrobial Susceptibility Tests for Bacteria That Grow Aerobically; Approved Standard—9th Edition", CLSI (Jan. 2012) M07-A9 32(2): 88 pages.
Clinical Trial NCT02168946, "A Phase 3, Multi-Center, Randomized, Open-Label Study of Carbavance (Meropenem/RPX7009) Versus Best Available Therapy in Subjects with Selected Serious Infecations Due to Carbapenem-Resistant Enterobacteriaceae", Oct. 6, 2014; retrieved online from URL:https://clinicaltrials.gov/archive/NCT02168946/20140_10_06.
Conte et al., "Intrapulmonary pharmacokinetics and pharmacodynamics of meropenem", Int J Antimicrob Agents (Dec. 2005) 26(6):449-456.
Coppa et al., "A Facile, Convenient and Selective Homolytic Carbamolylation of Heteroaromatic Bases", Heterocycles (1993) 36(12):2687-2696.
Coutts et al., "Two Efficient Methods for the Cleavage of Pinanediol Boronate Esters Yielding the Free Boronic Acids", Tetrahedron Lett. (1994) 35(29):5109-5112.
Craig WA., "Pharmacokinetic/pharmacodynamic parameters: rationale for antibacterial dosing of mice and men", Clin Infect Dis. (1998) 26(1): 1-10.
Cunha, "Meropenem in elderly and renally impaired patients", Int'l J Antimicro Agents (1998) 10: 107-117.
Danziger et al., "Automated Site-directed Drug Design: A General Algorithm for Knowledge Acquisition about Hydrogen-bonding Regions at Protein Surfaces", Proc. Royal Soc London, Series B, Biol. Sciences (1989) 236(1283):101-113.
Darses et al., "Potassium Organotrifluoroborates: New Perspectives in organic Synthesis", Chem Rev. (2008) 108:288-325.
Davoli et al., "Enantioselective total synthesis of (-)-microcarpalide", Tetrahedron (2005) 61:4427-4436.
De Meijere A. [Ed], Science of Synthesis—vol. 24; "Three Carbon-Heteroatom Bonds: Ketene Acetals and Yne-X Compounds", TOC 46 pages.
Di Gioia et al., "Optically Pure N-Hydroxy-O-triisopropylsilyl-alpha-L-amino Acid Methyl Esters from AlCl3-Assisted Ring Opening of Chiral Oxaziridines by Nitrogen Containing Nucleophiles", J Org Chem. (2005) 70(25):10494-10501.
Dörwald F.Z., Side Reactions in Organic Synthesis—A guide to Successful Synthesis Design, Wiley-VCH Verlag GmbH & Co. KGaA, Weinheim, Germany (2005); Preface in 4 pages.
Drawz et al., "Three Decades of beta-Lactamase Inhibitors", Clin Microbiol Reviews (Jan. 2010) 23(1):160-201.
Drusano et al., Meropenem: clinical response in relation to in vitro susceptibility. Clin Microbiol Infect. (2000) 6: 185-194.
Dunetz et al., "Large-scale applications of amide coupling reagents for the synthesis of pharmaceuticals", Org Process Res Develop. (2016) 20(2): 140-177.
Eggen et al., "Total synthesis of cryptophycin-24 (Arenastatin A) amenable to structural modifications in the C16 side chain", J Org Chem. (2000) 65(23): 7792-7799; and Supporting documents, 22 pages.
Eidam et al., "Design, synthesis, crystal structures and antimicrobial activity of sulfonamide boronic acids as beta-lactamase inhibitors", J Med Chem. (2010) 53(21):7852-7863.
Eissenstat et al., "Aminoalkylindoles: Structure—Activity Relationships of Novel Cannabinoid Mimetics", J Med Chem. (1995) 38(16):3094-3105.
El Nezhawy et al., "Synthesis and antioxidant activity of some thiazolidin-4-one derivatives", Springer; Chemical Monthly/Monatshefte für Chemie (2009) 140(5):531-539.
Endo et al., "Chemoselective Suzuki coupling of diborylmethane for facile synthesis of benzylboronates", Org Lett. (2011) 13(13):3368-3371.
Fan, et al. (2009): STN International HCAPLUS database, Columbus (OH), accession No. 2009: 425839; 6 pages.

(56) References Cited

OTHER PUBLICATIONS

Farquhar et al., "Intensely potent doxorubicin analogues: structure-activity relationship", J. Med. Chem. (1998) 41(6):965-972.
Ghosh et al., "Enantioselective total synthesis of (+)-largazole, a potent inhibitor of histone deacetylase", Org Lett. (2008) 10(17):3907-3909.
Giroux, A., "Synthesis of benzylic boronates via palladium-catalyzed cross-coupling reaction of bis(pinacolato)diboron with benzylic halides", Tetrahedron Lett. (2003) 44:233-235.
Goodman et al., [Eds.], "The Pharmacological Basis of Therapeutics", 8th. Edition, Pergamon Press (1990); TOC, 8 pages.
Gorovoy et al., "Boron-Containing Peptidomimetics—A Novel Class of Selective Anti-tubercular Drugs", Chem Biol Drug Des. (Jan. 2013) 81(3):408-413.
Gossinger et al., "Towards EPC-syntheses of the structural class of cochleamycins and macquarimicins. Part 3: EPC-syntheses of the beta-keto lactone subunits and first attempts towards the syntheses of the pentacyclic antibiotics of this group", Tetrahedron (2007) 63:8336-8350.
Graham et al., "D is for Drugs", Chemistry & Industry, Mar. 19, 2013, pp. 28-30, Downloaded from http://www.concertpharma.com/wp-content/uploads/2014/12/ChemistryIndustry-0313.pdf; 3 pages.
Greene, et al., "Greene's Protective Groups in Organic Synthesis", 4th Edition, (2007); pp. 774, 785 & 787.
Gunanathan et al., "Ruthenium catalyzed hydroboration of terminal alkynes to Z vinylboronates", J Am Chem Soc. (2012) 134(35): 14349-14352; Supporting Information, 32 pages.
Hall D.G., [Ed] Boronic Acids [vol. 2]: Preparations and applications in Organic Synthesis, Medicine and Materials, Wiley-VCH, Weinheim, 2nd Edition (2011); TOC.
Hama et al., "Palladium-Catalyzed alpha-Arylation of Zinc Enolates of Esters: Reaction Conditions and Substrate Scope", J Org Chem. (2013) 78(17):8250-8266.
Hartung et al., "Highly Z-selective and Enantioselective Ring Opening/Cross Metathesis Catalyzed by Resolved Stereogenic-At-Ru Complex", J Am Chem Soc. (Jul. 2013) 135(28): 10183-10185.
He et al., "Ligand-promoted borylation of C(sp3)—H bonds with palladium(II) catalysts", Angew Chem Int Ed., (2016) 55(2): 785-789.
Hecker et al., "Discovery of a Cyclic Boronic Acid beta-Lactamase Inhibitor (RPX7009) with Utility vs Class A Serine Carbapenemases", J Med Chem. (Mar. 2015) 58:3682-3692.
Higuchi et al., [Eds.] "Pro-drugs as Novel Drug Delivery Systems", ACS Sumposium Series 14 (1975); TOC, 3 pages.
Hoveyda A., "Evolution of catalytic stereoselective olefin metathesis: From ancillary transformation to purveyor of stereochemical identity", J Org Chem. (Jun. 2014) 79(11): 4763-4792.
Hu et al., "Ag(I)-catalyzed C—H borylation of terminal alkynes", Tetrahedron (2014) 70: 5815-5819.
Imanishi et al., "Discovery of a Novel Series of Biphenyl Benzoic Acid Derivatives as Potent and Selective Human beta3-Adrenergic Receptor Agonists with Good Oral Bioavailability. Part I", J Med Chem. (2008) 51(6):1925-1944.
Inglis et al., "Observations on the Deprotection of Pinanediol and Pinacol Boronate Esters via Fluorinated Intermediates", J Org Chem. (2010) 75(2):468-471; Supporting Information, S1-S-76.
Ishii et al, "In vitro potentiation of carbapenems with ME1071, a Novel metallo-β-lactamase inhibitor, against metallo-β-lactamase producing pseudomonas aeruginosa clinical isolates." Antimicrob. Agents Chemother. doi:10.1128/AAC.01397-09 (2010) 54(9):3625-3629.
Ishiyama et al., "Palladium(0)-catalyzed cross-coupling reaction of alkoxydiboron with haloarenes: A direct procedure for arylboronic esters", J Org Chem. (1995) 60(23): 7508-7510; Supporting Information, 35 pages.
Ito et al., "An efficient constructive method for a tricyclic system: an important intermediate for the synthesis of tricycloclavulone", Tetrahedron Lett. (2003) 44:1259-1261.

Jadhav et al., "Direct synthesis of [alpha-[(tert-Butoxycarbonyl)amino]alkyl]-boronates from (alpha-Haloalkyl)boronates", Org Chem. (1996) 61(22):7951-7954.
Jagannathan et al., "Synthesis of Boronic Acid Analogues of alpha-Amino Acids by Introducing Side Chains as Electrophiles", J Org Chem. (2001) 66(19):6375-6380.
Jang et al., Copper-catalyzed trans-hydroboration of terminal aryl alkynes: Stereodivergent synthesis of alkenylboron compounds. Org Letts. (2016) 18(6): 1390-1393; Supporting Information in 37 pages.
Jiang et al., "A Practical Synthesis of Cefcapene Pivoxil", Synthesis (2012) 44:207-214.
Johnson et al., "A drug targeting motif for glycosidase inhibitors: An iminosugar-boronate shows unexpectedly selective beta-galactosidase inhibition", Tetrahed Lttrs. (2002) 43(49):8905-8908.
Jordan V.C., "Tamoxifen: A most unlikely pioneering medicine", Drug Discovery (2003) 2:205-213.
Kabalka et al., "Synthesis of a series of bornonated unnatural cyclic amino acids as potential boron neutron capture therapy agents", Appl Organomet Chem. (2008) 22(9):516-522.
Kanai et al., "Synthesis of ortho-Acylbenzylboronates via Cross-Coupling Reaction of (Dialkoxyboryl)methylzinc Reagents with Haloarenes. A Stable ortho-Quinodimethane Precursor", Chem Letts. (1993) 22(5):845-848.
Kawamorita et al., "Synthesis of Primary and Secondary Alkylboronates through Site-Selective C(sp3)—H Activation with Silica-supported Monophosphine-Ir Catalysts", J Am Chem Soc. (2013) 135(8):2947-2950.
Kikuchi et al., "Comparison of the Pharmacodynamics of Biapenem in Bronchial Epithelial Lining Fluid in Healthy Volunteers Given Half-Hour and Three-Hour Intravenous Infusions", Antimicrob Agents Chemother. (Jul. 2009) 53(7):2799-2803.
Kint et al., "New-found fundamentals of bacterial persistence", Trends Microbiol. (2012) 20(12):577-585.
Kose et al., "Synthesis of photochromic 2,3-bis(5-methyl-2-phenyl-4-thiazolyl)-1,4-naphthoquinone derivatives", J Photochem Photobiol. A: Chemistry. (2011) 219(1):58-61.
Kotha et al., "Recent applications of the suzuki-miyaura cross-coupling reaction in organic synthesis", Tetrahedron (2002) 58:9633-9695.
Kuang et al., "Convenient and stereoselctive synthesis of (Z)-1-bromo-1-alkenes by microwave-induced reaction", Tetrahedron Letts. (2001) 42(23): 3893-3896.
Kumar et al., "Synthesis of intermediates for the lactone moiety of mevinic acids via tellurium chemistry", J. Org. Chem., (1994) 59(17):4760-4764.
Kumar et al., "Development of Practical Methodologies for the Synthesis of Functionalized Benzoboroxoles", Tetrahedron Lett. (Aug. 25, 2010) 51(34):4482-4485.
Kusakabe et al., "Preparation of Optically Acitve 2-Furylcarbinols by Kinetic Resolution Using the Sharpless Reagent and Their Application in Organic Synthesis", J org Chem (1989) 54(9):2085-2091.
Kuti et al., "Use of Monte Carlo simulation to design an optimized pharmacodynamic dosing strategy for meropenem", J Clin Pharmacol. (Oct. 2003) 43(10): 1116-1123 with Erratum (2005); 1 page.
Laitar et al., "Catalytic diboration of aldehydes via insertion into the copper-boron bond", J Am Chem Soc. (2006) 128(34):11036-11037.
Lapuebla et al., "Activity of Meropenem Combined with RPX7009, a Novel beta-Lactamase Inhibitor, against Gram-Negative Clinical Isolates in New York City", Antimicrob Agents Chemother. (Aug. 2015) 59(8):4856-4860.
Larock R. [Ed.] Comprehensive Organic Transformations, VCH Publishers 1989; TOC, 11 pages.
Lebel et al., "Boc-protected amines via a mild and efficient one-pot Curtius rearrangement", Org Letts. (2005) 7(19): 4107-4110.
Lee et al., "Vicinal Diboronates in High Enantiomeric Purity through Tandem Site-Selective NHC-Cu-Catalyzed Boron-Copper Additions to Terminal Alkynes", J Am Chem Soc. (Dec. 2009) 131(51):18234-18235.

(56) References Cited

OTHER PUBLICATIONS

Lee et al., "Comparison of 30-min and 3-h infusion regimens for imipenem/cilastatin and for meropenem evaluated by Monte Carlo simulation", Diagn Microbiol Infect Dis. (2010) 68: 251-258.
Li et al., "Population Pharmacokinetic Analysis and Dosing Regimen Optimization of Meropenem in Adult Patients", J Clin Pharmacol. (2006) 46(10): 1171-1178.
Li et al, "Novel macrocyclic HCV NS3 protease inhibitors derived from α-amino cyclic boronates", Bioorganic Med Chem Lett. (2010) 20:5695-5700.
Li et al., "Synthesis and evaluation of novel alpha-amino cyclic boronates as inhibitors of HCV NS3 protease", Bioorg Med Chem Lett. (2010) 20:3550-3556.
Li et al., "Stereoselective total synthesis of etnangien and etnangien methyl ester", J Org Chem. (2010) 75(8):2429-2444.
Liang et al., "The Efficient Copper(I) (Hexabenzyl)tren Catalyst and Dendritic Analogues for Green "Click" Reactions between Azides and Alkynes in Organic Solvent and in Water: Positive Dendritic Effects and Monometallic Mechanism", Advance Syn Catal. (2011) 353(18): 3434-3450.
Lieberman H.A. [Ed] Pharmaceutical Dosage Forms—Tablets; Marcel Dekker, Inc. (1989) 2nd Ed; TOC; 7 pages.
Lima et al., "Bioisosterism: A Useful Strategy for Molecular Modification and Drug Design", Curr Med Chem. (2005) 12:23-49.
Lin et al., "Enantioselective syn and anti homocrotylation of aldehydes: Application to the formal synthesis of spongidepsin", J Am Chem Soc. (2015) 137(40): 13176-13182; Supporting Information, 177 pages.
Liu et al., "Selective Protein tyrosine phosphatase 1B inhibitors: Targeting the second phosphotyrosine binding site with non-carboxylic acid-containing ligands", J Med Chem. (2003) 46(16):3437-3440; Supporting Information, 38 pages.
Liu et al., "Application of Stereoselective Ether Transfer to the Synthesis of Isotactic Polyethers", J Org Chem. (2010) 75(12):3953-3957.
Livermore et al., "Activities of NXL104 combinations with Ceftazidime and Aztreonam against Carbapenemase-producing Enterobacteriaceae", Antimicr Agents Chemother. (2011) 55(1):390-394.
Livermore et al., "Activity of biapenem (RPX2003) combined with the boronate beta-lactamase inhibitor RPX7009 against carbapenem-resistant Enterobacteriaceae", J Antimicrob Chemother. (Aug. 2013) 68(8):1825-1831.
Lodise et al., "Penetration of meropenem into epithelial lining fluid of patients with ventilator-associated pneumonia", Antimicrob Agents Chemother. (Apr. 2011) 55(4):1606-1610.
Louie et al., Impact of meropenem in combination with tobramycin in a murine model of Pseudomonas aeruginosa pneumonia. Antimicrob Agents Chemother (2013) 57: 2788-2792.
Luithle et al., "Synthesis of enantiomerically pure cis-cyclopropylboronic esters", Eur J Org Chem. (2000) 14: 2557-2562.
MacVane et al., Characterizing in vivo pharmacodynamics of carbapenems against Acinetobacter baumannii in a Murine thigh infection model to support breakpoint determinations. Antimicrob Agents Chemother (2014) 58: 599-601.
Maguire B. A., Inhibition of Bacterial Ribosome Assembly: a Suitable Drug Target? Microbiol Mol Biol Rev. (2009) 73(1):22-35.
Malfertheiner et al., "Current concepts in the management of Helicobacter pylori infection: the Maastricht III Consensus Report", Gut (2007) 56(6):772-781.
Matteson et al., "Iodomethaneboronic Esters and Aminomethaneboronic Esters", J Organomet. Chem. (1979) 170:259-264.
Matteson et al., "A Directed Chiral Synthesis of Amino Acids from Boronic Esters", Tetrahedron Lett. (1987) 28(39):4499-4502.
Matteson, D.S., "Asymmetric Synthesis with Boronic Esters", Acc Chem Res. (1988) 21(8):294-300.
Matteson, "Boronic esters in stereodirected synthesis", Tetrahedron (1989) 45(7):1859-1885.
Matteson et al., "A stereospecific convergent coupling of nucleophilic and electrophilic chiral carbons", J. Am. Chem. Soc. (1989) 111:4399-4402.
Matteson et al., "Synthesis of asymmetrically deuterated glycerol and dibenzylglyceraldehyde via boronic esters", J. Am. Chem. Soc. (1990) 112:3964-3969.
Matteson et al., "(Alkoxyalkyl)boronic Ester Intermediates for Asymmetric Synthesis", Organometallics (1996) 15:152-163.
Matteson, "Alpha-Halo Baronic Esters in Asymmetric Synthesis", Tetrahedron (1998) 54(36):10555-10607.
Matteson et al., "Glass-Catalyzed Conversion of Boronic Esters of Asymmetric Diols to Diol Sulfites and Amine Complexes of Boron Halides", Oranometallics (2001) 20(13):2920-2923 & supporting Information (9 pages).
Matteson et al., "Cesium Alkyltrifluoroborates from Asymmetric Boronic Esters", Synlett (Jul. 2006) 20:3501-3503.
Matteson et al., "Synthesis of a (Beta-acetamido-alpha-acetoxyethyl) boronic ester via azido boronic esters", J Organomet Chem. (2008) 693:2258-2262.
Matteson, "Boronic Esters in Asymmetric Synthesis", J Org Chem. (Oct. 2013) 78(20): 10009-10023.
McOmie J.R.W. [Ed], Protective Groups in Organic Chemistry, Plenum Press, London & New York (1973); TOC, 3 pages.
Meanwell, "Synopsis of some recent tactical application of bioisosteres in drug design", J. Med. Chem. (2011) 54:2529-2591.
McSharry et al., "Prediction of the pharmacodynamically linked variable of oseltamivir carboxylate for influenza A virus using an in vitro hollow-fiber infection model system", Antimicrob Agents Chemother (2009) 53(6): 2375-2381.
Mendoza et al., "Bis(phenylthio)methaneboronic Esters as Sources of Carbanions and Ketene Thioacetals", J Org Chem. (1979) 44(8):1352-1354.
Micalizio et al., "A Boronic Ester Annulation Strategy for Diversity-Oriented Organic Synthesis", Angew Chem Int Ed Engl. (2002) 41(1):152-154.
Mkhalid et al., "C—H activation for the construction of C—B bonds", Chem Rev. (2010) 110(2): 890-931.
Molander et al., "Highly stereoselective synthesis of cis-alkenyl pinacolboronates and potassium cis-alkenyltrifluoroborates via a hydroboration/protodeboronation approach", J Org Chem. (2008) 73(17): 6841-6844.
Montalbetti et al., "Amide bond formation and peptide coupling", Tetrahedron (2005) 61:10827-10852.
Montefour et al., "Acinetobacter baumannii: an emerging multidrug-resistant pathogen in critical care", Crit Care Nurse (2008) 28(1):15-25.
Morandi et al., "Structure-based optimization of cephalothin-analogue boronic acids as beta-lactamase inhibitors", Bioorg Med Chem. (2008) 16(3):1195-205. Epub Nov. 7, 2007.
Mori et al., "Synthesis of 1,3-dienes from alkynes and ethylene: Acetic acid 2-methylene-3-phenethylbut-3-enyl ester", Org Synth. (2005) 81:1-13.
Morrill et al., "Treatment Options for Carbapenem-Resistant Enterobacteriaceae Infections", Open Forum Infectious Diseases [OFID] Apr. 2015; 15 pages.
Munar et al., "Drug Dosing Adjustments in Patients with Chronic Kidney Disease", Am Fam Physician (May 2007) 75(1): 1487-1496.
Nema et al., "Excipients and Their Role in Approved Injectable Products: Current Usage and Future Directions", PDA J Pharm Sci Technol. (2011) 65(3):287-332.
Ness et al., "Structure-based design guides the improved efficacy of deacylation transition state analogue inhibitors of TEM-1 beta-Lactamase", Biochemistry (2000) 39(18):5312-5321.
Nicasio et al., "Pharmacokinetics-Pharmacodynamics of Tazobactam in Combination with Piperacillin in an In Vitro Infection Model", Antimicrob Agents Chemother. (2016) 60: 20752080. doi: 10.1128/AAC.02747-15.
Nicolau DP., "Pharmacokinetic and pharmacodynamic properties of meropenem", Clin Infect Dis. (2008) 47 Suppl 1: S32-S40.
Noguchi et al., "Boron-masking strategy for the selective synthesis of oligoarenes via iterative Suzuki-Miyaura coupling", J Am Chem Soc. (2007) 129(4): 758-759; Supporting Information, 46 pages.
Nordmann et al., How to Detect NDM-1 Producers, J. Clin. Micro. (2011) 49:718-721.
Overman et al., "Organic Synthesis—Working with Hazardous Chemicals", Org Synth. (1990) 68: 182; 5 pages.

(56) References Cited

OTHER PUBLICATIONS

Panek et al., "Diastereoselectivity in the borane methyl sulfide promoted hydroboration of .alpha.-alkoxy-.beta, gamma.-unsaturated esters. Documentation of an alkoxy-directed hydroboration reaction", J. Org. Chem. (1992) 57(20):5288-5290.
Paquette L.A. [Ed.] Encyclopedia of Reagents for Organic Synthesis, vol. 1; J. Wiley & Sons (1995); Cover Only.
Patani et al., "Bioisosterism: A Rational Approach in Drug Design", Chem Rev. (1996) 96:3147-3176.
Paterson et al., "Extended-Spectrum beta-Lactamases: a Clinical Update", Clin Microbiol Rev. (2005) 18(4):657-686.
Pellissier, H., "Recent developments in asymmetric cyclopropanation", Tetrahedron (2008) 64(30-31): 7041-7095.
Perez et al., "Why are we afraid of Acinetobacter baumannii?", Expert Rev Anti Infect Ther. (2008) 6(3): 269-71.
Pietruszka et al., "Enantiomerically pure cyclopropylamines from cyclopropylboronic esters", Eur J Org Chem. (2009) 34: 5998-6008.
Pine et al., "Resonance vs. Tautomerism" in Organic Chemistry; McGraw-Hill, New York 4th Ed. (1980), pp. 218-219.
Pintaric et al., "An Opportunity for Mg-Catalyzed Grignard-Type Reactions: Direct Coupling of Benzylic Halides with Pinacolborane with 10 mol % of Magnesium", J Am Chem Soc. (2010) 132(34): 11825-11827.
Powell et al., "Compendium of excipients for parenteral formulations", PDA J Pharm Sci Technol. (1998) 52(5):238-311.
Rehm et al., "*Staphylococcus aureus*: Methicillin-susceptible *S. aureus* to Methicillin-resistant *S. aureus* and Vancomycin-resistant *S. aureus*", Clin Inf Diseases. (2010) 51(52):S176-S182.
Reissig et al.,"High diastereoselection in the alkylation of siloxy-substituted methyl cyclopropanecarboxylates: consequence of a pyramidal ester enolate anion?", J. Am. Chem. Soc. (1982) 104:1735-1737.
Robak et al., "Synthesis and applications of tert-butanesulfinamide", Chem Rev. (2010) 110(6):3600-3740.
Roche, E.B. (Ed.)., Bioreversible Carriers in Drug Design: Theory and Application. New York: Pergamon Press (1987); pp. 14-21.
Rodriguez-Martinez et al., "VIM-19, a Metallo-beta-lactamase with increased Carbapenemase Activity from *Escherichia coli* and *Klebsiella pneumoniae*", Antimicro Agents Chemother. (2010) 54(1):471-476.
Rubino et al., "Phase 1 Study of the Safety, Tolerability, and Pharmacokinetics of Vaborbactam and Meropenem Alone and in Combination following Single and Multiple Doses in Healthy Adult Subjects", Antimicrob Agents Chemother. (Apr. 2018) 62(4): E02228-17; 12 pages.
Sabet et al., "In Vivo Efficacy of Carbavance (Meropenem/RPX7009) Against KPC-producing Enterobacteriaceae", Abstracts of the 54th Interscience Conference on Antimicrobial Agents and Chemotherapy (Sep. 5-9, 2014) F-958; 3 pages.
Sabet et al., "Activity of Simulated Human Dosage Regimens of Meropenem and Vaborbactam against Carbapenem-Resistant Enterobacteriaceae in an In Vitro Hollow-Fiber Model", Antimicrob Agents Chemother (2017) 62. pii: e01969-17. doi: 10.1128/AAC.01969-17.
Sabet et al., "Activity of Meropenem-Vaborbactam in Mouse Models of Infection Due to KPC-Producing Carbapenem-Resistant Enterobacteriaceae", Antimicrob Agents Chemother. (2017) 62:1 10 e01446-379 17.
Sawant et al., "Synthesis of the C1—C13 Fragment of Biselyngbyaside", Synlett (2011) 20: 3002-3004.
Sawyer et al., "Physical properties and synthetic utility of a-alkoxyorganolithium species as studied through ligand selectivity in tin-lithium exchange", J. Am. Chem. Soc. (1988) 110:842-853.
Scriven et al., "Azides: Their preparation and synthetic uses", Chem Rev. (1988) 88(2): 297-368.
Selander et al., "Palladium-catalyzed allylic C—OH functionalization for efficient synthesis of functionalized allylsilanes", J Am Chem Soc. (2011) 133(3):409-411.
Shaffer, Robyn Kroop, "The Challenge of Antibiotic-Resistant *Staphylococcus*: Lessons from Hospital Nurseries in the mid-20th Century", Yale J Biol Med. (2013) 86:261-270.

Shao et al., "Asymmetric hydrogenation of 3,5-Dioxoesters catalyzed by Ru-binap complex: A short step asymmetric synthesis of 6-substituted 5,6-dehydro-2-pyrones", Tetrahedron (1993) 49(10):1997-2010.
Singer et al., "Catalytic, enantioselective acetate aldol additions to alpha-, beta-ynals: Preparation of optically active propargylic alcohols", Tetrahedron (1998) 54(25): 7025-7032.
Singh et al., "Asymmetric Homologation of Boronic Esters Bearing Azido and Silyloxy Substituents", J Org Chem. (2000) 65(20):6650-6653 and Erratum: J Org Chem. (2001) 66(22):7560.
Singh et al., "Confronting the challenges of discovery of novel antibacterial agents", Bioorg Med Chem Lett. (2014) 24(16):3683-3689.
Sliwka et al., "Synthetic Sulfur Carotenoids II: Optically Active Carotenoid Thiols", Tetrahedron: Asymmetry (1993) 4(3):361-368.
Solladié et al., "First Stereocontrolled Synthesis of the (3S,5R,7R,10R,11R)-C1—C13 Fragment of Nystatin A(1)", J Org Chem. (1999) 64(15):5447-5452.
Souto et al., "Synthesis and biological characterization of the histone deacetylase inhibitor largazole and c7-modified analogues", J. Med. Chem. (2010) 53(12):4654-4667.
Spiegel et al., "CP-263,114 synthetic studies. Construction of an isotwistane ring system via rhodium carbenoid C—H insertion", Tetrahedron (2002) 58:6545-6554.
Sumida et al., "Boron-selective biaryl coupling approach to versatile dibenzoxaborins and application to concise synthesis of defucogilvocarcin M", Org Ltt. (Dec. 2014) 16(23):6240-6243.
Sun et al., "A method for the deprotection of alkylpinacolyl boronate esters", J Org Chem. (2011) 76(9): 3571-3575; Supporting Information, 8 pages.
Sun et al., "Programmed Synthesis of a Contiguous Stereotriad Motif by Triple Stereospecific Reagent-controlled Homologation", Org Lttr. (Jul. 2013) 15(17):4500-4503.
Tam et al., "Optimization of meropenem minimum concentration/MIC ratio to suppress in vitro resistance of Pseudomonas aeruginosa", Antimicrob Agents Chemother. (2005) 49(12): 4920-4927.
Teo et al., "Efficient and highly aldehyde selective Wacker oxidation", Org Lett. (2012) 14(13):3237-3239.
Theuretzbacher et al., "Update on antibacterial and antifungal drugs—can we master the resistance crisis?", Curr Opin Pharmacol. (2011) 11:429-432.
U.S. Department of Health and Human Resources, "Antibiotic Resistance Threats in the United States, 2013"; 114 pages.
Valters et al., "Ring-Chain Tautomerism", Plenum Press, New York and London, Softcover reprint of the hardcover 1st Ed. 1985, Chapter 1, 23 pages.
VanScoy et al., "Pharmacokinetics-pharmacodynamics of tazobactam in 386 combination with ceftolozane in an in vitro infection model", Antimicrob Agents Chemother. (2013) 57: 2809-2814. doi: 10.1128/AAC.02513-12.
Vasil'Ev et al., (1977): STN International HCAPLUS database, Columbus (OH), accession No. 1977: 72730; 1 page.
Vitor et al., "Rhenium(I)- and technetium(I) tricarbonyl complexes anchored by bifunctional pyrazole-diamine and pyrazole-dithioether chelators", J Organometal Chem (2004) 689(25):4764-4774.
Voituriez et al., "Preparation of a storable zinc carbenoid species and its application in cyclopropanation, chain extension, and [2,3]-sigmatropic rearrangement reactions", J Org Chem. (2010) 75(4): 1244-1250; Supporting Information, 20 pages.
Waley, Stephen G., "A quick method for the determination of inhibition constants", Biochem J. (1982) 205(3):631-633.
Walker et al., "Pharmacodynamic activities of meropenem in an animal infection model", (1994), Abstracts of Papers #A91, 34th Interscience Conference on Antimicrobial Agents and Chemotherapy, Orlando, FL., 5 pages.
Walsh et al., "Metallo-beta-Lactamases: the Quiet before the Storm?", Clin Microbiol Rev. (2005) 18(2):306-325.
Wang et al., "Recognition and resistance in TEM beta-lactamase", Biochemistry (2003) 42(28):8434-8444.
Webb et al., "Metal catalysed hydroboration of vinyl sulfides, sulfoxides, sulfones, and sulfonates", J Mol Cat A: Chem. (2007) 275:91-100.

(56) References Cited

OTHER PUBLICATIONS

Wilson D.N., "The A-Z of bacterial translation inhibitors", Crit Rev Biochem Mol Biolog. (2009) 44(6):393-433.
Wohlrab et al., "Total synthesis of plusbacin A3: a depsipeptide antibiotic active against vancomycin-resistant bacteria", J. Am. Chem. Soc. (2007) 129:4175-4177.
Wong et al., "A chemoselective Reformatsky-Negishi approach to α-haloaryl esters", Tetrahedron (2014) 70(7): 1508-1515.
Xia et al., "Synthesis and SAR of novel benzoxaboroles as a new class of beta-lactamase inhibitors", Bioorg Med Chem Lett. (2011) 21:2533-2536.
Xie et al., "Group-assisted purification (GAP) chemistry for the synthesis of Velcade via asymmetric borylation of N-phosphinylimines", Beilstein J Org Chem (Mar. 2014) 10:746-751.
Yamamoto et al., "Iridium-catalyzed hydroboration of alkenes with pinacolborane", Tetrahedron (2004) 60:10695-10700.
Yanagisawa et al., "Nonpeptide angiotensin II receptor antagonists: synthesis, biological activities, and structure-activity relationships of imidazole-5-carboxylic acids bearing alkyl, alkenyl, and hydroxyalkyl substituents at the 4-position and their related compounds", J Med Chem. (1996) 39(1):323-338.
Yuen et al., "Deprotection of pinacolyl boronate esters via hydrolysis of intermediate potassium trifluoroborates", Tetrahed Lttr. (2005) 46(46):7899-7903.
Zhu et al., "Design, preparation, x-ray crystal structure, and reactivity of o-alkoxyphenyliodonium bis(methoxycarbonyl)methanide, a highly soluble carbene precursor", Org Lett. (2012) 14(12): 3170-3173; Supporting Information, 76 pages.
International Search Report and Written Opinion [Corrected Version] dated Jun. 6, 2016 for International Application No. PCT/US2016/022678, filed Mar. 16, 2016.
International Written Opinion (Rule 66) dated Feb. 8, 2017 for International Application No. PCT/US2016/022678, filed Mar. 16, 2016.
International Preliminary Report of Patentability dated May 10, 2017 for International Application No. PCT/US2016/022678, filed Mar. 16, 2016.
CAS Registry No. 2114651-20-4; "7-Benzofurancarboxylic acid", Aurora Fine Chemicals; Aug. 16, 2017; 1 page.
CAS Registry No. 1780853-40-8; "7-Benzofurancarboxylic acid", Aurora Fine Chemicals; Jun. 15, 2015; 1 page.
CAS Registry No. 1427326-65-5; "7-Benzofurancarboxylic acid", Ellanova Laboratories; Apr. 5, 2013; 1 page.
CAS Registry No. 1344904-36-4; "7-Benzofurancarboxylic acid", Asiba Pharmatech, Inc.; Nov. 13, 2011; 1 page.
CAS Registry No. 1890373-92-8; "Benzoic acid", Aurora Fine Chemicals; Apr. 15, 2016; 1 page.
Cheng et al., "Inhibitors of hepatitis C virus polymerase: Synthesis and characterization of novel 2-oxy-6-fluoro-N-((S)-1-hydroxy-3-phenylpropan-2-yl)-benzamides", Bioorg Med Chem Ltts. (2010) 20:2119-2124.

SUBSTITUTED BORONIC ACIDS AS ANTIMICROBIALS

CROSS-REFERENCE TO RELATED APPLICATIONS

This application is a continuation of and claims priority to U.S. application Ser. No. 15/558,544, filed Sep. 14, 2017, which is the U.S. National Phase of International Application No. PCT/US2016/022678, filed Mar. 16, 2016, which claims the benefit of U.S. Provisional Application No. 62/134,329, filed Mar. 17, 2015, and U.S. Provisional Application No. 62/191,221, filed Jul. 10, 2015, the disclosures of each of which are incorporated herein by reference in their entireties.

BACKGROUND

Field of the Invention

The present invention relates to the fields of chemistry and medicine. More particularly, the present invention relates to boronic acid antimicrobial compounds, compositions, their preparation, and their use as therapeutic agents.

Description of the Related Art

Antibiotics have been effective tools in the treatment of infectious diseases during the last half-century. From the development of antibiotic therapy to the late 1980s there was almost complete control over bacterial infections in developed countries. However, in response to the pressure of antibiotic usage, multiple resistance mechanisms have become widespread and are threatening the clinical utility of anti-bacterial therapy. The increase in antibiotic resistant strains has been particularly common in major hospitals and care centers. The consequences of the increase in resistant strains include higher morbidity and mortality, longer patient hospitalization, and an increase in treatment costs.

Various bacteria have evolved β-lactam deactivating enzymes, namely, β-lactamases, that counter the efficacy of the various β-lactam antibiotics. β-lactamases can be grouped into 4 classes based on their amino acid sequences, namely, Ambler classes A, B, C, and D. Enzymes in classes A, C, and D include active-site serine β-lactamases, and class B enzymes, which are encountered less frequently, are Zn-dependent. These enzymes catalyze the chemical degradation of β-lactam antibiotics, rendering them inactive. Some β-lactamases can be transferred within and between various bacterial strains and species. The rapid spread of bacterial resistance and the evolution of multi-resistant strains severely limits β-lactam treatment options available.

The increase of class D β-lactamase-expressing bacterium strains such as *Acinetobacter baumannii* has become an emerging multidrug-resistant threat. *A. baumannii* strains express A, C, and D class β-lactamases. The class D β-lactamases such as the OXA families are particularly effective at destroying carbapenem type β-lactam antibiotics, e.g., imipenem, the active carbapenems component of Merck's Primaxin® (Montefour, K.; et al. Crit. Care Nurse 2008, 28, 15; Perez, F. et al. Expert Rev. Anti Infect. Ther. 2008, 6, 269; Bou, G.; Martinez-Beltran, J. Antimicrob. Agents Chemother. 2000, 40, 428. 2006, 50, 2280; Bou, G. et al, J. Antimicrob. Agents Chemother. 2000, 44, 1556). This has imposed a pressing threat to the effective use of drugs in that category to treat and prevent bacterial infections. Indeed the number of catalogued serine-based β-lactamases has exploded from less than ten in the 1970s to over 300 variants. These issues fostered the development of five "generations" of cephalosporins. When initially released into clinical practice, extended-spectrum cephalosporins resisted hydrolysis by the prevalent class A β-lactamases, TEM-1 and SHV-1. However, the development of resistant strains by the evolution of single amino acid substitutions in TEM-1 and SHV-1 resulted in the emergence of the extended-spectrum β-lactamase (ESBL) phenotype.

New β-lactamases have recently evolved that hydrolyze the carbapenem class of antimicrobials, including imipenem, biapenem, doripenem, meropenem, and ertapenem, as well as other β-lactam antibiotics. These carbapenemases belong to molecular classes A, B, and D. Class A carbapenemases of the KPC-type predominantly in *Klebsiella pneumoniae* but now also reported in other *Enterobacteriaceae*, *Pseudomonas aeruginosa* and *Acinetobacter baumannii*. The KPC carbapenemase was first described in 1996 in North Carolina, but since then has disseminated widely in the US. It has been particularly problematic in the New York City area, where several reports of spread within major hospitals and patient morbidity have been reported. These enzymes have also been recently reported in France, Greece, Sweden, United Kingdom, and an outbreak in Germany has recently been reported. Treatment of resistant strains with carbapenems can be associated with poor outcomes.

The zinc-dependent class B metallo-β-lactamases are represented mainly by the VIM, IMP, and NDM types. IMP and VIM-producing *K. pneumonia* were first observed in 1990s in Japan and 2001 in Southern Europe, respectively. IMP-positive strains remain frequent in Japan and have also caused hospital outbreaks in China and Australia. However dissemination of IMP-producing *Enterobacteriaceae* in the rest of the word appears to be somewhat limited. VIM-producing enterobacteria can be frequently isolated in Mediterranean countries, reaching epidemic proportions in Greece. Isolation of VIM-producing strains remains low in Northern Europe and in the United States. In stark contrast, a characteristic of NDM-producing *K. pneumonia* isolates has been their rapid dissemination from their epicenter, the Indian subcontinent, to Western Europe, North America, Australia and Far East. Moreover, NDM genes have spread rapidly to various species other than *K. pneumonia*.

The plasmid-expressed class D carbapenemases belong to OXA-48 type. OXA-48 producing *K. pneumonia* was first detected in Turkey, in 2001. The Middle East and North Africa remain the main centers of infection. However, recent isolation of OXA-48-type producing organisms in India, Senegal and Argentina suggest the possibility of a global expansion. Isolation of OXA-48 in bacteria other than *K. pneumonia* underlines the spreading potential of OXA-48.

Treatment of strains producing any of these carbapenemases with carbapenems can be associated with poor outcomes.

Another mechanism of β-lactamase mediated resistance to carbapenems involves combination of permeability or efflux mechanisms combined with hyper production of beta-lactamases. One example is the loss of a porin combined in hyperproduction of ampC beta-lactamase results in resistance to imipenem in *Pseudomonas aeruginosa*. Efflux pump over expression combined with hyperproduction of the ampC β-lactamase can also result in resistance to a carbapenem such as meropenem.

Thus, there is a need for improved β-lactamase inhibitors.

SUMMARY

Some embodiments relate to a compound having the structure of structure of the formula I' or II':

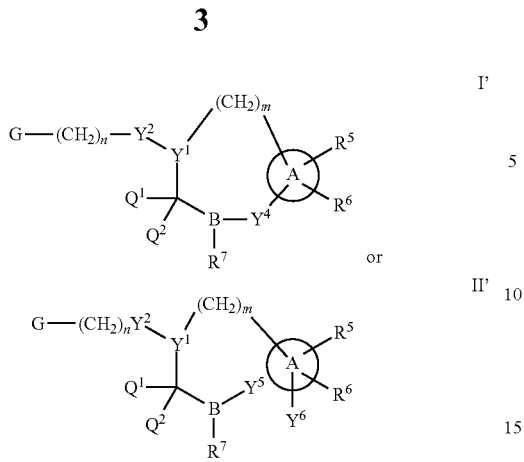

or a pharmaceutically acceptable salt thereof, wherein:
each G is independently selected from the group consisting of —C(O)R$^4$, C(O)(CH$_2$)$_{0-3}$SR$^3$, —C(O)(CH$_2$)$_{1-3}$R$^4$, —C(O)OR$^3$, —C(O)NR$^1$R$^2$, —C(O)NR$^1$OR$^3$, —NR$^1$C(O)R$^4$, —NR$^1$C(O)NR$^1$R$^2$, —NR$^1$C(O)OR$^3$, —NR$^1$S(O)$_2$R$^3$, —NR$^1$S(O)$_2$NR$^1$R$^2$, —C(=NR$^1$)R$^4$, —C(=NR$^1$)NR$^1$R$^2$, —NR$^1$CR$^4$(=NR$^2$), —NR$^1$C(=NR$^2$)NR$^1$R$^2$, —S(O)$_2$R$^3$, —S(O)(CH$_2$)$_{1-3}$R$^3$, —S(O)$_2$NR$^1$R$^2$, —S(O)$_2$NR$^1$OR$^3$, —NR$^1$S(O)$_2$NR$^1$OR$^3$, —CN, —OR$^1$, —SR$^1$, —NR$^1$R$^2$, optionally substituted C$_{1-10}$ alkyl, optionally substituted C$_{2-10}$alkenyl, optionally substituted C$_{2-10}$alkynyl, optionally substituted C$_{3-7}$ carbocyclyl, optionally substituted 5-10 membered heterocyclyl, optionally substituted C$_{6-10}$aryl, optionally substituted 5-10 membered heteroaryl, optionally substituted C$_{3-7}$carbocyclyl-C$_{1-6}$alkyl, optionally substituted 5-10 membered heterocyclyl-C$_{1-6}$alkyl, optionally substituted C$_{6-10}$aryl-C$_{1-6}$alkyl, and optionally substituted 5-10 membered heteroaryl-C$_{1-6}$alkyl;
Y$^1$ is selected from the group consisting of CR$^1$ and N;
each Y$^2$ is independently selected from the group consisting of —S—, —S(O)—, —S(O)$_2$—, —O—, —CR$^1$R$^2$, and —NR$^2$—, or Y$^2$—(CH$_2$)$_n$-G is CH$_3$;
Y$^4$ is selected from the group consisting of —O—, —S—, and —NR$^1$—;
Y$^5$ is selected from the group consisting of —OH, —SH, and —NHR$^1$;
Y$^6$ is selected from the group consisting of —OH, optionally substituted —O—C$_{1-6}$ alkyl, —NR$^1$R$^2$, and —N(OR$^3$)R$^2$,
Q$^1$ and Q$^2$ is each indecently H or —Y$^2$—(CH$_2$)$_n$-G;
each n is independently an integer from 0 to 3;
m is 0 or 1;
A is selected from the group consisting of C$_{3-10}$ carbocyclyl, C$_{6-10}$ aryl, 5-10 membered heteroaryl, and 5-10 membered heterocyclyl;
each R$^1$, R$^2$, R$^3$, and R$^4$ are independently selected from —H, halogen, optionally substituted C$_{1-4}$alkyl, optionally substituted O—C$_{1-4}$alkyl, optionally substituted C$_{3-7}$ carbocyclyl, optionally substituted 4-10 membered heterocyclyl, optionally substituted C$_{6-10}$aryl, and optionally substituted 5-10 membered heteroaryl;
R$^5$ is present 1 to 5 times and each R$^5$ is independently selected from the group consisting of H, OH, halogen, CN, —C(O)OR$^1$; —C(O)NR$^1$R$^2$; —C(O)NR$^1$OR$^2$; —NR$^1$C(O)R$^2$; —NR$^1$C(O)NR$^2$R$^3$; —NR$^1$C(O)OR$^2$; —NR$^1$S(O)$_2$R$^2$; —NR$^1$S(O)$_2$NR$^2$R$^3$; —C(=NR$^1$)R$^2$; —C(=NR$^1$)NR$^2$R$^3$; —NR$^1$CR$^2$(=NR$^3$); —NR$^1$C(=NR$^2$)NR$^3$R$^4$; —S(O)(CH$_2$)$_{1-3}$R$^4$, —S(O)$_2$NR$^1$R$^2$, —S(O)$_2$NR$^1$OR$^3$, —NR$^1$S(O)$_2$NR$^1$OR$^3$, optionally substituted C$_2$-C$_6$ alkenyl, optionally substituted C$_2$-C$_6$ alkynyl, optionally substituted C$_1$-C$_6$ heteroalkyl, optionally substituted C$_3$-C$_7$ carbocyclyl, optionally substituted 5-10 membered heterocyclyl, optionally substituted C$_{6-10}$aryl, optionally substituted 5-10 membered heteroaryl, cyano, C$_1$-C$_6$ alkoxy(C$_1$-C$_6$)alkyl, aryloxy, sulfhydryl (mercapto), and —(CH$_2$)$_p$—Y$^3$—(CH$_2$)$_q$M';
p and q are each independently 0, 1, or 2;
Y$^3$ is selected from the group consisting of —S—, —S(O)—, —S(O)$_2$—, —O—, —CR$^1$R$^2$—, and —NR$^1$—;
M' is selected from the group consisting of halogen, cycano, —OH, —C(O)NR$^1$R$^2$; —C(O)NR$^1$OR$^2$; —NR$^1$C(O)R$^2$; —NR$^1$C(O)NR$^2$R$^3$; —NR$^1$C(O)OR$^2$; —NR$^1$S(O)$_2$R$^2$; —NR$^1$S(O)$_2$NR$^2$R$^3$; —C(=NR$^1$)R$^2$; —C(=NR$^1$)NR$^2$R$^3$; —NR$^1$CR$^2$(=NR$^3$); —NR$^1$C(=NR$^2$)NR$^3$R$^4$; —S(O)$_2$R$^1$, —S(O)$_2$NR$^1$R$^2$, —S(O)$_2$NR$^1$OR$^3$, C$_{1-4}$ alkyl optionally substituted with 0-2 substituents selected from the group consisting of —OR$^1$, —CN, —NR$^1$R$^2$, -heterocyclyl, halogen, —C(O)NR$^1$R$^2$, and —NR$^1$C(O)R$^2$; C$_{2-4}$ alkenyl optionally substituted with 0-2 substituents selected from the group consisting of C$_{1-4}$ alkyl, —(CH$_2$)$_{0-4}$OR$^1$, —(CH$_2$)$_{0-4}$CN, —(CH$_2$)$_{0-4}$NR$^1$R$^2$, —(CH$_2$)$_{0-4}$-heterocyclyl, halogen, —C(O)NR$^1$R$^2$, and —NR$^1$C(O)R$^2$; C$_{2-4}$ alkynyl optionally substituted with 0-2 substituents selected from the group consisting of C$_{1-4}$ alkyl, —(CH$_2$)$_{0-4}$OR$^1$, —(CH$_2$)$_{0-4}$CN, —(CH$_2$)$_{0-4}$NR$^1$R$^2$, —(CH$_2$)$_{0-4}$-heterocyclyl, halogen, —C(O)NR$^1$R$^2$, and —NR$^1$C(O)R$^2$; C$_{6-10}$aryl optionally substituted with 0-2 substituents selected from the group consisting of C$_{1-4}$ alkyl, —(CH$_2$)$_{0-4}$OR$^1$, —(CH$_2$)$_{0-4}$CN, —(CH$_2$)$_{0-4}$NR$^1$R$^2$, —(CH$_2$)$_{0-4}$-heterocyclyl, halogen, —C(O)NR$^1$R$^2$, and —NR$^1$C(O)R$^2$; C$_{3-7}$ carbocyclyl optionally substituted with 0-2 substituents selected from the group consisting of C$_{1-4}$ alkyl, —(CH$_2$)$_{0-4}$OR$^1$, —(CH$_2$)$_{0-4}$CN, —(CH$_2$)$_{0-4}$NR$^1$R$^2$, —(CH$_2$)$_{0-4}$-heterocyclyl, halogen, —C(O)NR$^1$R$^2$, and —NR$^1$C(O)R$^2$; 5-10 membered heteroaryl optionally substituted with 0-2 substituents selected from the group consisting of C$_{1-4}$ alkyl, —(CH$_2$)$_{0-4}$OR$^1$, —(CH$_2$)$_{0-4}$CN, —(CH$_2$)$_{0-4}$NR$^1$R$^2$, —(CH$_2$)$_{0-4}$-heterocyclyl, halogen, —C(O)NR$^1$R$^2$, and —NR$^1$C(O)R$^2$; and 3-10 membered heterocyclyl optionally substituted with 0-2 substituents selected from the group consisting of C$_{1-4}$ alkyl, —(CH$_2$)$_{0-4}$OR$^1$, —(CH$_2$)$_{0-4}$CN, —(CH$_2$)$_{0-4}$NR$^1$R$^2$, —(CH$_2$)$_{0-4}$-heterocyclyl, halogen, —C(O)NR$^1$R$^2$, and —NR$^1$C(O)R$^2$;
R$^6$ is selected from the group consisting of is selected from the group consisting of —H, halogen, optionally substituted —C$_{1-6}$ alkyl, —OH, —C(O)OR, —P(O)(OR)$_2$, P(O)(OR)R$^1$, optionally substituted —O—C$_{1-6}$ alkyl, —NR$^1$R$^2$, —N(OR$^3$)R$^2$, optionally substituted —S—C$_{1-6}$ alkyl, —C(O)NR$^1$R$^2$, —S(O)$_2$NR$^1$R$^2$, CN, optionally substituted —S(O)—C$_{1-6}$ alkyl, optionally substituted —S(O)$_2$—C$_{1-6}$ alkyl, and a carboxylic acid isostere;
R is selected from —H, —C$_{1-9}$alkyl, —CR$^{10}$R$^{11}$OC(O)C$_{1-9}$alkyl, —CR$^{10}$R$^{11}$OC(O)OC$_{1-9}$alkyl, —CR$^{10}$R$^{11}$OC(O)C$_{6-10}$aryl, —CR$^{10}$R$^{11}$OC(O)OC$_{6-10}$aryl, —CR$^{10}$R$^{11}$OC(O)NR$^{10}$C$_{1-9}$alkyl, —CR$^{10}$R$^{11}$OC(O)NR$^{10}$C$_{6-10}$aryl, and

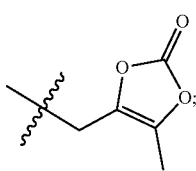 [SMILES: *Cc1oc(=O)oc1C]

$R^7$ is selected from the group consisting of OH, optionally substituted —O—$C_{1-6}$ alkyl, —$NR^1R^2$, and —$N(OR^3)R^2$; and $R^{10}$ and $R^{11}$ are independently selected from the group consisting of —H, optionally substituted $C_{1-4}$alkyl, optionally substituted $C_{3-7}$ carbocyclyl, optionally substituted 5-10 membered heterocyclyl, optionally substituted $C_{6-10}$aryl, and optionally substituted 5-10 membered heteroaryl.

A compound having the structure of the Formula (I) or (II):

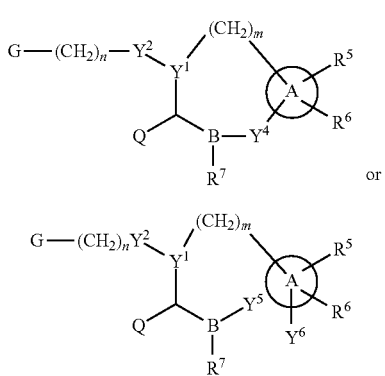

or a pharmaceutically acceptable salt thereof, wherein:

each G is independently selected from the group consisting of —C(O)$R^4$, —C(O)(CH$_2$)$_{0-3}$SR$^3$, C(O)(CH$_2$)$_{1-3}$R$^4$, —C(O)OR$^3$, —C(O)NR$^1$R$^2$, —C(O)NR$^1$OR$^3$, —NR$^1$C(O)R$^4$, NR$^1$C(O)NR$^1$R$^2$, —NR$^1$C(O)OR$^3$, —NR$^1$S(O)$_2$R$^3$, —NR$^1$S(O)$_2$NR$^1$R$^2$, —C(=NR$^1$)R$^4$, C(=NR$^1$)NR$^1$R$^2$, —NR$^1$CR$^4$(=NR$^2$), —NR$^1$C(=NR$^2$)NR$^1$R$^2$, —S(O)$_2$R$^3$, optionally substituted $C_{1-10}$ alkyl, optionally substituted $C_{2-10}$alkenyl, optionally substituted $C_{2-10}$alkynyl, optionally substituted $C_{3-7}$ carbocyclyl, optionally substituted 5-10 membered heterocyclyl, optionally substituted $C_{6-10}$aryl, optionally substituted 5-10 membered heteroaryl, optionally substituted $C_{3-7}$carbocyclyl-$C_{1-6}$alkyl, optionally substituted 5-10 membered heterocyclyl-$C_{1-6}$alkyl, optionally substituted $C_{6-10}$aryl-$C_{1-6}$alkyl, and optionally substituted 5-10 membered heteroaryl-$C_{1-6}$alkyl;

$Y^1$ is selected from the group consisting of $CR^1$ and N;

each $Y^2$ is independently selected from the group consisting of —S—, —S(O)—, —S(O)$_2$—, —O—, —CR$^1$R$^2$—, and —NR$^2$—;

$Y^4$ is selected from the group consisting of —O—, —S—, and —NR$^1$—;

$Y^5$ is selected from the group consisting of —OH, —SH, and —NHR$^1$;

$Y^6$ is selected from the group consisting of —OH, optionally substituted —O—$C_{1-6}$ alkyl, —NR$^1$R$^2$, and —N(OR$^3$)R$^2$;

Q is H or —$Y^2$—(CH$_2$)$_n$-G;

each n is independently an integer from 0 to 3;

m is 0 or 1;

A is selected from the group consisting of $C_{3-10}$ carbocyclyl, $C_{6-10}$ aryl, 5-10 membered heteroaryl, and 5-10 membered heterocyclyl;

each $R^1$, $R^2$, $R^3$, and $R^4$ are independently selected from —H, optionally substituted $C_{1-4}$alkyl, optionally substituted $C_{3-7}$ carbocyclyl, optionally substituted 4-10 membered heterocyclyl, optionally substituted $C_{6-10}$aryl, and optionally substituted 5-10 membered heteroaryl;

$R^5$ is present 1 to 5 times and each $R^5$ is independently selected from the group consisting of H, OH, halogen, —CF$_3$, optionally substituted $C_2$-$C_6$ alkenyl, optionally substituted $C_2$-$C_6$ alkynyl, optionally substituted $C_1$-$C_6$ heteroalkyl, optionally substituted $C_3$-$C_7$ carbocyclyl, optionally substituted 5-10 membered heterocyclyl, optionally substituted $C_{6-10}$aryl, optionally substituted 5-10 membered heteroaryl, cyano, $C_1$-$C_6$ alkoxy($C_1$-$C_6$)alkyl, aryloxy, sulfhydryl (mercapto), and —(CH$_2$)$_p$—Y$^3$—(CH$_2$)$_q$M';

p and q are each independently 0 or 1;

$Y^3$ is selected from the group consisting of —S—, —S(O)—, —S(O)$_2$—, —O—, —CH$_2$—, and —NR$^1$—;

M' is selected from the group consisting of —C(O)NR$^1$R$^2$; —C(O)NR$^1$OR$^2$; —NR$^1$C(O)R$^2$; —NR$^1$C(O)NR$^2$R$^3$; —NR$^1$C(O)OR$^2$; —NR$^1$S(O)$_2$R$^2$; —NR$^1$S(O)$_2$NR$^2$R$^3$; —C(=NR$^1$)R$^2$; —C(=NR$^1$)NR$^2$R$^3$; —NR$^1$CR$^2$(=NR$^3$); —NR$^1$C(=NR$^2$)NR$^3$R$^4$; $C_{1-4}$ alkyl optionally substituted with 0-2 substituents selected from the group consisting, —OR$^1$, —NR$^1$R$^2$, halogen, —C(O)NR$^1$R$^2$, and —NR$^1$C(O)R$^2$; $C_{6-10}$ aryl optionally substituted with 0-2 substituents selected from the group consisting of $C_{1-4}$ alkyl, —OR$^1$, —NR$^1$R$^2$, halogen, —C(O)NR$^1$R$^2$, and —NR$^1$C(O)R$^2$; $C_{3-7}$ carbocyclyl optionally substituted with 0-2 substituents selected from the group consisting of $C_{1-4}$ alkyl, —OR$^1$, —NR$^1$R$^2$, halogen, —C(O)NR$^1$R$^2$, and —NR$^1$C(O)R$^2$; 5-10 membered heteroaryl optionally substituted with 0-2 substituents selected from the group consisting of $C_{1-4}$ alkyl, —OR$^1$, —NR$^1$R$^2$, halogen, —C(O)NR$^1$R$^2$, and —NR$^1$C(O)R$^2$; and 3-10 membered heterocyclyl optionally substituted with 0-2 substituents selected from the group consisting of $C_{1-4}$ alkyl, —OR$^1$, —NR$^1$R$^2$, halogen, —C(O)NR$^1$R$^2$, and —NR$^1$C(O)R$^2$;

$R^6$ is selected from the group consisting of is selected from the group consisting of —H, halogen, optionally substituted —$C_{1-6}$ alkyl, —OH, —C(O)OR, optionally substituted —O—$C_{1-6}$ alkyl, —NR$^1$R$^2$, —N(OR$^3$)R$^2$, optionally substituted —S—$C_{1-6}$ alkyl, —C(O)NR$^1$R$^2$, —S(O)$_2$NR$^1$R$^2$, CN, optionally substituted —S(O)—$C_{1-6}$ alkyl, optionally substituted —S(O)$_2$—$C_{1-6}$ alkyl, and a carboxylic acid isostere;

R is selected from —H, —$C_{1-9}$alkyl, —CR$^{10}$R$^{11}$OC(O)$C_{1-9}$alkyl, —CR$^{10}$R$^{11}$OC(O)OC$_{1-9}$alkyl, —CR$^{10}$R$^{11}$OC(O)$C_{6-10}$aryl, —CR$^{10}$R$^{11}$OC(O)OC$_{6-10}$aryl and

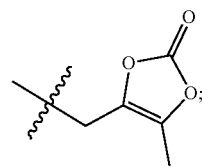 [SMILES: *Cc1oc(=O)oc1C]

$R^7$ is selected from the group consisting of OH, optionally substituted —O—$C_{1-6}$ alkyl, —NR$^1$R$^2$, and —N(OR$^3$)R$^2$; and $R^{10}$ and $R^{11}$ are independently selected from the group consisting of —H, optionally substituted $C_{1-4}$alkyl, optionally substituted C$_{3-7}$ carbocyclyl, optionally substituted 5-10 membered heterocyclyl, optionally substituted C$_{6-10}$aryl, and optionally substituted 5-10 membered heteroaryl.

Some embodiments relate to compound having the structure of the formula I' or IV':

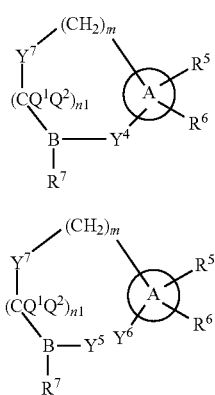

or a pharmaceutically acceptable salt thereof, wherein:

A is selected from the group consisting of C$_{3-10}$ carbocyclyl, C$_{6-10}$ aryl, 5-10 membered heteroaryl, and 5-10 membered heterocyclyl;

m is 0, 1 or 2;

Y$^7$ is selected from the group consisting of —CH$_2$—, —O—, —S— and —NR$^1$—;

n$^1$ is 1, 2 or 3;

Q$^1$ and Q$^2$ are H;

each R$^7$ is independently selected from the group consisting of OH, optionally substituted —O—C$_{1-6}$ alkyl, —NR$^1$R$^2$, and —N(OR$^1$)R$^2$; and Y$^4$ is selected from the group consisting of —O—, —S—, and —NR$^1$—;

Y$^5$ is selected from the group consisting of —OH, —SH, and —NHR$^1$;

Y$^6$ is selected from the group consisting of —OH, optionally substituted —O—C$_{1-6}$ alkyl, —NR$^1$R$^2$, and —N(OR$^1$)R$^2$;

each R$^1$, R$^2$, R$^3$ and R$^4$ are independently selected from —H, halogen, optionally substituted C$_{1-4}$alkyl, optionally substituted O—C$_{1-4}$alkyl, optionally substituted C$_{3-7}$ carbocyclyl, optionally substituted 4-10 membered heterocyclyl, optionally substituted C$_{6-10}$aryl, and optionally substituted 5-10 membered heteroaryl;

R$^5$ is present 1 to 5 times and each R$^5$ is independently selected from the group consisting of H, OH, halogen, —C(O)OR$^1$; —C(O)NR$^1$R$^2$; —C(O)NR$^1$OR$^2$; —C(=NR$^1$)R$^2$; —C(=NR$^1$)NR$^2$R$^3$; —NR$^1$C(O)R$^2$; —NR$^1$C(O)NR$^2$R$^3$; —NR$^1$C(O)OR$^2$; —NR$^1$S(O)$_2$R$^2$; —NR$^1$S(O)$_2$NR$^2$R$^3$; —NR$^1$CR$^2$(=NR$^3$); —NR$^1$C(=NR$^2$)NR$^3$R$^4$; —S(O)(CH$_2$)$_{1-3}$R$^4$, —S(O)$_2$NR$^1$R$^2$, —S(O)$_2$NR$^1$OR$^3$, —NR$^1$S(O)$_2$NR$^1$OR$^3$, optionally substituted C$_2$-C$_6$ alkenyl, optionally substituted C$_2$-C$_6$ alkynyl, optionally substituted C$_1$-C$_6$ heteroalkyl, optionally substituted C$_3$-C$_7$ carbocyclyl, optionally substituted 5-10 membered heterocyclyl, optionally substituted C$_{6-10}$aryl, optionally substituted 5-10 membered heteroaryl, cyano, C$_1$-C$_6$ alkoxy(C$_1$-C$_6$)alkyl, aryloxy, sulfhydryl (mercapto), and —(CH$_2$)$_p$—Y$^3$—(CH$_2$)$_q$M';

p and q are each independently 0, 1, or 2;

Y$^3$ is selected from the group consisting of —S—, —S(O)—, —S(O)$_2$—, —O—, —CR$^1$R$^2$, and —NR$^1$—;

M' is selected from the group consisting of halogen, cyano, —OH, —C(O)NR$^1$R$^2$; —C(O)NR$^1$OR$^2$; —NR$^1$C(O)R$^2$; —NR$^1$C(O)NR$^2$R$^3$; —NR$^1$C(O)OR$^2$; —NR$^1$S(O)$_2$R$^2$; —NR$^1$S(O)$_2$NR$^2$R$^3$; —C(=NR$^1$)R$^2$; —C(=NR$^1$)NR$^2$R$^3$; —NR$^1$CR$^2$(=NR$^3$); —NR$^1$C(=NR$^2$)NR$^3$R$^4$; —S(O)$_2$R$^1$, —S(O)$_2$NR$^1$R$^2$, —S(O)$_2$NR$^1$OR$^3$, C$_{1-4}$ alkyl optionally substituted with 0-2 substituents selected from the group consisting of —OR$^1$, —CN, —NR$^1$R$^2$, -heterocyclyl, halogen, —C(O)NR$^1$R$^2$, and —NR$^1$C(O)R$^2$; C$_{2-4}$ alkenyl optionally substituted with 0-2 substituents selected from the group consisting of C$_{1-4}$ alkyl, —(CH$_2$)$_{0-4}$OR$^1$, —(CH$_2$)$_{0-4}$CN, —(CH$_2$)$_{0-4}$NR$^1$R$^2$, —(CH$_2$)$_{0-4}$-heterocyclyl, halogen, —C(O)NR$^1$R$^2$, and —NR$^1$C(O)R$^2$; C$_{2-4}$ alkynyl optionally substituted with 0-2 substituents selected from the group consisting of C$_{1-4}$ alkyl, —(CH$_2$)$_{0-4}$OR$^1$, —(CH$_2$)$_{0-4}$CN, —(CH$_2$)$_{0-4}$NR$^1$R$^2$, —(CH$_2$)$_{0-4}$-heterocyclyl, halogen, —C(O)NR$^1$R$^2$, and —NR$^1$C(O)R$^2$; C$_{6-10}$ aryl optionally substituted with 0-2 substituents selected from the group consisting of C$_{1-4}$ alkyl, —(CH$_2$)$_{0-4}$OR$^1$, —(CH$_2$)$_{0-4}$CN, —(CH$_2$)$_{0-4}$NR$^1$R$^2$, —(CH$_2$)$_{0-4}$-heterocyclyl, halogen, —C(O)NR$^1$R$^2$, and —NR$^1$C(O)R$^2$; C$_{3-7}$ carbocyclyl optionally substituted with 0-2 substituents selected from the group consisting of C$_{1-4}$ alkyl, —(CH$_2$)$_{0-4}$OR$^1$, —(CH$_2$)$_{0-4}$CN, —(CH$_2$)$_{0-4}$NR$^1$R$^2$, —(CH$_2$)$_{0-4}$-heterocyclyl, halogen, —C(O)NR$^1$R$^2$, and —NR$^1$C(O)R$^2$; 5-10 membered heteroaryl optionally substituted with 0-2 substituents selected from the group consisting of C$_{1-4}$ alkyl, —(CH$_2$)$_{0-4}$OR$^1$, —(CH$_2$)$_{0-4}$CN, —(CH$_2$)$_{0-4}$NR$^1$R$^2$, —(CH$_2$)$_{0-4}$-heterocyclyl halogen, —C(O)NR$^1$R$^2$, and —NR$^1$C(O)R$^2$; and 3-10 membered heterocyclyl optionally substituted with 0-2 substituents selected from the group consisting of C$_{1-4}$ alkyl, —(CH$_2$)$_{0-4}$OR$^1$, —(CH$_2$)$_{0-4}$CN, —(CH$_2$)$_{0-4}$NR$^1$R$^2$, —(CH$_2$)$_{0-4}$-heterocyclyl, halogen, —C(O)NR$^1$R$^2$, and —NR$^1$C(O)R$^2$;

R$^6$ is selected from the group consisting of H, halogen, optionally substituted —C$_{1-6}$ alkyl, —OH, —C(O)OR, —P(O)(OR)$_2$, P(O)(OR)R$^1$, optionally substituted —O—C$_{1-6}$ alkyl, —NR$^1$R$^2$, —N(OR$^1$)R$^2$, optionally substituted —S—C$_{1-6}$ alkyl, —C(O)NR$^1$R$^2$, —S(O)$_2$NR$^1$R$^2$, CN, optionally substituted —S(O)—C$_{1-6}$ alkyl, optionally substituted —S(O)$_2$—C$_{1-6}$ alkyl, and a carboxylic acid isostere;

R is selected from —H, alkali metal, NH$_4$$^+$, —C$_{1-9}$alkyl, —CR$^{10}$R$^{11}$OC(O)C$_{1-9}$alkyl, —CR$^{10}$R$^{11}$OC(O)OC$_{1-9}$alkyl, —CR$^{10}$R$^{11}$OC(O)C$_{6-10}$aryl, —CR$^{10}$R$^{11}$OC(O)OC$_{6-10}$aryl, —CR$^{10}$R$^{11}$OC(O)NR$^{10}$C$_{1-9}$alkyl, —CR$^{10}$R$^{11}$OC(O) NR$^{10}$C$_{6-10}$aryl, and

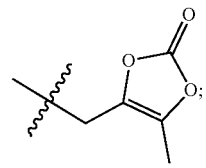 [SMILES: *Cc1oc(=O)oc1C]

R$^{10}$ and R$^{11}$ are independently selected from the group consisting of —H, optionally substituted C$_{1-4}$alkyl, optionally substituted C$_{3-7}$ carbocyclyl, optionally substituted 5-10 membered heterocyclyl, optionally substituted C$_{6-10}$aryl, and optionally substituted 5-10 membered heteroaryl.

Some embodiments relate to a compound having the structure of Formula (III) or (IV):

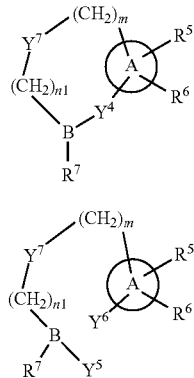

or a pharmaceutically acceptable salt thereof, wherein:

A is selected from the group consisting of $C_{3-10}$ carbocyclyl, $C_{6-10}$ aryl, 5-10 membered heteroaryl, and 5-10 membered heterocyclyl;

m is 0, 1 or 2;

$Y^7$ is selected from the group consisting of $CH_2$, O, S and NH;

$n^1$ is 1, 2 or 3;

each $R^7$ is independently selected from the group consisting of OH, optionally substituted —O—$C_{1-6}$ alkyl, —$NR^1R^2$, and —$N(OR^1)R^2$; and $Y^4$ is selected from the group consisting of —O—, —S—, and —$NR^1$—;

$Y^5$ is selected from the group consisting of —OH, —SH, and —$NHR^1$;

$Y^6$ is selected from the group consisting of —OH, optionally substituted —O—$C_{1-6}$ alkyl, —$NR^1R^2$, and —$N(OR^1)R^2$;

each $R^1$, $R^2$, $R^3$ and $R^4$ are independently selected from —H, optionally substituted $C_{1-4}$alkyl, optionally substituted $C_{3-7}$ carbocyclyl, optionally substituted 4-10 membered heterocyclyl, optionally substituted $C_{6-10}$aryl, and optionally substituted 5-10 membered heteroaryl;

$R^5$ is present 1 to 5 times and each $R^5$ is independently selected from the group consisting of H, OH, halogen, —$CF_3$, optionally substituted $C_2$-$C_6$ alkenyl, optionally substituted $C_2$-$C_6$ alkynyl, optionally substituted $C_1$-$C_6$ heteroalkyl, optionally substituted $C_3$-$C_7$ carbocyclyl, optionally substituted 5-10 membered heterocyclyl, optionally substituted $C_{6-10}$aryl, optionally substituted 5-10 membered heteroaryl, cyano, $C_1$-$C_6$ alkoxy($C_1$-$C_6$)alkyl, aryloxy, sulfhydryl (mercapto), and —$(CH_2)_p$—$Y^3$—$(CH_2)_q$M';

p and q are each independently 0 or 1;

$Y^3$ is selected from the group consisting of —S—, —S(O)—, —$S(O)_2$—, —O—, —$CH_2$—, and —$NR^1$—;

M' is selected from the group consisting of —C(O)$NR^1R^2$; —C(O)$NR^1OR^2$; —$NR^1C(O)R^2$; —$NR^1C(O)NR^2R^3$; —$NR^1C(O)OR^2$; —$NR^1S(O)_2R^2$; —$NR^1S(O)_2NR^2R^3$; —$C(=NR^1)R^2$; —$C(=NR^1)NR^2R^3$; —$NR^1CR^2(=NR^3)$; —$NR^1C(=NR^2)NR^3R^4$; $C_{1-4}$ alkyl optionally substituted with 0-2 substituents selected from the group consisting, —$OR^1$, —$NR^1R^2$, halogen, —C(O)$NR^1R^2$, and —$NR^1C(O)R^2$; $C_{6-10}$ aryl optionally substituted with 0-2 substituents selected from the group consisting of $C_{1-4}$ alkyl, —$OR^1$, —$NR^1R^2$, halogen, —C(O)$NR^1R^2$, and —$NR^1C(O)R^2$; $C_{3-7}$ carbocyclyl optionally substituted with 0-2 substituents selected from the group consisting of $C_{1-4}$ alkyl, —$OR^1$, —$NR^1R^2$, halogen, —C(O)$NR^1R^2$, and —$NR^1C(O)R^2$; 5-10 membered heteroaryl optionally substituted with 0-2 substituents selected from the group consisting of $C_{1-4}$ alkyl, —$OR^1$, —$NR^1R^2$, halogen, —C(O)$NR^1R^2$, and —$NR^1C(O)R^2$; and 3-10 membered heterocyclyl optionally substituted with 0-2 substituents selected from the group consisting of $C_{1-4}$ alkyl, —$OR^1$, —$NR^1R^2$, halogen, —C(O)$NR^1R^2$, and —$NR^1C(O)R^2$;

$R^6$ is selected from the group consisting of H, halogen, optionally substituted —$C_{1-6}$ alkyl, —OH, —C(O)OR, optionally substituted —O—$C_{1-6}$ alkyl, —$NR^1R^2$, —$N(OR^1)R^2$, optionally substituted —S—$C_{1-4}$ alkyl, —C(O)$NR^1R^2$, —$S(O)_2NR^1R^2$, CN, optionally substituted —S(O)—$C_6$ alkyl, optionally substituted —$S(O)_2$—$C_{1-6}$ alkyl, and a carboxylic acid isostere;

R is selected from —H, alkali metal, $NH_4^+$, —$C_{1-9}$alkyl, —$CR^{10}R^{11}OC(O)C_{1-9}$alkyl, —$CR^{10}R^{11}OC(O)OC_{1-9}$alkyl, —$CR^{10}R^{11}OC(O)C_{6-10}$aryl, —$CR^{10}R^{11}OC(O)OC_{6-10}$aryl and

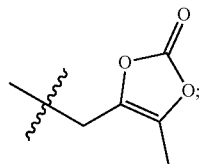 [SMILES: *Cc1oc(=O)oc1C]

$R^{10}$ and $R^{11}$ are independently selected from the group consisting of —H, optionally substituted $C_{1-4}$alkyl, optionally substituted $C_{3-7}$ carbocyclyl, optionally substituted 5-10 membered heterocyclyl, optionally substituted $C_{6-10}$aryl, and optionally substituted 5-10 membered heteroaryl.

Some embodiments relate to a compound having the structure selected from the group consisting of

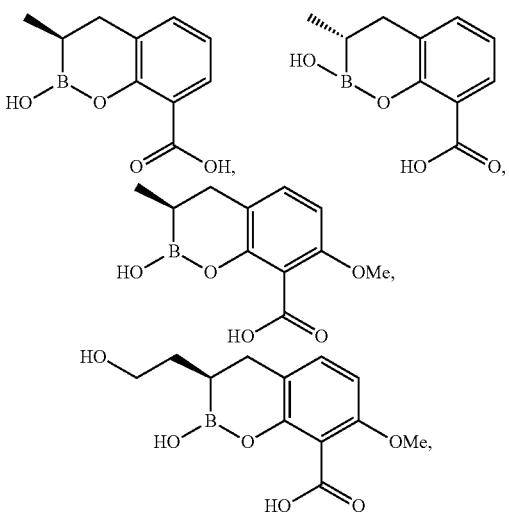

and pharmaceutically acceptable salts thereof.

Other embodiments disclosed herein include a pharmaceutical composition comprising a therapeutically effective amount of a compound disclosed herein and a pharmaceutically acceptable excipient.

Other embodiments disclosed herein include a method of treating or preventing a bacterial infection, comprising administering to a subject in need thereof a compound disclosed herein.

DETAILED DESCRIPTION

In some embodiments, compounds that contain a boronic acid moiety are provided that act as antimicrobial agents and/or as potentiators of antimicrobial agents Various embodiments of these compounds include compounds having the structures of Formula (I) as described above or pharmaceutically acceptable salts thereof.

In some embodiments, the compound described herein has the structure of Formula (I') or a pharmaceutically acceptable salt thereof. In some embodiments, the compound described herein has the structure of Formula (II') or a pharmaceutically acceptable salt thereof.

In some embodiments, the compound described herein has the structure of Formula (I) or a pharmaceutically acceptable salt thereof. In some embodiments, the compound described herein has the structure of Formula (II) or a pharmaceutically acceptable salt thereof.

In some embodiments, $Q^1$ and $Q^2$ are deuterium. In some embodiments, $Q^1$ is hydrogen and $Q^2$ is deuterium. In some embodiments, $Q^1$ is —$Y^2$—$(CH_2)_n$-G and $Q^2$ is deuterium. In some embodiments, $Q^1$ is —$Y^2$—$(CH_2)_n$-G and $Q^2$ is hydrogen.

In some embodiments, Q is —$Y^2$—$(CH_2)_n$-G. In some embodiments, Q is H.

Some embodiments of compounds of Formula (I') or (I) include compounds having the structure of Formula (I-1)

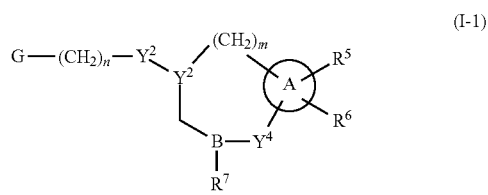

(I-1)

or a pharmaceutically acceptable salt thereof, wherein:

G is selected from the group consisting of —C(O)$R^4$, —C(O)(CH$_2$)$_{0-3}$S$R^3$, —C(O)O$R^3$, —C(O)N$R^1R^2$, —C(O)N$R^1$O$R^3$, —N$R^1$C(O)$R^4$, —N$R^1$C(O)N$R^1R^2$, —N$R^1$C(O)O$R^3$, —N$R^1$S(O)$_2R^3$, —N$R^1$S(O)$_2$N$R^1R^2$, —C(=N$R^1$)$R^4$, —C(=N$R^1$)N$R^1R^2$, —N$R^1$C$R^4$(=N$R^2$), —N$R^1$C(=N$R^2$)N$R^1R^2$, —S(O)$_2R^3$, optionally substituted $C_{1-10}$ alkyl, optionally substituted $C_{2-10}$alkenyl, optionally substituted $C_{2-10}$alkynyl, optionally substituted $C_{3-7}$ carbocyclyl, optionally substituted 5-10 membered heterocyclyl, optionally substituted $C_{6-10}$aryl, optionally substituted 5-10 membered heteroaryl, optionally substituted $C_{3-7}$carbocyclyl-$C_{1-6}$alkyl, optionally substituted 5-10 membered heterocyclyl-$C_{1-6}$alkyl, optionally substituted $C_{6-10}$aryl-$C_{1-6}$alkyl, and optionally substituted 5-10 membered heteroaryl-$C_{1-6}$alkyl;

each $R^1$, $R^2$, $R^3$, and $R^4$ are independently selected from —H, optionally substituted $C_{1-4}$alkyl, optionally substituted $C_{3-7}$ carbocyclyl, optionally substituted 5-10 membered heterocyclyl, optionally substituted $C_{6-10}$aryl, and optionally substituted 5-10 membered heteroaryl; and R is selected from —H, —$C_{1-9}$alkyl, —C$R^{10}R^{11}$OC(O)$C_{1-9}$alkyl, —C$R^{10}R^{11}$OC(O)OC$_{1-9}$alkyl, and

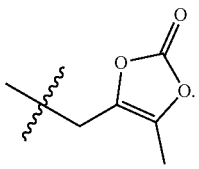 [SMILES: *Cc1oc(=O)oc1C]

Some embodiments of compounds of Formula (I-A), Formula (I) or Formula (I-1) include compounds having the structure of Formula (Ia):

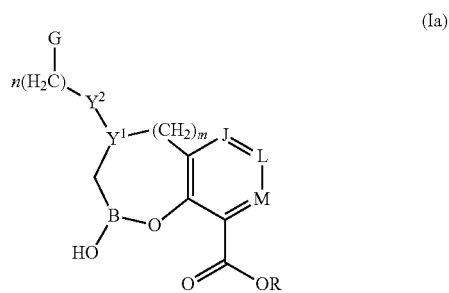

(Ia)

or a pharmaceutically acceptable salt thereof, wherein: n is 0 or 1; and J, L, and M are each independently selected from the group consisting of C$R^5$ and N.

Some embodiments of compounds of Formula (I'), Formula (I), Formula (I-1), or Formula (Ia) or their pharmaceutically acceptable salts have the following stereochemistry as shown in the structure of formula (Ib)

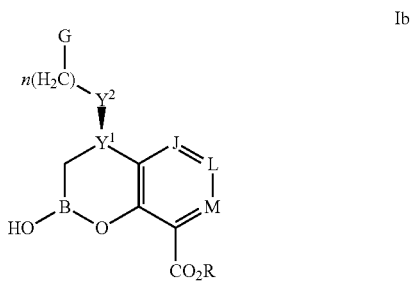

Ib

Some embodiments of compounds of Formula (I'), Formula (I), Formula (I-1), or Formula (Ia) or their pharmaceutically acceptable salts have the following stereochemistry as shown in the structure of formula (Ic)

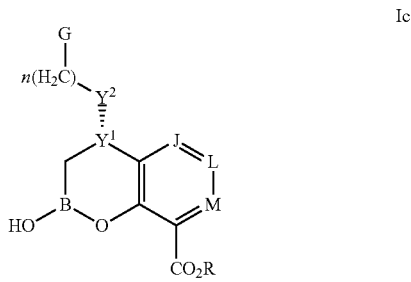

Ic

Some embodiments of compounds of Formula (II') or Formula (II) include compounds having the structure of Formula (IIa):

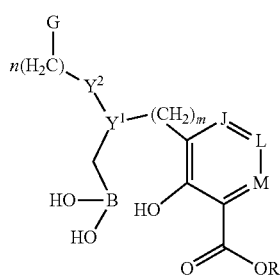

(IIa)

or a pharmaceutically acceptable salt thereof, wherein: n is 0 or 1; and J, L, and M are each independently selected from the group consisting of $CR^5$ and N.

Some embodiments of compounds of Formula (II'), Formula (III) or Formula (IIa) or their pharmaceutically acceptable salts include compounds having the structure of Formula (IIb):

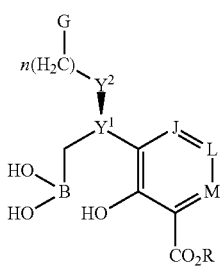

(IIb)

Some embodiments of compounds of Formula (II'), Formula (II), Formula (IIa), or Formula (IIb) or their pharmaceutically acceptable salts include compounds having the structure of Formula (IIc):

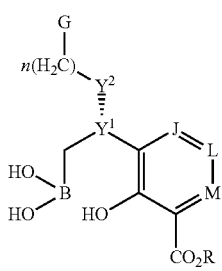

(IIc)

In some embodiments of Formula (I'), (I), (I-1), (Ia), (Ib) (Ic), (II'), (II), (IIa), (IIb), or (IIc), $Y^2$ is selected from the group consisting of —S—, —SO$_2$—, —O—, or —NH—. In some embodiments of Formula (I'), (I), (I-1), (Ia), (Ib) (Ic), (II), (IIa), (IIb), or (IIc), $Y^2$ is selected from the group consisting of —S—, —SO$_2$—, —O—, or —NR$^1$—.

In some embodiments of Formula (I') or (I), $Y^4$ is —O—.

In some embodiments of Formula (Ia), (Ib) (Ic), (IIa), (IIb), or (IIc), M is N. In some embodiments of Formula (Ia), (Ib) (Ic), (IIa), (IIb), or (IIc), M is $CR^5$. In some embodiments of Formula (Ia), (Ib) (Ic), (IIa), (IIb), or (IIc), J and L are each independently $CR^5$. In some embodiments, J and L are CH. In some embodiments of Formula (Ia), (Ib) (Ic), (IIa), (IIb), or (IIc), J is N. In some embodiments of Formula (Ia), (Ib) (Ic), (IIa), (IIb), or (IIc), L and M are each independently $CR^5$. In some embodiments of Formula (Ia), (IIb) (Ic), (IIa), (IIb), or (IIc), L is N. In some embodiments of Formula (Ia), (Ib) (Ic), (IIa), (IIb), or (IIc), J and M are each independently $CR^5$.

In some embodiments of Formula (I), $R^7$ is —OH.

Some embodiments of the compounds of Formula (I') or Formula (I) or their pharmaceutically acceptable salts can have the structure of Formula (Id):

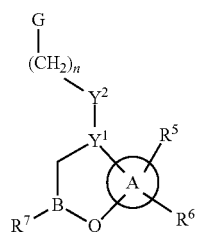

Id

In some embodiments of Formula (I'), (II'), (I), (II), (Ia), (Ib) (Ic), (Id), (IIa), (IIb), or (IIc), $Y^2$ is —O— or —S—; G is selected from the group consisting of $C_{1-4}$alkyl, phenyl, imidazole, pyrazole, triazole, tetrazole, thiazole, thiadiazole, oxazole, oxadiazole, isoxazole, isothiazole, pyridine, pyrazine, pyrimidine, pyridazine, and pyrazine, each optionally substituted by 0-2 substituents selected from the group consisting of hydroxy, $C_1$-$C_6$ alkoxy, $C_1$-$C_6$ alkoxy($C_1$-$C_6$) alkyl, aryloxy, halo($C_1$-$C_6$)alkoxy, amino, C-amido, and N-amido; and J, L and M are $CR^5$.

In some embodiments of Formula (I'), (II'), (I), (II), (Ia), (Ib), (Ic), (Id), (IIa), (IIb), or (IIc), G is $C_{1-4}$alkyl. In some embodiments, G is —CH$_3$.

In some embodiments of Formula (I'), (II'), (I), (II), (Ia), (Ib), (Ic), (Id), (IIa), (IIb), or (IIc), G is thiadiazole optionally substituted with amino. In some embodiments, G is

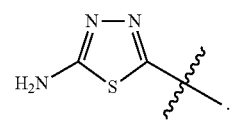 [SMILES: *c1nnc(N)s1]

In some embodiments of Formula (I'), (II'), (I), (II), (Ia), (Ib), (Ic), (Id), (IIa), (IIb), or (IIc), M is $CR^5$; and each $R^5$ is independently selected from the group consisting of —H, —$C_{1-4}$alkyl, and halogen, —CF$_3$, and —(CH$_2$)$_p$—$Y^3$—(CH$_2$)$_q$M'.

In some embodiments, $R^5$ is CN, —C(O)OR$^1$; —C(O)NR$^1$R$^2$; —C(O)NR$^1$OR$^2$; —NR$^1$C(O)R$^2$; —NR$^1$C(O)NR$^2$R$^3$; —NR$^1$C(O)OR$^2$; —NR$^1$S(O)$_2$R$^2$; —NR$^1$S(O)$_2$NR$^2$R$^3$; —C(=NR$^1$)R$^2$; —C(=NR$^1$)NR$^2$R$^3$; —NR$^1$CR$^2$(=NR$^3$); —NR$^1$C(=NR$^2$)NR$^3$R$^4$; —S(O)(CH$_2$)$_{1-3}$R$^4$, —S(O)$_2$NR$^1$R$^2$, —S(O)$_2$NR$^1$OR$^3$, or —NR$^1$S(O)$_2$NR$^1$OR$^3$.

In some embodiments, $R^5$ is —(CH$_2$)$_p$—$Y^3$—(CH$_2$)$_q$M'.

In some embodiments, p and q are each independently 0, 1, or 2. In some embodiments, p and q are each independently 0 or 1.

In some embodiments of Formula (I'), (II'), (I), (II), (Ia), (Ib), (Ic), (Id), (IIa), (IIb), or (IIc), $R^5$ is —(CH$_2$)$_p$—$Y^3$—(CH$_2$)$_q$M'; m is 0; p is 0; $Y^3$ is S or O; and M' is hydrogen; hydroxyl; $C_1$-$C_4$ alkyl optionally substituted with one or more substituents selected from the group consisting of —O—$C_1$-$C_6$alkyl, —S—$C_1$-$C_6$alkyl, amino, —C(O)- amino, —S(O)₂-amino, hydroxy, cyano, azido, and halogen; $C_{3-10}$ cycloalkyl optionally substituted with one or more substituents selected from the group consisting of $C_1$-$C_6$alkyl, —O—$C_1$-$C_6$alkyl, —S—$C_1$-$C_6$alkyl, amino, —C(O)-amino, —S(O)₂-amino, hydroxy, cyano, azido, and halogen; $C_6$-$C_{10}$ aryl optionally substituted with one or more substituents selected from the group consisting of $C_1$-$C_6$alkyl, —O—$C_1$-$C_6$alkyl, —S—$C_1$-$C_6$alkyl, amino, —C(O)-amino, —S(O)₂-amino, hydroxy, cyano, azido, and halogen; 5 to 10 membered heteroaryl optionally substituted with one or more substituents selected from the group consisting of $C_1$-$C_6$alkyl, —O—$C_1$-$C_6$alkyl, —S—$C_1$-$C_6$alkyl, amino, —C(O)-amino, —S(O)₂-amino, hydroxy, cyano, azido, and halogen; and 4 to 10 membered heterocyclyl optionally substituted with one or more substituents selected from the group consisting of $C_1$-$C_6$alkyl, —O—$C_1$-$C_6$alkyl, —S—$C_1$-$C_6$alkyl, amino, —C(O)-amino, —S(O)₂-amino, hydroxy, cyano, azido, and halogen.

In some embodiments, M' is selected from the group consisting of halogen, cycano, —OH, —S(O)₂R¹, —S(O)₂NR¹R², —S(O)₂NR¹OR³, $C_{1-4}$ alkyl optionally substituted with 0-2 substituents selected from the group consisting of —OR¹, —CN, —NR¹R², -heterocyclyl, halogen, —C(O)NR¹R², and —NR¹C(O)R²; $C_{2-4}$ alkenyl optionally substituted with 0-2 substituents selected from the group consisting of $C_{1-4}$ alkyl, —(CH₂)₀₋₄OR¹, —(CH₂)₀₋₄CN, —(CH₂)₀₋₄NR¹R², —(CH₂)₀₋₄-heterocyclyl, halogen, —C(O)NR¹R², and —NR¹C(O)R²; $C_{2-4}$ alkynyl optionally substituted with 0-2 substituents selected from the group consisting of $C_{1-4}$ alkyl, —(CH₂)₀₋₄OR¹, —(CH₂)₀₋₄CN, —(CH₂)₀₋₄NR¹R², —(CH₂)₀₋₄-heterocyclyl, halogen, —C(O)NR¹R², and —NR¹C(O)R²; $C_{6-10}$ aryl optionally substituted with 0-2 substituents selected from the group consisting of $C_{1-4}$ alkyl, —(CH₂)₀₋₄OR¹, —(CH₂)₀₋₄CN, —(CH₂)₀₋₄NR¹R², —(CH₂)₀₋₄-heterocyclyl, halogen, —C(O)NR¹R², and —NR¹C(O)R²; $C_{3-7}$ carbocyclyl optionally substituted with 0-2 substituents selected from the group consisting of $C_{1-4}$ alkyl, —(CH₂)₀₋₄OR¹, —(CH₂)₀₋₄CN, —(CH₂)₀₋₄NR¹R², —(CH₂)₀₋₄-heterocyclyl, halogen, —C(O)NR¹R², and —NR¹C(O)R²; 5-10 membered heteroaryl optionally substituted with 0-2 substituents selected from the group consisting of $C_{1-4}$ alkyl, —(CH₂)₀₋₄OR¹, —(CH₂)₀₋₄CN, —(CH₂)₀₋₄NR¹R², —(CH₂)₀₋₄-heterocyclyl, halogen, —C(O)NR¹R², and —NR¹C(O)R²; and 3-10 membered heterocyclyl optionally substituted with 0-2 substituents selected from the group consisting of $C_{1-4}$ alkyl, —(CH₂)₀₋₄OR¹, —(CH₂)₀₋₄CN, —(CH₂)₀₋₄NR¹R², —(CH₂)₀₋₄-heterocyclyl, halogen, —C(O)NR¹R², and —NR¹C(O)R².

In some embodiments of Formula (I'), (I'), (I), (I), (Ia), (Ib), (Ic), (Id), (IIa), (IIb), or (IIc), R⁵ is halogen. In some embodiments, R⁵ is F.

In some embodiments, R⁵ is —S—$C_1$-$C_6$alkyl, —S—$C_1$-$C_6$ cycloalkyl, or —S-4 to 10 membered heterocyclyl. In some embodiments, R⁵ is —S—CH₃.

In some embodiments, R⁵ is —O—$C_1$-$C_6$alkyl, —O—$C_1$-$C_6$ cycloalkyl, or —O-4 to 10 membered heterocyclyl. In some embodiments, R⁵ is

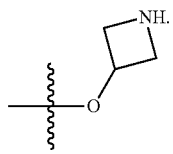 [SMILES: *OC1CNC1]

In some embodiments, R⁵ is —OCH₃.

In some embodiments of Formula (I'), (I'), (I), (Ia), (Ib), (Ic), (Id), (IIa), (IIb), or (IIc), n is 0 or 1; Y² is —NH—; G is selected from the group consisting of —C(O)R⁴, —C(O)(CH₂)₀₋₃SR³, —C(O)(CH₂)₁₋₃R⁴, —C(O)OR³, —C(O)NR¹R², —S(O)₂R³, —C(=NR¹)R⁴, and —C(=NR¹)NR¹R².

In some embodiments, G is selected from the group consisting of —C(O)R⁴, —C(O)(CH₂)₀₋₃SR³, —C(O)OR³, —C(O)NR¹R², —S(O)₂R³, —C(=NR¹)R⁴, and —C(=NR¹)NR¹R². In some embodiments, G is —C(O)R⁴. In some embodiments, G is —C(O)(CH₂)R⁴.

In some embodiments of Formula (I), (Ia), (Ib), (Ic), (Id), (IIa), (IIb), or (IIc), G is —C(O)R⁴; wherein R⁴ is optionally substituted $C_{1-4}$alkyl or R⁴ is $C_{1-4}$alkyl substituted with $C_1$-$C_4$ alkylthio or R⁴ is $C_{1-4}$alkyl substituted with 5-10 membered heteroaryl optionally substituted with halo, $C_1$-$C_6$ alkyl, $C_1$-$C_6$ alkoxy, $C_1$-$C_6$ haloalkyl, and $C_1$-$C_6$ haloalkoxy or R⁴ is optionally substituted 5-10 membered heteroaryl or R⁴ is 5-10 membered heteroaryl substituted with amino. In some embodiments, for the R⁴ in G, R⁴ is optionally substituted $C_{1-4}$alkyl. R⁴ is $C_{1-4}$alkyl substituted with $C_1$-$C_4$ alkylthio. In some embodiments, for the R⁴ in G, R⁴ is —CH₂SCH₃. In some embodiments, for the R⁴ in G, R⁴ is $C_{1-4}$alkyl substituted with 5-10 membered heteroaryl optionally substituted with halo, $C_1$-$C_6$ alkyl, $C_1$-$C_6$ alkoxy, $C_1$-$C_6$ haloalkyl, and $C_1$-$C_6$ haloalkoxy. In some embodiments, for the R⁴ in G, R⁴ is

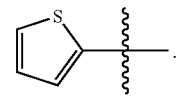

In some embodiments, for the R⁴ in G, R⁴ is optionally substituted 5-10 membered heteroaryl. In some embodiments, for the R⁴ in G, R⁴ is 5-10 membered heteroaryl substituted with amino. In some embodiments, R⁴ is

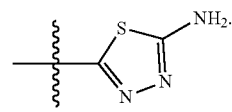

In some embodiments, G is

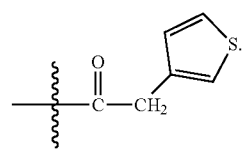 [SMILES: *C(=O)Cc1ccsc1]

In some embodiments, G is

In some embodiments, G is optionally substituted $C_{6-10}$aryl.
In some embodiments, G is —S(O)(CH$_2$)$_{1-3}$R$^3$, —S(O)$_2$NR$^1$R$^2$, —S(O)$_2$NR$^1$OR$^3$, —NR$^1$S(O)$_2$NR$^1$OR$^3$, —CN, —OR$^1$, —SR$^1$, or —NR$^1$R$^2$.

In some embodiments of Formula (I'), (II'), (I), (Ia), (Ib), (Ic), (Id), (IIa), (IIb), or (IIc), G is —C(O)CH$_2$SR$^3$.

In some embodiments of Formula (I'), (II'), (I), (Ia), (Ib), (Ic), (Id), (IIa), (IIb), or (IIc), when G is —C(O)CH$_2$SR$^3$, R$^3$ is $C_{1-4}$alkyl. In some embodiments, G is —C(O)(CH$_2$)SCH$_3$.

In some embodiments of Formula (I'), (II'), (I), (Ia), (Ib), (Ic), (Id), (IIa), (IIb), or (IIc), when G is —C(O)CH$_2$SR$^3$, R$^3$ is 5-10 membered heterocyclyl.

In some embodiments of Formula (I'), (II'), (I), (Ia), (Ib), (Ic), (Id), (IIa), (IIb), or (IIc), Y$^2$ is —S(O)$_2$—.

In some embodiments of Formula (I'), (II'), (I), (Ia), (Ib), (Ic), (Id), (IIa), (IIb), or (IIc), wherein Y$^2$ is —S(O)$_2$—, G is optionally substituted $C_{6-10}$aryl.

In some embodiments of Formula (I'), (I'), (I), (Ia), (Ib), (Ic), (Id), (IIa), (IIb), or (IIc), Y$^1$ is CH or N. In some embodiments, Y$^1$ is CH. In some embodiments, Y$^1$ is N.

Some embodiments include a compound selected from the group consisting of:

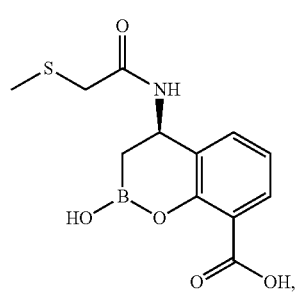

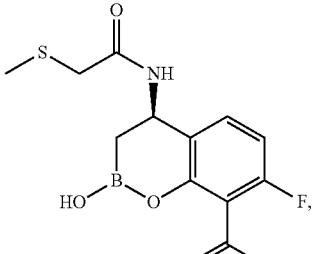

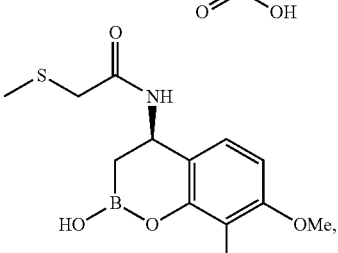

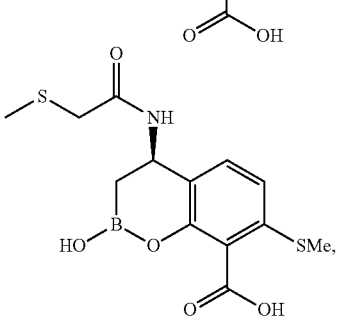

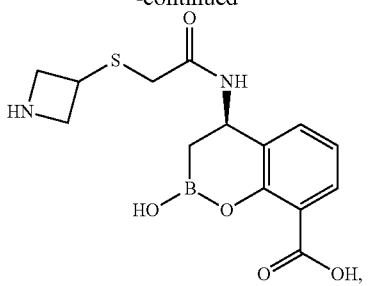

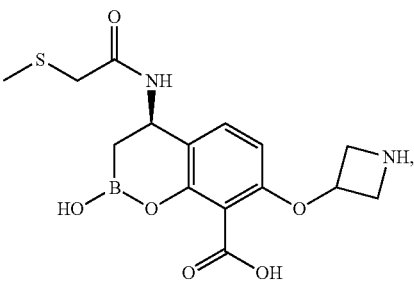

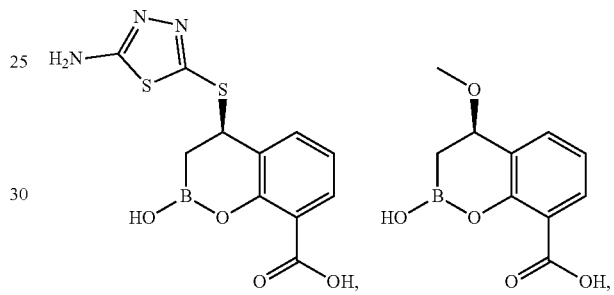

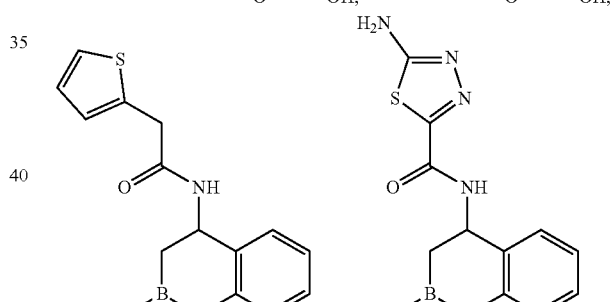

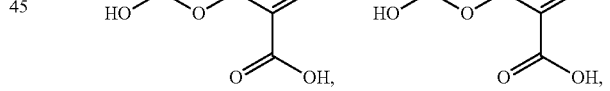

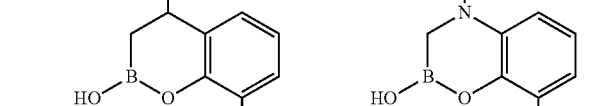

or a pharmaceutically acceptable salt thereof.

Some embodiments of the compounds of Formula (III') or (III) can have the structure of Formula (IIIa):

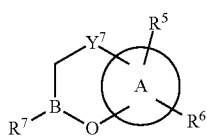

or its pharmaceutically acceptable salts

Some embodiments of the compounds of Formula (III') or (III) can have the structure of Formula (IIIb):

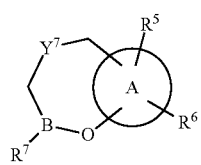

or its pharmaceutically acceptable salts.

Some embodiments of the compounds of Formula (III') or (III) can have the structure of Formula (IIIc):

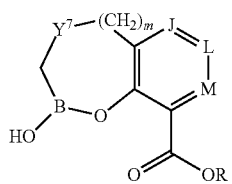

or its pharmaceutically acceptable salts, wherein:
m is 0, 1, or 2; and
J, L, and M are each independently selected from the group consisting of $CR^5$ and N.

Some embodiments of the compounds of Formula (III'), (III), or (IIIc) can have the structure of Formula (IIId):

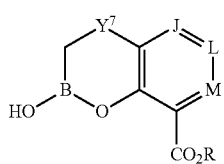

or its pharmaceutically acceptable salts.

Some embodiments of the compounds of Formula (IV') or (IV) can have the structure of Formula (IVa):

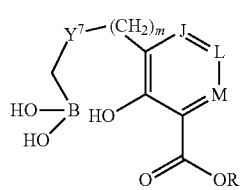

or its pharmaceutically acceptable salts, wherein:
m is 0, 1, or 2; and
J, L, and M are each independently selected from the group consisting of $CR^5$ and N.

Some embodiments of the compounds of Formula (IV'), (IV), or (IVa) can have the structure of Formula (IVb):

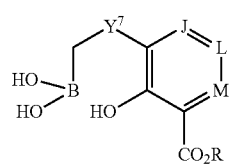

or its pharmaceutically acceptable salts.

Some embodiments of the compounds of Formula (III'), (IV'), (III) or (IV) can have the structure of Formula (III-1) or (IV-1):

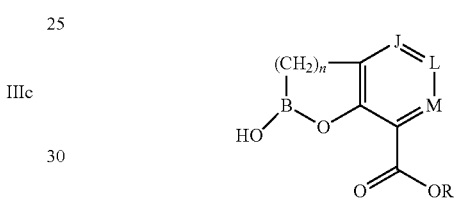

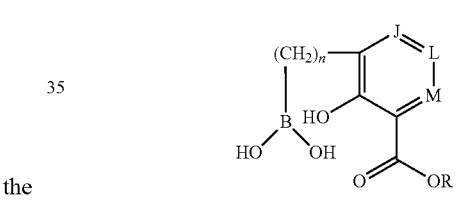

wherein J, L, and M are each independently selected from the group consisting of $CR^5$ and N.

In some embodiments, for the compounds of Formula (III') or (IV'), $n^1$ is 1 and $Q^1$ and $Q^2$ are deuterium. In some embodiments, $Q^1$ is hydrogen and $Q^2$ is deuterium.

In some embodiments, for the compounds of Formula (III'), (IV'), (III), (IV), (III-1), or (IV-1), $Y^7$ is $CH_2$, O, or S. In some embodiments, $Y^7$ is $CH_2$. In some embodiments, $Y^7$ is O. In some embodiments, $Y^7$ is S. In some embodiments, $Y^7$ is NH. In some embodiments, $Y^7$ is O, $n^1$ is 1, and m is 1.

Some embodiments of the compounds of Formula (III'), (IV'), (III), (IV), (III-1), (IV-1), or their pharmaceutically acceptable salts can have the structure of Formula (III-2), or (IV-2):

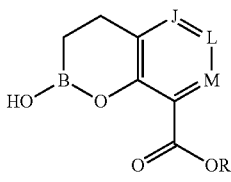

-continued (IV-2)

$$\text{HO-B(OH)... structure with J, L, M ring, OH, C(O)OR}$$

In some embodiments, M is CR⁵. In some embodiments, M is N. In some embodiments, M is CH. In some embodiments, J is N, and L and M are each independently CR⁵. In some embodiments, L is N, and J and M are each independently CR⁵. In some embodiments, M is N, and J and L are each independently CR⁵.

In some embodiments, J and L are each independently CR⁵. In some embodiments, J and L are CH. In some embodiments, MJ and M are CH. In some embodiments, L and M are CH.

In some embodiments, R⁵ is selected from the group consisting of $C_1$-$C_6$alkyl, $C_2$-$C_6$ alkenyl, $C_2$-$C_6$ alkynyl, $C_3$-$C_7$ carbocyclyl, $C_1$-$C_6$ heteroalkyl, 5-10 membered heterocyclyl, $C_6$-$C_{10}$ aryl, 5-10 membered heteroaryl, cyano, hydroxy, —OR³, —SR³, —S(O)₂M', —P(O)R¹M', and halogen. In some embodiments, R⁵ is halogen. In some embodiments, R⁵ is F. In some embodiments, R⁵ is alkoxy. In some embodiments, R⁵ is —OCH₃. In some embodiments, R⁵ is —OCH₂CH₃. In some embodiments, R⁵ is —OH. In some embodiments, R⁵ is —SH. In some embodiments, R⁵ is —SCH₃. In some embodiments, R⁵ is —S(O)₂M'. In some embodiments, R⁵ is —S(O)₂CH₃. In some embodiments, R⁵ is —SOM'. In some embodiments, R⁵ is —S(O)₂CH₃. In some embodiments, R⁵ is cyano. In some embodiments, R⁵ is —C≡CH. In some embodiments, R⁵ is —CHF₂. In some embodiments, R⁵ is —CF₃. In some embodiments, R⁵ is —C(O)NR¹R². In some embodiments, R⁵ is —C(O)NH₂. In some embodiments, R⁵ is —C(=NR¹)R². In some embodiments, R⁵ is —CH=N—OCH₃. In some embodiments, R⁵ is —COOR¹. In some embodiments, R⁵ is —COOH. In some embodiments, R⁵ is a $C_{2-4}$ alkynyl, triazole, or diazole, optionally substituted with 0-2 substituents selected from —(CH₂)₀₋₄OR¹, —(CH₂)₀₋₄CN, —(CH₂)₀₋₄NR¹R², —(CH₂)₀₋₄-heterocyclyl, halogen, —C(O)NR¹R², and —NR¹C(O)R². In some embodiments, R⁵ is

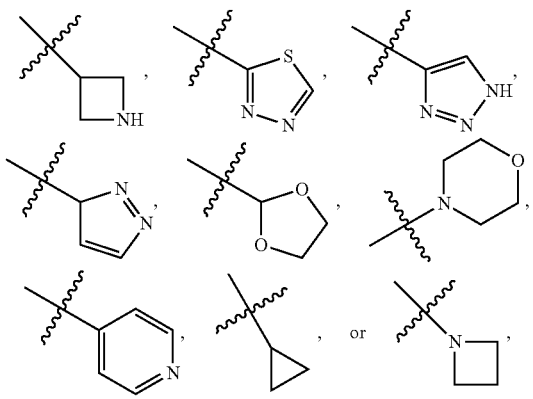

In some embodiments, R⁵ is —(CH₂)$_p$—Y³—(CH₂)$_q$M'.
In some embodiments, Y³ is —S—, —O—, or —NH—. In some embodiments, Y³ is —S—. In some embodiments, Y³ is —O—. In some embodiments, Y³ is —NH—. In some embodiments, Y³ is —S(O)— or —S(O)₂—. In some embodiments, Y³ is —S(O)—. In some embodiments, Y³ is —S(O)₂—.

In some embodiments, M' is a 5-10 membered heteroaryl or 3-10 membered heterocyclyl, each optionally substituted with 0-2 substituents selected from the group consisting of $C_{1-4}$ alkyl, —(CH₂)₀₋₄OR¹, —(CH₂)₀₋₄CN, —(CH₂)₀₋₄NR¹R², —(CH₂)₀₋₄-heterocyclyl, halogen, —C(O)NR¹R², and —NR¹C(O)R². In some embodiments, M' is azetine, thiadiazole, triazole, dioxolane, pyridine, morpholine, or cyclopropyl, each optionally substituted with 0-2 substituents selected from the group consisting of $C_{1-4}$ alkyl, —(CH₂)₀₋₄OR¹, —(CH₂)₀₋₄CN, —(CH₂)₀₋₄NR¹R², —(CH₂)₀₋₄-heterocyclyl, halogen, —C(O)NR¹R², and —NR¹C(O)R². In some embodiments, M' is

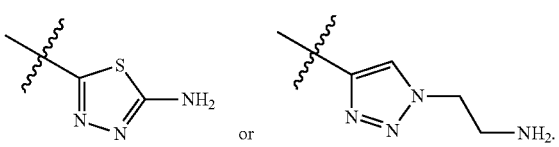 [SMILES: *c1nnc(N)s1 ; *c1cn(CCN)nn1 ; "or"]

each optionally substituted with 0-2 substituents selected from the group consisting of $C_{1-4}$ alkyl, —(CH₂)₀₋₄OR¹, —(CH₂)₀₋₄CN, —(CH₂)₀₋₄NR¹R², —(CH₂)₀₋₄-heterocyclyl, halogen, —C(O)NR¹R², and —NR¹C(O)R². In some embodiments, M' is

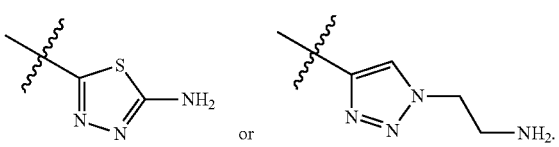 [SMILES: *c1nnc(N)s1 ; *c1cn(CCN)nn1 ; "or"]

In some embodiments, M' is cyano. In some embodiments, M' is —OH. In some embodiments, M' is —S(O)₂R¹ or —S(O)₂NR¹R². In some embodiments, M' is —S(O)₂CH₃ or —S(O)₂NH₂. In some embodiments, M' is —C(O)NR¹R². In some embodiments, M' is —C(O)NH₂. In some embodiments, M' is $C_{1-4}$ alkyl optionally substituted with 0-2 substituents selected from the group consisting of —OR¹, —CN, —NR¹R², -heterocyclyl, halogen, —C(O)NR¹R², and —NR¹C(O)R²; $C_{2-4}$ alkenyl optionally substituted with 0-2 substituents selected from the group consisting of $C_{1-4}$ alkyl, —(CH₂)₀₋₄OR¹, —(CH₂)₀₋₄CN, —(CH₂)₀₋₄NR¹R², —(CH₂)₀₋₄-heterocyclyl, halogen, —C(O)NR¹R², and —NR¹C(O)R²; or $C_{2-4}$ alkynyl optionally substituted with 0-2 substituents selected from the group consisting of $C_{1-4}$ alkyl, —(CH₂)₀₋₄OR¹, —(CH₂)₀₋₄CN, —(CH₂)₀₋₄NR¹R², —(CH₂)₀₋₄-heterocyclyl, halogen, —C(O)NR¹R², and —NR¹C(O)R². In some embodiments, M' is —C≡CH. In some embodiments, M' is —C≡C—(CH₂)₀₋₄OR¹, —C≡C—(CH₂)₀₋₄NR¹R², or —C≡C—(CH₂)₀₋₄-heterocyclyl. In some embodiments, M' is —C≡C—(CH₂)—OCH₃, —C≡C—(CH₂)—OH, —C≡C—(CH₂)—NH₂, or

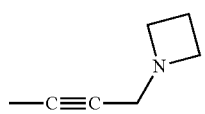

In some embodiments, M' is —(CH$_2$)$_3$NH$_2$, CH$_2$F, CHF$_2$, CF$_3$, CH(CH$_2$OH)$_2$, or CH$_2$N(CH$_3$)$_2$. In some embodiments, M' is C$_{1-4}$ alkyl.

In some embodiments, R$^5$ is present twice. In some embodiments, L and M are each independently CR$^5$; J is CH; and each R$^5$ is independently selected from from the group consisting of OH, halogen, CN, —C(O)OR$^1$; —C(O)NR$^1$R$^2$; —C(O)NR$^1$OR$^2$; —NR$^1$C(O)R$^2$; —NR$^1$C(O)NR$^2$R$^3$; —NR$^1$C(O)OR$^2$; —NR$^1$S(O)$_2$R$^2$; —NR$^1$S(O)$_2$NR$^2$R$^3$; —C(=NR$^1$)R$^2$; —C(=NR$^1$)NR$^2$R$^3$; —NR$^1$CR$^2$(=NR$^3$); —NR$^1$C(=NR$^2$)NR$^3$R$^4$; —S(O)(CH$_2$)$_{1-3}$R$^4$, —S(O)$_2$NR$^1$R$^2$, —S(O)$_2$NR$^1$OR$^3$, —NR$^1$S(O)$_2$NR$^1$OR$^3$, optionally substituted C$_2$-C$_6$ alkenyl, optionally substituted C$_2$-C$_6$ alkynyl, optionally substituted C$_1$-C$_6$ heteroalkyl, optionally substituted C$_3$-C$_7$ carbocyclyl, optionally substituted 5-10 membered heterocyclyl, optionally substituted C$_{6-10}$aryl, optionally substituted 5-10 membered heteroaryl, cyano, C$_1$-C$_6$ alkoxy(C$_1$-C$_6$)alkyl, aryloxy, sulfhydryl (mercapto), and —(CH$_2$)$_p$—Y$^3$—(CH$_2$)$_q$M'. In some embodiments, each R$^5$ is independently halogen or —OM'. In some embodiments, each R$^5$ is independently F or —OCH$_3$. In some embodiments, each R$^5$ is independently Cl or —OCH$_3$.

In some embodiments, R$^6$ is —COOR or —P(O)(OR)$_2$. In some embodiments, R$^1$ is —COOH or —P(O)(OH)$_2$.

In some embodiments, R is H. In some embodiments, R is alkali metal or NH$_4^+$. In some embodiments, R is Na.

Some specific embodiments of the compounds described herein have the structure selected from the group consisting of

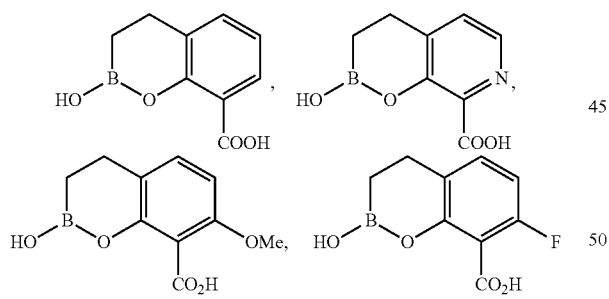

and pharmaceutically acceptable salts thereof.

Some specific embodiments of the compounds described herein have the structure selected from the group consisting of

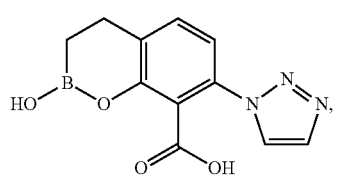

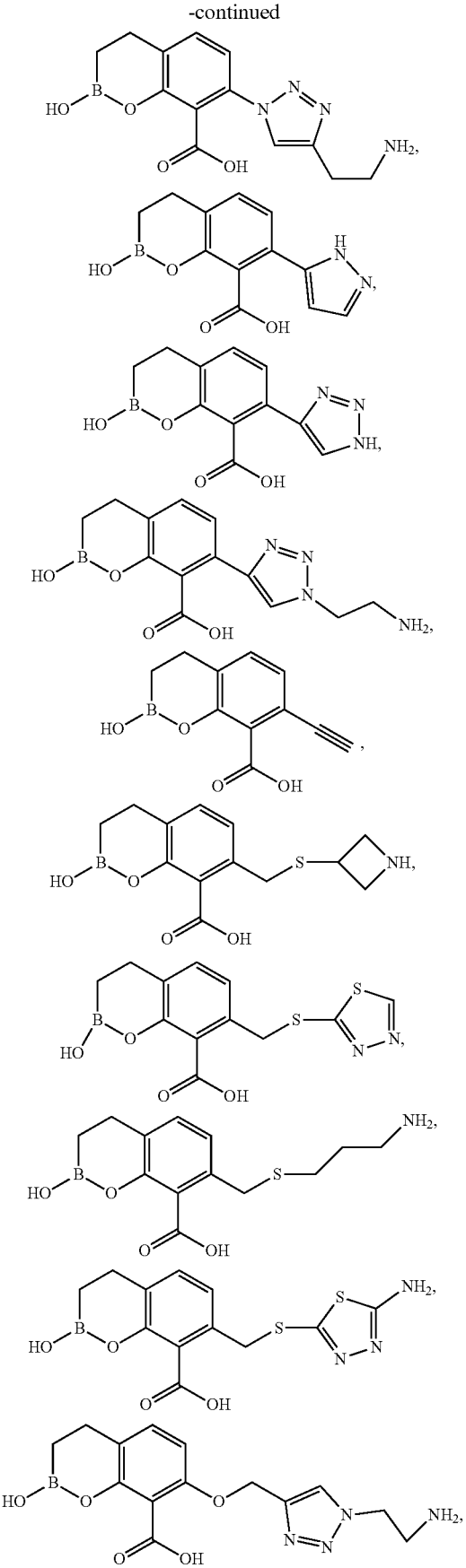

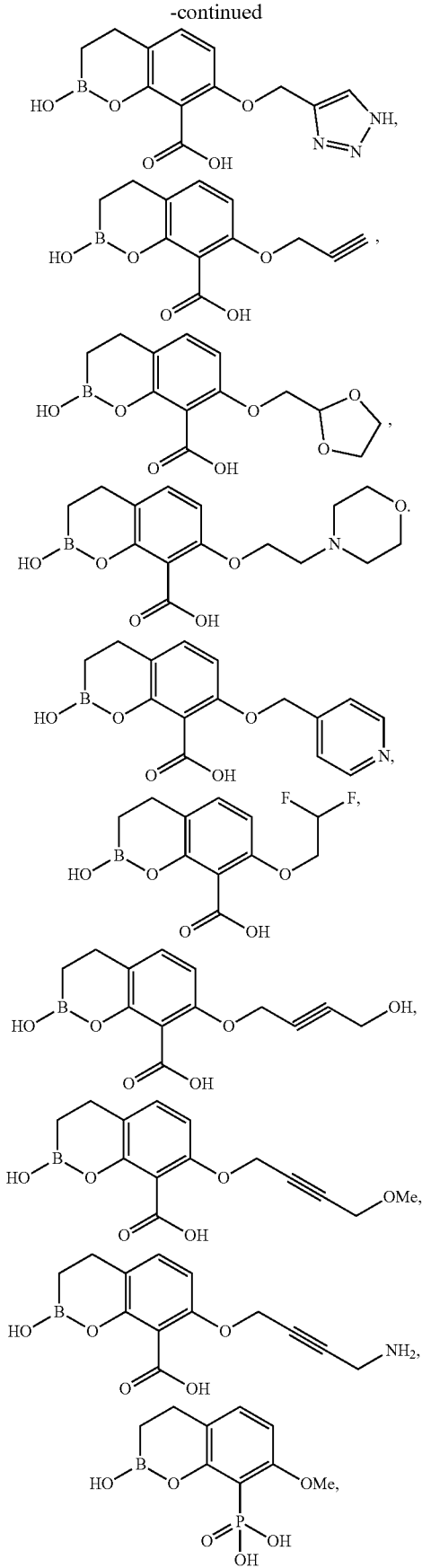
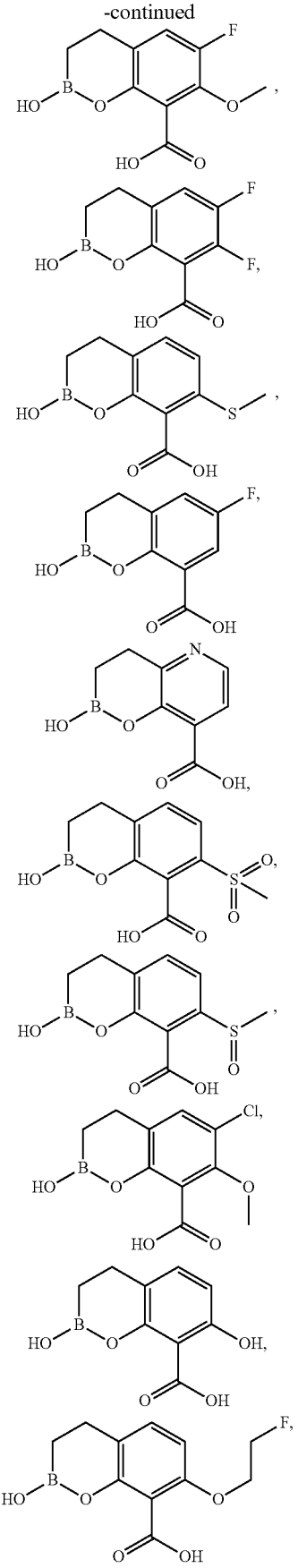

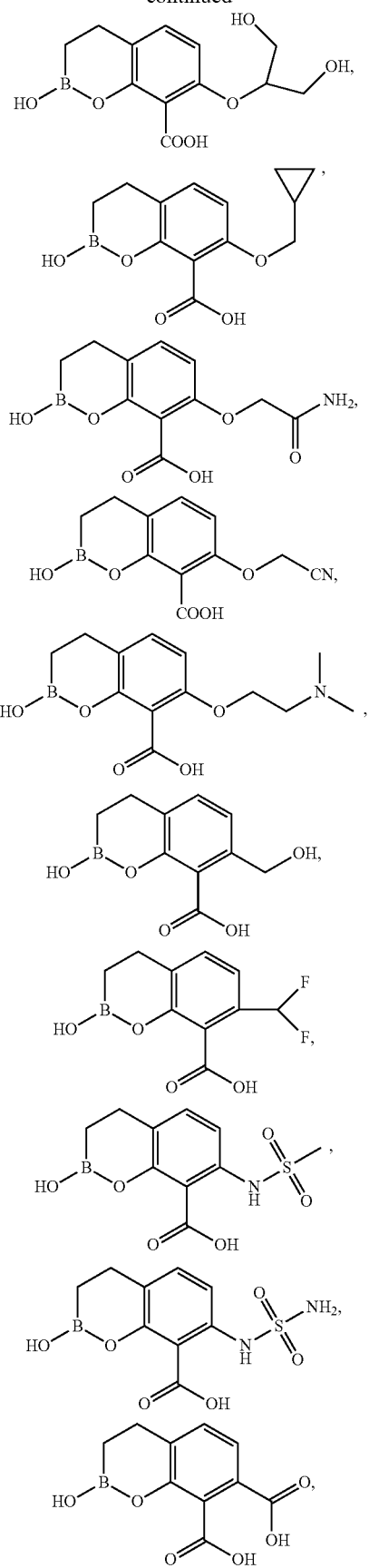
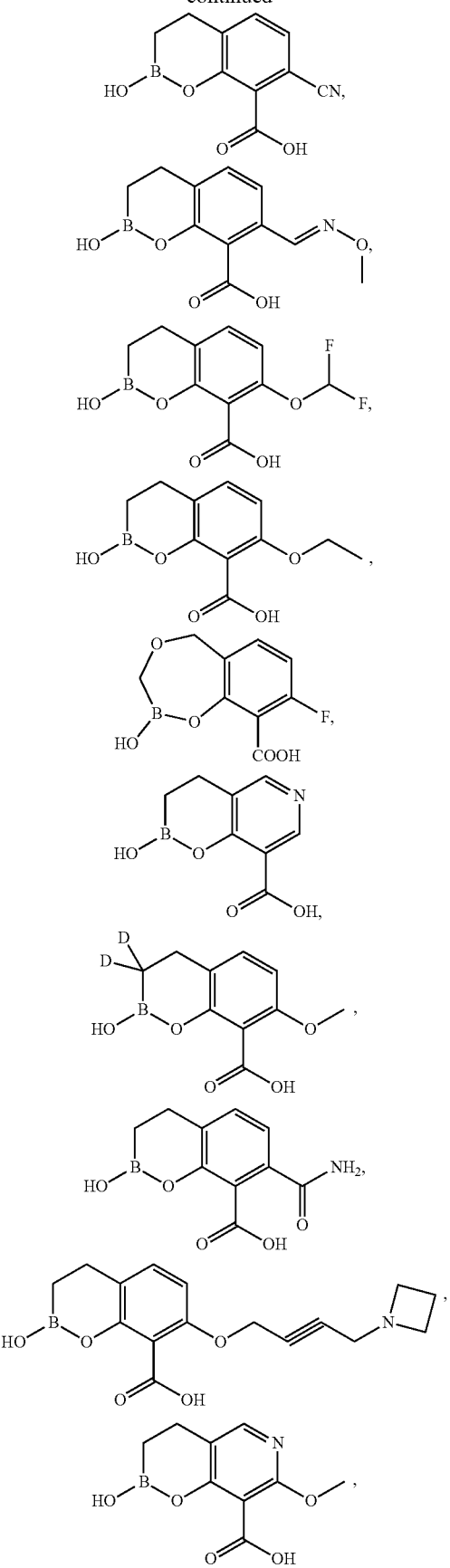

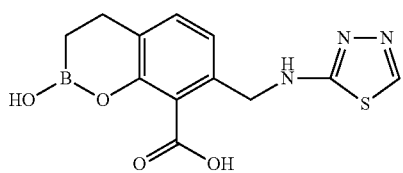

pharmaceutically acceptable salts thereof.

In some embodiments, the pharmaceutically acceptable salt is an alkaline metal salt or ammonium salt. In some embodiments, the pharmaceutically acceptable salt is a sodium salt.

In some embodiments, the compound of formula (III) or (IV) can have the structure selected from

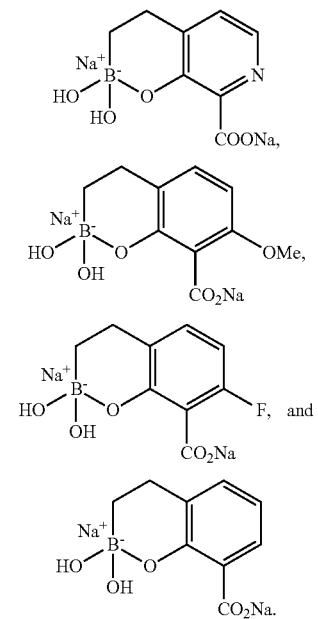

In some embodiments, the compound of formula (III'), (III), (IV) and (IV') can have the structure selected from

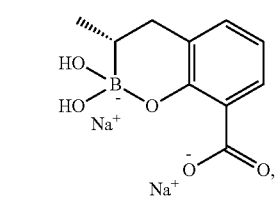

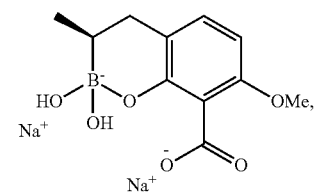

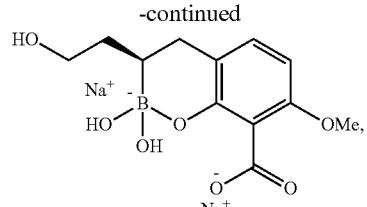

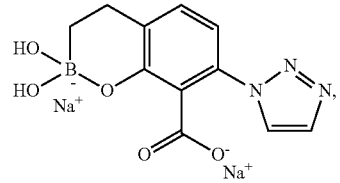

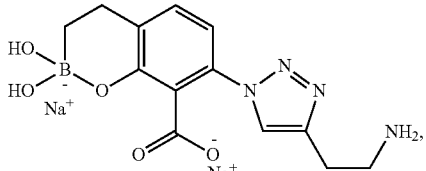

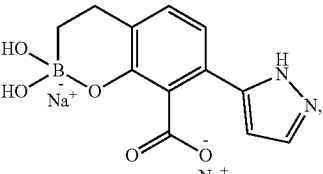

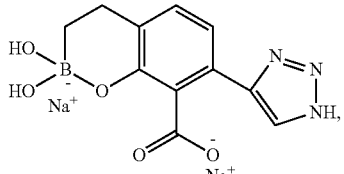

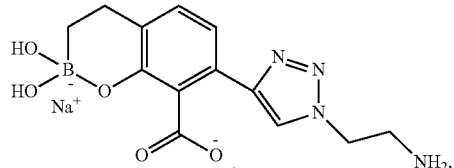

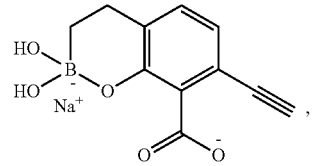

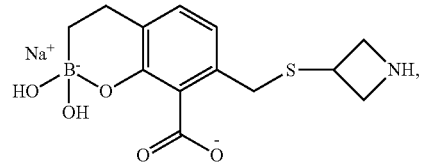

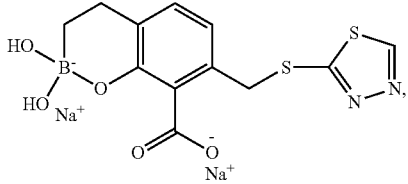

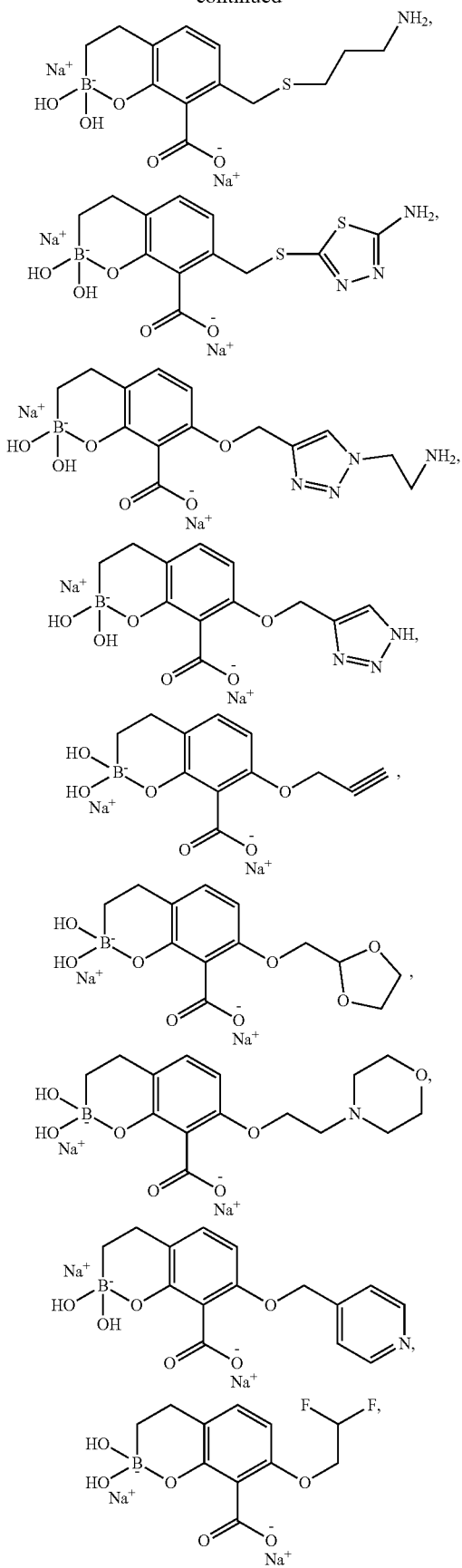
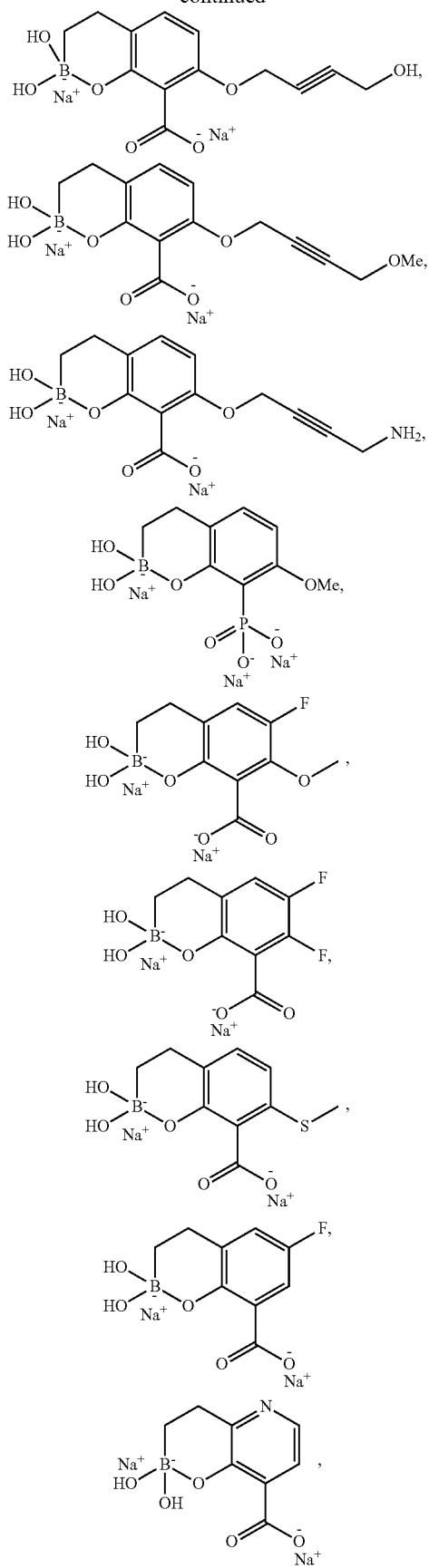

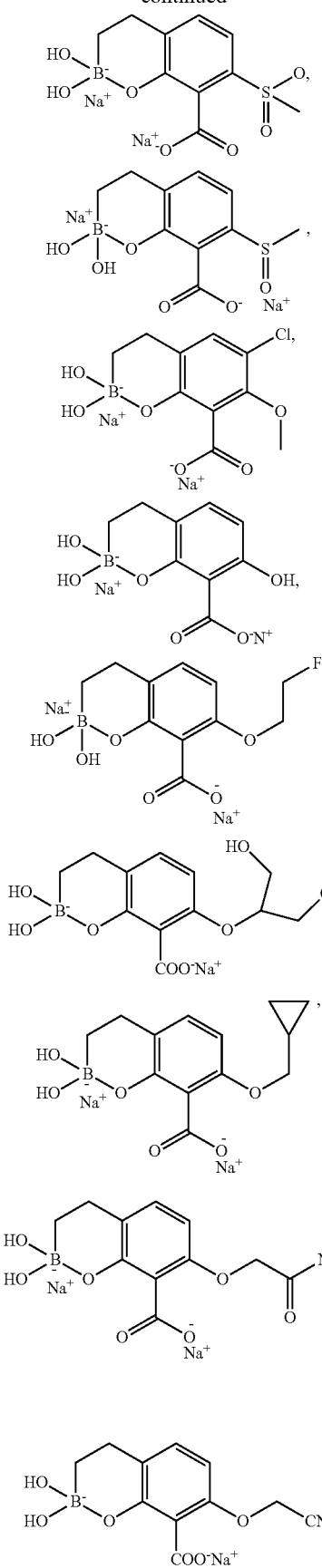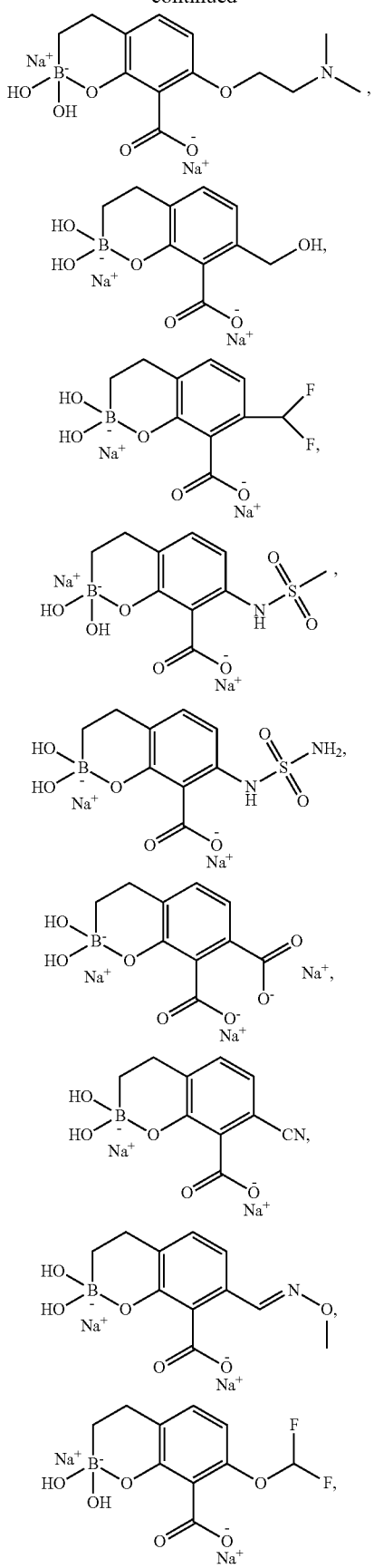

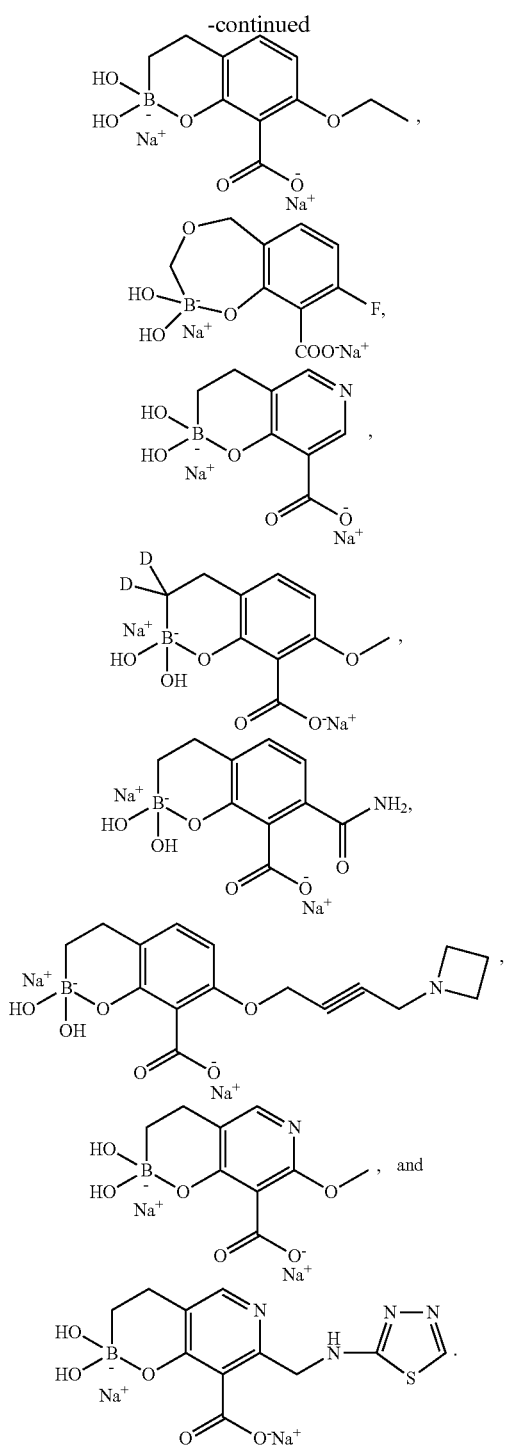

Where the compounds disclosed herein have at least one chiral center, they may exist as individual enantiomers and diastereomers or as mixtures of such isomers, including racemates. Separation of the individual isomers or selective synthesis of the individual isomers is accomplished by application of various methods which are well known to practitioners in the art. Unless otherwise indicated, all such isomers and mixtures thereof are included in the scope of the compounds disclosed herein. Furthermore, compounds disclosed herein may exist in one or more crystalline or amorphous forms. Unless otherwise indicated, all such forms are included in the scope of the compounds disclosed herein including any polymorphic forms. In addition, some of the compounds disclosed herein may form solvates with water (i.e., hydrates) or common organic solvents. Unless otherwise indicated, such solvates are included in the scope of the compounds disclosed herein.

The skilled artisan will recognize that some structures described herein may be resonance forms or tautomers of compounds that may be fairly represented by other chemical structures, even when kinetically; the artisan recognizes that such structures may only represent a very small portion of a sample of such compound(s). Such compounds are considered within the scope of the structures depicted, though such resonance forms or tautomers are not represented herein.

Isotopes may be present in the compounds described. Each chemical element as represented in a compound structure may include any isotope of said element. For example, in a compound structure a hydrogen atom may be explicitly disclosed or understood to be present in the compound. At any position of the compound that a hydrogen atom may be present, the hydrogen atom can be any isotope of hydrogen, including but not limited to hydrogen-1 (protium) and hydrogen-2 (deuterium). Thus, reference herein to a compound encompasses all potential isotopic forms unless the context clearly dictates otherwise.

In some embodiments, due to the facile exchange of boron esters, the compounds described herein may convert to or exist in equilibrium with alternate forms. Accordingly, in some embodiments, the compounds described herein may exist in combination with one or more of these forms. For example, as shown below, the compounds disclosed herein may exist in cyclic boronate monoesters as formula I' or in acyclic form as boronic acids as formula II', or may exist as a mixture of the two forms depending on the medium; the compounds disclosed herein may exist in cyclic form as cyclic boronate monoesters as formula III-1 or in acyclic form as boronic acids as formula IV-1, or may exist as a mixture of the two forms depending on the medium; the compounds disclosed herein may exist in cyclic boronate monoesters as formula I or in acyclic form as boronic acids as formula II, or may exist as a mixture of the two forms depending on the medium. In another example, the compounds disclosed herein may exist in cyclic form as cyclic boronate monoesters as formula III' or in acyclic form as boronic acids as formula IV', or may exist as a mixture of the two forms depending on the medium; the compounds disclosed herein may exist in cyclic form as cyclic boronate monoesters as formula III-1 or in acyclic form as boronic acids as formula IV-1, or may exist as a mixture of the two forms depending on the medium.

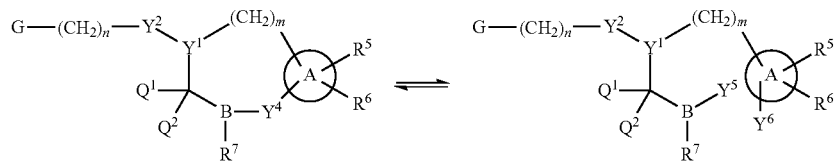

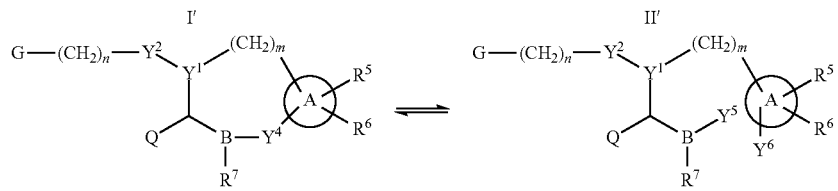

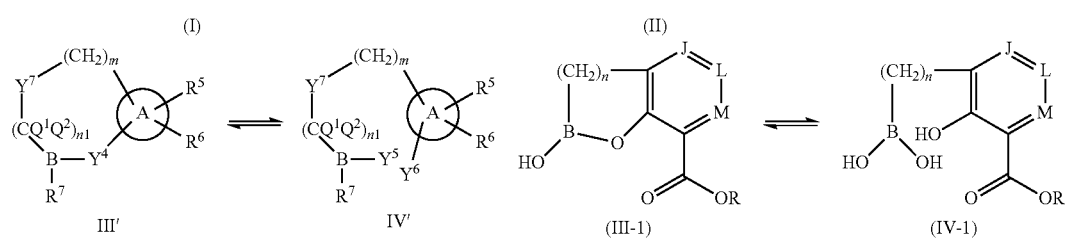

In some embodiments, the compounds described herein may exist in cyclic dimeric form as Formula (C) or trimeric form as Formula (D), tetrameric form as Formula (E) as shown below, or acylic dimeric, trimeric or tetrameric forms and the like. In some embodiments, Q can be H or —$Y^2$—$(CH_2)_n$-G; $Y^1$ can be $CR^1$ or N; and X' can be —$Y^2$—$(CH_2)_n$-G in Formula C, D and E.

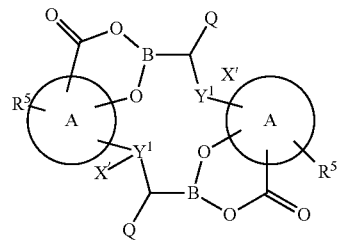

C

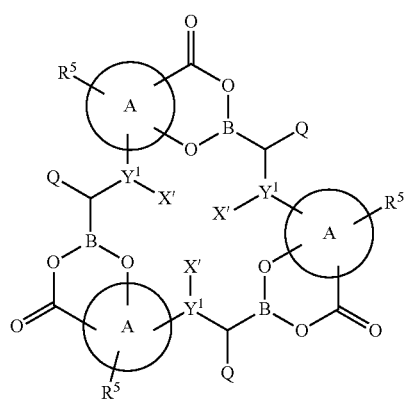

D

-continued

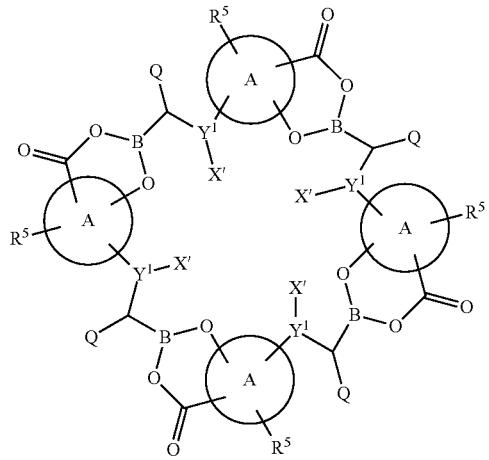

E

Definitions

Unless defined otherwise, all technical and scientific terms used herein have the same meaning as is commonly understood by one of ordinary skill in the art to which this disclosure belongs. All patents, applications, published applications, and other publications are incorporated by reference in their entirety. In the event that there is a plurality of definitions for a term herein, those in this section prevail unless stated otherwise.

A "prodrug" refers to an agent that is converted into the parent drug in vivo. Prodrugs are often useful because, in some situations, they may be easier to administer than the parent drug. They may, for instance, be bioavailable by oral administration whereas the parent is not. The prodrug may also have improved solubility in pharmaceutical compositions over the parent drug. An example, without limitation, of a prodrug would be a compound which is administered as an ester (the "prodrug") to facilitate transmittal across a cell membrane where water solubility is detrimental to mobility but which then is metabolically hydrolyzed to the carboxylic acid, the active entity, once inside the cell where water-solubility is beneficial. A further example of a prodrug might be a short peptide (polyaminoacid) bonded to an acid group where the peptide is metabolized to reveal the active moiety. Conventional procedures for the selection and preparation of suitable prodrug derivatives are described, for example, in *Design of Prodrugs*, (ed. H. Bundgaard, Elsevier, 1985), which is hereby incorporated herein by reference in its entirety.

The term "pro-drug ester" refers to derivatives of the compounds disclosed herein formed by the addition of any of several ester-forming groups that are hydrolyzed under physiological conditions. Examples of pro-drug ester groups include pivoyloxymethyl, acetoxymethyl, phthalidyl, indanyl and methoxymethyl, as well as other such groups known in the art, including a (5-R-2-oxo-1,3-dioxolen-4-yl)methyl group. Other examples of pro-drug ester groups can be found in, for example, T. Higuchi and V. Stella, in "Pro-drugs as Novel Delivery Systems", Vol. 14, A.C.S. Symposium Series, American Chemical Society (1975); and "Bioreversible Carriers in Drug Design: Theory and Application", edited by E. B. Roche, Pergamon Press: New York, 14-21 (1987) (providing examples of esters useful as prodrugs for compounds containing carboxyl groups). Each of the above-mentioned references is herein incorporated by reference in their entirety.

"Metabolites" of the compounds disclosed herein include active species that are produced upon introduction of the compounds into the biological milieu.

"Solvate" refers to the compound formed by the interaction of a solvent and a compound described herein, a metabolite, or salt thereof. Suitable solvates are pharmaceutically acceptable solvates including hydrates.

The term "pharmaceutically acceptable salt" refers to salts that retain the biological effectiveness and properties of a compound, which are not biologically or otherwise undesirable for use in a pharmaceutical. In many cases, the compounds herein are capable of forming acid and/or base salts by virtue of the presence of amino and/or carboxyl groups or groups similar thereto. Pharmaceutically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese, aluminum, and the like; particularly preferred are the ammonium, potassium, sodium, calcium and magnesium salts. Organic bases from which salts can be derived include, for example, primary, secondary, and tertiary amines, substituted amines including naturally occurring substituted amines, cyclic amines, basic ion exchange resins, and the like, specifically such as isopropylamine, trimethylamine, diethylamine, triethylamine, tripropylamine, and ethanolamine. Many such salts are known in the art, as described in WO 87/05297, Johnston et al., published Sep. 11, 1987 (incorporated by reference herein in its entirety). Some examples of pharmaceutically acceptable base addition salts of the compounds disclosed herein have the structure of Formula (IIc-salt) or (IVa-salt):

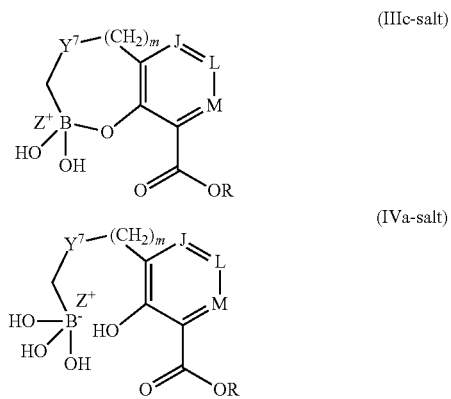

wherein Z can be an alkali metal or $NH_4^+$; and R can be an alkali metal or $NH_4^+$. Some additional examples of pharmaceutically acceptable base addition salts of the compounds described herein have the structure of Formula (IIId-salt) or (Ivb-salt):

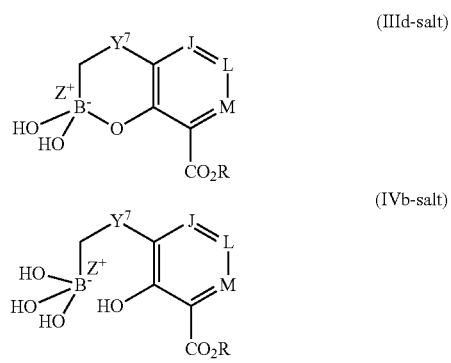

Some other examples of pharmaceutically acceptable base addition salts of the compounds described herein have the structure of Formula (I-salt) or (II-salt):

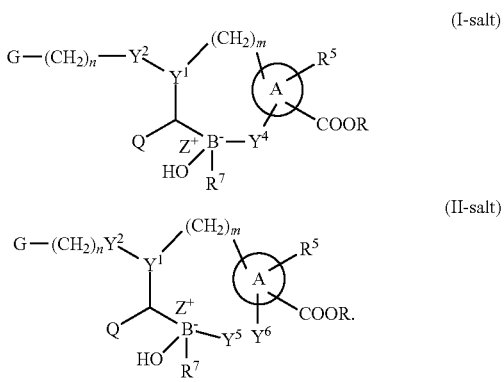

As used herein, "$C_a$ to $C_b$" or "$C_{a-b}$" in which "a" and "b" are integers refer to the number of carbon atoms in the specified group. That is, the group can contain from "a" to "b", inclusive, carbon atoms. Thus, for example, a "$C_1$ to $C_4$ alkyl" or "$C_{1-4}$ alkyl" group refers to all alkyl groups having from 1 to 4 carbons, that is, $CH_3$—, $CH_3CH_2$—, $CH_3CH_2CH_2$—, $(CH_3)_2CH$—, $CH_3CH_2CH_2CH_2$—, $CH_3CH_2CH(CH_3)$— and $(CH_3)_3C$—.

The term "halogen" or "halo," as used herein, means any one of the radio-stable atoms of column 7 of the Periodic Table of the Elements, e.g., fluorine, chlorine, bromine, or iodine, with fluorine and chlorine being preferred.

As used herein, "alkyl" refers to a straight or branched hydrocarbon chain that is fully saturated (i.e., contains no double or triple bonds). The alkyl group may have 1 to 20 carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc., up to and including 20 carbon atoms, although the present definition also covers the occurrence of the term "alkyl" where no numerical range is designated). The alkyl group may also be a medium size alkyl having 1 to 9 carbon atoms. The alkyl group could also be a lower alkyl having 1 to 4 carbon atoms. The alkyl group of the compounds may be designated as "$C_{1-4}$ alkyl" or similar designations. By way of example only, "$C_{1-4}$ alkyl" indicates that there are one to four carbon atoms in the alkyl chain, i.e., the alkyl chain is selected from the group consisting of methyl, ethyl, propyl, iso-propyl, n-butyl, iso-butyl, sec-butyl, and t-butyl. Typical alkyl groups include, but are in no way limited to, methyl, ethyl, propyl, isopropyl, butyl, isobutyl, tertiary butyl, pentyl, hexyl, and the like.

As used herein, "alkoxy" refers to the formula —OR wherein R is an alkyl as is defined above, such as "$C_{1-9}$ alkoxy", including but not limited to methoxy, ethoxy, n-propoxy, 1-methylethoxy (isopropoxy), n-butoxy, iso-butoxy, sec-butoxy, and tert-butoxy, and the like.

As used herein, "alkylthio" refers to the formula —SR wherein R is an alkyl as is defined above, such as "$C_{1-9}$ alkylthio" and the like, including but not limited to methylmercapto, ethylmercapto, n-propylmercapto, 1-methylethylmercapto (isopropylmercapto), n-butylmercapto, iso-butylmercapto, sec-butylmercapto, tert-butylmercapto, and the like.

As used herein, "alkenyl" refers to a straight or branched hydrocarbon chain containing one or more double bonds. The alkenyl group may have 2 to 20 carbon atoms, although the present definition also covers the occurrence of the term "alkenyl" where no numerical range is designated. The alkenyl group may also be a medium size alkenyl having 2 to 9 carbon atoms. The alkenyl group could also be a lower alkenyl having 2 to 4 carbon atoms. The alkenyl group of the compounds may be designated as "$C_{2-4}$ alkenyl" or similar designations. By way of example only, "$C_{2-4}$ alkenyl" indicates that there are two to four carbon atoms in the alkenyl chain, i.e., the alkenyl chain is selected from the group consisting of ethenyl, propen-1-yl, propen-2-yl, propen-3-yl, buten-1-yl, buten-2-yl, buten-3-yl, buten-4-yl, 1-methyl-propen-1-yl, 2-methyl-propen-1-yl, 1-ethyl-ethen-1-yl, 2-methyl-propen-3-yl, buta-1,3-dienyl, buta-1,2-dienyl, and buta-1,2-dien-4-yl. Typical alkenyl groups include, but are in no way limited to, ethenyl, propenyl, butenyl, pentenyl, and hexenyl, and the like.

As used herein, "alkynyl" refers to a straight or branched hydrocarbon chain containing one or more triple bonds. The alkynyl group may have 2 to 20 carbon atoms, although the present definition also covers the occurrence of the term "alkynyl" where no numerical range is designated. The alkynyl group may also be a medium size alkynyl having 2 to 9 carbon atoms. The alkynyl group could also be a lower alkynyl having 2 to 4 carbon atoms. The alkynyl group of the compounds may be designated as "$C_{2-4}$ alkynyl" or similar designations. By way of example only, "$C_{2-4}$ alkynyl" indicates that there are two to four carbon atoms in the alkynyl chain, i.e., the alkynyl chain is selected from the group consisting of ethynyl, propyn-1-yl, propyn-2-yl, butyn-1-yl, butyn-3-yl, butyn-4-yl, and 2-butynyl. Typical alkynyl groups include, but are in no way limited to, ethynyl, propynyl, butynyl, pentynyl, and hexynyl, and the like.

As used herein, "heteroalkyl" refers to a straight or branched hydrocarbon chain containing one or more heteroatoms, that is, an element other than carbon, including but not limited to, nitrogen, oxygen and sulfur, in the chain backbone. The heteroalkyl group may have 1 to 20 carbon atoms although the present definition also covers the occurrence of the term "heteroalkyl" where no numerical range is designated. The heteroalkyl group may also be a medium size heteroalkyl having 1 to 9 carbon atoms. The heteroalkyl group could also be a lower heteroalkyl having 1 to 4 carbon atoms. The heteroalkyl group of the compounds may be designated as "$C_{1-4}$ heteroalkyl" or similar designations. The heteroalkyl group may contain one or more heteroatoms. By way of example only, "$C_{1-4}$ heteroalkyl" indicates that there are one to four carbon atoms in the heteroalkyl chain and additionally one or more heteroatoms in the backbone of the chain.

The term "aromatic" refers to a ring or ring system having a conjugated pi electron system and includes both carbocyclic aromatic (e.g., phenyl) and heterocyclic aromatic groups (e.g., pyridine). The term includes monocyclic or fused-ring polycyclic (i.e., rings which share adjacent pairs of atoms) groups provided that the entire ring system is aromatic.

As used herein, "aryl" refers to an aromatic ring or ring system (i.e., two or more fused rings that share two adjacent carbon atoms) containing only carbon in the ring backbone. When the aryl is a ring system, every ring in the system is aromatic. The aryl group may have 6 to 18 carbon atoms, although the present definition also covers the occurrence of the term "aryl" where no numerical range is designated. In some embodiments, the aryl group has 6 to 10 carbon atoms. The aryl group may be designated as "$C_{6-10}$ aryl," "$C_6$ or $C_{10}$ aryl," or similar designations. Examples of aryl groups include, but are not limited to, phenyl, naphthyl, azulenyl, and anthracenyl.

As used herein, "aryloxy" and "arylthio" refers to RO— and RS—, in which R is an aryl as is defined above, such as "$C_{6-10}$ aryloxy" or "$C_{6-10}$ arylthio" and the like, including but not limited to phenyloxy.

An "aralkyl" or "arylalkyl" is an aryl group connected, as a substituent, via an alkylene group, such "$C_{7-14}$ aralkyl" and the like, including but not limited to benzyl, 2-phenylethyl, 3-phenylpropyl, and naphthylalkyl. In some cases, the alkylene group is a lower alkylene group (i.e., a $C_{1-4}$ alkylene group).

As used herein, "heteroaryl" refers to an aromatic ring or ring system (i.e., two or more fused rings that share two adjacent atoms) that contain(s) one or more heteroatoms, that is, an element other than carbon, including but not limited to, nitrogen, oxygen and sulfur, in the ring backbone. When the heteroaryl is a ring system, every ring in the system is aromatic. The heteroaryl group may have 5-18 ring members (i.e., the number of atoms making up the ring backbone, including carbon atoms and heteroatoms), although the present definition also covers the occurrence of the term "heteroaryl" where no numerical range is designated. In some embodiments, the heteroaryl group has 5 to 10 ring members or 5 to 7 ring members. The heteroaryl group may be designated as "5-7 membered heteroaryl," "5-10 membered heteroaryl," or similar designations. Examples of heteroaryl rings include, but are not limited to, furyl, thienyl, phthalazinyl, pyrrolyl, oxazolyl, thiazolyl, imidazolyl, pyrazolyl, isoxazolyl, isothiazolyl, triazolyl, thiadiazolyl, pyridinyl, pyridazinyl, pyrimidinyl, pyrazinyl, triazinyl, quinolinyl, isoquinlinyl, benzimidazolyl, benzoxazolyl, benzothiazolyl, indolyl, isoindolyl, and benzothienyl.

A "heteroaralkyl" or "heteroarylalkyl" is heteroaryl group connected, as a substituent, via an alkylene group. Examples include but are not limited to 2-thienylmethyl, 3-thienylmethyl, furylmethyl, thienylethyl, pyrrolylalkyl, pyridylalkyl, isoxazollylalkyl, and imidazolylalkyl. In some cases, the alkylene group is a lower alkylene group (i.e., a $C_{1-4}$ alkylene group).

As used herein, "carbocyclyl" means a non-aromatic cyclic ring or ring system containing only carbon atoms in the ring system backbone. When the carbocyclyl is a ring system, two or more rings may be joined together in a fused, bridged or spiro-connected fashion. Carbocyclyls may have any degree of saturation provided that at least one ring in a ring system is not aromatic. Thus, carbocyclyls include cycloalkyls, cycloalkenyls, and cycloalkynyls. The carbocyclyl group may have 3 to 20 carbon atoms, although the present definition also covers the occurrence of the term "carbocyclyl" where no numerical range is designated. The carbocyclyl group may also be a medium size carbocyclyl having 3 to 10 carbon atoms. The carbocyclyl group could also be a carbocyclyl having 3 to 6 carbon atoms. The carbocyclyl group may be designated as "$C_{3-6}$ carbocyclyl" or similar designations. Examples of carbocyclyl rings include, but are not limited to, cyclopropyl, cyclobutyl, cyclopentyl, cyclohexyl, cyclohexenyl, 2,3-dihydro-indene, bicycle[2.2.2]octanyl, adamantyl, and spiro[4.4]nonanyl.

A "(carbocyclyl)alkyl" is a carbocyclyl group connected, as a substituent, via an alkylene group, such as "$C_{4-10}$ (carbocyclyl)alkyl" and the like, including but not limited to, cyclopropylmethyl, cyclobutylmethyl, cyclopropylethyl, cyclopropylbutyl, cyclobutylethyl, cyclopropylisopropyl, cyclopentylmethyl, cyclopentylethyl, cyclohexylmethyl, cyclohexylethyl, cycloheptylmethyl, and the like. In some cases, the alkylene group is a lower alkylene group.

As used herein, "cycloalkyl" means a fully saturated carbocyclyl ring or ring system. Examples include cyclopropyl, cyclobutyl, cyclopentyl, and cyclohexyl.

As used herein, "cycloalkenyl" means a carbocyclyl ring or ring system having at least one double bond, wherein no ring in the ring system is aromatic. An example is cyclohexenyl.

As used herein, "heterocyclyl" means a non-aromatic cyclic ring or ring system containing at least one heteroatom in the ring backbone. Heterocyclyls may be joined together in a fused, bridged or spiro-connected fashion. Heterocyclyls may have any degree of saturation provided that at least one ring in the ring system is not aromatic. The heteroatom(s) may be present in either a non-aromatic or aromatic ring in the ring system. The heterocyclyl group may have 3 to 20 ring members (i.e., the number of atoms making up the ring backbone, including carbon atoms and heteroatoms), although the present definition also covers the occurrence of the term "heterocyclyl" where no numerical range is designated. The heterocyclyl group may also be a medium size heterocyclyl having 3 to 10 ring members. The heterocyclyl group could also be a heterocyclyl having 3 to 6 ring members. The heterocyclyl group may be designated as "3-6 membered heterocyclyl" or similar designations. In preferred six membered monocyclic heterocyclyls, the heteroatom(s) are selected from one up to three of O, N or S, and in preferred five membered monocyclic heterocyclyls, the heteroatom(s) are selected from one or two heteroatoms selected from O, N, or S. Examples of heterocyclyl rings include, but are not limited to, azepinyl, acridinyl, carbazolyl, cinnolinyl, dioxolanyl, imidazolinyl, imidazolidinyl, morpholinyl, oxiranyl, oxepanyl, thiepanyl, piperidinyl, piperazinyl, dioxopiperazinyl, pyrrolidinyl, pyrrolidonyl, pyrrolidionyl, 4-piperidonyl, pyrazolinyl, pyrazolidinyl, 1,3-dioxinyl, 1,3-dioxanyl, 1,4-dioxinyl, 1,4-dioxanyl, 1,3-oxathianyl, 1,4-oxathiinyl, 1,4-oxathianyl, 2H-1,2-oxazinyl, trioxanyl, hexahydro-1,3,5-triazinyl, 1,3-dioxolyl, 1,3-dioxolanyl, 1,3-dithiolyl, 1,3-dithiolanyl, isoxazolinyl, isoxazolidinyl, oxazolinyl, oxazolidinyl, oxazolidinonyl, thiazolinyl, thiazolidinyl, 1,3-oxathiolanyl, indolinyl, isoindolinyl, tetrahydrofuranyl, tetrahydropyranyl, tetrahydrothiophenyl, tetrahydrothiopyranyl, tetrahydro-1,4-thiazinyl, thiamorpholinyl, dihydrobenzofuranyl, benzimidazolidinyl, and tetrahydroquinoline.

A "(heterocyclyl)alkyl" is a heterocyclyl group connected, as a substituent, via an alkylene group. Examples include, but are not limited to, imidazolinylmethyl and indolinylethyl.

As used herein, "acyl" refers to —C(=O)R, wherein R is hydrogen, $C_{1-6}$ alkyl, $C_{2-6}$ alkenyl, $C_{2-6}$ alkynyl, $C_{3-7}$ carbocyclyl, aryl, 5-10 membered heteroaryl, and 5-10 membered heterocyclyl, as defined herein. Non-limiting examples include formyl, acetyl, propanoyl, benzoyl, and acryl.

An "O-carboxy" group refers to a "—OC(=O)R" group in which R is selected from hydrogen, $C_{1-6}$ alkyl, $C_{2-6}$ alkenyl, $C_{2-6}$ alkynyl, $C_{3-7}$ carbocyclyl, aryl, 5-10 membered heteroaryl, and 5-10 membered heterocyclyl, as defined herein.

A "C-carboxy" group refers to a "—C(=O)OR" group in which R is selected from hydrogen, $C_{1-6}$ alkyl, $C_{2-6}$ alkenyl, $C_{2-6}$ alkynyl, $C_{3-7}$ carbocyclyl, aryl, 5-10 membered heteroaryl, and 5-10 membered heterocyclyl, as defined herein. A non-limiting example includes carboxyl (i.e., —C(=O)OH).

A "cyano" group refers to a "—CN" group.

A "cyanato" group refers to an "—OCN" group.

An "isocyanato" group refers to a "—NCO" group.

A "thiocyanato" group refers to a "—SCN" group.

An "isothiocyanato" group refers to an "—NCS" group.

A "sulfinyl" group refers to an "—S(=O)R" group in which R is selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

A "sulfonyl" group refers to an "—SO$_2$R" group in which R is selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "S-sulfonamido" group refers to a "—SO$_2$NR$_A$R$_B$" group in which R$_A$ and R$_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "N-sulfonamido" group refers to a "—N(R$_A$)SO$_2$R$_B$" group in which R$_A$ and R$_b$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "O-carbamyl" group refers to a "—OC(=O)NR$_A$R$_B$" group in which R$_A$ and R$_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "N-carbamyl" group refers to an "—N($R_A$)OC(=O)$R_B$" group in which $R_A$ and $R_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "O-thiocarbamyl" group refers to a "—OC(=S)N$R_A R_B$" group in which $R_A$ and $R_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "N-thiocarbamyl" group refers to an "—N($R_A$)OC(=S)$R_B$" group in which $R_A$ and $R_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

A "C-amido" group refers to a "—C(=O)N$R_A R_B$" group in which $R_A$ and $R_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "N-amido" group refers to a "—N($R_A$)C(=O)$R_B$" group in which $R_A$ and $R_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "amino" group refers to a "—N$R_A R_B$" group in which $R_A$ and $R_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "aminoalkyl" group refers to an amino group connected via an alkylene group.

An "alkoxyalkyl" group refers to an alkoxy group connected via an alkylene group, such as a "$C_{2-8}$ alkoxyalkyl" and the like.

As used herein, a substituted group is derived from the unsubstituted parent group in which there has been an exchange of one or more hydrogen atoms for another atom or group. Unless otherwise indicated, when a group is deemed to be "substituted," it is meant that the group is substituted with one or more substituents independently selected from $C_1$-$C_6$ alkyl, $C_1$-$C_6$ alkenyl, $C_1$-$C_6$ alkynyl, $C_1$-$C_6$ heteroalkyl, $C_3$-$C_7$ carbocyclyl (optionally substituted with halo, $C_1$-$C_6$ alkyl, $C_1$-$C_6$ alkoxy, $C_1$-$C_6$ haloalkyl, and $C_1$-$C_6$ haloalkoxy), $C_3$-$C_7$-carbocyclyl-$C_1$-$C_6$-alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heterocyclyl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heterocyclyl-$C_1$-$C_6$-alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), aryl (optionally substituted with halo, $C_1$-$C_6$ alkyl, $C_1$-$C_6$ alkoxy, $C_1$-$C_6$ haloalkyl, and $C_1$-$C_6$ haloalkoxy), aryl($C_1$-$C_6$)alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heteroaryl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heteroaryl($C_1$-$C_6$)alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), halo, cyano, hydroxy, $C_1$-$C_6$ alkoxy, $C_1$-$C_6$ alkoxy($C_1$-$C_6$)alkyl (i.e., ether), aryloxy, sulfhydryl (mercapto), halo($C_1$-$C_6$) alkyl (e.g., —CF$_3$), halo($C_1$-$C_6$)alkoxy (e.g., —OCF$_3$), $C_1$-$C_6$ alkylthio, arylthio, amino, amino($C_1$-$C_6$)alkyl, nitro, O-carbamyl, N-carbamyl, O-thiocarbamyl, N-thiocarbamyl, C-amido, N-amido, S-sulfonamido, N-sulfonamido, C-carboxy, O-carboxy, acyl, cyanato, isocyanato, thiocyanato, isothiocyanato, sulfinyl, sulfonyl, and oxo (=O). Wherever a group is described as "optionally substituted" that group can be substituted with the above substituents.

In some embodiments, substituted group(s) is (are) substituted with one or more substituent(s) individually and independently selected from $C_1$-$C_4$ alkyl, amino, hydroxy, and halogen.

It is to be understood that certain radical naming conventions can include either a mono-radical or a di-radical, depending on the context. For example, where a substituent requires two points of attachment to the rest of the molecule, it is understood that the substituent is a di-radical. For example, a substituent identified as alkyl that requires two points of attachment includes di-radicals such as —CH$_2$—, —CH$_2$CH$_2$—, —CH$_2$CH(CH$_3$)CH$_2$—, and the like. Other radical naming conventions clearly indicate that the radical is a di-radical such as "alkylene" or "alkenylene."

As used herein, "alkylene" means a branched, or straight chain fully saturated di-radical chemical group containing only carbon and hydrogen that is attached to the rest of the molecule via two points of attachment (i.e., an alkanediyl). The alkylene group may have 1 to 20 carbon atoms, although the present definition also covers the occurrence of the term alkylene where no numerical range is designated. The alkylene group may also be a medium size alkylene having 1 to 9 carbon atoms. The alkylene group could also be a lower alkylene having 1 to 4 carbon atoms. The alkylene group may be designated as "$C_{1-4}$ alkylene" or similar designations. By way of example only, "$C_{1-4}$ alkylene" indicates that there are one to four carbon atoms in the alkylene chain, i.e., the alkylene chain is selected from the group consisting of methylene, ethylene, ethan-1,1-diyl, propylene, propan-1,1-diyl, propan-2,2-diyl, 1-methyl-ethylene, butylene, butan-1,1-diyl, butan-2,2-diyl, 2-methyl-propan-1,1-diyl, 1-methyl-propylene, 2-methyl-propylene, 1,1-dimethyl-ethylene, 1,2-dimethyl-ethylene, and 1-ethyl-ethylene.

As used herein, "alkenylene" means a straight or branched chain di-radical chemical group containing only carbon and hydrogen and containing at least one carbon-carbon double bond that is attached to the rest of the molecule via two points of attachment. The alkenylene group may have 2 to 20 carbon atoms, although the present definition also covers the occurrence of the term alkenylene where no numerical range is designated. The alkenylene group may also be a medium size alkenylene having 2 to 9 carbon atoms. The alkenylene group could also be a lower alkenylene having 2 to 4 carbon atoms. The alkenylene group may be designated as "$C_{2-4}$ alkenylene" or similar designations. By way of example only, "$C_{2-4}$ alkenylene" indicates that there are two to four carbon atoms in the alkenylene chain, i.e., the alkenylene chain is selected from the group consisting of ethenylene, ethen-1,1-diyl, propenylene, propen-1,1-diyl, prop-2-en-1,1-diyl, 1-methyl-ethenylene, but-1-enylene, but-2-enylene, but-1,3-dienylene, buten-1,1-diyl, but-1,3-dien-1,1-diyl, but-2-en-1,1-diyl, but-3-en-1,1-diyl, 1-methyl-prop-2-en-1,1-diyl, 2-methyl-prop-2-en-1,1-diyl, 1-ethyl-ethenylene, 1,2-dimethyl-ethenylene, 1-methyl-propenylene, 2-methyl-propenylene, 3-methyl-propenylene, 2-methyl-propen-1,1-diyl, and 2,2-dimethyl-ethen-1,1-diyl.

When two R groups are said to form a ring (e.g., a carbocyclyl, heterocyclyl, aryl, or heteroaryl ring) "together with the atom to which they are attached," it is meant that the collective unit of the atom and the two R groups are the recited ring. The ring is not otherwise limited by the definition of each R group when taken individually. For example, when the following substructure is present:

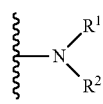

and $R^1$ and $R^2$ are defined as selected from the group consisting of hydrogen and alkyl, or $R^1$ and $R^2$ together with the nitrogen to which they are attached form a heteroaryl, it is meant that $R^1$ and $R^2$ can be selected from hydrogen or alkyl, or alternatively, the substructure has structure:

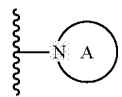

where ring A is a heteroaryl ring containing the depicted nitrogen.

Similarly, when two "adjacent" R groups are said to form a ring "together with the atoms to which they are attached," it is meant that the collective unit of the atoms, intervening bonds, and the two R groups are the recited ring. For example, when the following substructure is present:

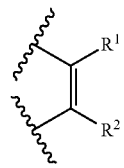

and $R^1$ and $R^2$ are defined as selected from the group consisting of hydrogen and alkyl, or $R^1$ and $R^2$ together with the atoms to which they are attached form an aryl or carbocylyl, it is meant that $R^1$ and $R^2$ can be selected from hydrogen or alkyl, or alternatively, the substructure has structure:

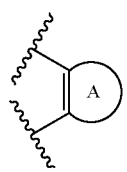

where A is an aryl ring or a carbocylyl containing the depicted double bond.

Wherever a substituent is depicted as a di-radical (i.e., has two points of attachment to the rest of the molecule), it is to be understood that the substituent can be attached in any directional configuration unless otherwise indicated. Thus, for example, a substituent depicted as -AE- or

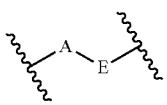

includes the substituent being oriented such that the A is attached at the leftmost attachment point of the molecule as well as the case in which A is attached at the rightmost attachment point of the molecule.

As used herein, "isosteres" of a chemical group are other chemical groups that exhibit the same or similar properties. For example, tetrazole is an isostere of carboxylic acid because it mimics the properties of carboxylic acid even though they both have very different molecular formulae. Tetrazole is one of many possible isosteric replacements for carboxylic acid. Other carboxylic acid isosteres contemplated include —$SO_3H$, —$SO_2HNR$, —$PO_2(R)_2$, —$PO_3(R)_2$, —$CONHNHSO_2R$, —$COHNSO_2R$, and —$CONRCN$, where R is selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 3-10 membered heterocyclyl, as defined herein. In addition, carboxylic acid isosteres can include κ-7 membered carbocycles or heterocycles containing any combination of $CH_2$, O, S, or N in any chemically stable oxidation state, where any of the atoms of said ring structure are optionally substituted in one or more positions. The following structures are non-limiting examples of carbocyclic and heterocyclic isosteres contemplated. The atoms of said ring structure may be optionally substituted at one or more positions with R as defined above.

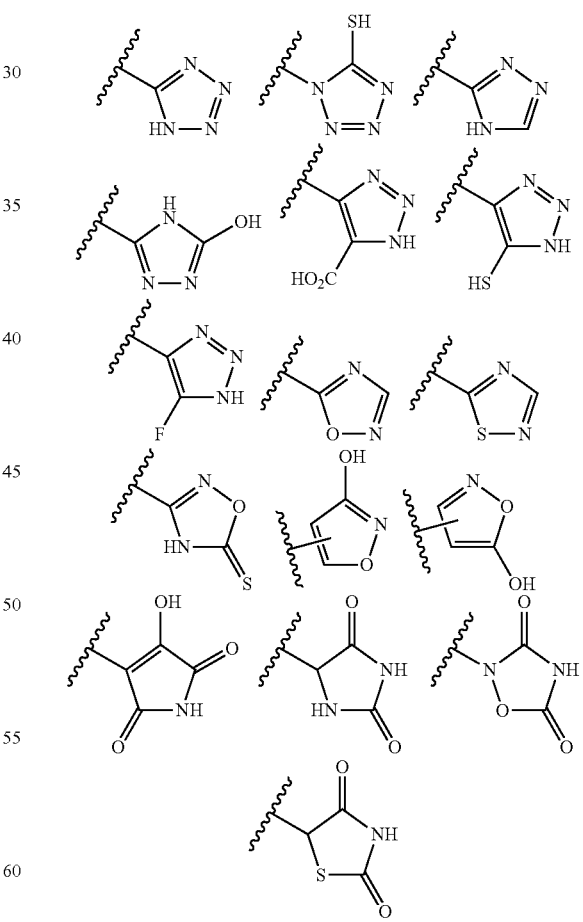

It is also contemplated that when chemical substituents are added to a carboxylic isostere, the compound retains the properties of a carboxylic isostere. It is contemplated that when a carboxylic isostere is optionally substituted with one or more moieties selected from R as defined above, then the substitution and substitution position is selected such that it does not eliminate the carboxylic acid isosteric properties of the compound. Similarly, it is also contemplated that the placement of one or more R substituents upon a carbocyclic or heterocyclic carboxylic acid isostere is not a substitution at one or more atom(s) that maintain(s) or is/are integral to the carboxylic acid isosteric properties of the compound, if such substituent(s) would destroy the carboxylic acid isosteric properties of the compound.

Other carboxylic acid isosteres not specifically exemplified in this specification are also contemplated.

The term "agent" or "test agent" includes any substance, molecule, element, compound, entity, or a combination thereof. It includes, but is not limited to, e.g., protein, polypeptide, peptide or mimetic, small organic molecule, polysaccharide, polynucleotide, and the like. It can be a natural product, a synthetic compound, or a chemical compound, or a combination of two or more substances. Unless otherwise specified, the terms "agent", "substance", and "compound" are used interchangeably herein.

The term "analog" is used herein to refer to a molecule that structurally resembles a reference molecule but which has been modified in a targeted and controlled manner, by replacing a specific substituent of the reference molecule with an alternate substituent. Compared to the reference molecule, an analog would be expected, by one skilled in the art, to exhibit the same, similar, or improved utility. Synthesis and screening of analogs, to identify variants of known compounds having improved characteristics (such as higher binding affinity for a target molecule) is an approach that is well known in pharmaceutical chemistry.

The term "mammal" is used in its usual biological sense. Thus, it specifically includes, but is not limited to, primates, including simians (chimpanzees, apes, monkeys) and humans, cattle, horses, sheep, goats, swine, rabbits, dogs, cats, rats and mice but also includes many other species.

The term "microbial infection" refers to the invasion of the host organism, whether the organism is a vertebrate, invertebrate, fish, plant, bird, or mammal, by pathogenic microbes. This includes the excessive growth of microbes that are normally present in or on the body of a mammal or other organism. More generally, a microbial infection can be any situation in which the presence of a microbial population(s) is damaging to a host mammal. Thus, a mammal is "suffering" from a microbial infection when excessive numbers of a microbial population are present in or on a mammal's body, or when the effects of the presence of a microbial population(s) is damaging the cells or other tissue of a mammal. Specifically, this description applies to a bacterial infection. Note that the compounds of preferred embodiments are also useful in treating microbial growth or contamination of cell cultures or other media, or inanimate surfaces or objects, and nothing herein should limit the preferred embodiments only to treatment of higher organisms, except when explicitly so specified in the claims.

The term "pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. In addition, various adjuvants such as are commonly used in the art may be included. Considerations for the inclusion of various components in pharmaceutical compositions are described, e.g., in Gilman et al. (Eds.) (1990); Goodman and Gilman's: The Pharmacological Basis of Therapeutics, 8th Ed., Pergamon Press, which is incorporated herein by reference in its entirety.

"Subject" as used herein, means a human or a non-human mammal, e.g., a dog, a cat, a mouse, a rat, a cow, a sheep, a pig, a goat, a non-human primate or a bird, e.g., a chicken, as well as any other vertebrate or invertebrate.

An "effective amount" or a "therapeutically effective amount" as used herein refers to an amount of a therapeutic agent that is effective to relieve, to some extent, or to reduce the likelihood of onset of, one or more of the symptoms of a disease or condition, and includes curing a disease or condition. "Curing" means that the symptoms of a disease or condition are eliminated; however, certain long-term or permanent effects may exist even after a cure is obtained (such as extensive tissue damage).

"Treat," "treatment," or "treating," as used herein refers to administering a pharmaceutical composition for prophylactic and/or therapeutic purposes. The term "prophylactic treatment" refers to treating a subject who does not yet exhibit symptoms of a disease or condition, but who is susceptible to, or otherwise at risk of, a particular disease or condition, whereby the treatment reduces the likelihood that the patient will develop the disease or condition. The term "therapeutic treatment" refers to administering treatment to a Methods of Preparation The compounds disclosed herein may be synthesized by methods described below, or by modification of these methods. Ways of modifying the methodology include, among others, temperature, solvent, reagents etc., known to those skilled in the art. In general, during any of the processes for preparation of the compounds disclosed herein, it may be necessary and/or desirable to protect sensitive or reactive groups on any of the molecules concerned. This may be achieved by means of conventional protecting groups, such as those described in *Protective Groups in Organic Chemistry* (ed. J. F. W. McOmie, Plenum Press, 1973); and P. G. M. Green, T. W. Wutts, *Protecting Groups in Organic Synthesis* (3rd ed.) Wiley, New York (1999), which are both hereby incorporated herein by reference in their entirety. The protecting groups may be removed at a convenient subsequent stage using methods known from the art. Synthetic chemistry transformations useful in synthesizing applicable compounds are known in the art and include e.g. those described in R. Larock, *Comprehensive Organic Transformations*, VCH Publishers, 1989, or L. Paquette, ed., *Encyclopedia of Reagents for Organic Synthesis*, John Wiley and Sons, 1995, which are both hereby incorporated herein by reference in their entirety. The routes shown and described herein are illustrative only and are not intended, nor are they to be construed, to limit the scope of the claims in any manner whatsoever. Those skilled in the art will be able to recognize modifications of the disclosed syntheses and to devise alternate routes based on the disclosures herein; all such modifications and alternate routes are within the scope of the claims.

In the following schemes, protecting groups for oxygen atoms are selected for their compatibility with the requisite synthetic steps as well as compatibility of the introduction and deprotection steps with the overall synthetic schemes (P. G. M. Green, T. W. Wutts, Protecting Groups in Organic Synthesis (3rd ed.) Wiley, New York (1999)). Handling of protecting and/or sterodirecting groups specific to boronic acid derivatives is described in a recent review of chemistry of boronic acids: D. G. Hall (Ed.), Boronic Acids. Preparation and Application in Organic Synthesis and Medicine, Wiley VCH (2005) and in earlier reviews: Matteson, D. S. (1988). Asymmetric synthesis with boronic esters. Accounts of Chemical Research, 21(8), 294-300, and Matteson, D. S. (1989). Tetrahedron, 45(7), 1859-1885), all of which are incorporated herein by reference in their entirety. The latter review articles also describe methodology for stereoselective insertion of halomethine functionality next to the boronate which is employed in the synthetic schemes below.

In addition to standard acid catalyzed deprotection, special methods for removal of boronic acid protecting and/or sterodirecting groups methods using fluorides (Yuen, A. K. L., & Hutton, C. A. (2005). Tetrahedron Letters, 46(46), 7899-7903—incorporated herein by reference in its entirety) or periodate oxidation (Coutts, S. J., et al. (1994). Tetrahedron Letters, 35(29), 5109-5112—incorporated herein by reference in its entirety) can also be employed in preparations of the compounds disclosed herein.

In strategies employing pinanediol or other diol-based chiral auxiliaries for stereospecific introduction of new chiral centers, the early stages of chemistry on boronic intermediates can be performed on chiral boronate esters or alternatively nonchiral borate/boronate intermediates can be used in early stages followed by transesterification with chiral diols prior to the step where stereoselection is required.

Synthesis of Compounds of Formula I', I, III' and III

The following example schemes are provided for the guidance of the reader, and collectively represent an example method for making the compounds encompassed herein. Furthermore, other methods for preparing compounds described herein will be readily apparent to the person of ordinary skill in the art in light of the following reaction schemes and examples. Unless otherwise indicated, all variables are as defined above.

Compounds of formula Ib where R is H can be prepared as depicted in schemes 1-4 from key intermediates VI, VIII and XII, which may be assembled by known reactions (Boronic Acids: Preparations and Applications in Organic Synthesis, Medicine and Materials, D. G. Hall, ed., Wiley-VCH, Weinheim, 2011, which is incorporated herein by reference in its entirety).

Scheme 1

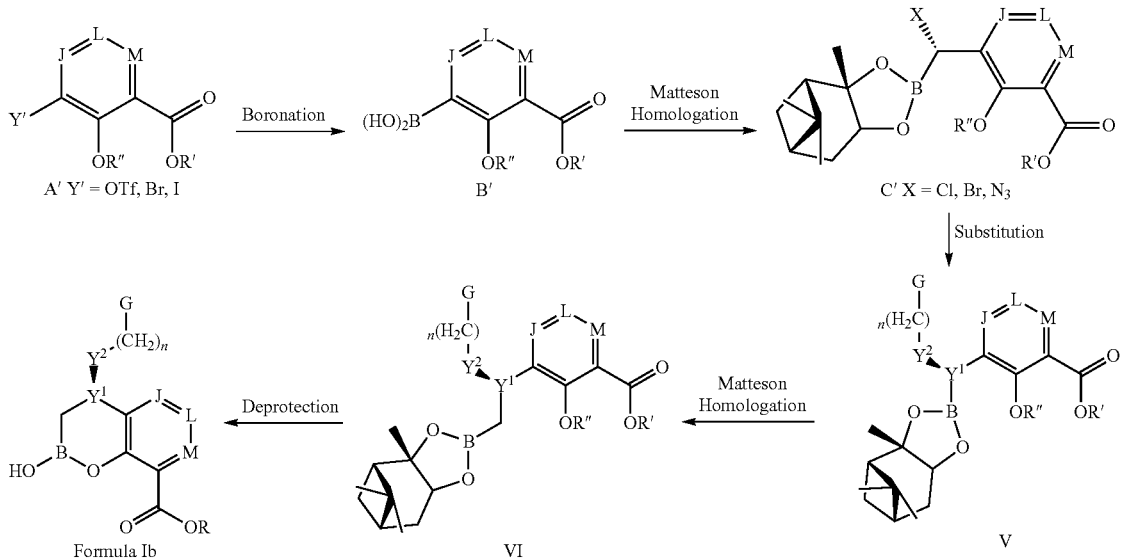

Compounds of formula Ib can be made starting from protected aryl or heteroaryl intermediates of formula B' via a double Matteson homologation sequence (J. Org. Chem., 2013, 78, 10009-10023, which is incorporated herein by reference in its entirety). The compounds of formula B' may be attained from A' by means of several earlier known methods (WO0458679, which is incorporated herein by reference in its entirety) with conventional protecting groups for R' and R", such as those described in Protective Groups in Organic Chemistry (ed. J. F. W. McOmie, Plenum, 1973, which is incorporated herein by reference in its entirety); and Protecting Groups in Organic Synthesis P. G. M. Wutts, T. W. Green, Wiley, New York, 1999, which is incorporated herein by reference in its entirety) from commercially available salicylic acid derivatives. Aryl compounds of formula A' upon boronation by well-known available methods (Chem. Rev. 2010, 110, 890-931, which is incorporated herein by reference in its entirety) and boronate ester formation with desired chiral auxiliary give precursor for Matteson homologation. Compounds of formula C' where X=Cl and R' is Boc and R" is t-Butyl or R' and R" are protected together as isopropylidine or any other groups protected separately or together in cyclic form may be made from compounds of formula B' via homologation upon chloromethylene insertion with good stereocontrol by Matteson reaction conditions (WO0946098, which is incorporated herein by reference in its entirety). Compounds of formula C' where X is bromo may be made analogously to the chloro compounds of Scheme 1, utilizing dibromomethane (J. Am. Chem. Soc. 1990, 112, 3964-969, which is incorporated herein by reference in its entirety). The halo derivatives of formula C' where X is Cl or Br undergo stereospecific substitution to form thioethers (WO 04064755, which is incorporated herein by reference in its entirety), ethers (WO 12067664, which is incorporated herein by reference in its entirety), amines (J. Organomet. Chem. 1979, 170, 259-64, which is incorporated herein by reference in its entirety) or acetates (*Tetrahedron* 2005, 61, 4427-4536, which is incorporated herein by reference in its entirety), to give compounds of formula V. In an alternate approach, compounds of formula C' where Y² is S can be made via a thiol intermediate by alkylation or arylation to introduce various G groups. Such compounds may also be made via alkyl or thiomethylene boronate esters by reaction with substituted benzyl halides (U.S. Pat. No. 6,586,615, which is incorporated herein by reference in its entirety). The resulting products of formula V where Y² is S or O can be further homologated by a methylene insertion in a second Matteson reaction to give compounds of formula VI. Additionally, halo derivatives of formula C' where X is Cl or Br undergo stereospecific substitution to form azides which can be further elaborated to compounds of formula VI where Y²=—NR2- by homologation, reduction, alkylation or amide formation sequence (WO 01002424, which is incorporated herein by reference in its entirety).

Simultaneous deprotection of pinane ester and salicylic acid protective groups of compounds of formula VI can be achieved by heating with dilute HCl, affording the desired compounds of structure Ib. This transformation may also be achieved by treatment with BCl₃ or BBr₃ (WO09064414), which is incorporated herein by reference in its entirety. Alternatively, the deprotection may be attained via transesterification with isobutyl boronic acid in presence of dilute acid (WO09064413, which is incorporated herein by reference in its entirety) or via other known methods (*J. Org. Chem.* (2010), 75, 468-471, which is incorporated herein by reference in its entirety).

Salicylic acid derivatives of formula A' where Y' is a leaving group undergo coupling reaction with Reformatsky reagent of acetate in Negishi conditions to give intermediates of formula VII where X' is OR'" (*Tetrahedron*, 2014, 1508-1515, *J. Org. Chem.*, 2013, 78, 8250-8266, which is incorporated herein by reference in its entirety) (Scheme 2).

Such intermediates may be alkylated with halomethylene boronate derivative (VIIA) to give compounds of formula VIII in high stereoselectivity (*J. Am. Chem. Soc.*, 2011, 133, 11936-11939, which is incorporated herein by reference in its entirety). Intermediates of formula VII undergo methylenation to give derivatives of IX (*J. Org. Chem.*, 1986, 51, 2981-2988, which is incorporated herein by reference in its entirety). Intermediates of formula IX undergo asymmetric boronation in known conditions to give compounds of formula VIII (*J. Am. Chem. Soc.*, 2010, 132, 10630-10633, which is incorporated herein by reference in its entirety). Such asymmetric boronation may also feasible where X' is —NR¹R². Intermediates of formula VIII can be further transformed to compound of formula Ib under the conditions described in scheme 1.

Scheme 2

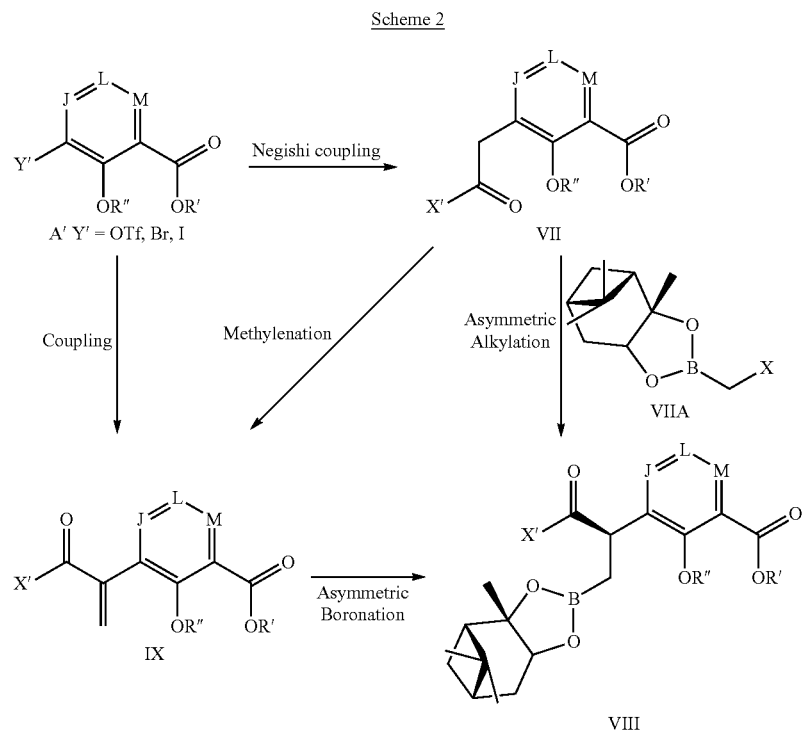

In an alternative sequence, compounds of formula Ib can be made via boracarboxylation followed by asymmetric hydrogenation of acetylene intermediate X as shown in scheme 3. Aryl or heteroaryl derivatives formula A' can undergo Pd mediated coupling reaction to give acetylene substituted compound with TMS-acetylene. Boracarboxylation of alkynes with a diborane compound and carbon dioxide in presence of an N-heterocyclic carbene copper (1) complex as a catalyst gives α,β-unsaturated β-boralactone derivatives regio- and stereoselectively via a borylcupration/carboxylation (*J. Am. Chem. Soc.* 2012, 134, 14314-14317, which is incorporated herein by reference in its entirety). Such resulting derivatives can be transformed to esters of carboxylate and boronate to give intermediates of formula XI. Asymmetric hydrogenation of intermediates of formula XI (*Chem. Rev.* 2003, 103, 3029-3070, which is incorporated herein by reference in its entirety) may be utilized to give enatiomerically pure compounds of XII. Such compounds may be further transformed to compounds of formula Ib via VI by derivatization and hydrolysis as described above in scheme 1.

Scheme 3

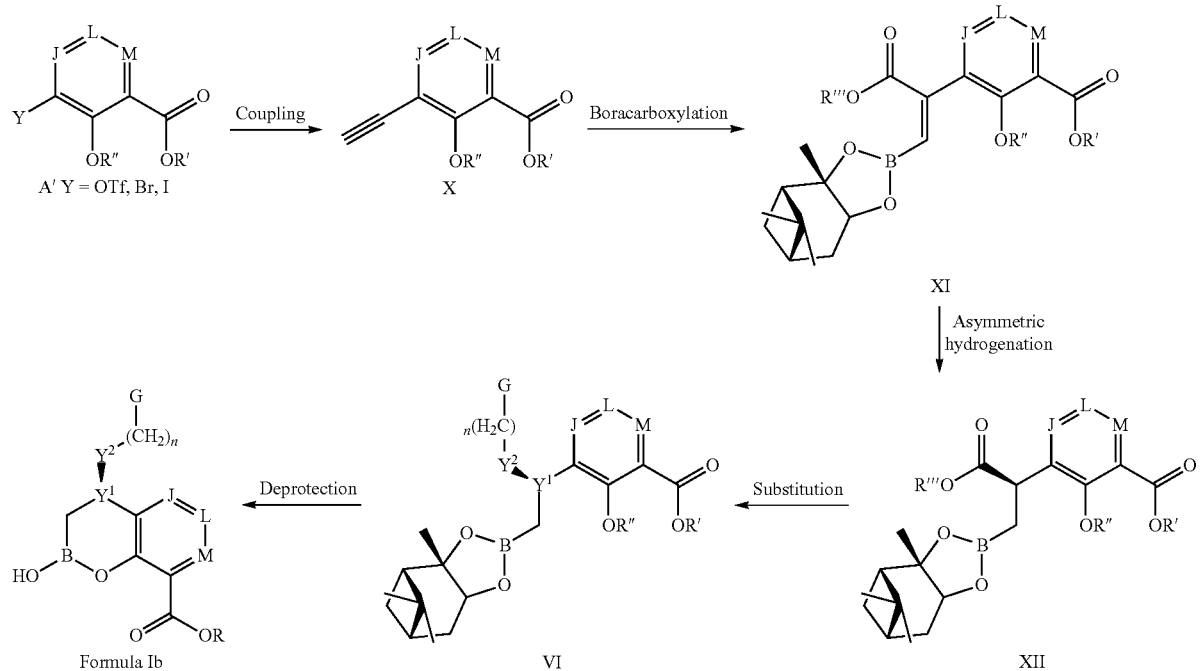

Compounds of formula Ib where $Y^1$ =CH, $Y^2$=—NHC(O)— may be prepared from carboxylic acid of formula XII ($R'''$=OH) as shown in scheme 4. Such compounds may be converted to amides via Curtius rearrangement (*Chem. Rev.* 1988, 88, 297-368; *Org. Lett.*, 2005, 4107-4110, which is incorporated herein by reference in its entirety) followed by deprotection, amide formation to give compounds of formula XIV. Compounds of formula XIII may also be transformed to compounds of formula Ib where $Y^2$ is —NHC(O)—O— by hydrolysis.

Scheme 4

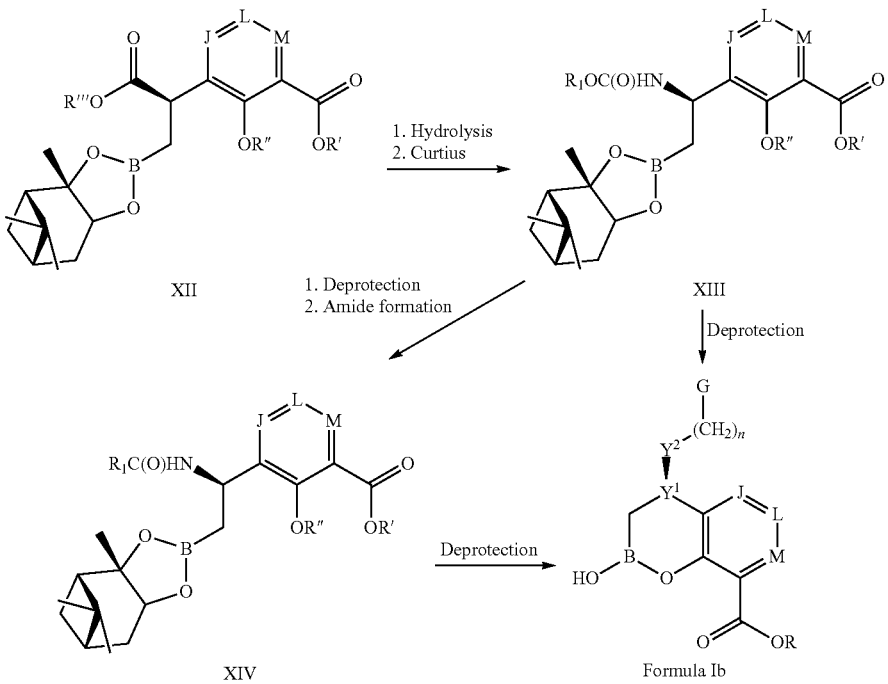

Intermediates of formula XVII to attain compounds of formula Ib may be prepared as shown in scheme 5. Such intermediates of formula XVII can be synthesized from XIV where X' is a triflate or bromo or iodo group by utilizing Reformatsky reagent of bromomethylene acetate ester (*J. Org. Chem.*, 2013, 78, 8250-8266; *Chem Lett.*, 1993, 845-848, which is incorporated herein by reference in its entirety). Compounds where X' is substituted with bromo or iodo groups can be attained from appropriately protected commercial 2,5-hydroxy-benzoic acid derivatives (*J. Med. Chem.*, 2003, 46, 3437-3440, which is incorporated herein by reference in its entirety). Intermediates of XIV can also be prepared via carboxylation of derivatives of formula XV where Z' is a fluoro or OR' or SR' by earlier described methods (WO12106995, which is incorporated herein by reference in its entirety).

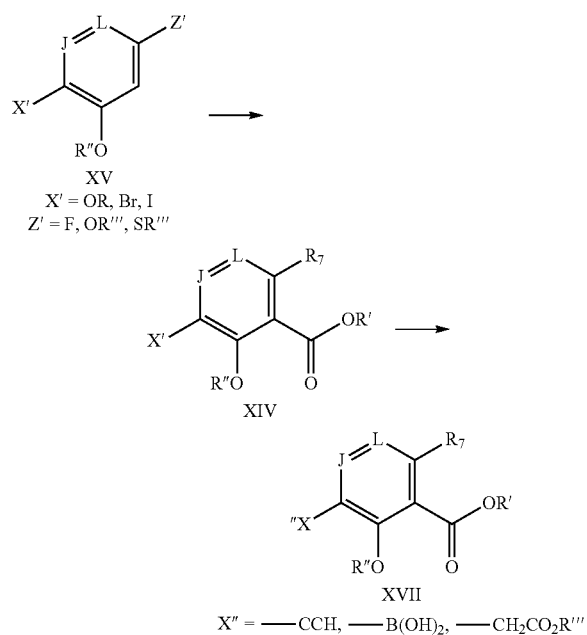

In another exemplary synthetic scheme 6, the compound of formula XX can be prepared from a salicylic acid derivative of formula XVIII. The compounds of formula XVIII upon diallylation under basic conditions followed by thermal Claisen rearrangement (*Org. React.* 1975, 22, 1-252, which is incorporated herein by reference in its entirety) and ester hydrolysis give compounds of formula XIX. Such compounds upon protection and oxidation followed by esterification result in phenylacetic acid compounds of formula XX. Compounds of formula XX can be further transformed as shown above in scheme 2. The compound of formula XVIII can also undergo the steps listed above in Scheme 5 to form an ortho-carboxylate-substituted compound of formula XIX.

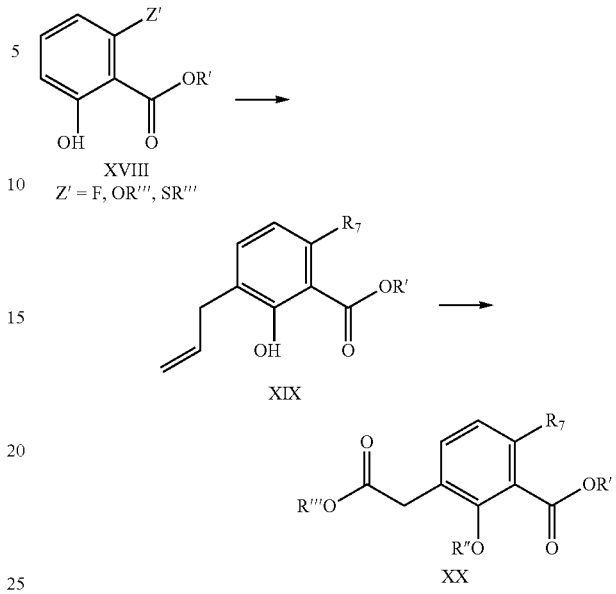

Synthesis of Prodrugs

Compounds of formula Ib where the R is a prodrug moiety may be synthesized by a variety of known methods of different carboxylic acid prodrugs (*Prodrugs: Challenges and Rewards*, V. J. Stella, et al., ed., Springer, New York, 2007, which is incorporated herein by reference in its entirety). These prodrugs include but are not limited to substituted or non-substituted alkyl esters, (acyloxy)alkyl (*Synthesis* 2012, 44, 207, which is incorporated herein by reference in its entirety), [(alkoxycarbonyl)oxy]methyl esters (WO10097675, which is incorporated herein by reference in its entirety), or (oxodioxolyl)methyl esters (*J. Med. Chem.* 1996, 39, 323-338, which is incorporated herein by reference in its entirety). Such prodrugs can be made from compounds of formula Ib where R=H by treatment with acid or in neutral conditions (e.g., carbodiimide coupling) in the presence of alcohols (ROH) or via base promoted esterification with RX where X is a leaving group in the presence of an appropriate base.

One exemplary but non-limiting general synthetic scheme for preparing prodrugs is shown in Scheme 7 below. The boronic acid of Formula Ib where R is hydrogen can react with a chloro/bromo-substituted prodrug moiety to form a prodrug of Formula Ib where R is a prodrug moiety. Examples of the prodrug moiety R can be —$C_{1-9}$alkyl, —$CR^{10}R^{11}OC(O)C_{1-9}$alkyl, —$CR^{10}R^{11}OC(O)OC_{1-9}$alkyl, and

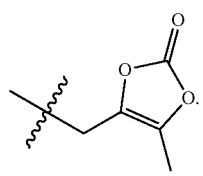 [SMILES: *Cc1oc(=O)oc1C]

Scheme 7

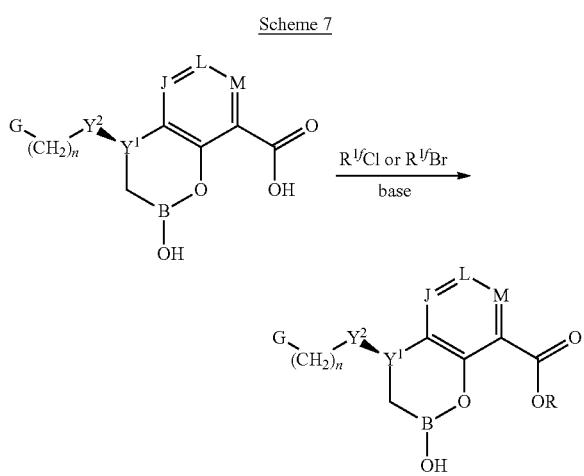

Alternatively, boronate esters of formula XXI or corresponding tetrafluoroborates (*Chem. Rev.* 2008, 108, 288-325, which is incorporated herein by reference in its entirety) may be also utilized for introduction of prodrugs and convert them to final prodrugs (Scheme 8). Such carboxylic acids (XXI) can be made from compounds of formula VI by selective deprotection of OR'. The prodrug group may also be introduced earlier in the sequence in compounds of formula V where R' is R. Such sequence where prodrug is introduced in earlier intermediates is only feasible when the ester is stable under the final deprotection conditions to remove the phenol protective group and boronate ester group.

Scheme 8

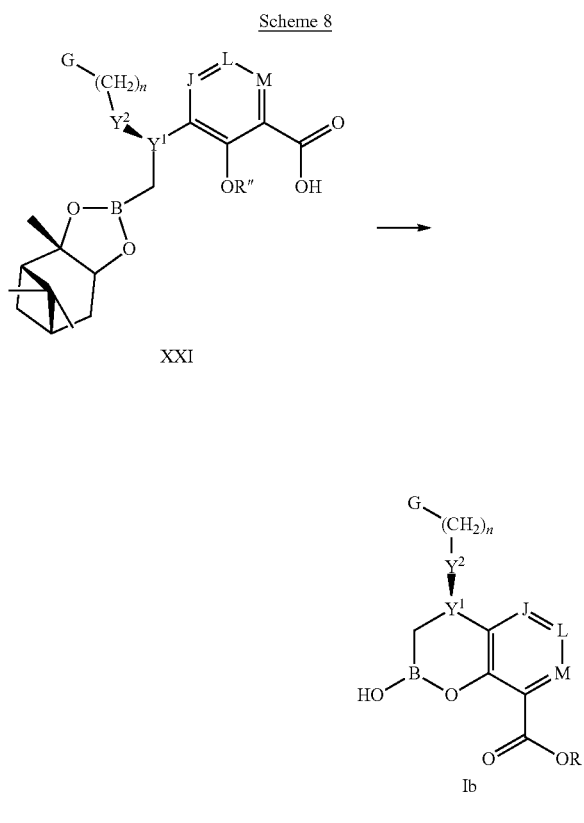

Compounds of Formula IIIC may be prepared as shown in scheme 9. Compounds of formula IIIc where m is 0 and $Y^7$ is —$CH_2$— may be synthesized via intermediate A' by coupling of vinyl boronate in Heck reaction conditions (*J. Med. Chem.*, 2015, 58, 147-169, which is incorporated herein by reference in its entirety) or by coupling of an acetylene derivative of protected boronate via Sonagashira conditions (*Tet.*, 2011, 67, 4306-4312, which is incorporated herein by reference in its entirety). The protection of such boronate substituted vinyl/acetylene intermediates can be selected from pinacol or pinanediol or dimethylaminonaphthalene (*Org. Lett.*, 2008, 10, 377-380, which is incorporated herein by reference in its entirety) or MIDA (*J. Am. Chem. Soc.*, 2009, 131, 6961-6963, which is incorporated herein by reference in its entirety) groups. The resulting coupling products can be hydrogenated under catalytic conditions to give intermediate XXIII which can be further transformed to compounds of formula IIIc as described earlier in scheme 1 or by other methods known in the art. Alternatively, aryl intermediates of formula A' of desired substitution can be converted to vinyl substituted intermediates such as XXII which readily undergo Ir (*Tetrahedron*, 2004, 60, 10695-10700, which is incorporated herein by reference in its entirety) or Cu (*Tetrahedron Lett.*, 2015, 56, 2297-2302, which is incorporated herein by reference in its entirety) mediated borylation to form intermediates of formula XXIII. Compounds of formula XXIII can also be made from acetylene substituted compounds of formula X via borylation of corresponding lithiated acetylide (*Angew. Chem., Int. Ed.*, 2012, 51, 2947-2950, which is incorporated herein by reference in its entirety) or in a Pd catalyzed reaction (*Org. Lett.*, 2016, 18, 432-435, which is incorporated herein by reference in its entirety) followed by hydrogenation of resulting products. Aryl intermediates of formula A' where Y'=H can be utilized via Claisen rearrangement (*Chem. Rev.*, 2004, 104, 2939-3002, which is incorporated herein by reference in its entirety). Allyl ethers of A' intermediate where R" is allyl undergo Claisen rearrangement. Such rearrangement products can be converted to haloethylene substitution via ozonolysis or periodate reaction of terminal olefin to aldehydes followed by reduction and conversion of resulting alcohols to halides. These primary or secondary halides can be transformed to boronate esters of formula XXIII under a variety of conditions including via reactions catalyzed by Cu (*Angew. Chem. Int. Ed.*, 2012, 51, 528-532; and *Org. Lett.*, 2012, 14, 890-893, which are incorporated herein by reference in their entireties), Pd (*J. Org. Chem.*, 2012, 77, 6629-6633, which is incorporated herein by reference in its entirety), Fe (*J. Am. Chem. Soc.*, 2014, 136, 9521-9523, which is incorporated herein by reference in its entirety) Zn (*Angew. Chem. Int. Ed.* 2014, 53, 1799-1803), Ni (*J. Am. Chem. Soc.*, 2012, 134, 10693-10697, which is incorporated herein by reference in its entirety). Compounds of formula IIIC where m=1 and Y is O, S or NR' can be synthesized through intermediate XXIV where $Y^1$ is —OH, —SH or —NHR, by alkylation of bromo/iodomethylene boronate ester of pinacol or pinanediol (WO 09046098, which is incorporated herein by reference in its entirety) (Scheme 9).

Scheme 9

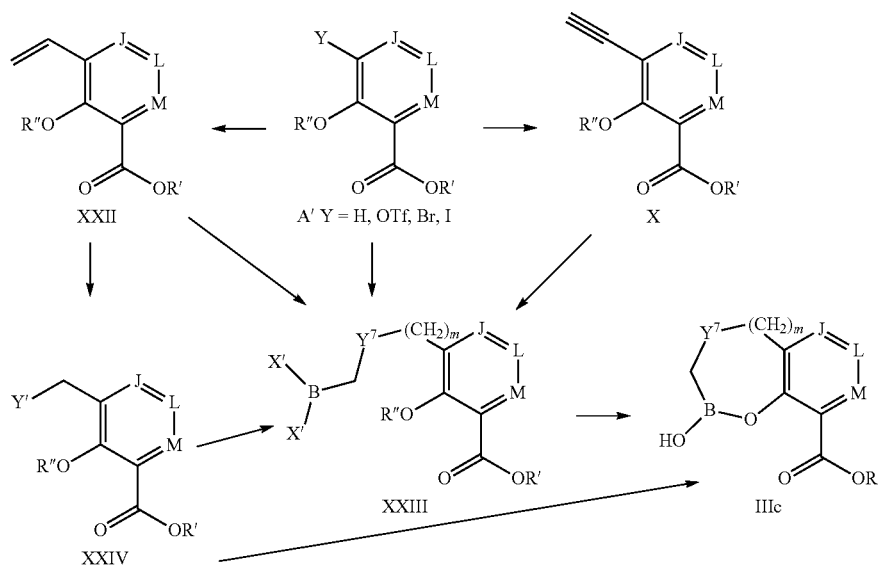

A non-limiting example for making compounds of formula Ic is shown in Scheme 10. Compounds of formula IIIc-1 where M is $R^5$ is —$(CH_2)_p$—$Y^3$—$(CH_2)_q$M can be made from intermediates of formula XXVI. Such compounds of XXVI can be made from XXV where $R^5$ is already introduced. Alternatively, $R^5$ can also be substituted at XXVI stage by deprotection of —OR' or SR' or $CR^1R^2OR^1$, $CR^1R^2SR'$, $CR^1R^2NHR'$ and reaction with appropriate protected building blocks of $R^5$ (scheme 10). Compounds of formula IIIc wherein J and/or L is $R^5$ is —$(CH_2)_p$—$Y^3$—$(CH_2)_q$M can also be made from the appropriate intermediates XXV and XXVI using this scheme.

Scheme 10

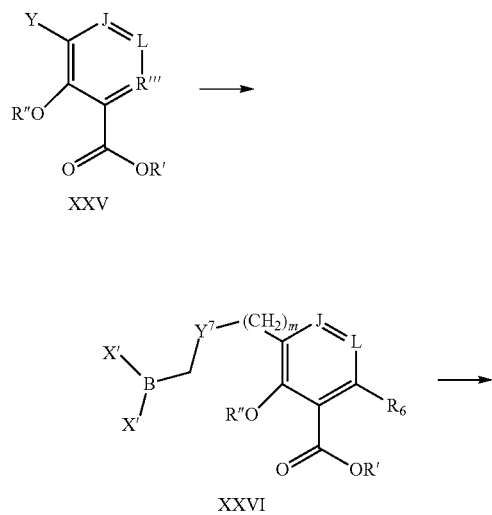

-continued

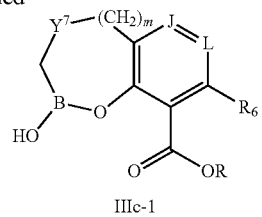

Y = H, OTf, Br, I

Administration and Pharmaceutical Compositions

The compounds are administered at a therapeutically effective dosage. While human dosage levels have yet to be optimized for the compounds described herein, generally, a daily dose may be from about 0.25 mg/kg to about 120 mg/kg or more of body weight, from about 0.5 mg/kg or less to about 70 mg/kg, from about 1.0 mg/kg to about 50 mg/kg of body weight, or from about 1.5 mg/kg to about 10 mg/kg of body weight. Thus, for administration to a 70 kg person, the dosage range would be from about 17 mg per day to about 8000 mg per day, from about 35 mg per day or less to about 7000 mg per day or more, from about 70 mg per day to about 6000 mg per day, from about 100 mg per day to about 5000 mg per day, or from about 200 mg to about 3000 mg per day. The amount of active compound administered will, of course, be dependent on the subject and disease state being treated, the severity of the affliction, the manner and schedule of administration and the judgment of the prescribing physician.

Administration of the compounds disclosed herein or the pharmaceutically acceptable salts thereof can be via any of the accepted modes of administration for agents that serve similar utilities including, but not limited to, orally, subcutaneously, intravenously, intranasally, topically, transdermally, intraperitoneally, intramuscularly, intrapulmonarilly, vaginally, rectally, or intraocularly. Oral and parenteral administrations are customary in treating the indications that are the subject of the preferred embodiments.

The compounds useful as described above can be formulated into pharmaceutical compositions for use in treatment of these conditions. Standard pharmaceutical formulation techniques are used, such as those disclosed in Remington's The Science and Practice of Pharmacy, 21st Ed., Lippincott Williams & Wilkins (2005), incorporated by reference in its entirety. Accordingly, some embodiments include pharmaceutical compositions comprising: (a) a safe and therapeutically effective amount of a compound described herein (including enantiomers, diastereoisomers, tautomers, polymorphs, and solvates thereof), or pharmaceutically acceptable salts thereof; and (b) a pharmaceutically acceptable carrier, diluent, excipient or combination thereof.

In addition to the selected compound useful as described above, come embodiments include compositions containing a pharmaceutically-acceptable carrier. The term "pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. In addition, various adjuvants such as are commonly used in the art may be included. Considerations for the inclusion of various components in pharmaceutical compositions are described, e.g., in Gilman et al. (Eds.) (1990); Goodman and Gilman's: The Pharmacological Basis of Therapeutics, 8th Ed., Pergamon Press, which is incorporated herein by reference in its entirety.

Some examples of substances, which can serve as pharmaceutically-acceptable carriers or components thereof, are sugars, such as lactose, glucose and sucrose; starches, such as corn starch and potato starch; cellulose and its derivatives, such as sodium carboxymethyl cellulose, ethyl cellulose, and methyl cellulose; powdered tragacanth; malt; gelatin; talc; solid lubricants, such as stearic acid and magnesium stearate; calcium sulfate; vegetable oils, such as peanut oil, cottonseed oil, sesame oil, olive oil, corn oil and oil of theobroma; polyols such as propylene glycol, glycerine, sorbitol, mannitol, and polyethylene glycol; alginic acid; emulsifiers, such as the TWEENS; wetting agents, such sodium lauryl sulfate; coloring agents; flavoring agents; tableting agents, stabilizers; antioxidants; preservatives; pyrogen-free water; isotonic saline; and phosphate buffer solutions.

The choice of a pharmaceutically-acceptable carrier to be used in conjunction with the subject compound is basically determined by the way the compound is to be administered.

The compositions described herein are preferably provided in unit dosage form. As used herein, a "unit dosage form" is a composition containing an amount of a compound that is suitable for administration to an animal, preferably mammal subject, in a single dose, according to good medical practice. The preparation of a single or unit dosage form however, does not imply that the dosage form is administered once per day or once per course of therapy. Such dosage forms are contemplated to be administered once, twice, thrice or more per day and may be administered as infusion over a period of time (e.g., from about 30 minutes to about 2-6 hours), or administered as a continuous infusion, and may be given more than once during a course of therapy, though a single administration is not specifically excluded. The skilled artisan will recognize that the formulation does not specifically contemplate the entire course of therapy and such decisions are left for those skilled in the art of treatment rather than formulation.

The compositions useful as described above may be in any of a variety of suitable forms for a variety of routes for administration, for example, for oral, nasal, rectal, topical (including transdermal), ocular, intracerebral, intracranial, intrathecal, intra-arterial, intravenous, intramuscular, or other parental routes of administration. The skilled artisan will appreciate that oral and nasal compositions comprise compositions that are administered by inhalation, and made using available methodologies. Depending upon the particular route of administration desired, a variety of pharmaceutically-acceptable carriers well-known in the art may be used. Pharmaceutically-acceptable carriers include, for example, solid or liquid fillers, diluents, hydrotropies, surface-active agents, and encapsulating substances. Optional pharmaceutically-active materials may be included, which do not substantially interfere with the inhibitory activity of the compound. The amount of carrier employed in conjunction with the compound is sufficient to provide a practical quantity of material for administration per unit dose of the compound. Techniques and compositions for making dosage forms useful in the methods described herein are described in the following references, all incorporated by reference herein: Modern Pharmaceutics, 4th Ed., Chapters 9 and 10 (Banker & Rhodes, editors, 2002); Lieberman et al., Pharmaceutical Dosage Forms: Tablets (1989); and Ansel, Introduction to Pharmaceutical Dosage Forms 8th Edition (2004).

Various oral dosage forms can be used, including such solid forms as tablets, capsules, granules and bulk powders. Tablets can be compressed, tablet triturates, enteric-coated, sugar-coated, film-coated, or multiple-compressed, containing suitable binders, lubricants, diluents, disintegrating agents, coloring agents, flavoring agents, flow-inducing agents, and melting agents. Liquid oral dosage forms include aqueous solutions, emulsions, suspensions, solutions and/or suspensions reconstituted from non-effervescent granules, and effervescent preparations reconstituted from effervescent granules, containing suitable solvents, preservatives, emulsifying agents, suspending agents, diluents, sweeteners, melting agents, coloring agents and flavoring agents.

The pharmaceutically-acceptable carrier suitable for the preparation of unit dosage forms for peroral administration is well-known in the art. Tablets typically comprise conventional pharmaceutically-compatible adjuvants as inert diluents, such as calcium carbonate, sodium carbonate, mannitol, lactose and cellulose; binders such as starch, gelatin and sucrose; disintegrants such as starch, alginic acid and croscarmellose; lubricants such as magnesium stearate, stearic acid and talc. Glidants such as silicon dioxide can be used to improve flow characteristics of the powder mixture. Coloring agents, such as the FD&C dyes, can be added for appearance. Sweeteners and flavoring agents, such as aspartame, saccharin, menthol, peppermint, and fruit flavors, are useful adjuvants for chewable tablets. Capsules typically comprise one or more solid diluents disclosed above. The selection of carrier components depends on secondary considerations like taste, cost, and shelf stability, which are not critical, and can be readily made by a person skilled in the art.

Peroral compositions also include liquid solutions, emulsions, suspensions, and the like. The pharmaceutically-acceptable carriers suitable for preparation of such compositions are well known in the art. Typical components of carriers for syrups, elixirs, emulsions and suspensions include ethanol, glycerol, propylene glycol, polyethylene glycol, liquid sucrose, sorbitol and water. For a suspension, typical suspending agents include methyl cellulose, sodium carboxymethyl cellulose, AVICEL RC-591, tragacanth and sodium alginate; typical wetting agents include lecithin and polysorbate 80; and typical preservatives include methyl paraben and sodium benzoate. Peroral liquid compositions may also contain one or more components such as sweeteners, flavoring agents and colorants disclosed above.

Such compositions may also be coated by conventional methods, typically with pH or time-dependent coatings, such that the subject compound is released in the gastrointestinal tract in the vicinity of the desired topical application, or at various times to extend the desired action. Such dosage forms typically include, but are not limited to, one or more of cellulose acetate phthalate, polyvinylacetate phthalate, hydroxypropyl methyl cellulose phthalate, ethyl cellulose, Eudragit coatings, waxes and shellac.

Compositions described herein may optionally include other drug actives.

Other compositions useful for attaining systemic delivery of the subject compounds include sublingual, buccal and nasal dosage forms. Such compositions typically comprise one or more of soluble filler substances such as sucrose, sorbitol and mannitol; and binders such as acacia, microcrystalline cellulose, carboxymethyl cellulose and hydroxypropyl methyl cellulose. Glidants, lubricants, sweeteners, colorants, antioxidants and flavoring agents disclosed above may also be included.

A liquid composition, which is formulated for topical ophthalmic use, is formulated such that it can be administered topically to the eye. The comfort should be maximized as much as possible, although sometimes formulation considerations (e.g. drug stability) may necessitate less than optimal comfort. In the case that comfort cannot be maximized, the liquid should be formulated such that the liquid is tolerable to the patient for topical ophthalmic use. Additionally, an ophthalmically acceptable liquid should either be packaged for single use, or contain a preservative to prevent contamination over multiple uses.

For ophthalmic application, solutions or medicaments are often prepared using a physiological saline solution as a major vehicle. Ophthalmic solutions should preferably be maintained at a comfortable pH with an appropriate buffer system. The formulations may also contain conventional, pharmaceutically acceptable preservatives, stabilizers and surfactants.

Preservatives that may be used in the pharmaceutical compositions disclosed herein include, but are not limited to, benzalkonium chloride, PHMB, chlorobutanol, thimerosal, phenylmercuric, acetate and phenylmercuric nitrate. A useful surfactant is, for example, Tween 80. Likewise, various useful vehicles may be used in the ophthalmic preparations disclosed herein. These vehicles include, but are not limited to, polyvinyl alcohol, povidone, hydroxypropyl methyl cellulose, poloxamers, carboxymethyl cellulose, hydroxyethyl cellulose and purified water.

Tonicity adjustors may be added as needed or convenient. They include, but are not limited to, salts, particularly sodium chloride, potassium chloride, mannitol and glycerin, or any other suitable ophthalmically acceptable tonicity adjustor.

Various buffers and means for adjusting pH may be used so long as the resulting preparation is ophthalmically acceptable. For many compositions, the pH will be between 4 and 9. Accordingly, buffers include acetate buffers, citrate buffers, phosphate buffers and borate buffers. Acids or bases may be used to adjust the pH of these formulations as needed.

In a similar vein, an ophthalmically acceptable antioxidant includes, but is not limited to, sodium metabisulfite, sodium thiosulfate, acetylcysteine, butylated hydroxyanisole and butylated hydroxytoluene.

Other excipient components, which may be included in the ophthalmic preparations, are chelating agents. A useful chelating agent is edetate disodium, although other chelating agents may also be used in place or in conjunction with it.

For topical use, creams, ointments, gels, solutions or suspensions, etc., containing the compound disclosed herein are employed. Topical formulations may generally be comprised of a pharmaceutical carrier, co-solvent, emulsifier, penetration enhancer, preservative system, and emollient.

For intravenous administration, the compounds and compositions described herein may be dissolved or dispersed in a pharmaceutically acceptable diluent, such as a saline or dextrose solution. Suitable excipients may be included to achieve the desired pH, including but not limited to NaOH, sodium carbonate, sodium acetate, HCl, and citric acid. In various embodiments, the pH of the final composition ranges from 2 to 8, or preferably from 4 to 7. Antioxidant excipients may include sodium bisulfite, acetone sodium bisulfite, sodium formaldehyde, sulfoxylate, thiourea, and EDTA. Other non-limiting examples of suitable excipients found in the final intravenous composition may include sodium or potassium phosphates, citric acid, tartaric acid, gelatin, and carbohydrates such as dextrose, mannitol, and dextran. Further acceptable excipients are described in Powell, et al., Compendium of Excipients for Parenteral Formulations, *PDA J Pharm Sci and Tech* 1998, 52 238-311 and Nema et al., Excipients and Their Role in Approved Injectable Products: Current Usage and Future Directions, *PDA J Pharm Sci and Tech* 2011, 65 287-332, both of which are incorporated herein by reference in their entirety. Antimicrobial agents may also be included to achieve a bacteriostatic or fungistatic solution, including but not limited to phenylmercuric nitrate, thimerosal, benzethonium chloride, benzalkonium chloride, phenol, cresol, and chlorobutanol.

The compositions for intravenous administration may be provided to caregivers in the form of one more solids that are reconstituted with a suitable diluent such as sterile water, saline or dextrose in water shortly prior to administration. In other embodiments, the compositions are provided in solution ready to administer parenterally. In still other embodiments, the compositions are provided in a solution that is further diluted prior to administration. In embodiments that include administering a combination of a compound described herein and another agent, the combination may be provided to caregivers as a mixture, or the caregivers may mix the two agents prior to administration, or the two agents may be administered separately.

The actual dose of the active compounds described herein depends on the specific compound, and on the condition to be treated; the selection of the appropriate dose is well within the knowledge of the skilled artisan.

Methods of Treatment

Some embodiments of the present invention include methods of treating bacterial infections with the compounds and compositions comprising the compounds described herein. Some methods include administering a compound, composition, pharmaceutical composition described herein to a subject in need thereof. In some embodiments, a subject can be an animal, e.g., a mammal (including a human). In some embodiments, the bacterial infection comprises a bacteria described herein. As will be appreciated from the foregoing, methods of treating a bacterial infection include methods for preventing bacterial infection in a subject at risk thereof.

In some embodiments, the subject is a human.

Further embodiments include administering a combination of compounds to a subject in need thereof. A combination can include a compound, composition, pharmaceutical composition described herein with an additional medicament.

Some embodiments include co-administering a compound, composition, and/or pharmaceutical composition described herein, with an additional medicament. By "co-administration," it is meant that the two or more agents may be found in the patient's bloodstream at the same time, regardless of when or how they are actually administered. In one embodiment, the agents are administered simultaneously. In one such embodiment, administration in combination is accomplished by combining the agents in a single dosage form. In another embodiment, the agents are administered sequentially. In one embodiment the agents are administered through the same route, such as orally. In another embodiment, the agents are administered through different routes, such as one being administered orally and another being administered i.v.

Examples of additional medicaments include an antibacterial agent, antifungal agent, an antiviral agent, an anti-inflammatory agent and an anti-allergic agent.

Preferred embodiments include combinations of a compound, composition or pharmaceutical composition described herein with an antibacterial agent such as a β-lactam. Examples of such β-lactams include Amoxicillin, Ampicillin (e.g., Pivampicillin, Hetacillin, Bacampicillin, Metampicillin, Talampicillin), Epicillin, Carbenicillin (Carindacillin), Ticarcillin, Temocillin, Azlocillin, Piperacillin, Mezlocillin, Mecillinam (Pivmecillinam), Sulbenicillin, Benzylpenicillin (G), Clometocillin, Benzathine benzylpenicillin, Procaine benzylpenicillin, Azidocillin, Penamecillin, Phenoxymethylpenicillin (V), Propicillin, Benzathine phenoxymethylpenicillin, Pheneticillin, Cloxacillin (e.g., Dicloxacillin, Flucloxacillin), Oxacillin, Methicillin, Nafcillin, Faropenem, Biapenem, Doripenem, Ertapenem, Imipenem, Meropenem, Panipenem, Cefazolin, Cefacetrile, Cefadroxil, Cefalexin, Cefaloglycin, Cefalonium, Cefaloridine, Cefalotin, Cefapirin, Cefatrizine, Cefazedone, Cefazaflur, Cefradine, Cefroxadine, Ceftezole, Cefaclor, Cefamandole, Cefminox, Cefonicid, Ceforanide, Cefotiam, Cefprozil, Cefbuperazone, Cefuroxime, Cefuzonam, Cefoxitin, Cefotetan, Cefmetazole, Loracarbef, Cefixime, Ceftazidime, Ceftriaxone, Cefcapene, Cefdaloxime, Cefdinir, Cefditoren, Cefetamet, Cefmenoxime, Cefodizime, Cefoperazone, Cefotaxime, Cefpimizole, Cefpiramide, Cefpodoxime, Cefsulodin, Cefteram, Ceftibuten, Ceftiolene, Ceftizoxime, Flomoxef, Latamoxef, Cefepime, Cefozopran, Cefpirome, Cefquinome, Ceftobiprole, Ceftaroline, Ceftiofur, Cefquinome, Cefovecin, Aztreonam, Tigemonam and Carumonam.

Preferred embodiments include β-lactams such as Ceftazidime, Biapenem, Doripenem, Ertapenem, Imipenem, Meropenem, Tebipenem, Tebipenem pivoxil, Apapenem, and Panipenem.

Additional preferred embodiments include β-lactams such as Aztreonam, Tigemonam, and Carumonam.

Some embodiments include a combination of the compounds, compositions and/or pharmaceutical compositions described herein with an additional agent, wherein the additional agent comprises a monobactam. Examples of monobactams include aztreonam, tigemonam, nocardicin A, carumonam, and tabtoxin. In some such embodiments, the compound, composition and/or pharmaceutical composition comprises a class A, C, or D beta-lactamase inhibitor. Some embodiments include co-administering the compound, composition or pharmaceutical composition described herein with one or more additional agents.

Some embodiments include a combination of the compounds, compositions and/or pharmaceutical compositions described herein with an additional agent, wherein the additional agent comprises a class B beta lactamase inhibitor. An example of a class B beta lactamase inhibitor includes ME1071 (Yoshikazu Ishii et al, "In Vitro Potentiation of Carbapenems with ME1071, a Novel Metallo-ß-Lactamase Inhibitor, against Metallo-ß-lactamase Producing *Pseudomonas aeruginosa* Clinical Isolates." Antimicrob. Agents Chemother. doi:10.1128/AAC.01397-09 (July 2010)). Some embodiments include co-administering the compound, composition or pharmaceutical composition described herein with one or more additional agents.

Some embodiments include a combination of the compounds, compositions and/or pharmaceutical compositions described herein with an additional agent, wherein the additional agent comprises one or more agents that include a class A, B, C, or D beta lactamase inhibitor. Some embodiments include co-administering the compound, composition or pharmaceutical composition described herein with the one or more additional agents.

Indications

The compounds and compositions comprising the compounds described herein can be used to treat bacterial infections. Bacterial infections that can be treated with the compounds, compositions and methods described herein can comprise a wide spectrum of bacteria. Example organisms include gram-positive bacteria, gram-negative bacteria, aerobic and anaerobic bacteria, such as *Staphylococcus, Lactobacillus, Streptococcus, Sarcina, Escherichia, Enterobacter, Klebsiella, Pseudomonas, Acinetobacter, Mycobacterium, Proteus, Campylobacter, Citrobacter, Nisseria, Bacillus, Bacteroides, Peptococcus, Clostridium, Salmonella, Shigella, Serratia, Haemophilus, Brucella* and other organisms.

More examples of bacterial infections include *Pseudomonas aeruginosa, Pseudomonas fluorescens, Pseudomonas acidovorans, Pseudomonas alcaligenes, Pseudomonas putida, Stenotrophomonas maltophilia, Burkholderia cepacia, Aeromonas hydrophilia, Escherichia coli, Citrobacter freundii, Salmonella typhimurium, Salmonella typhi, Salmonella paratyphi, Salmonella enteritidis, Shigella dysenteriae, Shigella flexneri, Shigella sonnei, Enterobacter cloacae, Enterobacter aerogenes, Klebsiella pneumoniae, Klebsiella oxytoca, Serratia marcescens, Francisella tularensis, Morganella morganii, Proteus mirabilis, Proteus vulgaris, Providencia alcalifaciens, Providencia rettgeri, Providencia stuartii, Acinetobacter baumannii, Acinetobacter calcoaceticus, Acinetobacter haemolyticus, Yersinia enterocolitica, Yersinia pestis, Yersinia pseudotuberculosis, Yersinia intermedia, Bordetella pertussis, Bordetella parapertussis, Bordetella bronchiseptica, Haemophilus influenzae, Haemophilus parainfluenzae, Haemophilus haemolyticus, Haemophilus parahaemolyticus, Haemophilus ducreyi, Pasteurella multocida, Pasteurella haemolytica, Branhamella catarrhalis, Helicobacter pylori, Campylobacter fetus, Campylobacter jejuni, Campylobacter coli, Borrelia burgdorferi, Vibrio cholerae, Vibrio parahaemolyticus, Legionella pneumophila, Listeria monocytogenes, Neisseria gonorrhoeae, Neisseria meningitidis, Kingella, Moraxella,*

*Gardnerella vaginalis, Bacteroides fragilis, Bacteroides distasonis, Bacteroides* 3452A homology group, *Bacteroides vulgatus, Bacteroides ovalus, Bacteroides thetaiotaomicron, Bacteroides uniformis, Bacteroides eggerthii, Bacteroides splanchnicus, Clostridium difficile, Mycobacterium tuberculosis, Mycobacterium avium, Mycobacterium intracellulare, Mycobacterium leprae, Corynebacterium diphtheriae, Corynebacterium ulcerans, Streptococcus pneumoniae, Streptococcus agalactiae, Streptococcus pyogenes, Enterococcus faecalis, Enterococcus faecium, Staphylococcus aureus, Staphylococcus epidermidis, Staphylococcus saprophyticus, Staphylococcus intermedius, Staphylococcus hyicus* subsp. *hyicus, Staphylococcus haemolyticus, Staphylococcus hominis*, or *Staphylococcus saccharolyticus*.

To further illustrate this invention, the following examples are included. The examples should not, of course, be construed as specifically limiting the invention. Variations of these examples within the scope of the claims are within the purview of one skilled in the art and are considered to fall within the scope of the invention as described, and claimed herein. The reader will recognize that the skilled artisan, armed with the present disclosure, and skill in the art is able to prepare and use the invention without exhaustive examples. The following examples will further describe the present invention, and are used for the purposes of illustration only, and should not be considered as limiting.

EXAMPLES

General Procedures

Materials used in preparing the cyclic boronic acid ester derivatives described herein may be made by known methods or are commercially available. It will be apparent to the skilled artisan that methods for preparing precursors and functionality related to the compounds claimed herein are generally described in the literature including, for example, procedures described in U.S. Pat. No. 7,271,186 and WO2009064414, each of which is incorporated by reference in its entirety. In these reactions, it is also possible to make use of variants which are themselves known to those of ordinary skill in this art, but are not mentioned in greater detail. The skilled artisan given the literature and this disclosure is well equipped to prepare any of the compounds.

It is recognized that the skilled artisan in the art of organic chemistry can readily carry out manipulations without further direction, that is, it is well within the scope and practice of the skilled artisan to carry out these manipulations. These include reduction of carbonyl compounds to their corresponding alcohols, oxidations, acylations, aromatic substitutions, both electrophilic and nucleophilic, etherifications, esterification and saponification and the like. These manipulations are discussed in standard texts such as March Advanced Organic Chemistry (Wiley), Carey and Sundberg, Advanced Organic Chemistry (incorporated herein by reference in their entirety) and the like.

The skilled artisan will readily appreciate that certain reactions are best carried out when other functionality is masked or protected in the molecule, thus avoiding any undesirable side reactions and/or increasing the yield of the reaction. Often the skilled artisan utilizes protecting groups to accomplish such increased yields or to avoid the undesired reactions. These reactions are found in the literature and are also well within the scope of the skilled artisan. Examples of many of these manipulations can be found for example in T. Greene and P. Wuts Protecting Groups in Organic Synthesis, 4th Ed., John Wiley & Sons (2007), incorporated herein by reference in its entirety.

The following example schemes are provided for the guidance of the reader, and represent preferred methods for making the compounds exemplified herein. These methods are not limiting, and it will be apparent that other routes may be employed to prepare these compounds. Such methods specifically include solid phase based chemistries, including combinatorial chemistry. The skilled artisan is thoroughly equipped to prepare these compounds by those methods given the literature and this disclosure. The compound numberings used in the synthetic schemes depicted below are meant for those specific schemes only, and should not be construed as or confused with same numberings in other sections of the application.

Trademarks used herein are examples only and reflect illustrative materials used at the time of the invention. The skilled artisan will recognize that variations in lot, manufacturing processes, and the like, are expected. Hence the examples, and the trademarks used in them are non-limiting, and they are not intended to be limiting, but are merely an illustration of how a skilled artisan may choose to perform one or more of the embodiments of the invention.

The following abbreviations have the indicated meanings:
DCM=dichloromethane
DMF=N,N-dimethylformamide
ESBL=extended-spectrum β-lactamase
EtOAc=ethyl acetate
HATU=2-(7-aza-1H-benzotriazole-1-yl)-1,1,3,3-tetramethyluronium hexafluorophosphate
MeCN=acetonitrile
NMR=nuclear magnetic resonance
TBDMSCl=tert-butyldimethylsilyl chloride
TBS=tert-butyldimethylsilyl
TFA=trifluoroacetic acid
THF=tetrahydrofuran
TLC=thin layer chromatography The following example schemes are provided for the guidance of the reader, and collectively represent an example method for making the compounds provided herein. Furthermore, other methods for preparing compounds described herein will be readily apparent to the person of ordinary skill in the art in light of the following reaction schemes and examples. Unless otherwise indicated, all variables are as defined above.

EXAMPLE 1

2-HYDROXY-4-(2-(THIOPHEN-2-YL)ACETAMIDO)-3,4-DIHYDRO-2H-BENZO[E][1,2]OXABORININE-8-CARBOXYLIC ACID (1)

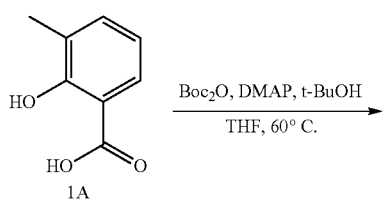

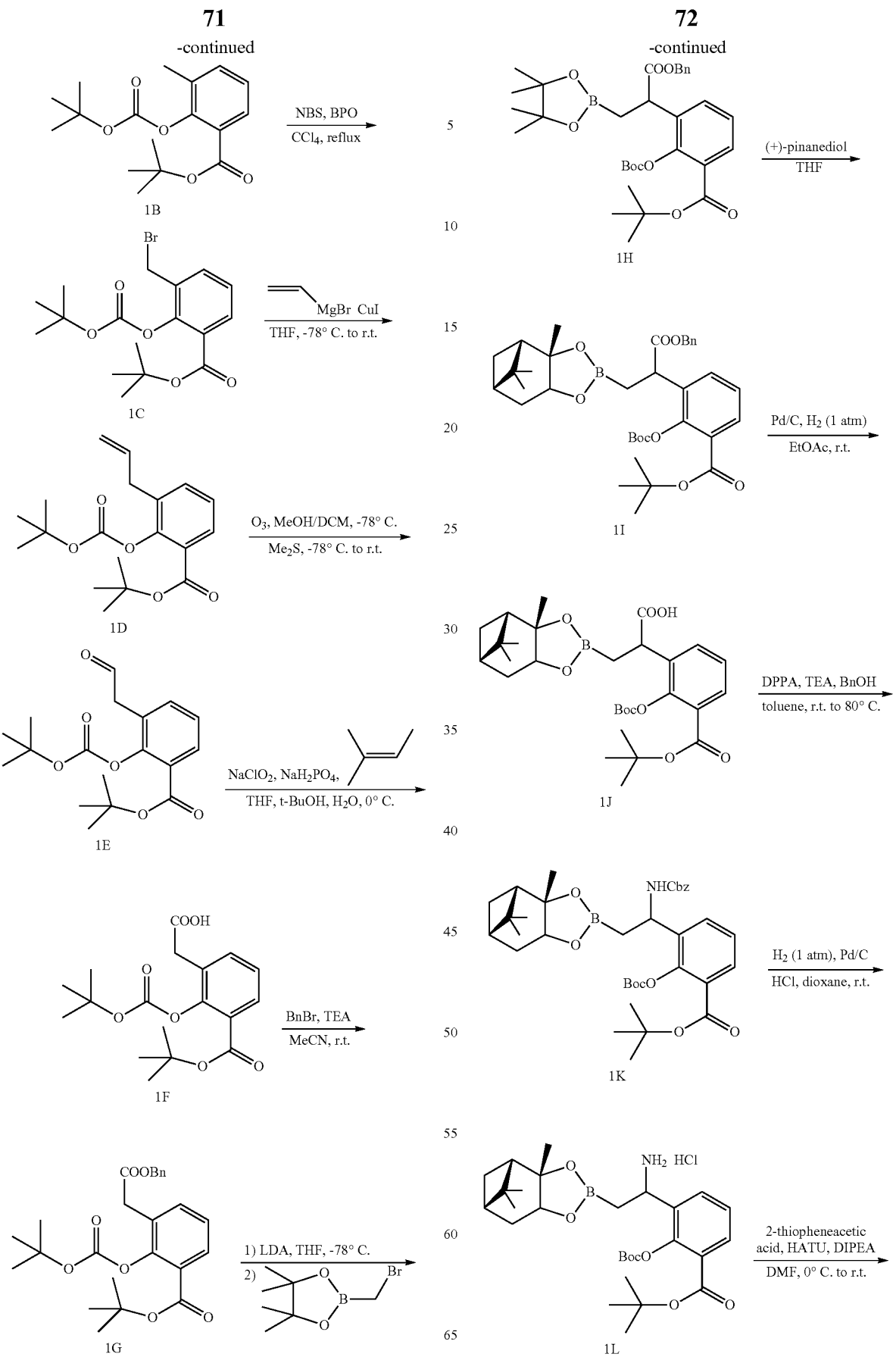

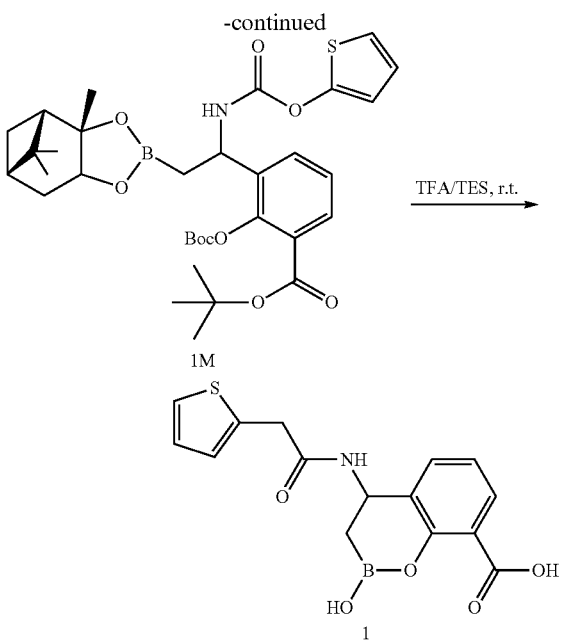

Step 1: Synthesis of Compound 1B

To the solution of compound 1A (200 g, 1.314 mol) in THF (500 mL) was added Boc₂O (1146 g, 5.26 mol), DMAP (48 g, 0.394 mol) and ᵗBuOH (1 L). The resulting solution was stirred at 60° C. for 6 hours before it was concentrated in vacuo. The residue was purified by flash column chromatography (ethyl acetate/hexanes, v/v, 1/200~1/100) to give the title compound 1B (192.8 g, 47.6% yield) as colorless oil.

$^1$H-NMR: (400 MHz, CDCl$_3$) δ 7.73 (d, 1H), 7.35 (d, 1H), 7.15 (t, 1H), 2.25 (s, 3H), 1.60 (s, 9H), 1.58 (s, 9H).

Step 2: Synthesis of Compound 1C

To the solution of compound 1B (192.8 g, 625 mmol) and NBS (122.4 g, 688 mmol) in CCl₄ (1 L) was added BPO (15.1 g, 62.5 mmol). The resulting mixture was refluxed at 80° C. for 15 hours. The solid was filtered off and the filtrate was concentrated in vacuo. The residue was recrystallized with hexanes to afford the title compound 1C (141 g, 58.2% yield) as white solid.

$^1$H-NMR: (400 MHz, CDCl$_3$) δ 7.87 (d, 1H), 7.55 (d, 1H), 7.26 (t, 1H), 4.49 (s, 2H), 1.59 (s, 9H), 1.55 (s, 9H).

Step 3: Synthesis of Compound 1D

To the suspension of CuI (480 mg, 2.51 mmol) in THF (100 mL) was added vinylmagnesium bromide (12.6 mL, 1.0M in THF, 12.6 mmol) dropwise at −50° C. in 5 minutes. After 10 minutes, a solution of compound 1C (3.24 g, 8.37 mmol) in THF (20 mL) was added via syringe in 3 minutes. The resulting reaction mixture was slowly warmed up to room temperature in 3 hours and stirred overnight. The dark reaction mixture was quenched with saturated NH₄Cl and extracted with EtOAc twice. After drying over Na₂SO₄, the organic solution was concentrated and chromatographed (ethyl acetate/hexanes, v/v, 1/20~1/8) to obtain the title compound 1D (1.81 g, 65% yield) as slightly yellow oil.

$^1$H-NMR: (300 MHz, CDCl$_3$) δ 7.78 (dd, 1H), 7.38 (dd, 1H), 7.20 (t, 1H), 5.80-5.96 (m, 1H), 5.08 (d, 1H), 5.03 (s, 1H), 3.39 (d, 2H), 1.59 (s, 9H), 1.56 (s, 9H).

Step 4: Synthesis of Compound 1E

To a solution of 1D (2.0 g, 6.0 mmol) in CH₂Cl₂ (35 mL) and MeOH (5 mL) at −78° C. was bubbled with O3 until light blue color appeared in the flask. Then Me₂S (2.64 mL, 36 mmol) was added, and the solution was slowly warmed up to room temperature where it was stirred for 16 h. The reaction solution was concentrated in vacuo to dryness and used directly for next step.

Step 5: Synthesis of Compound 1F

To a solution of crude 1E (about 6.0 mmol) in THF (80 mL), t-BuOH (35 mL) and water (35 mL) at 0° C. was added 2-methyl-2-butene (6.4 mL, 60 mmol), followed by NaClO₂ (3.26 g, ~80% purity, 36 mmol). After 30 min at 0° C., then reaction was quenched with NaHSO₃ (5 g). The solution was adjusted to pH=2 with 1N HCl, and extracted with EtOAc twice. The combined organic layers were washed with brine and dried over Na₂SO₄. After concentration, 1.2 g crude 1F was obtained as light yellow oil, which was used directly for next step.

$^1$H-NMR: (300 MHz, CDCl$_3$) δ 7.83 (dd, 1H), 7.43 (dd, 1H), 7.22 (t, 1H), 3.66 (s, 2H), 1.57 (s, 9H), 1.53 (s, 9H).

Step 6: Synthesis of Compound 1G

To a solution of crude 1F (about 3.4 mmol) in MeCN (9 mL) was added BnBr (0.81 mL, 6.8 mmol), followed by Et₃N (0.71 mL, 5.1 mmol). The resulting solution was stirred at room temperature for 6 hours. The reaction mixture was diluted with EtOAc and washed with water and brine. The aqueous layers were extracted with EtOAc. The combined organic layers were dried over Na₂SO₄. After concentration, the residue was purified by column chromatography (ethyl acetate/hexanes, v/v, 1/10~1/3) to obtain the title compound 1G (0.82 g) as slightly yellow oil.

$^1$H-NMR: (300 MHz, CDCl$_3$) δ 7.82 (d, 1H), 7.43 (d, 1H), 7.25-7.36 (m, 5H), 7.21 (t, 1H), 5.12 (s, 2H), 3.70 (s, 2H), 1.56 (s, 9H), 1.52 (s, 9H).

Step 7: Synthesis of Compound 1H

To the solution of 1G (5.9 g, 13.3 mmol) in THF (50 mL) was added LDA (freshly made from diisopropylamine (2.43 g, 17.3 mmol) and n-BuLi (6.65 mL, 2.5 M in hexanes, 16.6 mmol) in 30 mL THF, pre-cooled to −78° C.) at −78° C. via cannula. After 5 minutes, bromomethylboronic acid pinacol ester (4.1 g, 18.6 mmol) was added via syringe. After 30 minutes at −78° C., ZnCl₂ (30 mL, 1M in Et₂O, 30 mmol) was added slowly in 5 minutes. The resulting solution was slowly warmed up to room temperature for 3 hours before it was quenched with saturated NH₄Cl. The reaction mixture was extracted with EtOAc twice and dried over Na₂SO₄. After concentration, the residue was purified by column chromatography (ethyl acetate/hexanes, v/v, 1/10~1/5) to obtain the title compound 1H (4.7 g) as slightly yellow oil.

$^1$H-NMR: (300 MHz, CDCl$_3$) δ 7.80 (d, 1H), 7.42 (d, 1H), 7.20-7.36 (m, 5H), 7.20 (t, 1H), 4.92-5.19 (dd, 2H), 4.22 (dd, 1H), 1.58 (s, 9H), 1.55 (s, 9H), 1.24 (d, 2H), 1.15 (d, 12H).

Step 8: Synthesis of Compound 1I

Compound 1H (4.7 g, 8.1 mmol) and (+)-pinanediol (1.65 g, 9.7 mmol) were stirred in THF (50 mL) at room temperature for 24 hours. The reaction mixture was concentrated and purified by column chromatography (ethyl acetate/hexanes, v/v, 1/10~1/5) to obtain the title compound 1I (2.8 g) as slightly yellow oil.

$^1$H-NMR: (300 MHz, CDCl$_3$) δ 7.80 (d, 1H), 7.42 (d, 1H), 7.18-7.36 (m, 5H), 7.18 (t, 1H), 4.92-5.21 (m, 2H), 4.24 (m, 1H), 4.18 (m, 1H), 2.17-2.32 (m, 1H), 2.00-2.16 (m, 1H), 1.92-2.00 (m, 1H), 1.65-1.86 (m, 2H), 1.60 (s, 9H), 1.51 (s, 9H), 1.22-1.31 (m, 5H), 1.12-1.16 (m, 3H), 0.77-0.84 (m, 3H).

Step 9: Synthesis of Compound 1J

Compound 1I (2.8 g, 4.4 mmol) and Pd/C (400 mg, 10%) were stirred in EtOAc (50 mL) at room temperature under hydrogen (1 atm) for 18 hours. The reaction mixture was filtered through Celite and washed with EtOAc. After concentration, the mixture was purified by column chromatography (ethyl acetate/hexanes, v/v, 1/2~1/1) to obtain the title compound 1J (1.48 g) as white solid.
MS calcd for ($C_{29}H_{41}BO_9$): 544.
MS (ESI, negative) found: (M−1): 543.
Step 10: Synthesis of Compound 1K
Compound 1J (1.26 g, 2.3 mmol), DPPA (0.65 mL, 3.0 mmol) and $Et_3N$ (0.48 mL, 3.5 mmol) were dissolved in dry toluene (12 mL) at room temperature in nitrogen atmosphere. After 30 minutes, BnOH (2.4 mL, 23 mmol) was added and the reaction mixture was heated to 80° C. and stirred at this temperature for 16 hours. After cooling down, the solution was concentrated and purified by column chromatography (ethyl acetate/hexanes, v/v, 1/4~1/3) to obtain the title compound 1K (0.88 g) as colorless oil.
MS calcd for ($C_{36}H_{48}BNO_9$): 649.
MS (ESI, positive) found: (M+1): 650.
MS (ESI, negative) found: (M−1): 648.
Step 11: Synthesis of Compound 1L
To the solution of 1K (170 mg, 0.26 mmol) in 10 mL dioxane was added Pd/C (80 mg, 10%) and HCl solution (0.13 mL, 4 N in dioxane, 0.53 mmol). The resulting mixture was stirred at room temperature under hydrogen (1 atm) atmosphere for 2 hours. The reaction mixture was filtered through Celite and washed with dioxane. The filtrate was directly used for next step.
MS calcd for ($C_{28}H_{42}BNO_7$): 515.
MS (ESI, positive) found: (M+1): 516.

Step 12: Synthesis of Compound 1M
To the solution of 2-thiopheneacetic acid (75 mg, 0.53 mmol) in DMF (3 mL) was added HATU (209 mg, 0.55 mmol) at 0° C. After 20 minutes, the crude solution of 1 L (0.26 mmol) in 10 mL dioxane was added, followed by DIPEA (0.18 mL, 1.1 mmol). The resulting mixture was warmed to room temperature and stirred for 1 hour until LC-MS monitoring indicating the completion of reaction. The reaction mixture was concentrated to half volume and diluted with EtOAc/hexanes (4/1, v/v). After washed with 0.1N HCl, water and brine, the organic layer was dried over $Na_2SO_4$. After concentration, the residue was purified by column chromatography (ethyl acetate/hexanes, v/v, 1/3~1/1) to obtain the title compound 1M (85 mg) as slightly yellow solid.
MS calcd for ($C_{34}H_{46}BNO_8S$): 639.
MS (ESI, positive) found: (M+1): 640.
MS (ESI, negative) found: (M−1): 638.
Step 13: Synthesis of Compound 1
To the mixture of 1M (85 mg, 0.13 mmol) and triethylsaline (155 mg, 1.3 mmol) was added TFA (2 mL). The resulting solution was stirred at room temperature for 1.5 hours before it was concentrated to dryness. The residue was washed with hexanes twice and purified by prep-HPLC (18, acetonitrile and water as mobile phases, 0.1% formic acid) to obtain the title compound T110 (16 mg) as white solid.
MS calcd for ($C_{15}H_{14}BNO_5S$): 331.
MS (ESI, positive) found: (M+1): 332.
MS (ESI, negative) found: (M−1): 330.
$^1$H-NMR: (300 MHz, $CDCl_3$) δ 7.82 (dd, 1H), 7.31 (dd, 1H), 7.24 (dd, 1H), 6.87 (d, 2H), 6.83 (t, 1H), 4.70 (m, 1H), 3.85 (s, 2H), 0.68-0.82 (m, 2H). NMR:

EXAMPLE 2

4-(5-AMINO-1,3,4-THIADIAZOLE-2-CARBOXAMIDO)-2-HYDROXY-3,4-DIHYDRO-2H-BENZO[E][1,2]OXABORININE-8-CARBOXYLIC ACID (2)

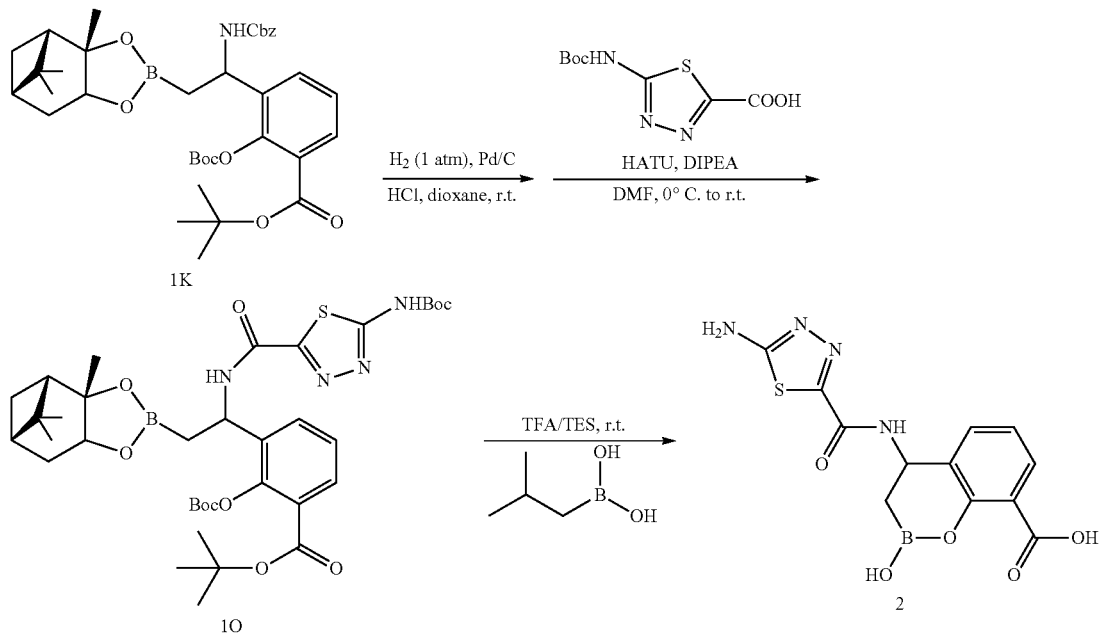

Step 1: Synthesis of Compound 1O
To the solution of 1K (200 mg, 0.31 mmol) in 10 mL dioxane was added Pd/C (110 mg, 10%) and HCl solution (0.16 mL, 4 N in dioxane, 0.62 mmol). The resulting mixture was stirred at room temperature under hydrogen (1 atm) atmosphere for 2 hours. The reaction mixture was filtered through Celite and washed with dioxane.
To the solution of 5-(N-Boc-amino)-1,3,4-thiadiazole-2-carboxylic acid (114 mg, 0.46 mmol) in DMF (4 mL) was added HATU (190 mg, 0.5 mmol) at 0° C. After 20 minutes, the above solution in 10 mL dioxane was added, followed by DIPEA (0.22 mL, 1.3 mmol). The resulting mixture was warmed to room temperature and stirred for 1 hour until LC-MS monitoring indicating the completion of reaction. The reaction mixture was concentrated to half volume and diluted with EtOAc/hexanes (4/1, v/v). After washed with 0.1N HCl, water and brine, the organic layer was dried over $Na_2SO_4$. After concentration, the residue was purified by column chromatography (ethyl acetate/hexanes, v/v, 1/3~1/1) to obtain the title compound 1O (102 mg) as white solid.

MS calcd for ($C_{36}H_{51}BN_4O_{10}S$): 742.
MS (ESI, negative) found: (M−1): 741.

Step 2: Synthesis of Compound 2

To the mixture of 1O (102 mg, 0.14 mmol) and triethylsaline (1 mL) was added TFA (4 mL) and isobutylboronic acid (35 mg, 0.34 mmol). The resulting solution was stirred at room temperature 4 hours before it was concentrated to dryness. The residue was purified by prep-HPLC (18, acetonitrile and water as mobile phases, 0.1% formic acid) to obtain the title compound T520 (8 mg) as white solid.

MS calcd for ($C_{12}H_{11}BN_4O_5S$): 334.
MS (ESI, positive) found: (M+1): 335.
MS (ESI, negative) found: (M−1): 333.
$^1$H-NMR: (300 MHz, $CDCl_3$) δ 7.88 (dd, 1H), 7.48 (dd, 1H), 6.93 (t, 1H), 4.80 (m, 1H), 1.05-1.35 (m, 2H).

EXAMPLE 3

2-HYDROXY-4-(2-(METHYLTHIO)ACETAMIDO)-3,4-DIHYDRO-2H-BENZO[E][1.2]OXABORININE-8-CARBOXYLIC ACID (3)

Step 1: Synthesis of Compound 1N

To the solution of 1K (345 mg, 0.53 mmol) in 12 mL dioxane was added Pd/C (2000 mg, 10%) and HCl solution (0.27 mL, 4 N in dioxane, 1.1 mmol). The resulting mixture was stirred at room temperature under hydrogen (1 atm) atmosphere for 2 hours. The reaction mixture was filtered through Celite and washed with dioxane.

To the solution of (methylthio)acetic acid (85 mg, 0.80 mmol) in DMF (5 mL) was added HATU (323 mg, 0.85 mmol) at 0° C. After 20 minutes, the above solution in 13 mL dioxane was added, followed by DIPEA (0.35 mL, 2.1 mmol). The resulting mixture was warmed to room temperature and stirred for 1 hour until LC-MS monitoring indicating the completion of reaction. The reaction mixture was concentrated to half volume and diluted with EtOAc/hexanes (4/1, v/v). After washed with 0.1N HCl, water and brine, the organic layer was dried over $Na_2SO_4$. After concentration, the residue was purified by column chromatography (ethyl acetate/hexanes, v/v, 1/3~1/1) to obtain the title compound 1N (150 mg) as white solid.

MS calcd for ($C_{31}H_{46}BNO_8S$): 603.
MS (ESI, positive) found: (M+1): 604.
MS (ESI, negative) found: (M−1): 602.

Step 2: Synthesis of Compound 3

To the mixture of 1N (150 mg, 0.25 mmol) and triethylsaline (150 mg) was added TFA (4 mL) and isobutylboronic acid (55 mg, 0.54 mmol). The resulting solution was stirred at room temperature 4 hours before it was concentrated to dryness. The residue was purified by prep-HPLC (18, acetonitrile and water as mobile phases, 0.1% formic acid) to obtain the title compound 3 (16 mg) as white solid.

MS calcd for ($C_{12}H_{14}BNO_5S$): 295.
MS (ESI, positive) found: (M+1): 296.
MS (ESI, negative) found: (M−1): 294.
$^1$H-NMR: (300 MHz, $CDCl_3$) δ 7.92 (dd, 1H), 7.43 (dd, 1H), 6.94 (t, 1H), 4.80 (m, 1H), 3.34 (s, 2H), 2.12 (s, 3H), 0.80-1.00 (m, 2H).

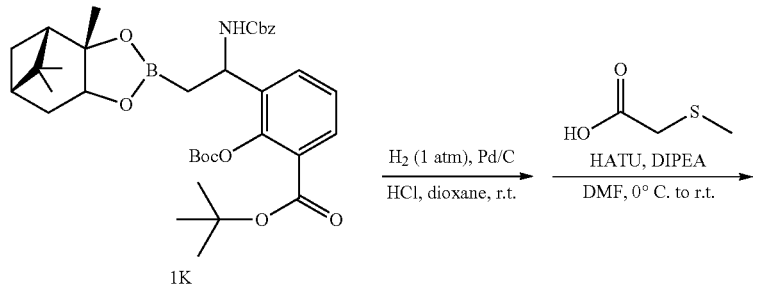

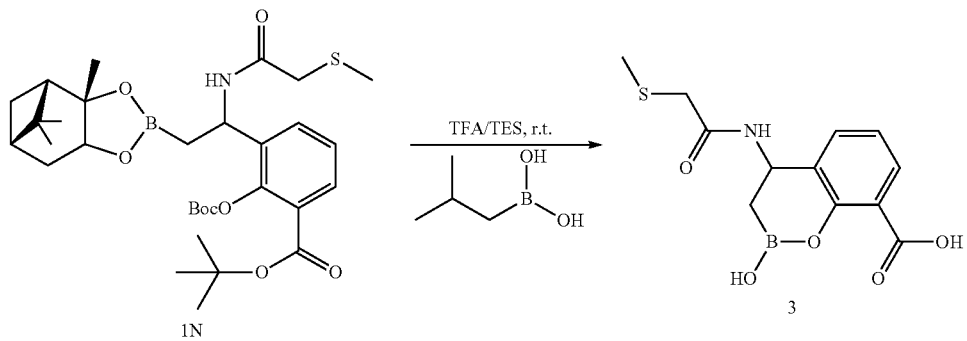

EXAMPLE 4

4-(BENZYLSULFONYL)-2-HYDROXY-3,4-DI-HYDRO-2H-BENZO[E][1,4,2]OXAZABORININE-8-CARBOXYLIC ACID (4)

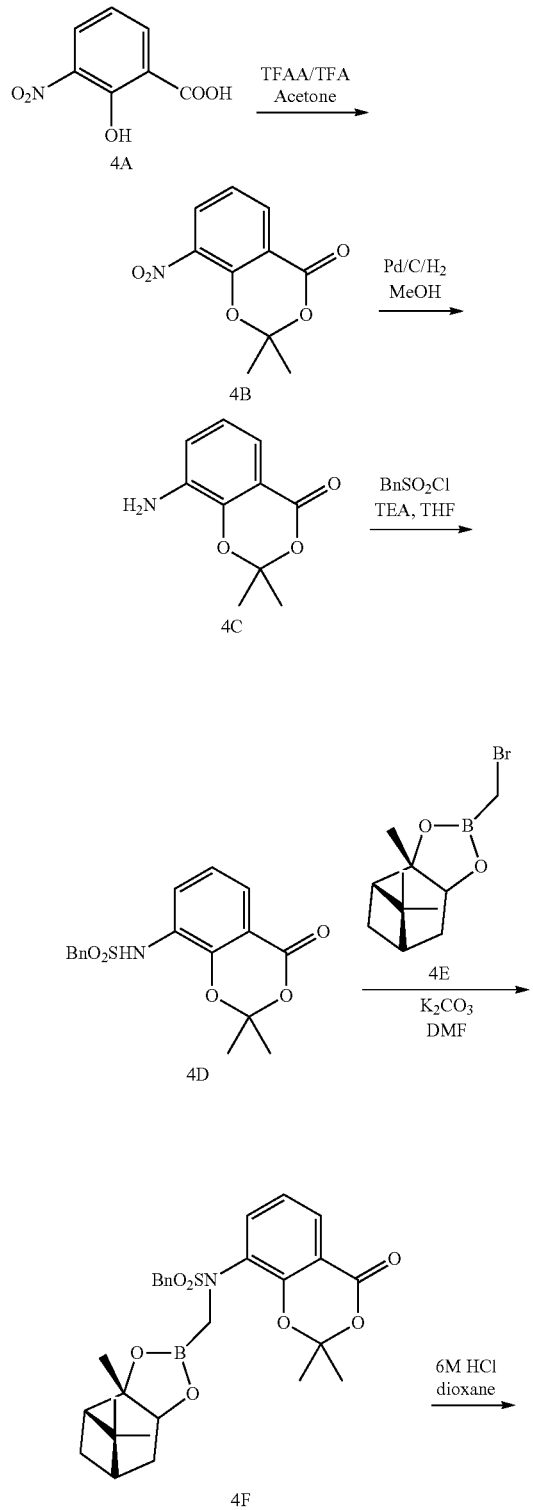

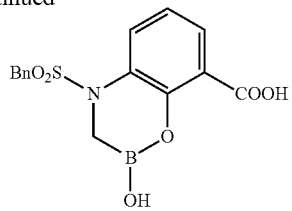

Step 1: Synthesis of 4B

To a mixture of TFAA/TFA (20 mL/30 mL) was added compound 4A (4.4 g, 24 mmol) at −4° C., followed by acetone (8 mL) dropwise over 30 mins. The solution was stirred at room temperature overnight and 30 hours at 90° C. The reaction mixture was diluted with DCM, washed with water and saturated NaHCO$_3$(aq), dried over Na$_2$SO$_4$. After concentration, the mixture was purified by silica gel chromatography to get the title compound 4B (4.1 g, 76% yield).

$^1$H NMR: (400 MHz, CDCl$_3$) δ 8.22-8.28 (m, 2H), 7.23-7.27 (m, 1H), 1.82 (s, 6H).

Step 2: Synthesis of 4C

The mixture of compound 4B (4.1 g) and Pd/C (1 g, 10%) in methanol (100 mL) was stirred under H$_2$ (1 atm) for 12 h at room temperature. After filtration, the filtrate was evaporated to dryness, and purified by silica gel chromatography to afford the title compound 4C (2.9 g, 81.7% yield).

$^1$H NMR: (400 MHz, CDCl$_3$) δ 7.33 (m, 1H), 6.88-6.95 (m, 2H), 3.83 (broad s, 2H), 1.74 (s, 6H).

Step 3: Synthesis of 4D

To a solution of compound 4C (2.8 g, 14.5 mmol) and triethylamine (4.4 g, 43.5 mmol) in DCM (30 mL) was added BnSO$_2$Cl (2.77 g, 14.5 mmol). The mixture was stirred at room temperature overnight before it was evaporated to dryness. The residue was purified by silica gel chromatography to get the title compound 4D (1 g, 20% yield).

$^1$H NMR: (400 MHz, CDCl$_3$) δ 7.70-7.72 (m, 2H), 7.31-7.37 (m, 3H), 7.23-7.26 (m, 2H), 7.06-7.09 (t, 1H), 6.58 (s, 1H), 4.39 (s, 2H), 1.69 (s, 6H).

Step 4: Synthesis of 4F

To a solution of compound 4D (1 g, 2.88 mmol) and K$_2$CO$_3$ (1.19 g, 8.64 mmol) in DMF was added compound 4E (1.18 g, 4.32 mmol) (WO2013/56163). The mixture was stirred at room temperature overnight before it was evaporated to dryness. The residue was purified by silica gel chromatography to get the title compound 4F (0.5 g, 32% yield).

$^1$H NMR: (400 MHz, CDCl$_3$) δ 7.88-7.91 (m, 1H), 7.46-7.47 (m, 2H), 7.32-7.37 (m, 4H), 6.98-7.00 (m, 1H), 4.40 (s, 2H), 4.22 (dd, 1H), 3.31 (s, 2H), 2.21-2.38 (m, 1H), 0.2.02-2.08 (m, 1H), 1.91-1.95 (m, 2H), 1.79-1.80 (s, 6H), 1.31 (s, 3H), 1.28 (s, 3H), 0.79 (s, 3H), 0.73 (d, 1H).

Step 5: Synthesis of 4

Compound 4F (500 mg) in HCl (6 mol/L, 2 mL) and 1,4-dioxane (2 mL) was heated to reflux (oil bath: 110° C.) for 3 hour before it was concentrated to dryness. The residue purified by prep-HPLC to afford 4 (82 mg) as white solid. The compound was obtained as a mixture of cyclic and acyclic boronate.

$^1$H NMR: (400 MHz, CD$_3$OD) δ 7.42-7.43 (d, 1H, J=4 Hz), 7.41-7.42 (d, 1H, J=4 Hz), 7.40-7.41 (d, 1H, J=4 Hz), 7.39-7.40 (m, 5H), 7.33-7.34 (m, 2H), 7.28-7.29 (m, 3H), 7.15-7.18 (m, 4H), 6.87-6.91 (m, 1H), 6.83-6.85 (m, 1H), 5.49 (s, 1H), 4.5 (s, 2H), 4.24 (s, 1H), 3.42 (s, 1H), 3.16 (s, 2H).

MS calcd for ($C_{15}H_{14}BNO_6S$): 347.2.

MS (ESI, positive) found: (M+1): 348.

EXAMPLE 5

2-HYDROXY-3,4-DIHYDRO-1,2-BENZOXA-BORININE-8-CARBOXYLIC ACID

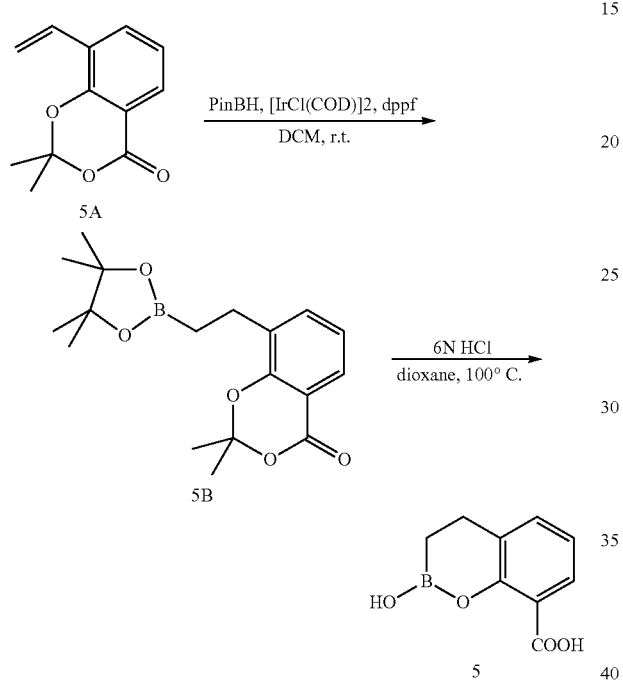

Step 1: Synthesis of 5B

To the solution of [IrCl(cod)]2 (11.1 mg, 0.0165 mmol) and dppe (13 mg, 0.033 mmol) in dichloromethane (1 mL) was added pinacolborane (0.095 mL, 0.66 mmol) under N2 atmosphere. The resulting solution was added into compound 5A (112 mg, 0.55 mmol) (WO 2014107535) in dichloromethane (2 mL) and stirred at room temperature for 18 hours. Crude NMR showed good conversion. The reaction mixture was concentrated and purified by column chromatography (silica gel, EtOAc/Hexanes, v/v, 1/4) to give the titled compound 5B (150 mg) as colorless oil.

Step 2: Synthesis of 5

To the solution of compound 5B (~140 mg) in dioxane (5 mL) was added 6N aqueous HCl (5 mL). The resulting solution was stirred at 100° C. for 1.5 hours before it was cooled down. The reaction mixture was concentrated and purified by C18 reverse-phase prep-HPLC (acetonitrile and water as mobile phases, 0.1% formic acid) to give titled compound 5 (39 mg) as white solid.

MS calcd for ($C_9H_9BO_4$): 192.

MS (ESI, negative) found: (2M−1): 383.

$^1$H NMR (300 MHz, CD$_3$OD) δ 7.68 (dd, 1H), 7.33 (dd, 1H), 6.79 (t, 1H), 2.69 (t, 2H), 1.09 (t, 2H).

EXAMPLE 6

DISODIUM; 4,4-DIHYDROXY-5-OXA-8-AZA-4-BORANUIDABICYCLO[4.4.0]DECA-1(6),7,9-TRIENE-7-CARBOXYLATE

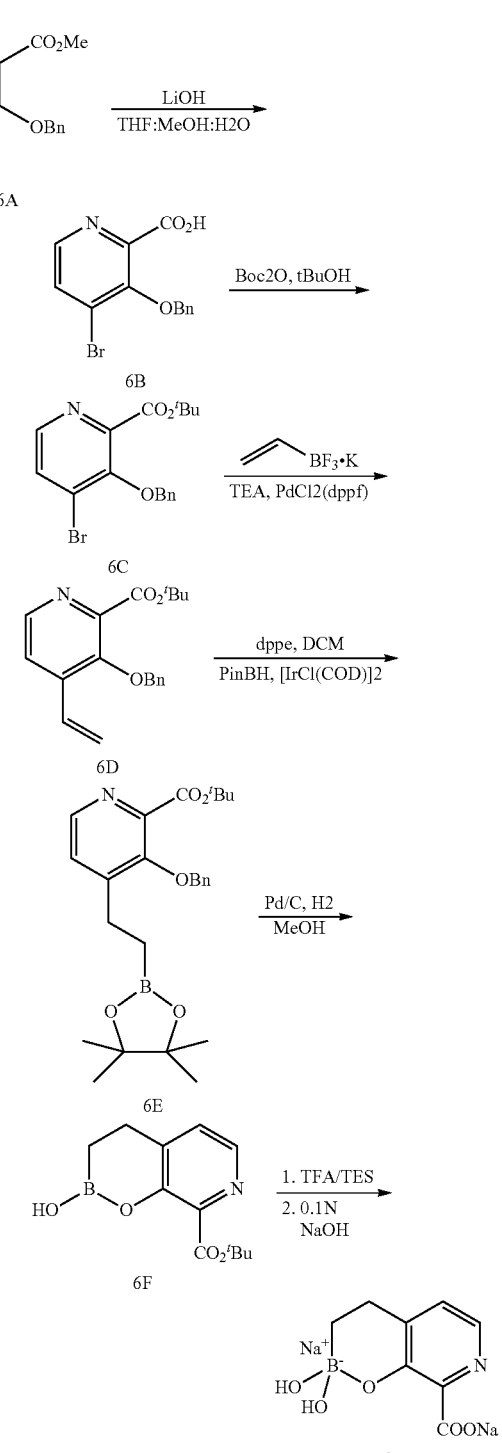

Step 1: Synthesis of 6B:

To a solution of known compound 6A (7 g, 21.73 mmol, 1.0 eq, *Tetrahedron*, 2011, 67, 8757) in THF:MeOH:H$_2$O (2:2:1, 100 mL) was added LiOH (1.37 g, 32.6 mmol, 1.5 eq) at room temperature. The mixture was stirred at rt for 1.5 hours. The solvent was removed under reduced pressure. The residue was redissolved in water, adjusted pH to 1 with 1N HCl, and extracted with ethyl acetate. The organics were dried over $Na_2SO_4$, and concentrated to yield residue, which was purified by column chromatography (DCM:MeOH=10:1) to give compound 6B (4.85 g, 72%). H NMR (CD$_3$OD, 300 MHz): δ 8.21 (d, J=4.8 Hz, 1H), 7.88 (d, J=4.8 Hz, 1H), 7.55-7.36 (m, 5H), 5.15 (s, 2H).

Step 2: Synthesis of 6C:

To a solution of compound 6B (4.8 g, 15.58 mmol, 1.0 eq) in $^t$BuOH (150 mL) was added DMAP (195 mg, 1.596 mmol, 0.1 eq) and Boc$_2$O (10.2 g, 46.74 mmol, 3 eq). The mixture was stirred overnight at 60° C. The solvent was removed under reduced pressure, and the resulting residue was purified by column chromatography (ethyl acetate:hexanes=1:3) to give compound 6C (4.9 g, 86%). H NMR (CDCl$_3$, 300 MHz): δ 8.23 (d, J=4.8 Hz, 1H), 7.63 (d, J=5.1 Hz, 1H), 7.55-7.38 (m, 5H), 5.13 (s, 2H), 1.58-1.57 (m, 9H).

Step 3: Synthesis of 6D:

To a solution of compound 6C (4.9 g, 13.45 mmol, 1.0 eq) in isopropyl alcohol (250 mL) was added PdCl$_2$(dppf) (878 mg, 1.08 mmol, 0.08 eq), potassium vinyltrifluroborate (4.5 g, 33.59 mmol, 2.5 eq), and triethylamine (2.04 g, 20.17 mmol, 1.5 eq). The mixture was purged with N$_2$ and stirred at 86° C. for 3 hours. The solvent was removed under reduced pressure, and the resulting residue was purified by column chromatography (ethyl acetate:hexanes=1:3) to give compound 6D (3.77 g, 90%). H NMR (CDCl$_3$, 300 MHz): δ 8.38 (d, 1H), 7.52-7.28 (m, 6H), 6.95 (dd, 1H), 5.95 (dd, 1H), 5.56 (dd, 1H), 5.01 (s, 2H), 1.6-1.58 (m, 9H).

Step 3: Synthesis of 6E:

To a solution of PinBH (1.86 g, 14.54 mmol, 1.2 eq), [IrCl(COD)]2 (163 mg, 0.263 mmol, 0.02 eq) and dppe (191 mg, 0.479 mmol, 0.04 eq) in DCM (100 mL) was added compound 6D (3.77 g, 12.11 mmol, 1.0 eq) in DCM (50 mL). The mixture was purged with N$_2$ and stirred overnight at room temperature. After addition of MeOH (10 mL), the solvent was removed under reduced pressure, and the resulting residue was purified by column chromatography (ethyl acetate:hexanes=1:3) to give compound 6E (2.58 g, 48%). H NMR (CDCl$_3$, 300 MHz): δ 8.36 (d, 1H), 7.51-7.29 (m, 6H), 5.03 (s, 2H), 2.80 (t, 2H), 1.59 (s, 9H). 1.29-1.18 (m, 14H).

Step 4: Synthesis of 6F:

To a solution of compound 6E (2.58 g, 5.87 mmol, 1.0 eq) in MeOH (100 mL) was added Pd/C. The mixture was stirred overnight at room temperature. The mixture was filtered through celite and concentrated under reduced pressure. The resulting residue was purified by column chromatography (DCM:MeOH=10:1) to give impure compound 6F (~1.5 g).

MS calcd for ($C_{12}H_{16}BNO_4$): 249.
MS (ESI, positive) found: (M+1): 250.

Step 5: Synthesis of 6:

Step 1: A solution of compound 6F (1.5 g, 6 mmol, 1.0 eq) in TFA (12 mL) and TES (3 mL) was stirred at rt for 1.5 h. The mixture was concentrated, and purified by C18 reverse-phase prep-HPLC (acetonitrile and water as mobile phases, 0.1% formic acid). After lyophilization, the obtained white solid was dissolved in MeCN/H$_2$O, and adjusted to pH about 7.9 using 0.1N aqueous NaOH. After stirred at room temperature overnight, the solution was concentrated, and re-purified by Cis reverse-phase prep-HPLC (acetonitrile and water as mobile phases, neutral) to give the desired 6 sodium salt as white solid.

MS calcd for ($C_8H_8BNO_4$): 193.
MS (ESI, positive) found: (M+1) 194; (M+1+H$_2$O) 212.
$^1$H NMR (300 MHz, D$_2$O): δ 7.59 (d, 1H), 7.08 (d, 1H), 2.55 (t, 2H), 0.48 (t, 2H).

EXAMPLE 7

DISODIUM; 4,4-DIHYDROXY-8-METHOXY-5-OXA-4-BORANUIDABICYCLO[4.4.0]DECA-1(6),7,9-TRIENE-7-CARBOXYLATE

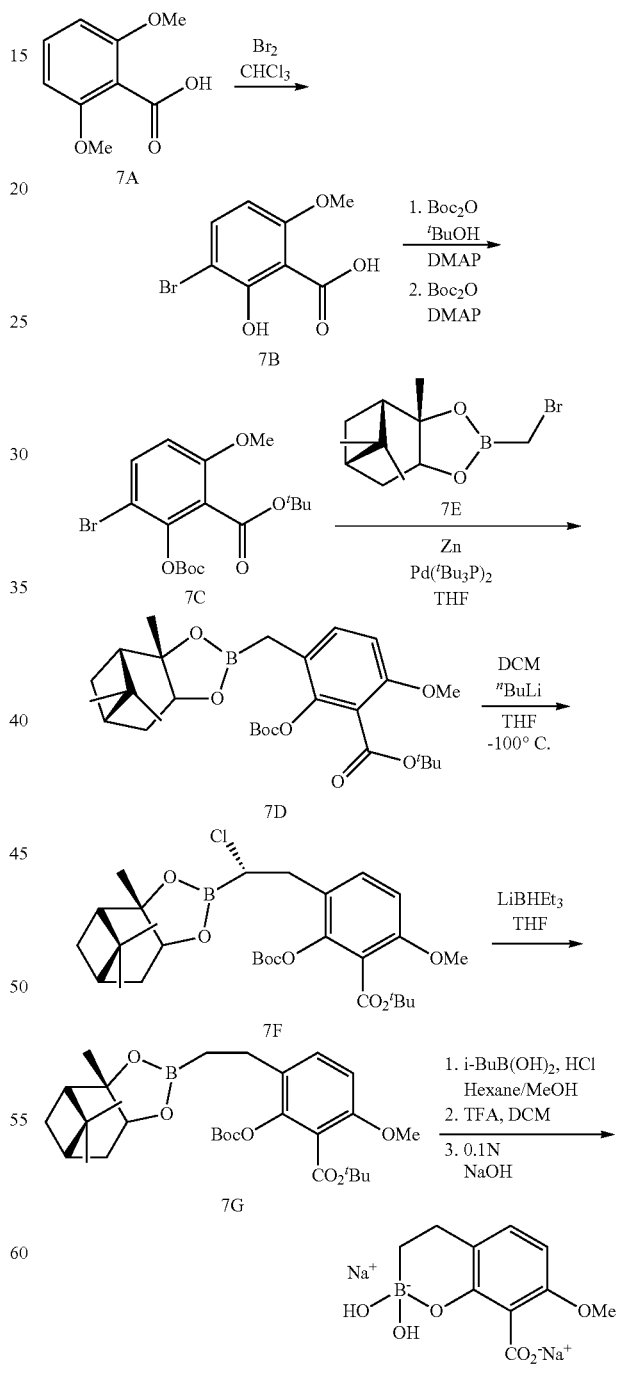

Step 1: Synthesis of 7B:
To a solution of 2, 6-dimethoxybenzoic acid (7A) (50 g, 0.275 mol) in CHCl$_3$ (1 L) at 0° C. was added dropwise bromine (14.4 mL, 0.263 mol). The reaction mixture was stirred at 25° C. for 30 hours, before it was concentrated to dryness. The residue was purified by column chromatography (ethyl acetate/hexanes) to afford compound 7B (32.5 g, 48%) as white solid.

Step 2: Synthesis of 7C:
To the solution of compound 7B (32.5 g, 0.132 mol) in THF (200 mL) was added Boc$_2$O (114.7 g, 0.526 mol), DMAP (4.8 g, 0.04 mol) and tBuOH (400 mL). The resulting solution was stirred at 60° C. for 6 hours before it was concentrated in vacuo. The residue was quickly passed through a silica gel column (ethyl acetate/hexanes) to give the corresponding t-butyl ester. To the solution of this ester and Boc$_2$O (17 g, 0.078 mol) in DCM (300 mL) was added DMAP (475 mg, 3.89 mmol). The resulting reaction mixture was stirred at room temperature for 1 hour before it was concentrated to dryness. The residue was purified by column chromatography (ethyl acetate/hexanes) to afford compound 7C (52.1 g, 98%) as white solid.

Step 3: Synthesis of 7D:
To a mixture of Zn powder (20 g, 0.302 mol) and compound 7E (100 mg, 0.37 mmol) in anhydrous THF (100 mL) was added DIBAL-H (2.45 mL, 6.05 mmol, 1.5 M in toluene) at room temperature. The mixture was stirred at room temperature for 5 min, then more compound 7E (33 g, 0.121 mol) in anhydrous THF (100 mL) was added dropwise into the mixture over 20 min. The reaction mixture was warmed up to 50° C. and stirred at this temperature for 1 hour before it was settled down at room temperature. The top layer of clear solution was transferred into a mixture of compound 7C (20 g, 50 mmol) and Pd(t-Bu3P)2 (917 mg, 1.79 mmol) in THF (300 mL) at room temperature under N$_2$. After stirring at room temperature for 1 hour, the reaction mixture was concentrated, and purified by column chromatography (ethyl acetate/hexanes) to afford compound 7D (21 g, 81%) as light yellow solid.

Step 4: Synthesis of 7F:
To a solution of dichloromethane (4.2 mL, 0.066 mol) in anhydrous THF (200 mL), was added dropwise n-butyllithium (2.5 M in hexane, 18.5 mL, 0.046 mol) along the wall of the flask over 1 h at −100° C. (cooled with liquid nitrogen and methanol), while keeping the internal temperature below −90° C. After the addition, the mixture was stirred at −100° C. for 30 min before slow addition of the solution of compound 7D (17 g, 0.033 mol) in anhydrous THF (60 mL) over 1 h at −100° C. The reaction mixture was slowly warmed up to room temperature over a period of 6 hours and stirred overnight. The solvent was evaporated and the residue was purified by column chromatography (ethyl acetate/hexanes) to afford compound 7F (16.5 g, 88%) as light yellow solid.

Step 5: Synthesis of 7G:
To a solution of compound 7F (3.0 g, 5.3 mmol, 1.0 eq) (WO 2014107536) in anhydrous THF (60 mL) was added a solution of LiBHEt$_3$ in THF (1 M, 13.27 mL, 13.3 mmol, 2.5 eq) over 20 min at −78° C. The mixture was stirred at rt overnight. The solvent was removed under reduced pressure. The crude was purified by column chromatography (PE/EA=50:1 to 9:1) to give compound 7G (2.2 g, 78%). H NMR (CDCl$_3$, 400 MHz): δ 7.24 (d, J=8.8 Hz, 1H), 6.74 (d, J=8.4 Hz, 1H), 4.28-4.23 (m, 1H), 3.79 (s, 3H), 2.60 (m, 2H), 2.39-2.25 (m, 2H), 2.20-2.12 (m, 1H), 2.04-2.01 (m, 1H), 1.95-1.88 (m, 1H), 1.85-1.75 (m, 1H), 1.57 (s, 9H), 1.53 (s, 9H), 1.35 (s, 3H), 1.27 (s, 3H), 1.11-1.02 (m, J=7.6 Hz, 2H), 0.83 (s, 3H).

Step 6: Synthesis of 7:
To a mixture of compound 7G (2.0 g, 3.77 mmol, 1.0 eq), i-BuB(OH)$_2$ (499 mg, 3.77 mmol, 1.3 eq) in hexane (20 mL) and methanol (20 mL) was added 1 mL of hydrochloric acid at 0° C. The reaction mixture was stirred at rt overnight. The methanol layer was concentrated to give crude product (1.7 g).

The crude product (1.7 g) was then dissolved in dichloromethane (7 mL) and TFA (7 mL) was added slowly at 0° C. The reaction was stirred at rt for 1 h. The mixture was concentrated and the residue was diluted with methanol (3 mL) and water (3 mL). The mixture was then adjusted to pH 12 with 0.1N aqueous solution of NaOH and stirred at rt overnight. The solid was filtered, washed with acetonitrile-water and dried to afford 7 (650 mg, 71%) as a white solid.

MS calcd for (C$_{10}$H$_{11}$BO$_5$): 222.

MS (ESI, positive) found: (M+1) 223.

H NMR (CD$_3$OD, 400 MHz): δ 6.71 (d, J=8.0 Hz, 1H), 6.18 (d, J=8.4 Hz, 1H), 3.70 (s, 3H), 2.55 (t, J=6.8 Hz, 2H), 0.43 (t, J=7.2 Hz, 2H).

EXAMPLE 8

DISODIUM; 8-FLUORO-4,4-DIHYDROXY-5-OXA-4-BORANUIDABICYCLO[4.4.0]DECA-1(6),7,9-TRIENE-7-CARBOXYLATE

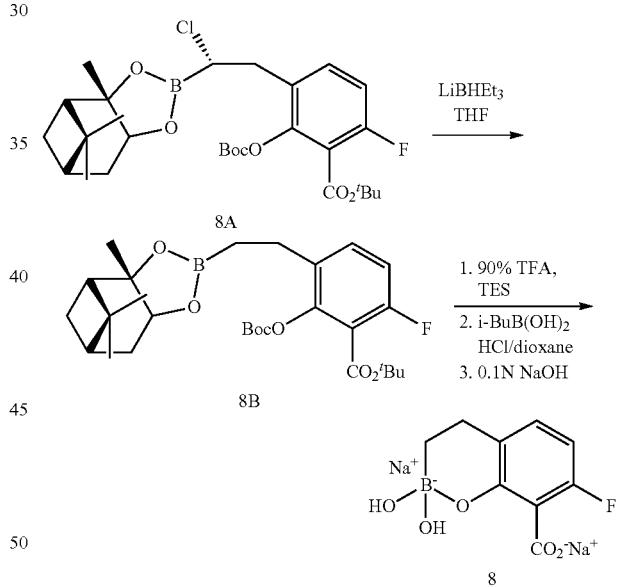

Step 1: Synthesis of 8B
The synthesis of the compound 8A can be found in WO 2014107536, which is incorporated herein by reference in its entirety. To a solution of compound 8A (3.0 g, 5.4 mmol, 1.0 eq) in anhydrous THF (80 mL) was added a solution of LiBHEt$_3$ in THF (1 M, 13.6 mL, 13.6 mmol, 2.5 eq) over 20 min at −78° C. The reaction was stirred at rt overnight and the solvent was removed under reduced pressure. The residue was purified by column chromatography (PE/EA=10:1) to give compound 8B (2.0 g, 71%).

$^1$H NMR (CDCl$_3$, 400 MHz): δ 7.32-7.26 (m, 1H), 6.92 (t, J=8.8 Hz, 1H), 4.25 (dd, J=8.8 Hz, 1.6 Hz, 1H), 2.65 (dd, J=8.4 Hz, 2H), 2.31-2.28 (m, 1H), 2.19-2.15 (m, 1H), 2.02 (t, J=5.6 Hz, 1H), 1.90-1.88 (m, 1H), 1.83-1.78 (m, 1H), 1.59 (s, 9H), 1.54 (s, 9H), 1.35 (s, 3H), 1.28 (s, 3H), 1.11 (dd, J=8.4 Hz, 2H), 1.03 (d, J=10.4 Hz, 1H), 0.83 (s, 3H).

Step 2: Synthesis of 8

A solution of compound 8B (2.0 g, 3.86 mmol, 1.0 eq) in 90% TFA (12 mL) and TES (4 mL) was stirred at rt for 1 h. The mixture was concentrated to give the crude product (1.5 g) which was used directly in next step without purification.

To a solution of the crude product (1.5 g) in dioxane (5 mL) and hydrochloric acid (5 mL) was added i-BuB(OH)$_2$ (590 mg, 5.79 mmol, 1.5 eq). The mixture was stirred at rt for 1 h. The solvent was removed under reduced pressure. The mixture was then adjusted to pH 12 with 0.1 N aqueous solution of NaOH and was stirred at rt for 48 h. The mixture was then purified by prep-HPLC to give 8 (370 mg, 41%) as white solid.

MS calcd for (C$_9$H$_8$BFO$_4$): 210.
MS (ESI, positive) found: (M+1) 211.
$^1$H NMR (D$_2$O, 400 MHz): δ 6.93 (m, 1H), 6.40 (m, J=8.8 Hz, 1H), 2.60 (t, J=6.4 Hz, 2H), 0.40 (t, J=7.2 Hz, 2H).

EXAMPLE 9

Disodium; (3S)-4,4-dihydroxy-3-methy-5-oxa-4-boranuidabicyclo[4.4.0]deca-1(6),7,9-triene-7-carboxylate

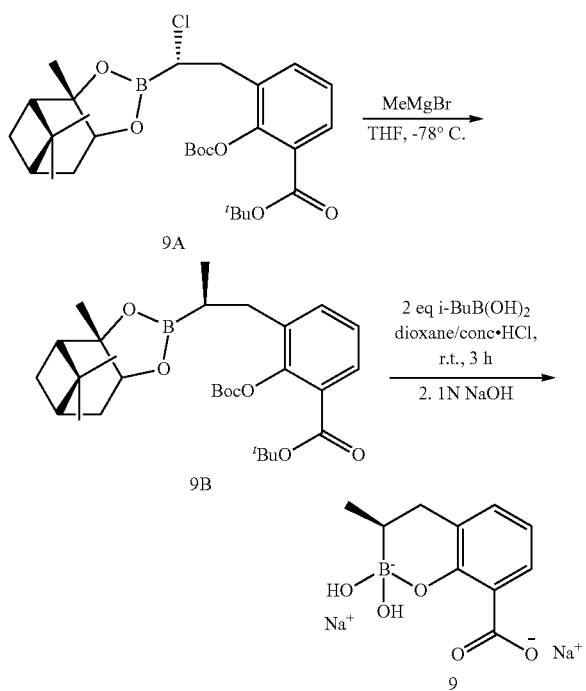

Step 1: Synthesis of 9B:

To a solution of compound 9A (US2014/194381) (1.1 g, 2.06 mmol, 1.0 eq) in anhydrous THF (10 mL) was added dropwise a solution of methyl magnesium bromide in THF (3 M, 1.03 mL, 3.1 mmol, 1.5 eq) over 5 min at −78° C. The reaction mixture was slowly warmed up to room temperature in 18 h before it was quenched with saturated aq NH$_4$Cl. The organic layer was concentrated and the residue was purified by column chromatography (PE/EA=10:1) to give compound 9B (0.9 g, 81%).

Step 2: Synthesis of 9:

To a solution of compound 9B (0.5 g) in dioxane (2 mL) and concentrated HCl (2 mL) was added i-BuB(OH)$_2$ (184 mg, 1.83 mmol, 2 eq) at room temperature. The mixture was stirred at rt for 3 h. The reaction mixture was concentrated in vacuo, and the residue was dissolved in H$_2$O/MeCN. The resulting solution was adjusted to pH=12 and purified by prep-HPLC (18, neutral) to give 9 (18 mg, 9%) as white solid.

MS calcd for (C$_{10}$H$_{11}$BO$_4$): 206.
MS (ESI, positive) found: (M+1): 207.
$^1$H NMR (CD$_3$OD, 400 MHz): δ 7.643-7.659 (d, J=6.4, 1H), 7.158-7.303 (dd, J=7.6, 1H), 6.710-6.883 (m, 1H), 2.598-2.758 (m, 2H), 1.255-1.295 (m, 3H), 0.796-0.885 (m, 1H).

EXAMPLE 10

Disodium; (3R)-4,4-dihydroxy-3-methyl-5-oxa-4-boranuidabicyclo[4.4.0]deca-1(6),7,9-triene-7-carboxylate

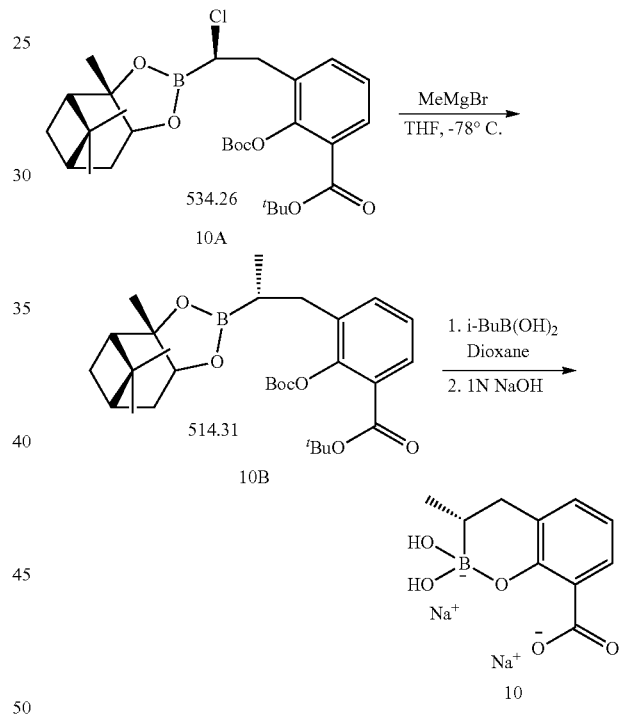

Step 1: Synthesis of 10B:

To a solution of compound 10A (prepared as 9A using (−)-Pinanediol) (2 g, 3.74 mmol, 1.0 eq) in anhydrous THF (20 mL) was added dropwise a solution of methyl magnesium bromide in THF (3 M, 1.87 mL, 5.61 mmol, 1.5 eq) over 10 min at −78° C. The reaction mixture was slowly warmed up to room temperature in 18 hours before it was quenched with saturated NH$_4$Cl. The organic layer was concentrated and the residue was purified by column chromatography (PE/EA=10:1) to give compound 10B (1.3 g, 66%).

Step 2: Synthesis of 10:

To a solution of compound 10B (1.3 g) in dioxane (6 mL) and hydrochloric acid (6 mL) was added i-BuB(OH)$_2$ (516 mg, 5.05 mmol, 2 eq) at room temperature. The mixture was stirred at rt for 3 hours. The reaction mixture was concentrated in vacuo, and the residue was dissolved in H$_2$O/MeCN. The resulting solution was adjusted to pH=12 and purified by prep-HPLC (18, neutral conditions) to give 10 (295 mg, 51%) as white solid.

MS calcd for (C$_{10}$H$_{11}$BO$_4$): 206.
MS (ESI, positive) found: (M+1): 207.
$^1$H NMR (CD$_3$OD, 400 MHz): δ 7.564 (s, 1H), 7.064-7.078 (d, J=5.6, 1H), 6.606-6.644 (d, J=15.2, 1H), 2.807-2.854 (m, 1H), 2.397-2.450 (m, 1H), 0.789-0.875 (m, 4H).

EXAMPLE 11

Disodium; (3S)-4,4-dihydroxy-8-methoxy-3-methyl-5-oxa-4-boranuidabicyclo[4.4.0]deca-1(6),7,9-triene-7-carboxylate

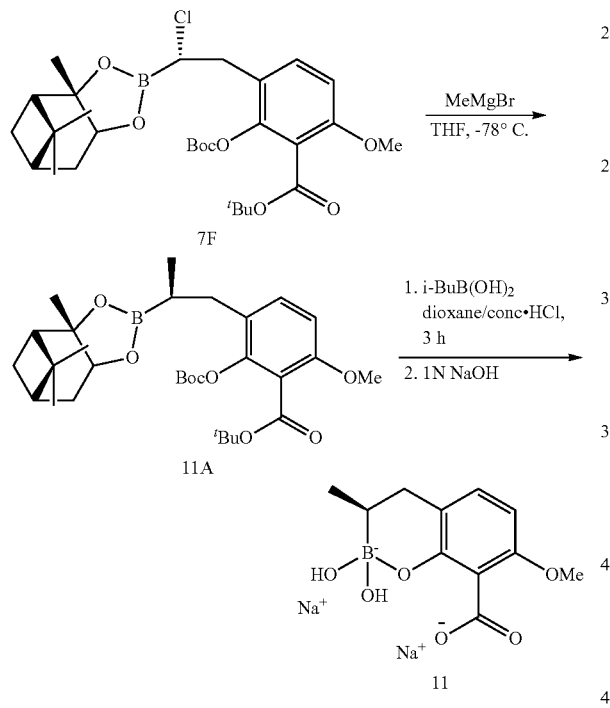

Step 1: Synthesis of 11A
To a solution of compound 7F (1.1 g, 1.95 mmol, 1.0 eq) in anhydrous THF (10 mL) was added dropwise a solution of methyl magnesium bromide in THF (3 M, 0.98 mL, 2.93 mmol, 1.5 eq) over 5 min at −78° C. The reaction mixture was slowly warmed up to room temperature in 18 hours before it was quenched with saturated NH$_4$Cl. The organic layer was concentrated and the residue was purified by column chromatography (PE/EA=10:1) to give compound 11A (0.9 g, 81%).

Step 2: Synthesis of 11
To a solution of compound 11A (0.45 g) in dioxane (3 mL) and hydrochloric acid (3 mL) was added i-BuB(OH)$_2$ (169 mg, 1.65 mmol, 2 eq) at room temperature. The mixture was stirred at rt for 3 hours. The reaction mixture was concentrated in vacuo, and the residue was dissolved in H$_2$O/MeCN. The resulting solution was adjusted to pH=12 and purified by prep-HPLC (18, neutral) to give 11 (75 mg, 38%) as white solid.

ESI-MS: [M+H]$^+$: 237.

H NMR (CD$_3$OD, 400 MHz): δ 6.747-6.767 (d, J=8, 1H), 6.226-6.247 (dd, J=8.4, 1H), 3.676-3.711 (m, 3H), 2.618-2.653 (m, 1H), 2.285-2.340 (m, 1H), 0.805-0.822 (m, 3H), 0.722-0.725 (m, 1H).

EXAMPLE 12

Disodium; (3R)-4,4-dihydroxy-3-(2-hydroxyethyl)-8-methoxy-5-oxa-4-boranuidabicyclo[4.4.0]deca-1(6),7,9-triene-7-carboxylate

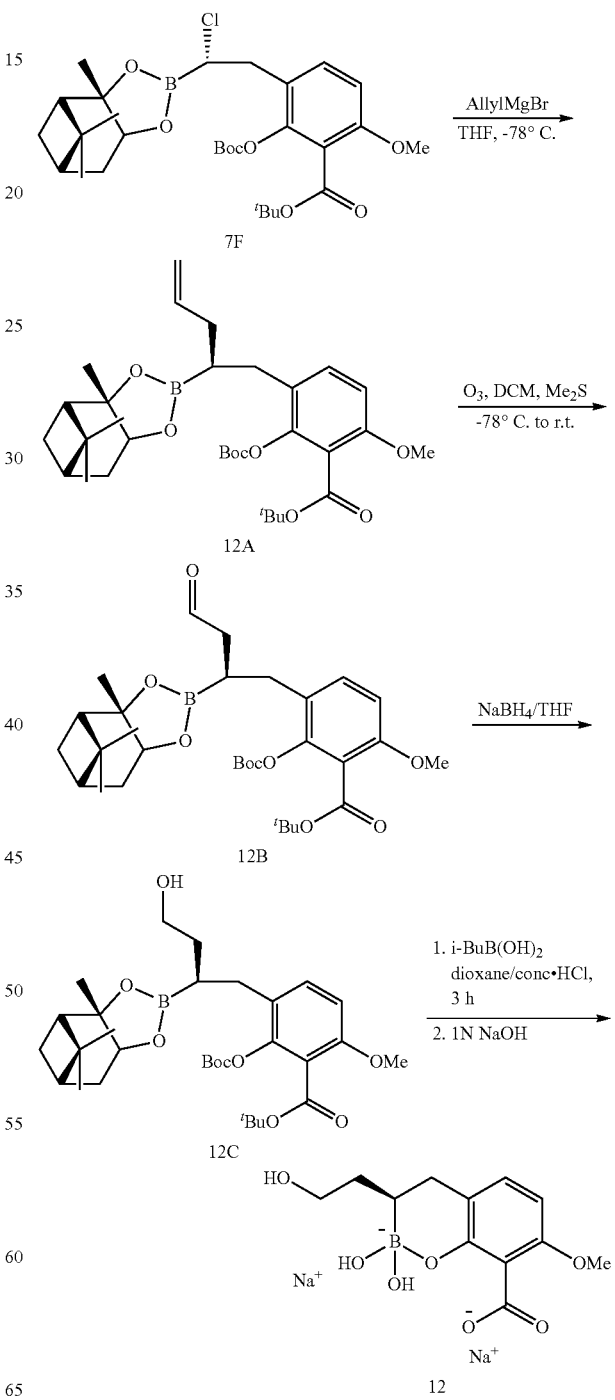

Step 1: Synthesis of 12

To a solution of compound 7F (5 g, 8.85 mmol, 1.0 eq) in anhydrous THF (50 mL) was added allylmagnesium bromide (11.5 mL, 1 M in THF, 11.5 mmol, 1.3 eq) dropwise over 10 minutes at −78° C. The reaction mixture was slowly warmed up to room temperature in 18 hours before it was quenched with saturated NH$_4$Cl. The organic layer was concentrated and the residue was purified by column chromatography (PE/EA=10:1) to give compound 12A (4.5 g, 89%).

Step 2: Synthesis of 12B

To a solution of compound 12A (730 mg, 1.28 mmol, 1.0 eq) in DCM (30 mL) was bubbled with 03 at −78° C. until the solution turned to slightly blue. The nitrogen was bubbled in to remove the color. The colorless solution was added dimethylsulfide (3 mL) and slowly warmed up to room temperature in 6 hours. The solvent was removed under reduced pressure and the residue was purified by column chromatography (PE/EA=3:1) to give compound 12B (400 mg, 55%).

Step 3: Synthesis of 12C

To a solution of compound 12B (400 mg, 0.69 mmol, 1.0 eq) in anhydrous THF (50 mL) was added NaBH$_4$ (31 mg, 0.83 mmol, 1.2 eq) at 0° C. The mixture was stirred at room temperature for 1 hour before it was concentrated under reduced pressure. The residue was purified by column chromatography (PE/EA=1:1) to give compound 12C (180 mg, 45%).

Step 4: Synthesis of 12

To a solution of compound 12C (180 mg) in dioxane (3 mL) and hydrochloric acid (3 mL) was added i-BuB(OH)$_2$ (64 mg, 0.63 mmol, 2 eq). The mixture was stirred at rt for 3 hours. The reaction mixture was concentrated in vacuo, and the residue was dissolved in H$_2$O/MeCN. The resulting solution was adjusted to pH=12 and purified by prep-HPLC (18, neutral) to give 12 (9 mg, 10%) as white solid.

ESI-MS: [M+H]: 267.

$^1$H NMR (CD$_3$OD, 400 MHz): δ 6.735-6.754 (d, J=7.6, 1H), 6.214-6.235 (dd, J=8.4, 1H), 3.701 (s, 3H), 3.607-3.685 (m, 2H), 2.518-2.553 (m, 1H), 2.485-2.496 (m, 1H), 1.758-1.823 (m, 1H), 1.458-1.495 (m, 1H), 1.005-1.012 (m, 1H).

EXAMPLE 13

Disodium; 4,4-dihydroxy-8-(triazol-1-yl)-5-oxa-4-boranuidabicyclo[4.4.0]deca-1(6),7,9-triene-7-carboxylate

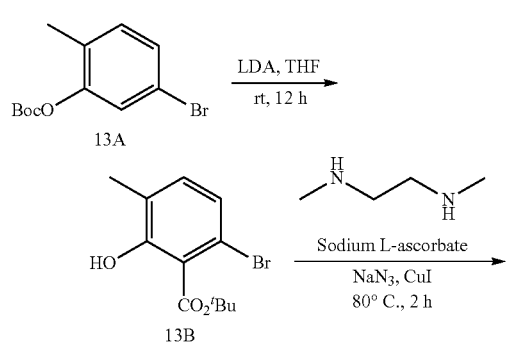

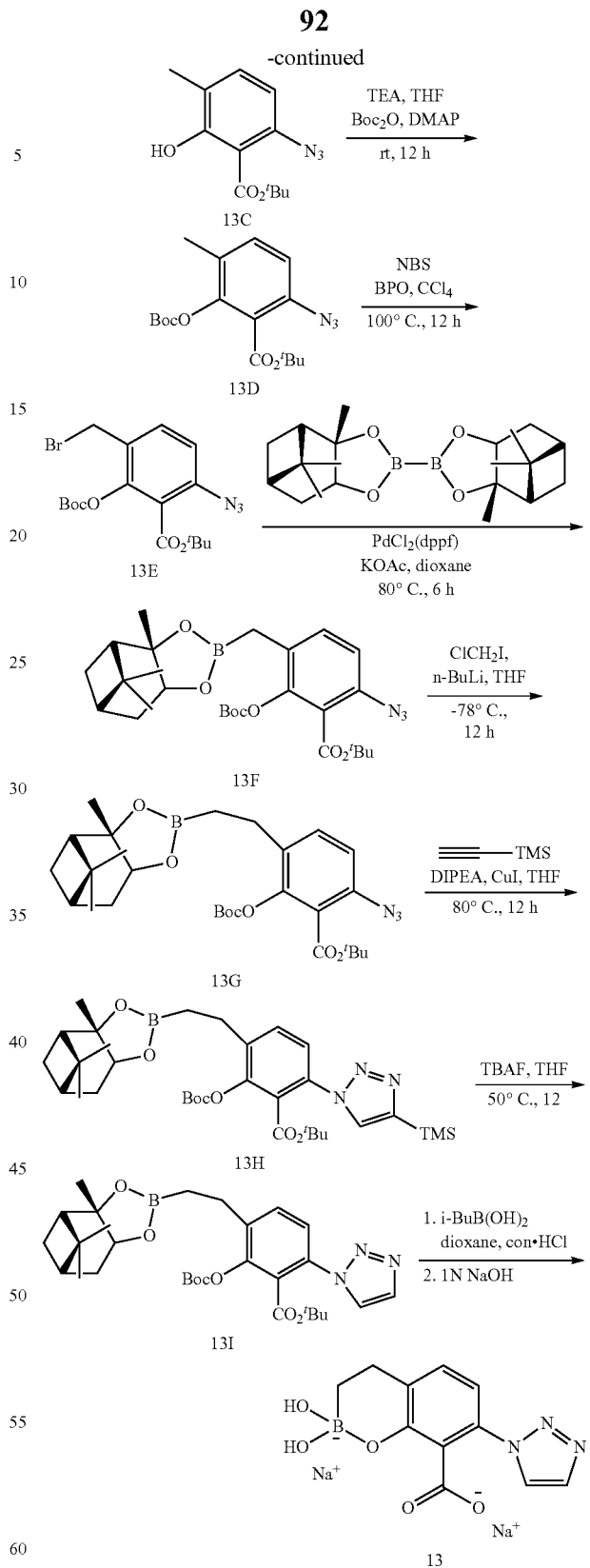

Step 1: Synthesis of 13B

To a solution of 13A (142.2 g, 497 mmol, 1.0 eq) in dry THF (350 mL) was added LDA (freshly made, 544 mmol, 1.1 eq) at −78° C. The mixture was slowly warmed up to room temperature for 12 hours under nitrogen atmosphere.

The mixture was concentrated and the residue was partitioned in EA and water. The aqueous layer was adjusted to PH=6 with 1N HCl. The organic layer was washed with brine, dried over $Na_2SO_4$ and then concentrated under reduced pressure to give 13B (142.6 g, 98%).

Step 2: Synthesis of 13C

To a solution of 13B (45 g, 156 mmol, 1.0 eq) in EtOH/$H_2O$ (200 mL, 7/3, v/v) was added $NaN_3$ (20.5 g, 3.15 mol, 2.0 eq), CuI (3 g, 157 mmol, 0.1 eq), N1,N2-dimethylethane-1,2-diamine (2.1 g, 23.8 mmol, 0.15 eq) and Sodium L-ascorbate (1.55 g, 7.82 mmol, 0.08 eq). The mixture was stirred at 80° C. for 2 hours under nitrogen atmosphere. The mixture was cooled to room temperature and quenched with 0.2 N HCl. The resulting mixture was extracted with EA (2×) and the organic layer was washed with water, brine. The solvent was removed in vacuo and the residue was purified by column chromatography on silica gel (PE:EA=100:1 to 30:1) to give 13C (25.8 g, 66%).

Step 3: Synthesis of 13D

To a solution of 13C (23 g, 92.4 mmol, 1.0 eq) in dry THF (250 mL) was added $Boc_2O$ (26.2 g, 120.1 mmol, 1.3 eq), DMAP (1.13 g, 9.24 mmol, 0.1 eq) and TEA (10.3 g, 101.6 mmol, 1.1 eq). The mixture was stirred at room temperature for 12 hours. The reaction was monitored by TLC. The mixture was concentrated and the residue was purified by column chromatography on silica gel (PE:EA=1:0-100:1) to give 13D (32.2 g, 86%).

Step 4: Synthesis of 13E

To a solution of 13D (20.1 g, 57.6 mmol, 1.0 eq) in $CCl_4$ (300 mL) was added NBS (11.3 g, 63.4 mmol, 1.1 eq) and BPO (2.8 g, 11.5 mmol, 0.2 eq). The mixture was stirred at 100° C. for 12 hours under nitrogen atmosphere. The reaction was monitored by TLC. The mixture was concentrated and the residue was purified by column chromatography on silica gel (PE:EA=300:1 to 20:1) to give 13E (18 g, 79%).

Step 5: Synthesis of 13F

To a solution of 13E (18.3 g, 42.7 mmol, 1.0 eq) in dioxane (550 mL) was added diboron reagent (18.4 g, 51.2 mmol, 1.2 eq), KOAc (8.4 g, 85.5 mmol, 2.0 eq) and $PdCl_2$(dppf) (1.7 g, 2.1 mmol, 0.05 eq). The mixture was stirred at 70° C. for 12 hours under nitrogen atmosphere. The reaction was monitored by TLC. The resulting mixture was filtered and the filtrate was concentrated under reduced pressure. The residue was purified by column chromatography on silica gel (PE:EA=20:1 to 10:1) to give 13F (8 g, 36%).

ESI-MS: [M+H]: 528.

Step 6: Synthesis of 13G

To a solution of 13F (6 g, 11.39 mmol, 1.0 eq) in dry THF (120 mL) was added $CH_2ICl$ (4.02 g, 22.77 mmol, 2.0 eq), followed by slow addition of n-BuLi (7.75 ml, 19.35 mmol, 1.7 eq) at −78° C. in 20 minutes under nitrogen atmosphere. The mixture was slowly warmed up to 0° C. in 12 hours. The reaction was monitored by TLC. The mixture was concentrated and the residue was purified by column chromatography on silica gel (PE:EA=200:1 to 10:1) to give 13G (3.67 g, 60%).

Step 7: Synthesis of 13H

A mixture of 13G (500 mg, 0.92 mmol, 1.0 eq), TMS-acetylene (2.27 g, 23.1 mmol, 25.0 eq), CuI (529 mg, 2.77 mmol, 3.0 eq) and DIPEA (1.08 g, 8.36 mmol, 9.0 eq) in THF (5 mL) was stirred at 80° C. for 12 hours under nitrogen atmosphere. The reaction was monitored by TLC. The resulting mixture was filtered and the filtrate was concentrated under reduced pressure. The residue was purified by column chromatography on silica gel (PE:EA=100:1 to 5:1) to give 13H (410 mg, 70%).

Step 8: Synthesis of 13I

To a solution of 13H (360 mg, 0.56 mmol, 1.0 eq) in THF (12 mL) was added TBAF (2.8 mL, 1M in THF, 2.8 mmol, 5.0 eq) under nitrogen atmosphere. After 2 hours at 50° C. reaction mixture was cooled down and concentrated. The residue was purified by column chromatography on silica gel (PE:EA=50:1 to 2:1) to give 13I (260 mg, 81%).

Step 9: Synthesis of 13

To the solution of 13I (50 mg, 0.08 mmol, 1.0 eq) in dioxane (1 mL) was added i-BuB(OH)$_2$ (23 mg, 0.22 mmol, 2.5 eq) and concentrated HCl (1 mL). The reaction mixture was stirred at rt for 1 hour. The reaction mixture was concentrated in vacuo, and the residue was dissolved in $H_2O$/MeCN. The resulting solution was adjusted to pH=12 and purified by prep-HPLC (18, neutral) to give 13 (10.4 mg, 46%) as white solid.

ESI-MS: [M+H]: 260.

$^1$H NMR (400 MHz, $D_2O$): δ 8.14 (s, 1H), 7.88 (s, 1H), 7.17 (d, J=8.8 Hz, 1H), 6.80 (d, J=7.6 Hz, 1H), 2.78-2.74 (m, 2H), 0.54 (d, J=7.2 Hz, 2H).

EXAMPLE 14

Disodium; 8-[4-(2-aminoethyl)triazol-1-yl]-4,4-dihydroxy-5-oxa-4-boranuidabicyclo[4.4.0]deca-1(6),7,9-triene-7-carboxylate

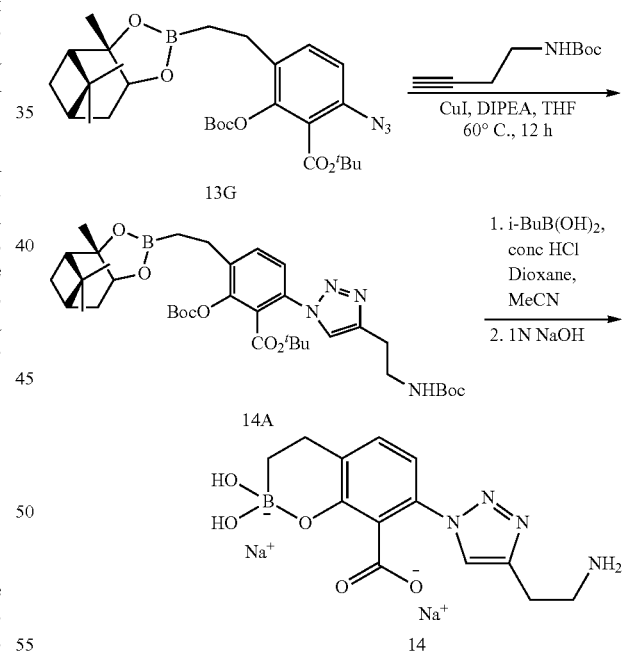

Step 1: Synthesis of 14A

To a solution of compound 13G (220 mg, 0.37 mmol, 1.0 eq) in THF (5 mL) was added tert-butyl but-3-yn-1-ylcarbamate (375 mg, 2.22 mmol, 6.0 eq), CuI (141 mg, 0.74 mmol, 2.0 eq) and DIPEA (287 mg, 2.22 mmol, 6.0 eq). The mixture was stirred at 60° C. for 12 hours under nitrogen atmosphere. The reaction was monitored by TLC. The mixture was filtered and concentrated. The residue was purified by column chromatography on silica gel (PE/EA=10:1 to 2:1) to give compound 14A (195 mg, 70%).

Step 2: Synthesis of 14

To the solution of 14A (250 mg, 0.35 mmol, 1.0 eq) in dioxane (3 mL) was added i-BuB(OH)$_2$ (90 mg, 0.88 mmol, 2.5 eq) and concentrated HCl (3 mL). The reaction mixture was stirred at rt for 1 hour. The reaction mixture was concentrated in vacuo, and the residue was dissolved in H$_2$O/MeCN. The resulting solution was adjusted to pH=12 and purified by prep-HPLC (18, neutral) to give 14 (10.4 mg, 46%) as white solid.

ESI-MS: [M+H]$^+$: 303.

$^1$H NMR (400 MHz, D$_2$O): δ 8.03 (s, 1H), 7.14 (d, J=7.6 Hz, 1H), 6.76 (d, J=7.6 Hz, 1H), 3.41-3.37 (m, 2H), 3.19-3.13 (m, 2H), 2.73 (d, J=6.0 Hz, 2H), 0.47 (d, J=5.2 Hz, 2H).

EXAMPLE 15

Disodium; 4,4-dihydroxy-8-(1H-pyrazol-5-yl)-5-oxa-4-boranuidabicyclo[4.4.0]deca-1(6),7,9-triene-7-carboxylate

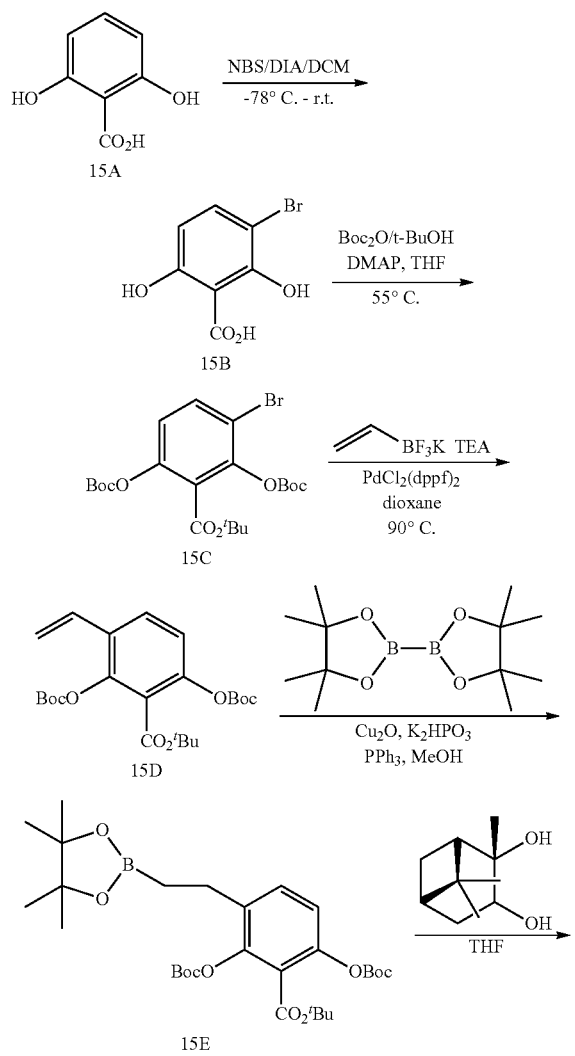

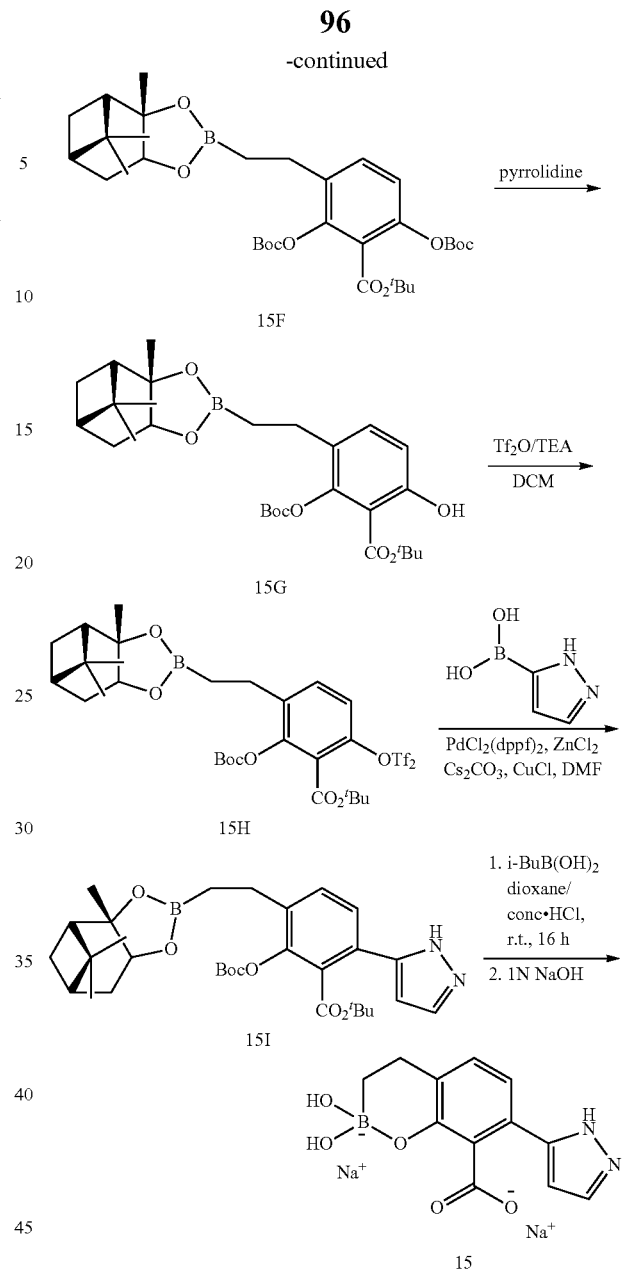

Step 1: Synthesis of 15B

To the solution of compound 15A (298 g, 1.93 mol, 1.0 eq) and DIA (98 g, 0.97 mol, 0.5 eq) in DCM (3.5 L) was added NBS (362 g, 2.03 mol, 1.05 eq) in small portions at −78° C. The mixture was slowly warmed to room temperature and stirred for 16 h as TLC monitoring showed the completion of reaction. The reaction mixture was evaporated to dryness, and the residue was stirred in 1 N HCl (2 L) 0.5 hour. The precipitate was filtrated to give compound 15B (370 g, 83%) as light yellow solid.

Step 2: Synthesis of 15C

A solution of compound 15B (370 g, 1.59 mol, 1.0 eq) in t-BuOH/THF (800 mL/1600 mL) was stirred at 55° C. for 10 minutes before Boc$_2$O (1750 g, 8.03 mol, 5.05 eq) and DMAP (155.2 g, 1.27 mol, 0.8 eq) were added in small portions. The mixture was stirred at 55° C. until compound 15B was fully consumed. The mixture was cooled to room temperature and more Boc$_2$O (693 g, 3.18 mol, 2 eq) and DMAP (155.2 g, 1.27 mol, 0.8 eq) were added. After 18 hours, the reaction mixture was concentrated to dryness in vacuo, purified by column chromatography to give compound 15C (700 g, 90%).

Step 3: Synthesis of 15D

The mixture of compound 15C (230 g, 0.47 mol, 1.0 eq), potassium vinyltrifluoroborate (126 g, 0.94 mol, 2.0 eq), TEA (143 g, 1.42 mol, 3.0 eq) and $PdCl_2(dppf)_2$ (20 g, 23.5 mmol, 0.05 eq) in dioxane (3.0 L) was stirred at 90° C. for 72 hours under $N_2$ atmosphere. Completion of the reaction was monitored by NMR. The mixture was concentrated and purified by column chromatography (eluted with PE) to give compound 15D (94 g, 46%).

Step 4: Synthesis of 15E

The mixture of compound 15D (94 g, 215.6 mmol, 1.0 eq), Bis(pinacolato)diboron (82 g, 323.4 mmol, 1.5 eq), $Cu_2O$ (1.54 g, 10.8 mmol, 0.05 eq), $K_2HPO_3$ (56.3 g, 323.4 mmol, 1.5 eq) and $PPh_3$ (2.82 g, 10.8 mmol, 0.05) in MeOH (1.2 L) was stirred at 50° C. for 16 hours. The reaction was monitored by HNMR. The reaction mixture was filtered, and the filtrated was concentrated in vacuo. The residue was purified by flash chromatography to give compound 15E (88.5 g, 73%).

ESI-MS: $[M+H]^+$: 565.

Step 5: Synthesis of 15F

The mixture of compound 15E (88.5 g, 157 mmol, 1.0 eq) and (+)-pinanediol (69.5 g, 0.409 mol, 2.61 eq) in THF (500 mL) was stirred at room temperature for 72 hours. The reaction mixture was concentrated in vacuo and the residue was purified by flash chromatography to give compound 15F (90 g, 100%).

ESI-MS: $[M+H]^+$: 617.

Step 6: Synthesis of 15G

A solution of compound 15F (100.6 g, 0.163 mol, 1.0 eq) in THF (500 mL) was added pyrrolidine (11.6 g, 14 mL, 0.163 mmol, 1.0 eq) at room temperature. The reaction mixture was stirred at 35° C. for 3 hours before it was concentrated in vacuo. The residue was purified by flash chromatography to give compound 15G (90 g, 98%).

ESI-MS: $[M+H]^+$: 517.

Step 7: Synthesis of 15H

To a solution of compound 15G (8.2 g, 15.9 mol, 1.0 eq) in DCM (50 mL) was added TEA (2.1 g, 20.8 mmol, 1.3 eq), followed by $Tf_2O$ (4.7 g, 16.7 mmol, 1.05 eq) dropwise at −78° C. The mixture was warmed to room temperature and stirred for 16 hours, LC-MS indicating the completion of reaction. The reaction solution was concentrated in vacuo, and the residue was stirred in 200 mL PE at room temperature for 0.5 hour. Then the solid was filtered off, and the PE layer was concentrated to give crude compound 15H (7.43 g, 72%) as yellow oil.

ESI-MS: [M+H]: 649.

Step 8: Synthesis of 151

The mixture of 3-pyrazoleboronic acid (155 mg, 1.39 mmol, 1.5 eq), $CuCl_2$ (9 mg, 0.091 mmol, 0.1 eq) and $ZnCl_2$ (126 mg, 0.926 mmol, 1.0 eq) in DMF (5 mL) was degassed and stirred at room temperature for 20 minutes. Then $Cs_2CO_3$ (603 mg, 1.85 mmol, 2.0 eq) and compound 15H (600 mg, 0.926 mmol, 1.0 eq) were added in sequence. The mixture was stirred for another 20 minutes before $PdCl_2$ $(dppf)_2$ (38 mg, 0.047 mmol, 0.05 eq) was added. The reaction mixture was degassed again and stirred at 85° C. for 20 hours. The reaction was monitored by LC-MS. After filtration through a short celite pad, the filtrate was concentrated and purified by flash chromatography (PE:EA=20:1 to 1:1) to give compound 151 (136 mg, 26%).

ESI-MS: [M+H]: 567.

Step 9: Synthesis of 15

To the solution of compound 151 (50 mg, 0.088 mmol, 1.0 eq) in dioxane (1 mL) was added $i-BuB(OH)_2$ (23 mg, 0.226 mmol, 2.5 eq), followed by concentrated HCl (1 mL). The reaction mixture was stirred at room temperature for 16 hours. The reaction was monitored by LC-MS. The reaction mixture was concentrated in vacuo, and the residue was dissolved in $H_2O/MeOH$. The resulting solution was adjusted to pH=12 and purified by prep-HPLC (18, neutral) to give 15 (9.0 mg, 35%) as white solid.

LC-MS: [M+1]=259

$^1H$ NMR (400 MHz, $D_2O$): δ 7.67 (s, 1H), 7.11 (d, J=7.6 Hz, 1H), 6.99 (d, J=6.4 Hz, 1H), 6.59 (s, 1H), 2.76-2.72 (m, 2H), 0.71 (m, 2H).

EXAMPLE 16

Disodium; 4,4-dihydroxy-8-(1H-triazol-5-yl)-5-oxa-4-boranuidabicyclo[4.4.0]deca-1(6),7,9-triene-7-carboxylate

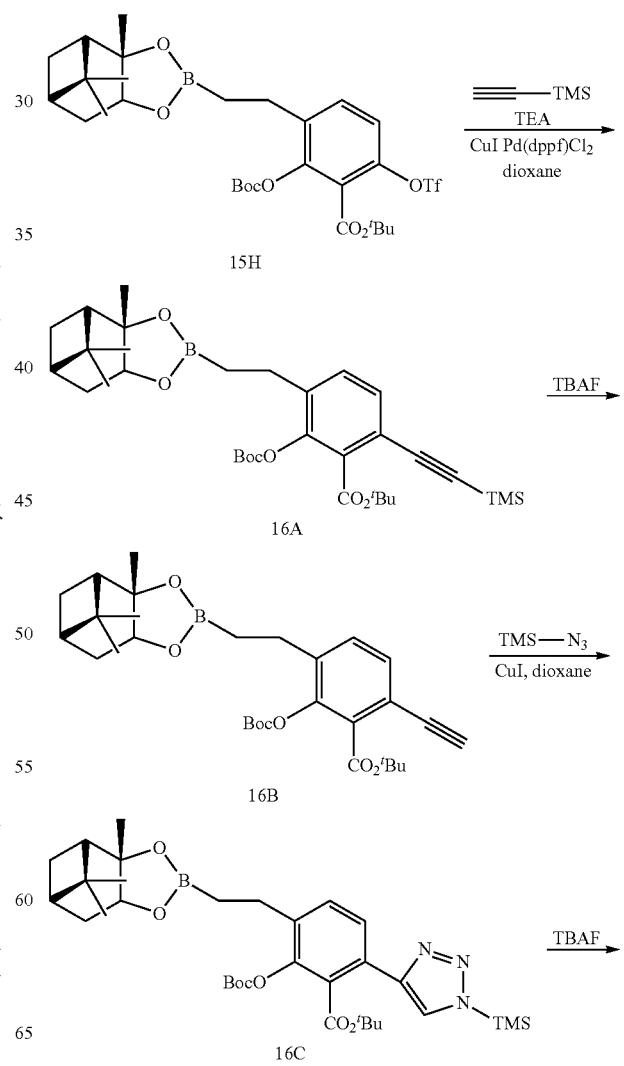

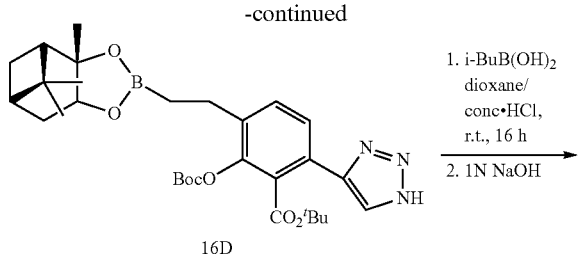

$^1$H NMR (400 MHz, CD$_3$OD): δ 8.01-7.99 (m, 1H), 7.02-6.98 (m, 2H), 2.72-2.65 (m, 2H), 1.31-1.25 (m, 2H).

EXAMPLE 17

Disodium; 8-[1-(2-aminoethyl)triazol-4-yl]-4,4-dihydroxy-5-oxa-4-boranuidabicyclo[4.4.0]deca-1(6),7,9-triene-7-carboxylate

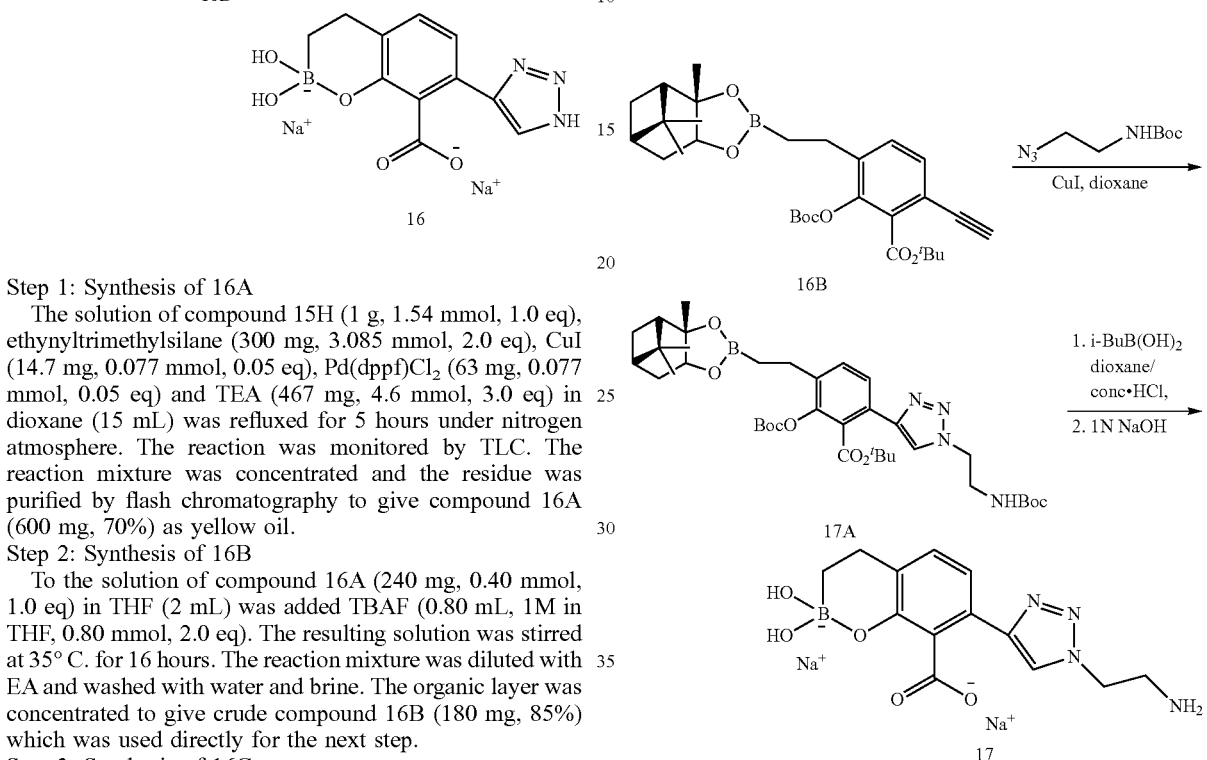

Step 1: Synthesis of 16A

The solution of compound 15H (1 g, 1.54 mmol, 1.0 eq), ethynyltrimethylsilane (300 mg, 3.085 mmol, 2.0 eq), CuI (14.7 mg, 0.077 mmol, 0.05 eq), Pd(dppf)Cl$_2$ (63 mg, 0.077 mmol, 0.05 eq) and TEA (467 mg, 4.6 mmol, 3.0 eq) in dioxane (15 mL) was refluxed for 5 hours under nitrogen atmosphere. The reaction was monitored by TLC. The reaction mixture was concentrated and the residue was purified by flash chromatography to give compound 16A (600 mg, 70%) as yellow oil.

Step 2: Synthesis of 16B

To the solution of compound 16A (240 mg, 0.40 mmol, 1.0 eq) in THF (2 mL) was added TBAF (0.80 mL, 1M in THF, 0.80 mmol, 2.0 eq). The resulting solution was stirred at 35° C. for 16 hours. The reaction mixture was diluted with EA and washed with water and brine. The organic layer was concentrated to give crude compound 16B (180 mg, 85%) which was used directly for the next step.

Step 3: Synthesis of 16C

The mixture of compound 16B (180 mg, 0.34 mmol, 1.0 eq), TMS-N$_3$ (1.18 g, 10.2 mmol, 30 eq) and CuI (195 mg, 1.02 mmol, 3.0 eq) in dioxane (2 mL) was stirred at 80° C. for 16 hours under nitrogen atmosphere. The reaction was monitored by LC-MS. After cooled to room temperature, the reaction mixture was filtrated through silica gel pad and washed with EA. The filtrate was concentrated to give crude compound 16C (200 mg, 91%) which was used directly for the next step.

Step 4: Synthesis of 16D

To the solution of compound 16C (200 mg, 0.31 mmol, 1.0 eq) in THF (2 mL) was added TBAF (0.62 mL, 1 M in THF, 0.62 mmol, 2.0 eq). The resulting solution was stirred at 35° C. for 16 hours. The reaction mixture was monitored by LC-MS. The reaction mixture was diluted with EA and washed with water and brine. The organic layer was concentrated to give crude compound 16D (150 mg, 85%) which was used directly for next step.

Step 5: Synthesis of 16

To the solution of 16D (150 mg, 0.26 mmol, 1.0 eq) in dioxane (3 mL) was added i-BuB(OH)$_2$ (54 mg, 0.53 mmol, 2.0 eq) and concentrated HCl (3 mL). The reaction mixture was stirred at rt for 16 hours. The reaction mixture was concentrated in vacuo, and the residue was dissolved in H$_2$O/MeOH. The resulting solution was adjusted to pH=12 and purified by prep-HPLC (18, neutral) to give 16 (33 mg, 48%) as white solid.

ESI-MS: [M+H]: 260.

Step 1: Synthesis of 17A

A mixture of compound 16B (180 mg, 0.34 mmol, 1.0 eq), N-Boc-2-azido-ethylamine (127 mg, 0.68 mmol, 2.0 eq) and CuI (65 mg, 0.34 mmol, 1.0 eq) in dioxane (2 mL) was stirred at 80° C. for 4 hours under nitrogen atmosphere. The reaction was monitored by LC-MS. After cooled to room temperature, the reaction mixture was filtrated through silica gel pad and washed with EA. The filtrate was concentrated to give crude compound 17A (200 mg, 82%) which was used directly for the next step.

ESI-MS: [M+H]$^+$: 711.

Step 2: Synthesis of 17

To the solution of 17A (200 mg, 0.28 mmol, 1.0 eq) in dioxane (3 mL) was added i-BuB(OH)$_2$ (62 mg, 0.56 mmol, 2.0 eq) and concentrated HCl (3 mL). The reaction mixture was stirred at rt for 16 hours. The reaction mixture was concentrated in vacuo, and the residue was dissolved in H$_2$O/MeOH. The resulting solution was adjusted to pH=12 and purified by prep-HPLC (18, neutral) to give 17 (31 mg, 36%) as white solid.

ESI-MS: [M+H]$^+$: 303.

$^1$H NMR (400 MHz, CD$_3$OD): δ 8.12 (s, 1H), 7.13 (d, J=8.0 Hz, 1H), 6.94 (d, J=8.0 Hz, 1H), 4.50-4.46 (m, 2H), 3.40 (d, J=1.2 Hz, 1H), 3.21-3.19 (m, 1H), 2.71-2.67 (m, 2H), 0.63 (d, J=6.4 Hz, 2H).

EXAMPLE 18

Disodium; 8-ethynyl-4,4-dihydroxy-5-oxa-4-boranuidabicyclo[4.4.0]deca-1(6),7,9-triene-7-carboxylate

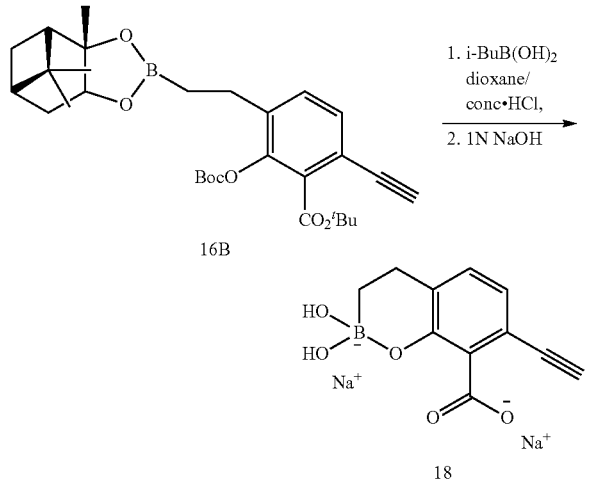

To the solution of 16B (140 mg, 0.27 mmol, 1.0 eq) in dioxane (3 mL) was added i-BuB(OH)$_2$ (58 mg, 0.54 mmol, 2.0 eq) and concentrated HCl (3 mL). The reaction mixture was stirred at rt for 16 hours. The reaction mixture was concentrated in vacuo, and the residue was dissolved in H$_2$O/MeOH. The resulting solution was adjusted to pH=12 and purified by prep-HPLC (18, neutral) to give 18 (8 mg, 13%) as white solid.

ESI-MS: [M+H]$^+$: 217.

$^1$H NMR (400 MHz, CD$_3$OD): δ 6.99 (d, J=7.6 Hz, 1H), 6.87 (d, J=7.6 Hz, 1H), 2.68-2.64 (m, 2H), 2.51 (s, 1H), 0.47-0.42 (m, 2H).

EXAMPLE 19

Disodium; 8-(azetidin-3-ylsulfanylmethyl)-4,4-dihydroxy-5-oxa-4-boranuidabicyclo[4.4.0]deca-1(6),7,9-triene-7-carboxylate

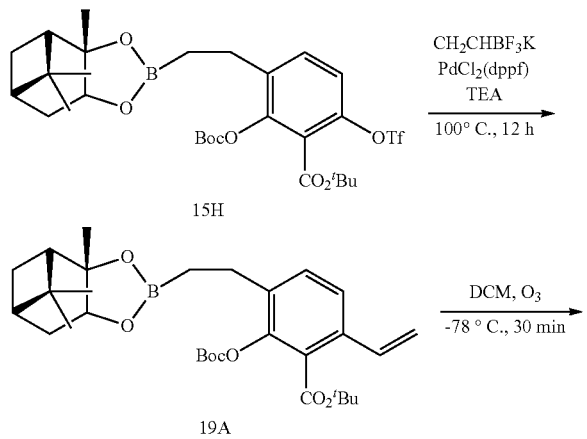

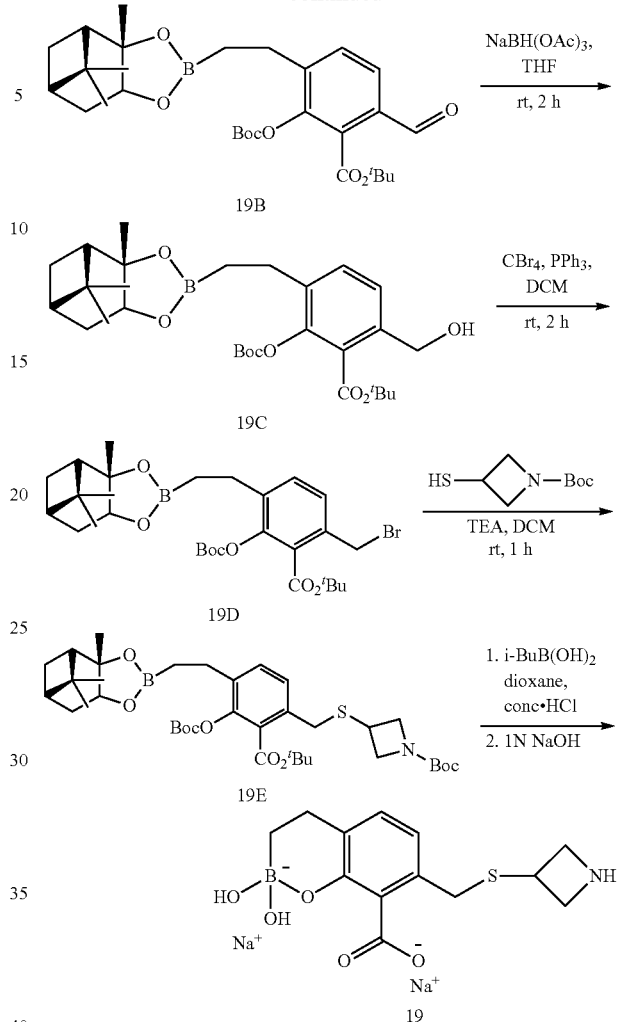

Step 1: Synthesis of 19A

To a solution of 15H (7.0 g, 10.8 mmol, 1.0 eq) in dioxane (100 mL) was added CH$_2$CHBF$_3$K (7.74 g, 12.96 mmol, 1.2 eq), PdCl$_2$(dppf) (790 mg, 1.08 mmol, 0.1 eq) and TEA (3.72 g, 32.4 mmol, 3.0 eq). The mixture was flushed with nitrogen and stirred at 100° C. for 12 hours. The resulting mixture was cooled down to room temperature and filtered. The filtrated was concentrated and the residue was purified by column chromatography on silica gel (PE/EA=10:1) to give 19A (4 g, 62%) as yellow oil.

Step 2: Synthesis of 19B

A solution of 19A (3 g, 5.7 mmol, 1.0 eq) in dichloromethane (30 mL) was bubbled with O3 at −78° C. until the color of the solution turned to light blue. Nitrogen gas was then bubbled and Me$_2$S (5 mL) was added. The solution was slowly warmed up to room temperature over 8 h and was concentrated under reduced pressure. The residue was purified by column chromatography on silica gel (PE/EA=10:1) to give 19B (1.7 g, 45%) as yellow solid.

Step 3: Synthesis of 19C

To a solution of 19B (1.7 g, 3.21 mmol, 1.0 eq) in THF (15 mL) was added NaBH(OAc)$_3$ (1.7 g, 8 mmol, 2.5 eq) at 0° C. The mixture slowly warmed up to room temperature in 2 hours before it was concentrated in vacuo. The residue was purified by column chromatography on silica gel (PE/EA=5:1) to give 19C (1.2 g, 86%) as yellow solid.

Step 4: Synthesis of 19D

To a solution of 19C (1.2 g, 2.26 mmol, 1.0 eq) in DCM (20 mL) was added CBr4 (1.1 g, 3.39 mmol, 1.5 eq) and PPh$_3$ (8.9 mg, 3.39 mmol, 1.5 eq). The mixture was stirred at room temperature for 2 hours and was concentrated in vacuo. The residue was purified by column chromatography on silica gel (PE/EA=5:1) to give 19D (450 mg, 48%) as yellow solid.

Step 5: Synthesis of 19E

To a solution of 19D (150 mg, 0.25 mmol, 1.0 eq) in DCM (5 mL) was added 1-Boc-3-mercapto-azetidine (52 mg, 0.27 mmol, 1.1 eq) and TEA (50.6 mg, 0.5 mmol, 2.0 eq). The mixture was stirred at room temperature for 1 hour. The reaction mixture was concentrated in vacuo and the residue was purified by prep-TLC (PE/EA=4:1) to give 19E (120 mg, 83%) as yellow solid.

Step 6: Synthesis of 19

To the solution of 19E (120 mg, 0.17 mmol, 1.0 eq) in dioxane (2 mL) was added i-BuB(OH)$_2$ (35 mg, 0.34 mmol, 2.0 eq) and concentrated HCl (2 mL). The reaction mixture was stirred at rt for 2 hours. The reaction mixture was concentrated in vacuo, and the residue was dissolved in H$_2$O/MeCN. The resulting solution was adjusted to pH=12 and purified by prep-HPLC (18, neutral) to give 19 (11 mg, 21%) as white solid.

ESI-MS: [M+H]$^+$: 294.

$^1$H NMR (400 MHz, CD$_3$OD/D$_2$O): δ 6.78 (d, J=7.6 Hz, 1H), 6.57 (d, J=7.2 Hz, 1H), 3.92 (s, 2H), 3.80 (s, 2H), 3.69-3.67 (m, 1H), 3.60-3.58 (m, 2H), 2.52-2.50 (m, 2H), 0.4-0.38 (m, 2H).

EXAMPLE 20

Disodium; 4,4-dihydroxy-8-(1,3,4-thiadiazol-2-yl-sulfanylmethyl)-5-oxa-4-boranuidabicyclo[4.4.0]deca-1(6),7,9-triene-7-carboxylate

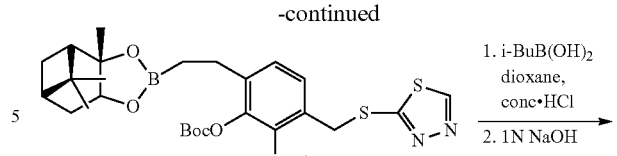

Step 1: Synthesis of 20A

To a solution of 19D (180 mg, 0.3 mmol, 1.0 eq) in DCM (2 mL) was added 2-mercapitothiadiazole (44 mg, 0.36 mmol, 1.2 eq) and TEA (61 mg, 0.6 mmol, 2.0 eq). The mixture was stirred at room temperature for 1 h before it was concentrated in vacuo. The residue was purified by prep-TLC (PE/EA=2:1) to give 20A (150 mg, 78%) as yellow solid.

Step 2: Synthesis of 20

To the solution of 20A (150 mg, 0.24 mmol, 1.0 eq) in dioxane (2 mL) was added i-BuB(OH)$_2$ (50 mg, 0.48 mmol, 2.0 eq) and concentrated HCl (2 mL). The reaction mixture was stirred at rt for 1 hour. The reaction mixture was concentrated in vacuo, and the residue was dissolved in H$_2$O/MeCN. The resulting solution was adjusted to pH=12 and purified by prep-HPLC (18, neutral) to give 20 (60 mg, 58%) as white solid.

ESI-MS: [M+H]$^+$: 323.

$^1$H NMR (400 MHz, CD$_3$OD/D$_2$O): δ 9.30 (s, 1H), 6.75 (d, J=4.4 Hz, 1H), 6.59 (d, J=7.6 Hz, 1H), 4.51 (s, 2H), 2.57 (s, 2H), 0.43 (s, 2H).

EXAMPLE 21

Disodium; 8-(3-aminopropylsulfanylmethyl)-4,4-dihydroxy-5-oxa-4-boranuidabicyclo[4.4.0]deca-1(6),7,9-triene-7-carboxylate

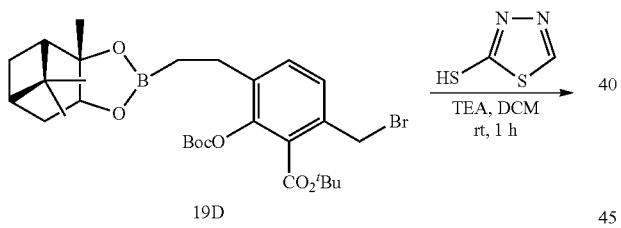

-continued

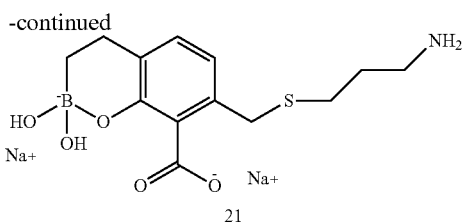

21

Step 1: Synthesis of 21A

To a solution of 19D (120 mg, 0.2 mmol, 1.0 eq) in DCM (3 mL) was added 3-aminopropane-1-thiol (31 mg, 0.24 mmol, 1.2 eq) and TEA (42 mg, 0.4 mmol, 2.0 eq). The reaction mixture was stirred at room temperature for 2 hours before it was concentrated in vacuo. The residue was purified by prep-TLC (PE/EA=4:1) to give 21A (100 mg, 76%) as light yellow oil.

Step 2: Synthesis of 21

To a solution of 21A (100 mg, 0.16 mmol, 1.0 eq) in dioxane (2 mL) was added i-BuB(OH)$_2$ (33 mg, 0.32 mmol, 2.0 eq) and concentrated HCl (2 mL). The mixture was stirred at room temperature for 2 hours. The reaction mixture was concentrated in vacuo, and the residue was dissolved in H$_2$O/MeCN. The resulting solution was adjusted to pH=12 and purified by prep-HPLC (18, neutral) to give 21 (26 mg, 32%) as white solid.

ESI-MS: [M+H]$^+$: 296.

$^1$H NMR (400 MHz, CD$_3$OD/D$_2$O): δ 6.89 (m, 1H), 6.75-6.68 (m, 1H), 3.96 (s, 2H), 2.86-2.80 (m, 2H), 2.67-2.62 (m, 2H), 2.59-2.55 (m, 2H), 1.88 (s, 2H), 1.33-1.26 (m, 2H).

EXAMPLE 22

Disodium; 8-[(5-amino-1,3,4-thiadiazol-2-yl)sulfanylmethyl]-4,4-dihydroxy-5-oxa-4-boranuidabicyclo[4.4.0]deca-1(6),7,9-triene-7-carboxylate

Step 1: Synthesis of 22A

To a solution of 19D (160 mg, 0.37 mmol, 1.0 eq) in DCM (20 mL) was added 2-amino-5-mercaptothiadiazole (45 mg, 0.52 mmol, 2.0 eq), TEA (61 mg, 0.52 mmol, 2.0 eq) and DMF (5 mL). The mixture was stirred at room temperature for 1 hour. The mixture was then partitioned in H$_2$O and DCM. The organic layer was washed with water and brine, dried over Na$_2$SO$_4$. After concentration under reduced pressure, crude 22A (240 mg) was obtained as yellow oil.

Step 2: Synthesis of 22

To a solution of 22A (240 mg, 0.37 mmol, 1.0 eq) in dioxane (5 mL) was added i-BuB(OH)$_2$ (77 mg, 0.74 mmol, 2.0 eq) and conc.HCl (5 mL). The mixture was stirred at room temperature for 2 hours. The reaction mixture was concentrated in vacuo, and the residue was dissolved in H$_2$O/MeCN. The resulting solution was adjusted to pH=12 and purified by prep-HPLC (18, neutral) to give 22 (70 mg, 30%) as white solid.

ESI-MS: [M+H]$^+$: 338.

$^1$H NMR (400 MHz, CD$_3$OD/D$_2$O): δ 7.00 (d, J=7.6 Hz, 1H), 6.57 (d, J=8.0 Hz, 1H), 4.79 (s, 2H), 2.67-2.62 (m, 2H), 1.29-1.25 (m, 2H).

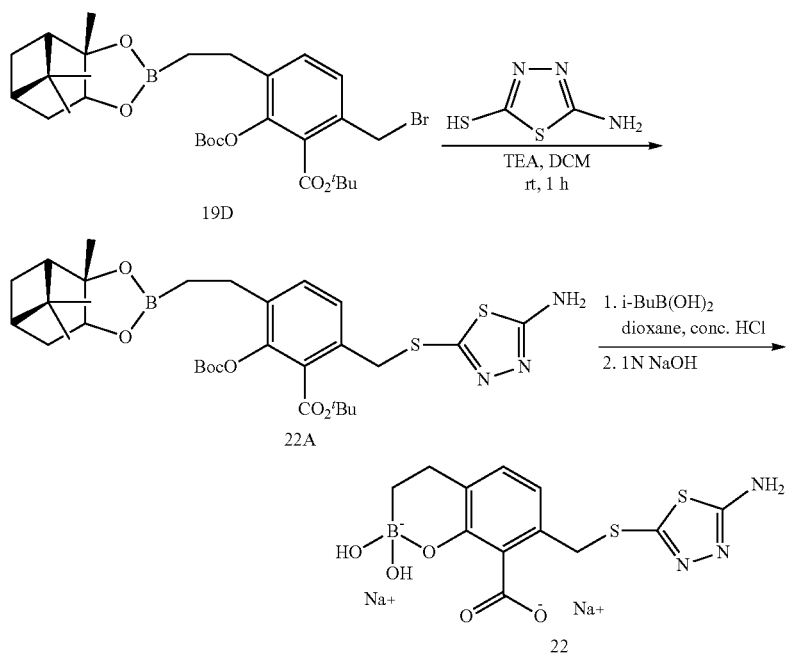

EXAMPLE 23

Disodium; 8-[[1-(2-aminoethyl)triazol-4-yl]methoxy]-4,4-dihydroxy-5-oxa-4-boranuidabicyclo[4.4.0]deca-1(6),7,9-triene-7-carboxylate

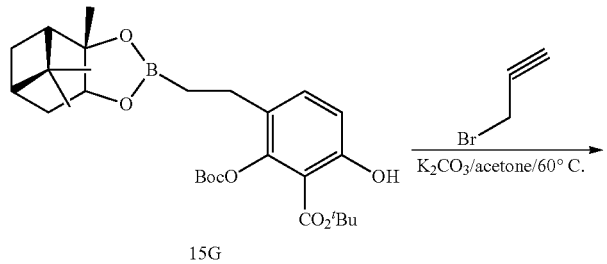

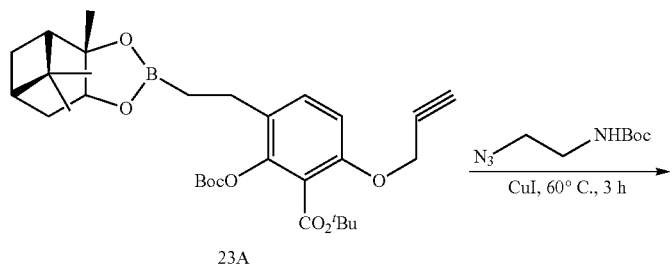

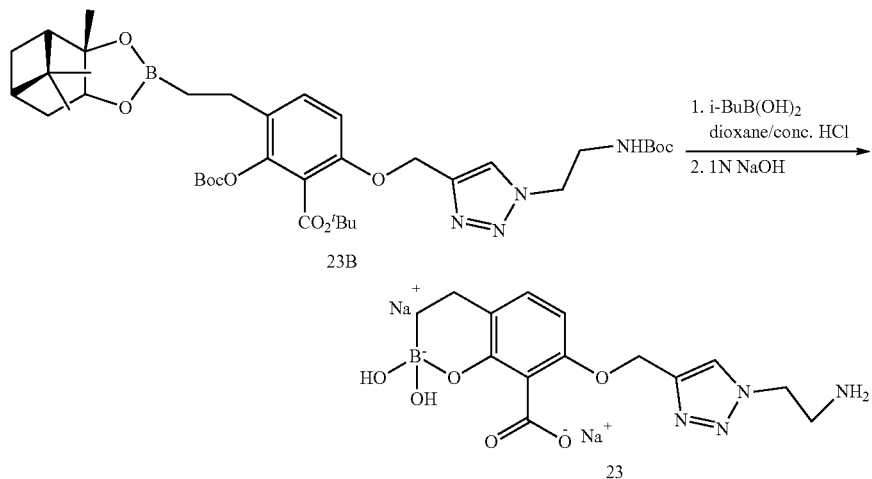

Step 1: Synthesis of 23A

The mixture of 19D (1.2 g, 2.33 mmol, 1.0 eq) and $K_2CO_3$ (0.963 g, 6.98 mmol, 3.0 eq) in acetone (10 mL) was stirred at room temperature for 10 minutes, followed by the addition of propargylbromide (0.83 g, 6.98 mmol, 3.0 eq). The resulting mixture was stirred at 60° C. for 40 hours. The reaction was monitored by LC-MS. After filtration through a short celite pad, the filtrate was concentrated under reduced pressure and the residue was purified by flash chromatography on silica (PE/EA=50:1 to 5:1) to give 23A (0.78 g, 60%).

Step 2: Synthesis of 23B

To a solution of 23A (100 mg, 0.181 mmol, 1.0 eq) in dioxane (2 mL) was added 2-azido-N-Bocethylamine (40 mg, 0.215 mmol, 1.2 eq) and CuI (70 mg, 0.362 mmol, 2.0 eq). The mixture was stirred at 60° C. for 3 hours under nitrogen atmosphere in a sealed tube. The reaction was monitored by LC-MS. After filtration and concentration, the crude residue was purified by prep-TLC (PE/EA=1:1) to give 23B (125 mg, 93%).

Step 3: Synthesis of 23

To a solution of 23B (100 mg, 0.18 mmol, 1.0 eq) in dioxane (3 mL) was added i-BuB(OH)$_2$ (37 mg, 0.36 mmol, 2.0 eq) and concentrated HCl (3 mL). The reaction mixture was stirred at room temperature for 16 hours. The reaction mixture was concentrated in vacuo, and the residue was dissolved in $H_2O$/MeOH. The resulting solution was adjusted to pH=12 and purified by prep-HPLC (18, neutral) to give 23 (14.2 mg, 32%).

ESI-MS: [M+H]$^+$: 333.

$^1$H NMR (400 MHz, $D_2O$): δ 8.06 (s, 1H), 7.08 (d, J=8.8 Hz, 1H), 6.65 (d, J=6.8 Hz, 1H), 5.29-5.22 (m, 2H), 4.74-4.62 (m, 2H), 3.80-3.25 (m, 2H), 2.69-2.64 (m, 2H), 0.93-0.73 (m, 2H).

EXAMPLE 24

Disodium; 4,4-dihydroxy-8-(1H-triazol-4-yl-methoxy)-5-oxa-4-boranuidabicyclo[4.4.0]deca-1(6),7,9-triene-7-carboxylate

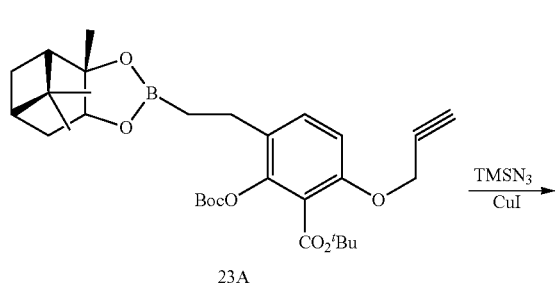

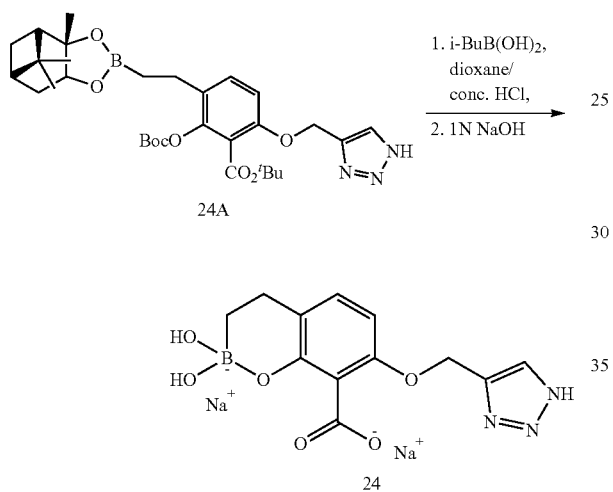

Step 1: Synthesis of 24A

To a solution of 23A (154 mg, 0.278 mmol, 1.0 eq) in dioxane (1.5 mL) were added TMSN$_3$ (560 mg, 4.86 mmol, 25.0 eq) and CuI (360 mg, 1.89 mmol, 10.0 eq). The reaction mixture was stirred at 80° C. for 48 h. The reaction was monitored by LC-MS. After filtration and concentration in vacuo to remove the excessive TMSN$_3$, the crude product 24A (175 mg, 94%) was obtained, which was used directly for the next step.

Step 2: Synthesis of 24

To a solution of 24A (170 mg, 0.285 mmol, 1.0 eq) in dioxane (1.0 mL) was added i-BuB(OH)$_2$ (73 mg, 0.713 mmol, 2.5 eq) and concentrated HCl (1.0 mL). The reaction mixture was stirred at room temperature for 16 hours. The reaction was monitored by LC-MS. The reaction mixture was concentrated in vacuo, and the residue was dissolved in H$_2$O/MeOH. The resulting solution was adjusted to pH=9 and purified by prep-HPLC (18, neutral) to give 24 (13.8 mg, 22%).

ESI-MS: [M+H]$^+$: 290.

$^1$H NMR (400 MHz, D$_2$O): δ 7.89 (s, 1H), 6.89 (d, J=7.6 Hz, 1H), 6.38 (d, J=8.4 Hz, 1H), 5.21 (s, 2H), 2.58-2.55 (m, 2H), 0.41 (t, J=6.8 Hz, 2H).

EXAMPLE 25

2-Hydroxy-7-prop-2-ynoxy-3,4-dihydro-1,2-benzoxaborinine-8-carboxylic acid

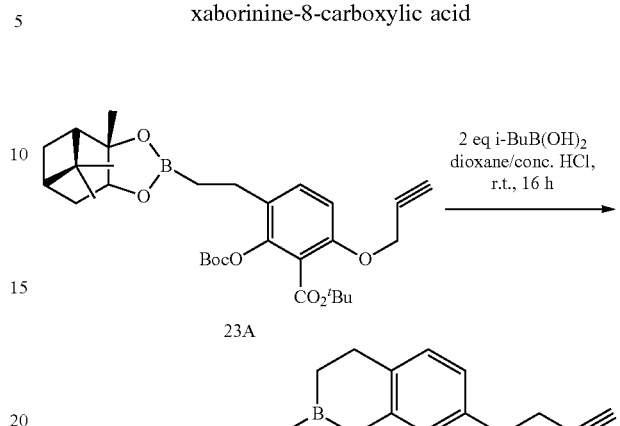

Step 1: Synthesis 25

To a solution of 23A (100 mg, 0.18 mmol, 1.0 eq) in dioxane (3 mL) was added i-BuB(OH)$_2$ (37 mg, 0.36 mmol, 2.0 eq) and concentrated HCl (3 mL). The reaction mixture was stirred at rt for 16 hours. The reaction was monitored by LC-MS. The reaction mixture was concentrated in vacuo, and the residue was purified by prep-HPLC (18, 0.1% HCOOH as buffer) to give 25 (14.2 mg, 32%).

ESI-MS: [M+H]$^+$: 247.

$^1$H NMR (400 MHz, CD$_3$OD): δ 7.19 (d, J=8.0 Hz, 1H), 6.70 (d, J=8.0 Hz, 1H), 4.80 (s, 2H), 2.99 (s, 1H), 2.69 (t, J=7.2 Hz, 2H), 1.06 (t, J=8.0 Hz, 2H).

EXAMPLE 26

7-(1,3-Dioxolan-2-ylmethoxy)-2-hydroxy-3,4-dihydro-1,2-benzoxaborinine-8-carboxylic acid

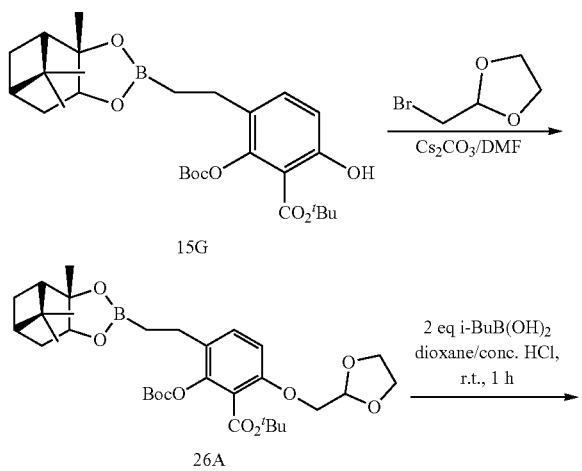

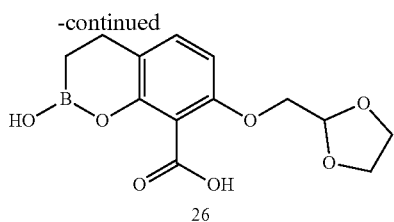

Step 1: Synthesis of 26A

A mixture of compound 15G (800 mg, 1.55 mmol, 1.0 eq), 2-(bromomethyl)-1,3-dioxolane (780 mg, 4.65 mmol, 3.0 eq) and $Cs_2CO_3$ (2.5 g, 7.75 mmol, 5.0 eq) in anhydrous DMF (40 mL) was stirred at room temperature overnight. The mixture was filtered and concentrated in vacuo. The residue was purified by column chromatography (PE/EA=10:1) to give compound 26A (140 mg, 16.4%).

Step 2: Synthesis of 26

To a solution of compound 26A (140 mg) in dioxane (4 mL) and hydrochloric acid (1 mL) was added i-BuB(OH)$_2$ (50 mg, 0.46 mmol, 2 eq). The mixture was stirred at room temperature for 1 hour and was directly purified by prep-HPLC to give 26 (14 mg, 9%) as white solid.

ESI-MS: [M+H]$^+$: 295.

H NMR (D$_2$O, 400 MHz): δ7.235-7.241 (m, 1H), 6.594-6.615 (d, J=8.4, 1H), 5.252 (m, 1H), 4.764-4.863 (m, 2H), 4.148-4.165 (m, 2H), 3.936-3.941 (m, 2H), 2.668-2.701 (m, 2H), 1.040-1.078 (m, 2H).

EXAMPLE 27

Disodium; 4,4-dihydroxy-8-(2-morpholinoethoxy)-5-oxa-4-boranuidabicyclo[4.4.0]deca-1(6),7,9-triene-7-carboxylate

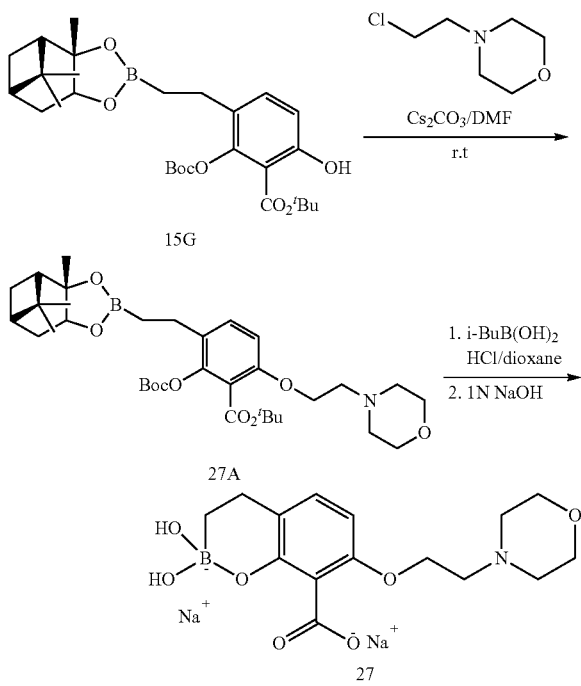

Step 1: Synthesis of 27A

A solution compound 15G (600 mg, 1.163 mmol, 1.0 eq), 4-(2-chloroethyl)morpholine hydrochloride (649 mg, 3.489 mmol, 3.0 eq) and $Cs_2CO_3$ (1.9 g, 5.8 mmol, 5.0 eq) in anhydrous DMF (12 mL) was stirred at room temperature overnight. The solvent was removed under reduced pressure and the residue was purified by column chromatography (PE/EA=10:1) to give compound 27A (120 mg, 16.4%) as yellow oil.

Step 2: Synthesis of 27

To a solution of compound 27A (120 mg) in dioxane (2 mL) and hydrochloric acid (2 mL) was added i-BuB(OH)$_2$ (38.4 mg, 0.38 mmol, 2 eq). The mixture was stirred at room temperature for 1 hour before it was concentrated under reduced pressure. The residue was dissolved in H$_2$O/MeOH. The resulting solution was adjusted to pH=12 and purified by prep-HPLC (18, neutral) to give 27 (54 mg, 9%) as white solid.

ESI-MS: [M+H]$^+$: 322.

$^1$H NMR (D$_2$O, 400 MHz): δ6.907-6.929 (d, J=8.8, 1H), 6.336-6.357 (d, J=8.4, 1H), 4.151-4.175 (m, 2H), 3.790-3.813 (m, 4H), 2.924-2.949 (m, 2H), 2.790-2.798 (m, 4H), 2.573-2.607 (m, 2H), 0.391-0.425 (m, 2H).

EXAMPLE 28

Disodium; 4,4-dihydroxy-8-(4-pyridylmethoxy)-5-oxa-4-boranuidabicyclo[4.4.0]deca-1(6),7,9-triene-7-carboxylate

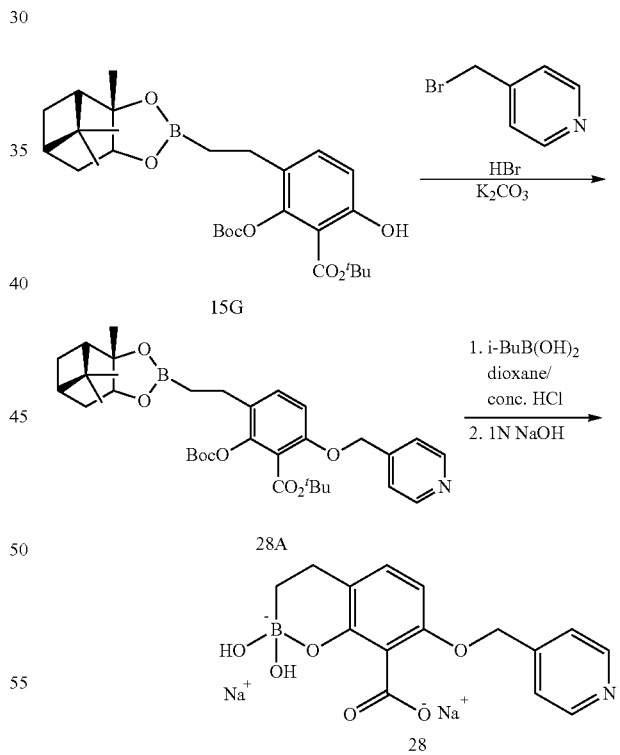

Step 1: Synthesis of 28A

The mixture of 15G (350 mg, 0.678 mmol, 1.0 eq) and K$_2$CO$_3$ (562 mg, 4.07 mmol, 6.0 eq) in DMF (5 mL) was stirred at room temperature for 10 minutes, followed by the addition of 4-(bromomethyl)pyridine hydrobromide (515 mg, 2.04 mmol, 3.0 eq). The resulting mixture was stirred at room temperature for 16 hours. The reaction was monitored by LC-MS. After filtration through a short celite pad, the filtrate was concentrated under reduced pressure and the residue was purified by flash chromatography on silica (PE/EA=10:1-0:1) to give compound 28A (100 mg, 24%).
Step 2: Synthesis of 28

To a solution of 28A (60 mg, 0.099 mmol, 1.0 eq) in dioxane (2 mL) was added i-BuB(OH)$_2$ (25 mg, 0.247 mmol, 2.5 eq) and concentrated HCl (2 mL). The mixture was stirred at rt for 3 hours. The reaction mixture was concentrated in vacuo, and the residue was dissolved in H$_2$O/MeOH. The resulting solution was adjusted to pH=8 and purified by prep-HPLC (18, neutral) to give 28 (5 mg, 20%) as white solid.

ESI-MS: [M+H]$^+$: 300.

$^1$H NMR (400 MHz, D$_2$O): δ 8.47 (s, 2H), 7.49 (s, 2H), 6.84 (s, 1H), 6.28 (d, J=8.0 Hz, 1H), 5.17 (s, 2H), 2.57 (s, 2H), 0.41 (s, 2H).

EXAMPLE 29

Disodium; 8-(2,2-difluoroethoxy)-4,4-dihydroxy-5-oxa-4-boranuidabicyclo[4.4.0]deca-1(6),7,9-triene-7-carboxylate

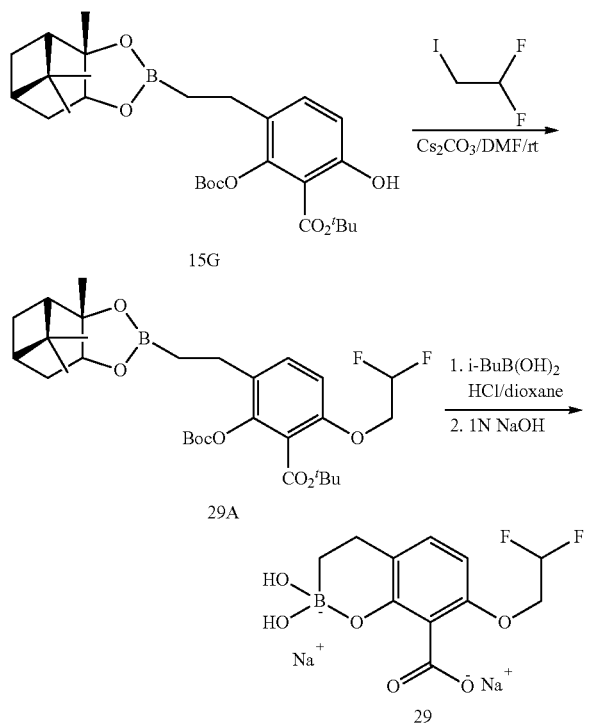

Step 1: Synthesis 29A

A mixture of compound 15G (500 mg, 0.968 mmol, 1.0 eq), 1,1-difluoro-2-iodoethane (278.8 mg, 1.452 mmol, 1.5 eq) and Cs$_2$CO$_3$ (946 mg, 2.90 mmol, 3.0 eq) in DMF (5 mL) was stirred at room temperature for 2 hours. The reaction was monitored by LC-MS. After filtration through a short celite pad, the filtrate was concentrated under reduced pressure and the residue was purified by prep-TLC (PE/EA=10:1) to give compound 29A (160 mg, 28%).
Step 2: Synthesis 29

To a solution of 29A (150 mg, 0.259 mmol, 1.0 eq) in dioxane (1 mL) was added i-BuB(OH)$_2$ (52.4 mg, 0.518 mmol, 2.0 eq) and concentrated HCl (1 mL). The reaction mixture was stirred at room temperature for 24 hours. The reaction mixture was concentrated in vacuo, and the residue was dissolved in H$_2$O/MeCN. The resulting solution was adjusted to pH=12 and purified by prep-HPLC (18, neutral) to give 29 (55 mg, 72%).

ESI-MS: [M+H]: 273.

$^1$H NMR (400 MHz, CD$_3$OD/DMSO): δ 6.89 (d, J=8.0 Hz, 1H), 6.38-6.30 (m, 1H), 6.17-6.15 (m, 1H), 4.24-4.17 (m, 2H), 3.32-3.29 (m, 2H), 0.53-0.49 (m, 2H).

EXAMPLE 30

Disodium; 4,4-dihydroxy-8-(4-hydroxybut-2-ynoxy)-5-oxa-4-boranuidabicyclo[4.4.0]deca-1(6),7,9-triene-7-carboxylate

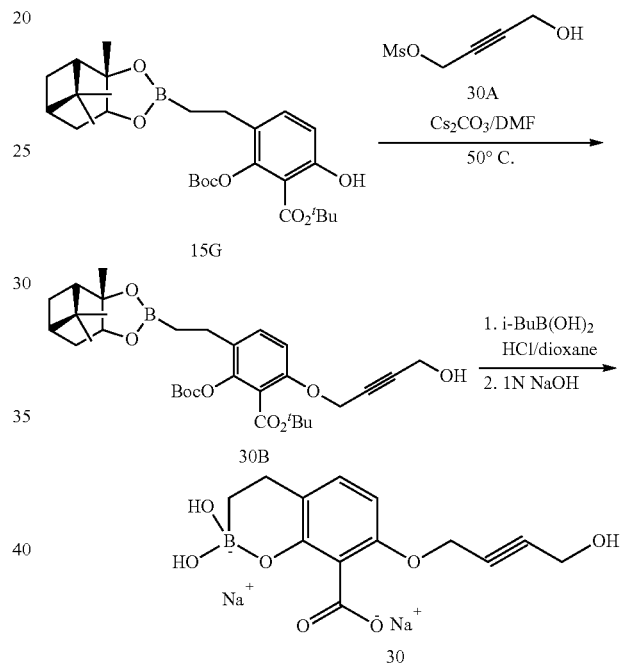

Step 1: Synthesis of 30B

A mixture of Compound 15G (500 mg, 0.969 mmol, 1.0 eq), compound 30A (*J. Med. Chem.*, 1994, 37, 3739-48) (238 mg, 1.45 mmol, 1.5 eq) and Cs$_2$CO$_3$ (948 mg, 2.91 mmol, 3.0 eq) in DMF (8 mL) was stirred at 50° C. for 12 hours. The reaction was monitored by LC-MS. After filtration through a short celite pad, the filtrate was concentrated under reduced pressure and the residue was purified by prep-TLC (PE/EA=5:1) to give compound 30B (58 mg, 10%).

Step 2: Synthesis of 30

To a solution of compound 30B (58 mg, 0.099 mmol, 1.0 eq) in dioxane (1 mL) was added i-BuB(OH)$_2$ (20 mg, 0.198 mmol, 2.0 eq) and concentrated HCl (1 mL). The reaction mixture was stirred at rt for 30 minutes. The reaction mixture was concentrated in vacuo, and the residue was dissolved in H$_2$O/MeCN. The resulting solution was adjusted to pH=12 and purified by prep-HPLC (18, neutral) to give compound 30 (24 mg, 81%).

ESI-MS: [M+H]$^+$: 277.

¹H NMR (400 MHz, CD₃OD): δ 6.72 (d, J=8.0 Hz, 1H), 6.29 (d, J=8.4 Hz, 1H), 4.64-4.60 (m, 2H), 4.22-4.16 (m, 2H), 3.71-3.67 (m, 1H), 3.62-3.56 (m, 1H), 2.53 (s, 1H), 0.42 (s, 2H).

EXAMPLE 31

Disodium; 4,4-dihydroxy-8-(4-methoxybut-2-ynoxy)-5-oxa-4-boranuidabicyclo[4.4.0]deca-1(6),7,9-triene-7-carboxylate

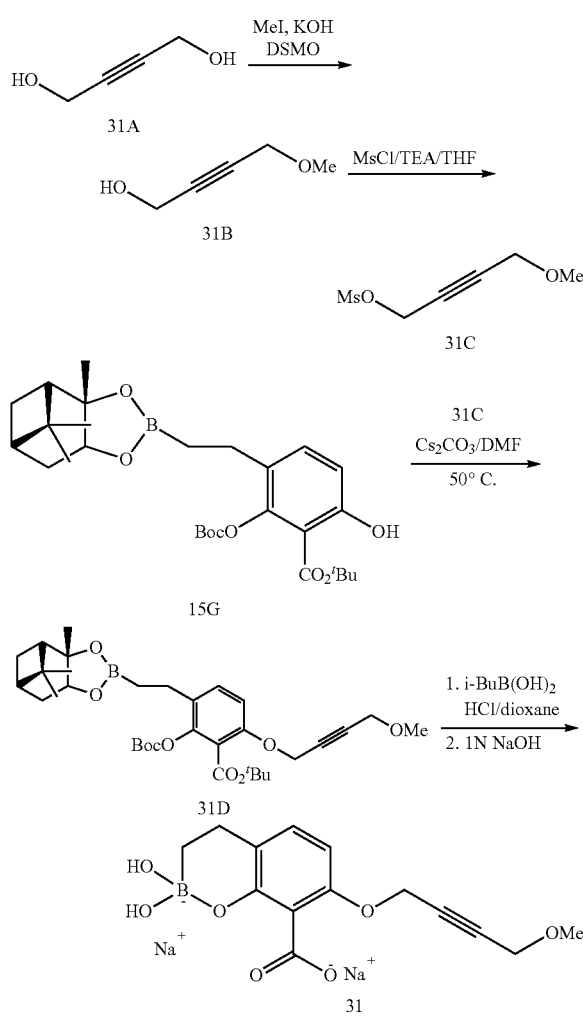

Step 1: Synthesis of 31B

To a solution of compound 31A (10 g, 0.116 mol, 1.0 eq) in DMSO (200 mL) was added KOH (6.6 g, 0.116 mol, 1.0 eq). The mixture was stirred at room temperature for 30 min before MeI (16.5 g, 0.116 mol, 1.0 eq) was added dropwise. After 30 minutes at room temperature, the reaction mixture was poured into water and extracted with DCM (2×). The organic layer was concentrated in vacuo and the residue was purified by flash chromatography on silica (PE/EA=5:1) to give compound 31B (2.3 g, 20%).

Step 2: Synthesis of 31C

To a solution of compound 31B (1.0 g, 10 mmol, 1.0 eq) in THF (10 mL) was added TEA (1.0 g, 10 mmol, 1.0 eq) at 0° C., followed by dropwise addition of MsCl (1.15 g, 10 mmol, 1.0 eq). The mixture was stirred at room temperature for 30 minutes before it was concentrated to dryness. The residue was dissolved in EA and washed with water and brine. The organic phase was dried over Na₂SO₄ before it was concentrated in vacuo to give crude compound 31C (1.8 g, 100%).

Step 3: Synthesis of 31D

The mixture of compound 15G (1.0 g, 1.94 mmol, 1.0 eq), compound 31C (690 mg, 3.87 mmol, 2.0 eq) and Cs₂CO₃ (1.9 g, 5.81 mmol, 3.0 eq) in DMF (15 mL) was stirred at 50° C. for 12 hours under nitrogen atmosphere. The reaction was monitored by LC-MS. The mixture was filtered, concentrated under reduced pressure, and the residue was purified by flash chromatography on silica (PE/EA=5:1) to give compound 31D (600 mg, 52%).

Step 4: Synthesis of 31

To a solution of compound 31D (300 mg, 0.50 mmol, 1.0 eq) in dioxane (2 mL) was added i-BuB(OH)₂ (101 mg, 1.00 mmol, 2.0 eq) and concentrated HCl (2 mL). The reaction mixture was stirred at rt for 1 hour. The reaction mixture was concentrated in vacuo, and the residue was dissolved in H₂O/MeCN. The resulting solution was adjusted to pH=12 and purified by prep-HPLC (18, neutral) to give compound 31 (52 mg, 33%).

ESI-MS: [M+H]: 291.

¹H NMR (400 MHz, CD₃OD): δ 6.82 (d, J=8.4 Hz, 1H), 6.38 (d, J=8.0 Hz, 1H), 4.76 (s, 2H), 4.14-4.09 (m, 2H), 3.37-3.35 (m, 3H), 2.62-2.56 (m, 2H), 0.54-0.50 (m, 2H).

EXAMPLE 32

Disodium; 8-(4-aminobut-2-ynoxy)-4,4-dihydroxy-5-oxa-4-boranuidabicyclo[4.4.0]deca-1(6),7,9-triene-7-carboxylate

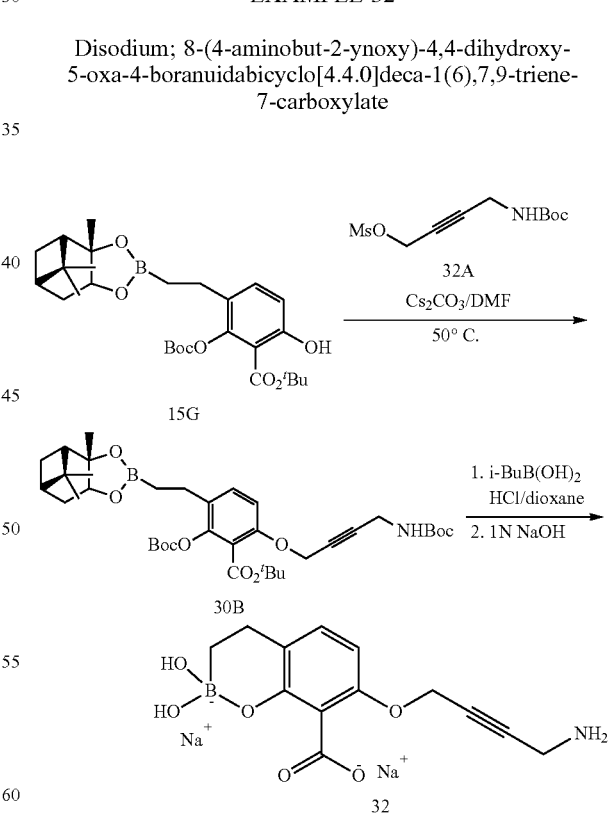

Step 1: Synthesis of 32B

The mixture of compound 15G (600 mg, 1.16 mmol, 1.0 eq), 32A (*Bioorg. Med. Chem. Lett.*, 2010, 20, 3165-68) (450 mg, 1.71 mmol, 1.5 eq) and Cs₂CO₃ (1.1 g, 3.38 mmol, 3.0 eq) in DMF (10 mL) was stirred at 50° C. for 12 hours under nitrogen atmosphere. The reaction was monitored by LC-MS. The mixture was filtered and concentrated under reduced pressure. The residue was purified by flash chromatography on silica (PE/EA=4:1) to give compound 32B (340 mg, 43%).

Step 6: Synthesis of 32

To a solution of compound 32B (300 mg, 0.44 mmol, 1.0 eq) in dioxane (3 mL) was added i-BuB(OH)$_2$ (89 mg, 0.88 mmol, 2.0 eq) and concentrated HCl (2 mL). The reaction mixture was stirred at rt for 1 hour. The reaction mixture was concentrated in vacuo, and the residue was dissolved in H$_2$O/MeCN. The resulting solution was adjusted to pH=12 and purified by prep-HPLC (18, neutral) to give compound 32 (31 mg, 24%).

ESI-MS: [M+H]$^+$: 276.

$^1$H NMR (400 MHz, CD$_3$OD): δ 6.96 (d, J=7.6 Hz, 1H), 6.45 (d, J=8.8 Hz, 1H), 5.57 (s, 4H), 3.65-3.41 (m, 2H), 2.62-2.57 (m, 2H), 0.81-0.76 (m, 2H).

EXAMPLE 33

(2-Hydroxy-7-methoxy-3,4-dihydro-1,2-benzoxaborinin-8-yl)phosphonic acid

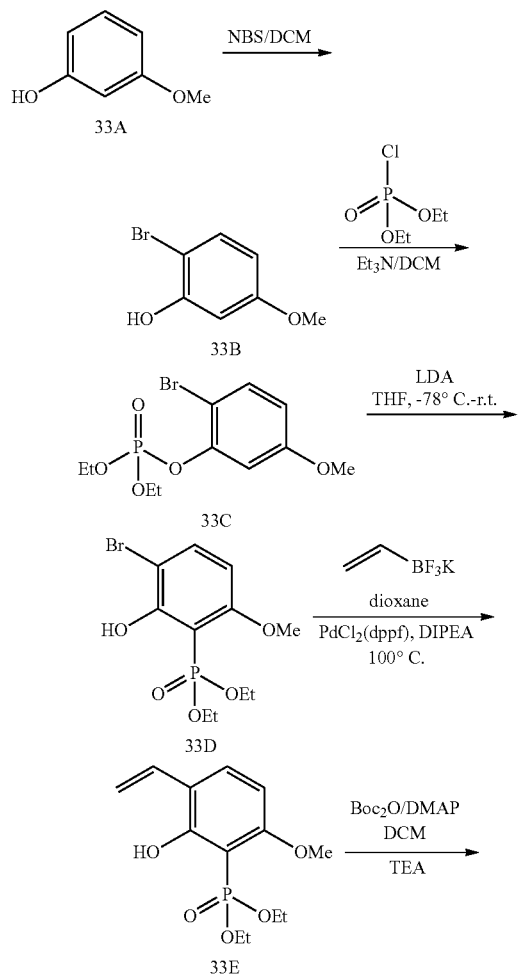

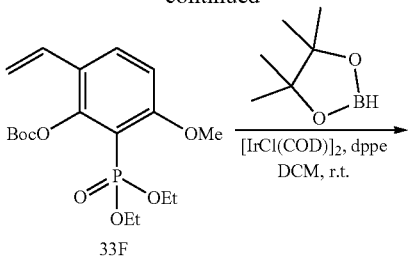

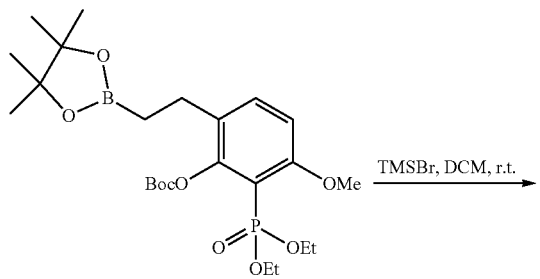

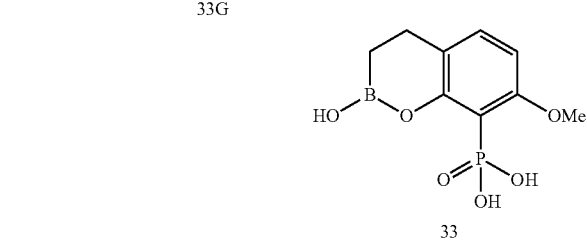

Step 1: Synthesis of 33B

To the solution of 33A (9.8 g, 79 mmol, 1.0 eq) in DCM (100 mL) was added NBS (14.8 g, 82.9 mmol, 1.05 eq) in DCM (150 mL) dropwise at 0° C. The reaction mixture was stirred at room temperature for 2 hours under nitrogen atmosphere before it was concentrated in vacuo to dryness. The residue was purified by flash chromatography on silica (PE/EA=20:1 to 5:1) to give 33B (10.2 g, 64%).

Step 2: Synthesis of 33C

To a solution of 33B (9.2 g, 45.5 mmol, 1.0 eq) in DCM (100 mL) was added diethyl phosphorochloridate (8.64 g, 50.1 mmol, 1.1 eq) and Et$_3$N (6.9 g, 68.3 mmol, 1.5 eq) dropwise. The mixture was stirred at room temperature for 16 hours before it was concentrated to dryness. The residue was purified by column chromatography (PE/EA=10:1 to 5:1) to give 33C (13.9 g, 90%).

Step 3: Synthesis of 33D

To a solution of 33C (13.9 g, 0.04 mol, 1.0 eq) in anhydrous THF (150 mL) was added LDA (36 mL, 2M in THF, 0.072 mol, 1.8 eq) dropwise at −78° C. The reaction mixture was slowly warmed to room temperature in 2 hours before it was quenched with saturated aqueous NH$_4$Cl. The mixture was extracted with EA and dried over Na$_2$SO$_4$. The crude product was purified by column chromatography (PE/EA=20:1 to 5:1) to give 33D (8.8 g, 63%).

Step 4: Synthesis of 33E

A mixture of 33D (3.0 g, 8.88 mmol, 1.0 eq), CH$_2$CHBF$_3$K (2.38 g, 17.75 mmol, 2.0 eq), PdCl$_2$(dppf) (579 mg, 0.71 mmol, 0.08 eq) and DIPEA (3.4 g, 26.6 mmol, 3.0 eq) in dioxane (30 mL) was stirred at 100° C. for 16 hours under nitrogen atmosphere. The reaction was monitored by TLC. The mixture was filtered, evaporated to dryness, and purified by column chromatography (PE/EA=20:1 to 10:1) to give compound 33E (1.4 g, 55%).

Step 5: Synthesis of 33F

To the solution of 33E (1.4 g, 4.89 mmol, 1.0 eq) in DCM (15 mL) was added Boc$_2$O (1.6 g, 7.34 mmol, 1.5 eq), TEA (1.49 g, 14.7 mmol, 3.0 eq) and DMAP (60 mg, 0.49 mmol, 0.1 eq). The mixture was stirred at room temperature for 16 hours before it was evaporated to dryness. The residue was purified by column chromatography (PE/EA=5:1 to 2:1) to give 33F (1.9 g, 100%).

Step 6: Synthesis of 33G

To a mixture of 33F (300 mg, 0.78 mmol, 1.0 eq) in DCM (3 mL) was added 4,4,5,5-tetramethyl-1,3,2-dioxaborolane (199 mg, 1.55 mmol, 2.0 eq), [IrCl(COD)]2 (10.4 mg, 0.016 mmol, 0.02 eq) and dppe (12.4 mg, 0.03 mmol, 0.04 eq). The mixture was stirred at room temperature for 16 hours before it was evaporated to dryness. The residue was purified by column chromatography (PE/EA=5:1 to 1:1) to give 33G (350 mg, 88%).

ESI-MS: [M+H]$^+$: 515.

Step 7: Synthesis of 33

To a solution of 33G (200 mg, 0.39 mmol, 1.0 eq) in DCM (5 mL) was added TMSBr (298 mg, 1.95 mmol, 8.0 eq). The mixture was stirred at room temperature for 16 hours before it was concentrated. The residue was purified by pre-HPLC (18) to give 33 (39.5 mg, 39%) as white solid.

ESI-MS: [M+H]$^+$: 259.

$^1$H NMR (400 MHz, CD$_3$OD): δ 7.19 (d, J=8.4 Hz, 1H), 6.43-6.38 (m, 1H), 3.82 (d, J=12.4 Hz, 3H), 2.61-2.56 (m, 2H), 1.06-1.01 (m, 2H).

EXAMPLE 34

6-Fluoro-2-hydroxy-7-methoxy-3,4-dihydro-1,2-benzoxaborinine-8-carboxylic acid

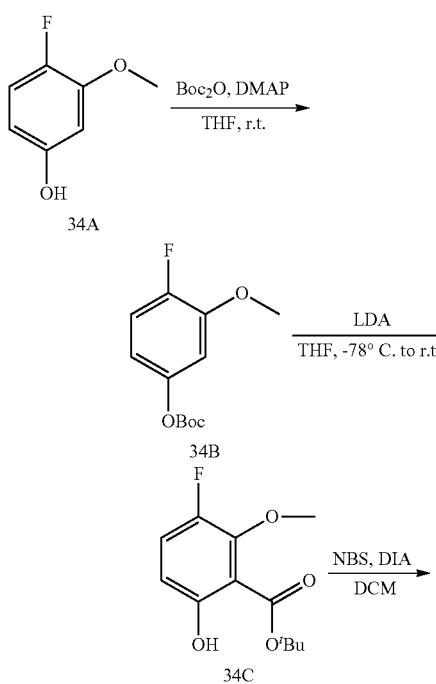
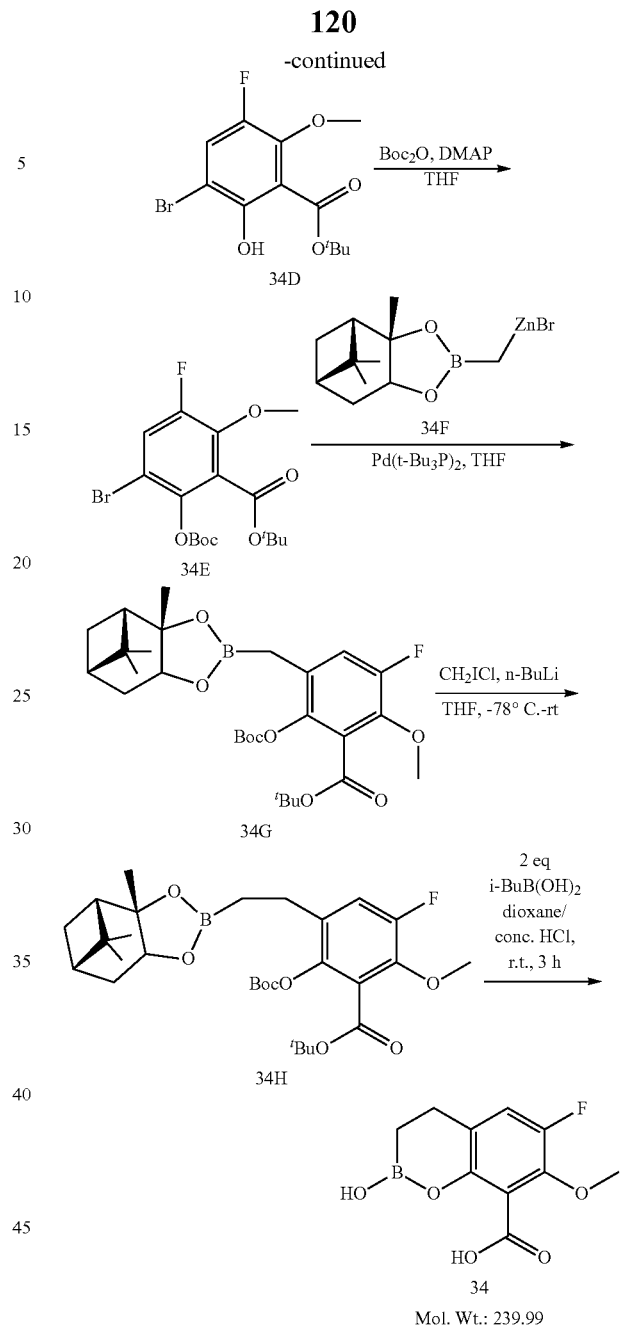

Step 1: Synthesis of 34B

To a solution of 34A (500 mg, 3.52 mmol, 1.0 eq) in THF (5 mL) was added Boc$_2$O (921 mg, 4.23 mmol, 1.2 eq) and DMAP (22 mg, 0.17 mmol, 0.05 eq). The mixture was stirred at room temperature for 2 hours before it was concentrated in vacuo. The residue was purified by column chromatography (PE/EA=20:1 to 5:1) to give 34B (767 mg, 90%).

Step 2: Synthesis of 34C

To a solution of 34B (5.0 g, 20.7 mmol, 1.0 eq) in anhydrous THF (50 mL) was added LDA (26 mL, 2M in THF, 52 mmol, 2.5 eq, freshly made) dropwise −78° C. The reaction mixture was slowly warmed to room temperature in 2 hours before it was quenched with saturated aqueous NH$_4$Cl. The mixture was extracted with EA and dried over Na$_2$SO$_4$. The crude product was purified by column chromatography (PE/EA=20:1 to 5:1) to give 34C (3.6 g, 75%).

Step 3: Synthesis of 34D

To a solution of 34C (3.6 g, 14.9 mmol, 1.0 eq) in DCM (40 mL) was added NBS (2.9 g, 16.4 mmol, 1.1 eq) and DIA (300 mg, 2.98 mmol, 0.2 eq). The reaction mixture was stirred at room temperature for 0.5 hour. The reaction was monitored by TLC. The mixture was evaporated to dryness, and the residue was purified by column chromatography (PE/EA=20:1 to 5:1) to give 34D (1.9 g, 40%).

Step 4: Synthesis of 34E

To a solution of 34D (1.9 g, 5.9 mmol, 1.0 eq) in THF (20 mL) was added $Boc_2O$ (1.5 g, 7.08 mmol, 1.2 eq) and DMAP (36 mg, 0.295 mmol, 0.05 eq). The mixture was stirred at room temperature for 2 hours before it was concentrated in vacuo. The residue was purified by column chromatography (PE/EA=20:1 to 5:1) to give 34E (2.5 g, 100%).

Step 5: Synthesis of 34G

To a solution of 34E (2.47 g, 5.9 mmol, 1.0 eq) and $Pd(t-Bu3P)_2$ (300 mg, 0.59 mmol, 0.1 eq) in THF (30 mL) was added 34F (WO 0946098) (freshly made, about 8.8 mmol in THF, 1.5 eq) dropwise over 10 min under $N_2$. The mixture was stirred at room temperature overnight before it was concentrated in vacuo. The residue was purified by column chromatography (PE/EA=10:1) to give 34G (660 mg, 23%).

ESI-MS: $[M+H]^+$: 535.

Step 6: Synthesis of 34H

To a solution of 34G (300 mg, 0.56 mmol, 1.0 eq) and $CH_2ICl$ (198 mg, 1.12 mmol, 2.0 eq) in THF (3 mL) was added n-BuLi (0.4 mL, 2.5 M in hexanes, 0.96 mmol, 1.7 eq) dropwise in 10 minutes at −78° C. The mixture was slowly warmed up to room temperature overnight. The mixture was concentrated in vacuo and the residue was purified by prep-TLC (PE/EA=5:1) to give 34H (220 mg, 71%).

ESI-MS: $[M+H]^+$: 549.

Step 7: Synthesis of 34

To a solution of 34H (220 mg, 0.40 mmol, 1.0 eq) in dioxane (3 mL) was added i-BuB(OH)$_2$ (82 mg, 0.80 mmol, 2.0 eq) and concentrated HCl (2 mL). The reaction mixture was stirred at room temperature for 3 hours. The reaction mixture was concentrated in vacuo, and the residue was dissolved in $H_2O$/MeCN. The resulting solution was adjusted to pH=10-12 with 1N NaOH and purified by prep-HPLC (18, neutral) to give 34 (18 mg, 19%).

ESI-MS: $[M+H]^+$: 241.

$^1$H NMR (400 MHz, CD$_3$OD): δ 7.06 (s, 1H), 3.80 (s, 3H), 2.72-2.68 (m, 2H), 1.10-1.05 (m, 2H).

EXAMPLE 35

6,7-Difluoro-2-hydroxy-3,4-dihydro-1,2-benzoxaborinine-8-carboxylic acid

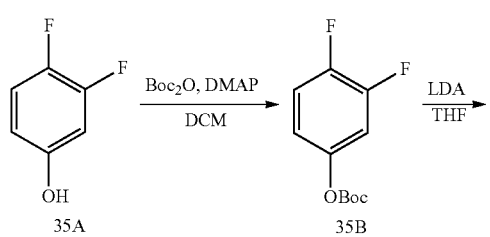

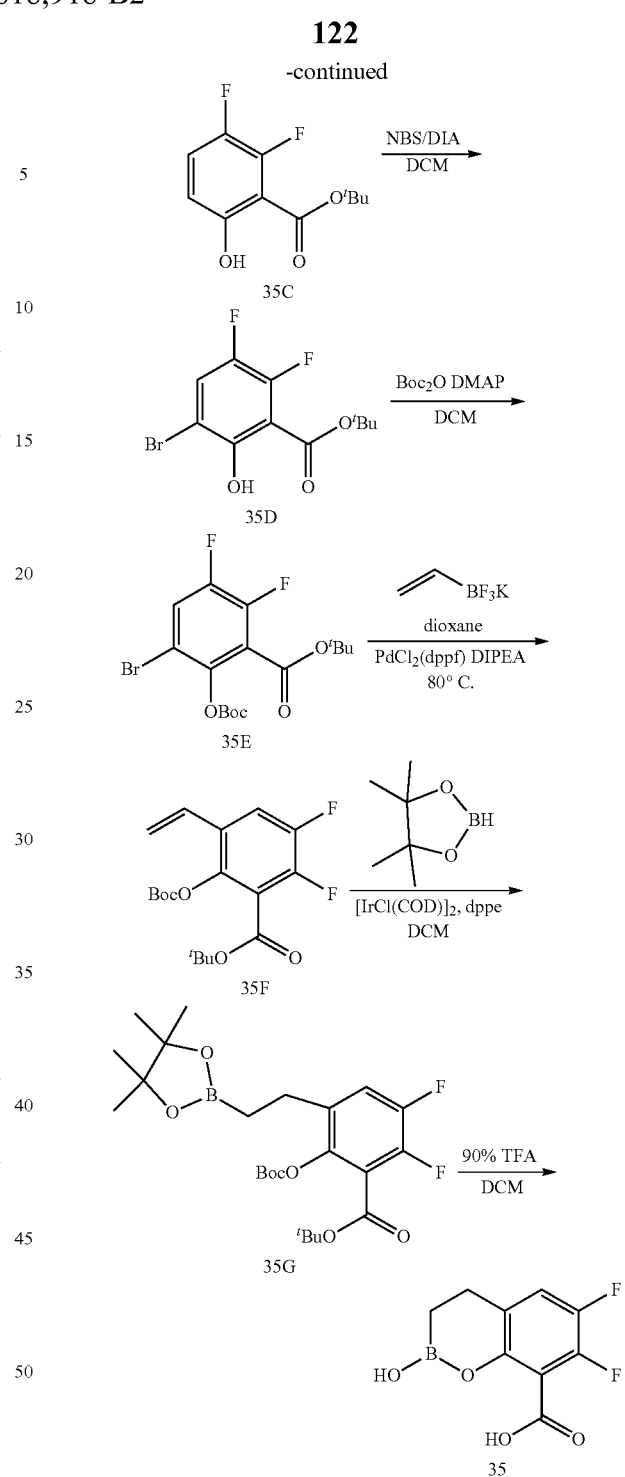

Step 1: Synthesis of 35B

To a solution of 35A (400 mg, 3.1 mmol, 1.0 eq) in THF (5 mL) was added $Boc_2O$ (811 mg, 3.7 mmol, 1.2 eq) and DMAP (20 mg, 0.16 mmol, 0.05 eq). The mixture was stirred at rt for 2 hours before it was concentrated in vacuo. The residue was purified by column chromatography (PE/EA=10:1) to give 35B (470 mg, 66%).

Step 2: Synthesis of 35C

To a solution of 35B (470 mg, 2.04 mmol, 1.0 eq) in anhydrous THF (20 mL) was added LDA (1.5 mL, 2M in THF, 3.06 mmol, 1.5 eq) dropwise at −78° C. The mixture was slowly warmed up to room temperature in 6 hours before it was quenched with saturated aqueous NH₄Cl solution. The mixture was extracted with EA and dried over Na₂SO₄. The organic layer was concentrated, and the residue was purified by column chromatography (PE/EA=20:1) to give 35C (317 mg, 67%).

Step 3: Synthesis of 35D

To a solution of 35C (317 mg, 1.38 mmol, 1.0 eq) in DCM (100 mL) was added DIA (27.9 mg, 0.276 mmol, 0.2 eq) and NBS (259 mg, 82.9 mmol, 1.05 eq). The mixture was stirred at room temperature for 16 hours before it was filtered and concentrated under vacuum to give crude 35D (436 mg, 100%).

Step 4: Synthesis of 35E

To a solution of 35D (436 mg, 1.41 mmol, 1.0 eq) in DCM (2 mL) was added Boc₂O (323 mg, 1.48 mmol, 1.05 eq) and DMAP (9 mg, 0.07 mmol, 0.05 eq). The mixture was stirred at room temperature for 1 hours before it was evaporated to dryness. The residue was purified by column chromatography (PE/EA=200:1 to 100:1) to give 35E (475 mg, 82%).

Step 5: Synthesis of 35F

A mixture of 35E (475 mg, 1.16 mmol, 1.0 eq), CH₂CHBF₃K (310 mg, 2.32 mmol, 2.0 eq), PdCl₂(dppf) (76 mg, 0.09 mmol, 0.08 eq) and DIPEA (448 mg, 3.47 mmol, 3.0 eq) in dioxane (5 mL) was stirred at 80° C. for 16 hours under nitrogen atmosphere. The reaction was monitored by TLC. The mixture was filtered and the filtrate was purified by column chromatography (PE/EA=100:1 to 30:1) to give 35F (240 mg, 58%).

Step 6: Synthesis of 35G

To a solution of 35F (240 mg, 0.67 mmol, 1.0 eq) in DCM (2 mL) was added 4,4,5,5-tetramethyl-1,3,2-dioxaborolane (172 mg, 1.34 mmol, 2.0 eq), [IrCl(COD)]₂ (9 mg, 0.013 mmol, 0.02 eq) and dppe (11 mg, 0.027 mmol, 0.04 eq). The mixture was stirred at room temperature for 16 hours under nitrogen atmosphere. The reaction was monitored by TLC. The mixture was concentrated and purified by prep-TLC (PE/EA=20:1) to give 35G (107 mg, 33%).

ESI-MS: [M+H]⁺: 485.

Step 7: Synthesis of 35

To a solution of 35G (100 mg, 0.207 mmol, 1.0 eq) in DCM (2 mL) at 0° C. was added 90% TFA (0.5 mL). The mixture was stirred at room temperature for 5 hours before it was concentrated in vacuo. The residue was purified by pre-HPLC (18) to give 35 (12.9 mg, 27%) as white solid.

ESI-MS: [M+CH₃CN+H]⁺=270.

¹H NMR (400 MHz, CD₃OD): δ 7.27-7.16 (m, 1H), 2.70-2.56 (m, 2H), 1.07-0.95 (m, 2H).

EXAMPLE 36

Disodium; 4,4-dihydroxy-8-methylsulfanyl-5-oxa-4-boranuidabicyclo[4.4.0]deca-1(6),7,9-triene-7-carboxylate

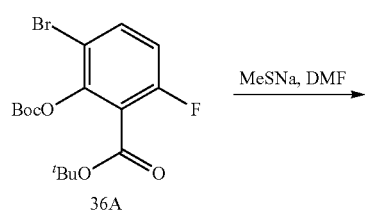

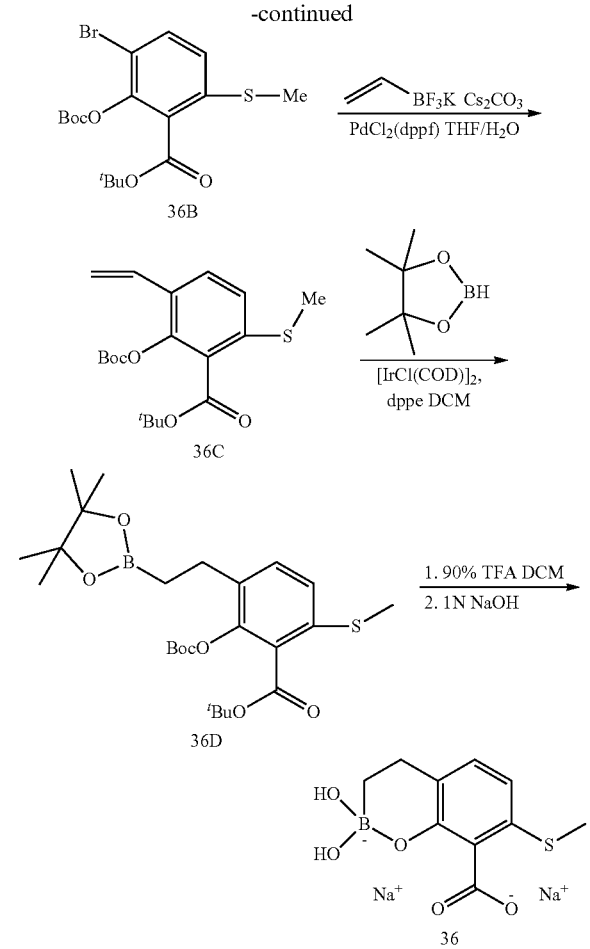

Step 1: Synthesis of 36B

A mixture of 36A (WO 15179308) (3.0 g, 7.7 mmol, 1.0 eq) and MeSNa (1.08 g, 15.4 mmol, 2.0 eq) in DMF (20 mL) was stirred at room temperature for 16 hours under nitrogen atmosphere. The reaction was monitored by TLC. The reaction mixture was concentrated in vacuo and purified by column chromatography (EA/PE, 1:5) to obtain 36B (1.41 g, 44%).

Step 2: Synthesis of 36C

To a mixture of 36B (1 g, 2.39 mmol, 1.0 eq), CH₂CHBF₃K (801 mg, 5.98 mmol, 2.5 eq) and Cs₂CO₃ (2.34 g, 7.18 mmol, 3.0 eq) in THF/H₂O (9 mL/1 mL) was added PdCl₂(dppf) (300 mg, 0.367 mmol, 0.15 eq). The reaction mixture was stirred at room temperature for 16 hours under nitrogen atmosphere. The mixture was filtered and washed with EA. The filtrate was concentrated and purified by column chromatography (PE/EA=20:1) to give 36C (600 mg, 68%).

Step 3: Synthesis of 36D

To a solution of 36C (700 mg, 1.91 mmol, 1.0 eq) in DCM (7 mL) was added 4,4,5,5-tetramethyl-1,3,2-dioxaborolane (489 mg, 3.82 mmol, 2.0 eq), [IrCl(COD)]2 (38.5 mg, 0.057 mmol, 0.03 eq) and dppe (46 mg, 0.114 mmol, 0.06 eq). The mixture was stirred at room temperature for 20 hours under nitrogen atmosphere before it was concentrated in vacuo. The residue was purified by column chromatography (PE/EA=20:1 to 5:1) to give 36D (130 mg, 14%).

ESI-MS: [M+H]⁺: 495.

Step 4: Synthesis of 36E

A solution of 36D (120 mg, 0.243 mmol, 1.0 eq) in 90% THF (1 mL) and DCM (1 mL) was stirred at room temperature for 2 hours. The reaction mixture was concentrated and the residue was dissolved in MeCN/water. The resulting solution was adjusted to pH=10 with 1N NaOH and purified by prep-HPLC (18, neutral) to give 36E (28 mg, 44%) as white solid.

ESI-MS: [M−H2O+H]$^+$: 221.

$^1$H NMR (400 MHz, CD$_3$OD/D$_2$O): δ 7.06 (d, J=8.4 Hz, 1H), 6.60 (d, J=8.0 Hz, 1H), 2.65-2.61 (m, 2H), 2.32 (s, 3H), 0.71-0.67 (m, 2H).

EXAMPLE 37

Disodium; 9-fluoro-4,4-dihydroxy-5-oxa-4-boranuidabicyclo[4.4.0]deca-1(6),7,9-triene-7-carboxylate

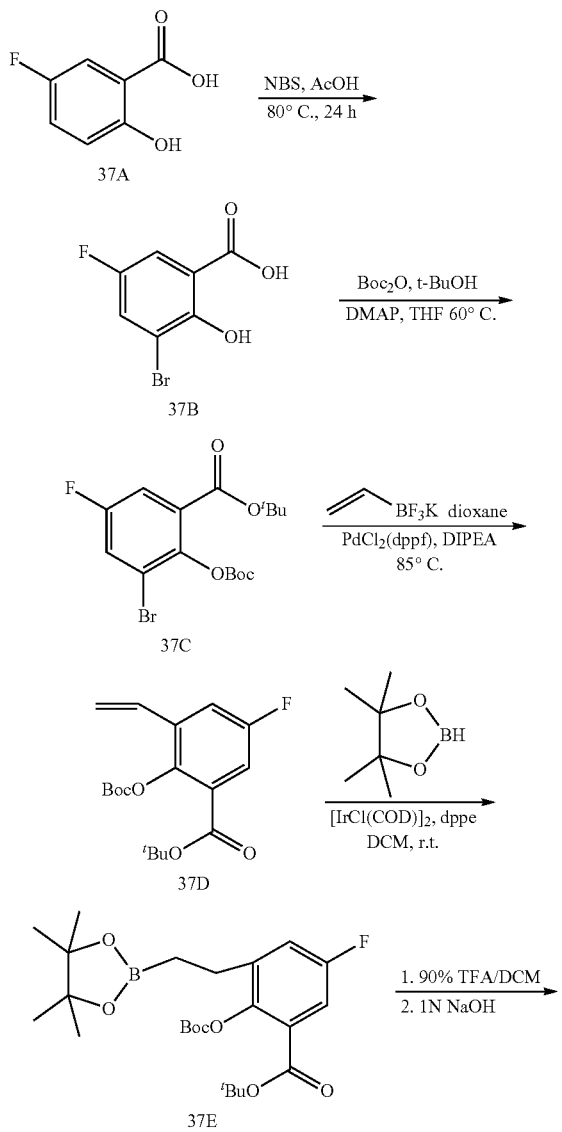

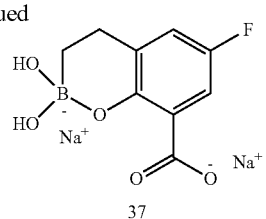

Step 1: Synthesis of 37B

A mixture of 37A (5.1 g, 33 mmol, 1.0 eq) and NBS (6.4 g, 36 mmol, 1.1 eq) in AcOH (25 mL) was stirred at 80° C. for 24 hours. The reaction was monitored by TLC. The mixture was concentrated in vacuo and the residue was purified by column chromatography (PE/EA=2:1 to 1:1) to give 37B (6.5 g, 85%).

ESI-MS: [M−H]$^−$: 233, 235.

Step 2: Synthesis of 37C

A mixture of 37B (6.1 g, 26 mmol, 1.0 eq), Boc$_2$O (28 g, 130 mmol, 5.0 eq) and DMAP (3.2 g, 26 mmol, 1.0 eq) in t-BuOH/THF (60 mL/40 mL) was stirred at 60° C. for 16 hours. The mixture was concentrated in vacuo and the residue was purified by column chromatography (PE/EA=10:1 to 5:1) to give 37C (1.5 g, 15%).

Step 3: Synthesis of 37D

A mixture of 37C (1.6 g, 4.75 mmol, 1.0 eq), CH$_2$CHBF$_3$K (1.27 g, 9.5 mmol, 2.0 eq), DIPEA (1.84 g, 14.2 mmol, 3.0 eq) and PdCl$_2$(dppf) (310 mg, 0.38 mmol, 0.08 eq) in dioxane (20 mL) was stirred at 85° C. for 16 hours under nitrogen atmosphere. The mixture was filtered and washed with EA. The filtrate was concentrated and purified by column chromatography (PE/EA=20:1) to give 37D (900 mg, 65%).

Step 4: Synthesis of 37E

To a solution of 37D (347 mg, 1.03 mmol, 1.0 eq) in DCM (4 mL) was added 4,4,5,5-tetramethyl-1,3,2-dioxaborolane (263 mg, 2.05 mmol, 2.0 eq), [IrCl(COD)]2 (21 mg, 0.031 mmol, 0.03 eq) and dppe (25 mg, 0.062 mmol, 0.06 eq). The mixture was stirred at room temperature for 5 hours before it was concentrated. The residue was purified by column chromatography (PE/EA=10:1 to 5:1) to give 37E (120 mg, 25%).

ESI-MS: [M+H]$^+$: 467.

Step 5: Synthesis of 37

A solution of 37E (100 mg, 0.215 mmol, 1.0 eq) in 90% THF (2.5 mL) and DCM (2.5 mL) was stirred at room temperature for 2 hours. The mixture was concentrated and purified by prep-HPLC (18). The obtained solid was dissolved in MeCN/H$_2$O and was adjusted to pH=9 with 0.1 N NaOH. After lyophilization, the Na salt of 37 (70 mg, 100%) was obtained as white solid.

ESI-MS: [M+MeCN+H]$^+$: 252.

$^1$H NMR (400 MHz, CD$_3$OD): δ 6.98 (d, J=6.4 Hz, 1H), 6.61 (d, J=6.4 Hz, 1H), 2.65-2.60 (m, 2H), 0.48-0.44 (m, 2H).

EXAMPLE 38

Disodium; 8,8-dihydroxy-7-oxa-2-aza-8-boranuid-abicyclo[4.4.0]deca-1,3,5-triene-5-carboxylate

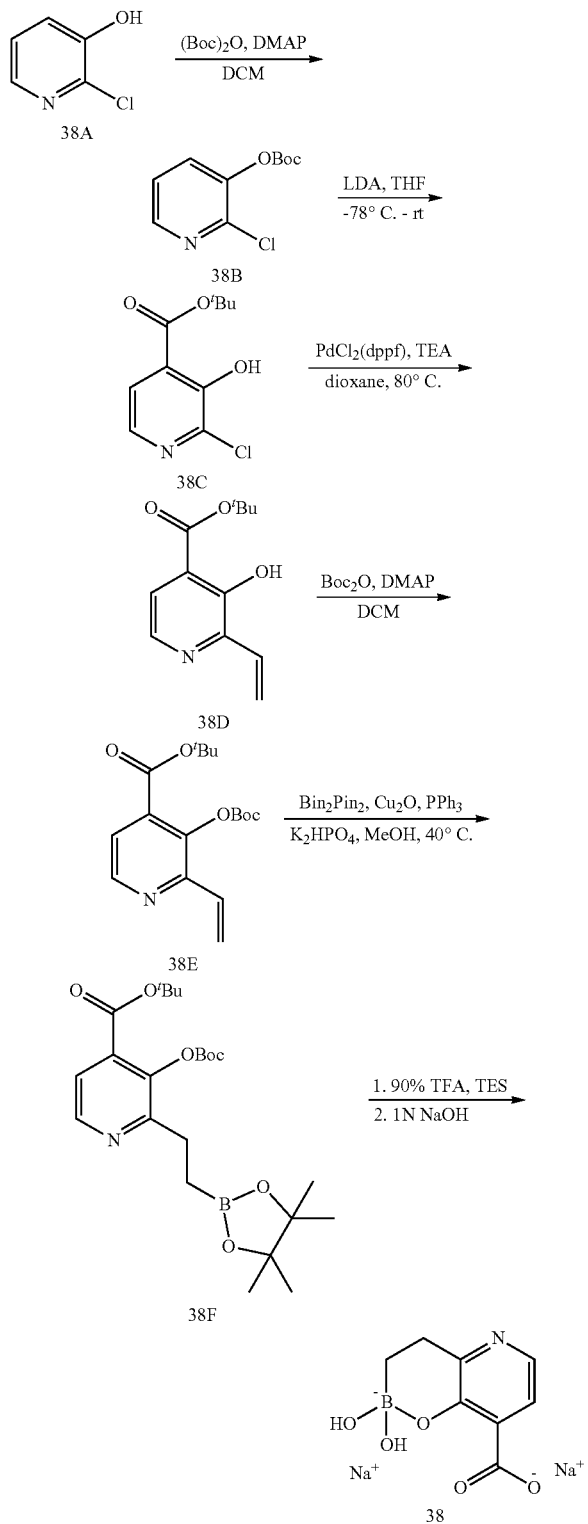

Step 1: Synthesis of 38B

A solution of compound 38A (5.0 g, 38.6 mmol, 1.0 eq), (Boc)₂O (9.17 g, 42.4 mmol, 1.1 eq) and DMAP (0.472 g, 3.86 mmol, 0.1 eq) in anhydrous DCM (100 mL) was stirred at room temperature for 0.5 hour. The solvent was removed under reduced pressure and the residue was purified by column chromatography (PE/EA=5:1) to give compound 38B (8.0 g, 90%).

ESI-MS: [M+H]⁺: 230.

Step 2: Synthesis of 38C

To a solution of compound 38B (4.0 g, 17.4 mmol, 1.0 eq) in anhydrous THF (50 ml) was slowly added LDA (10.5 mL, 2 M in THF, 20.9 mmol, 1.2 eq) over 10 minutes at −78° C. The mixture was warmed up and stirred at room temperature for 2 hours before it was quenched by saturated NH₄Cl solution. The organic layer was concentrated under reduced pressure and the residue was purified by column chromatography (PE/EA=51) to give compound 38C (0.9 g, 23%).

ESI-MS: [M+H]⁺: 230.

Step 3: Synthesis of 38D

A solution of compound 38C (0.8 g, 3.5 mmol, 1.0 eq), potassium vinyltrifluoroborate (0.61 g, 4.53 mmol, 1.3 eq), TEA (1.06 g, 10.5 mmol, 3.0 eq) and PdCl₂(dppf) (0.256 g, 0.35 mmol, 0.1 eq) in dioxane (10 ml) was stirred at 80° C. for 10 hours under N₂. After cooled down, the mixture was filtered and the filtrate was concentrated under reduced pressure. The residue was purified by column chromatography (PE/EA=10:1) to give compound 38D (0.58 g, 67%).

ESI-MS: [M+H]: 222.

Step 4: Synthesis of 38E

A solution of compound 38D (0.53 g, 2.4 mmol, 1.0 eq), (Boc₂)O (0.68 g, 3.1 mmol, 1.3 eq) and DMAP (0.147 g, 1.2 mmol, 0.5 eq) in anhydrous DCM (6 mL) was stirred at room temperature for 1 hour. The solution was concentrated under reduced pressure and the residue was purified by column chromatography (PE/EA=10:1) to give compound 38E (0.76 g, 98%).

ESI-MS: [M+H]: 322.

Step 5: Synthesis of 38F

A solution of compound 38E (0.3 g, 0.94 mmol, 1.0 eq), Bin₂Pin₂ (0.275 g, 1.08 mmol, 1.15 eq), Cu₂O (11 mg, 0.076 mmol, 0.08 eq), K₂HPO₄ (0.197 g, 1.13 mmol, 1.2 eq) and PPh₃ (0.028 g, 0.104 mmol, 0.11 eq) in MeOH (3 mL) was stirred at 85° C. for 4 hours under N₂. The mixture was filtered and the filtrate was concentrated in vacuo to give crude compound 38F (400 mg, 94%).

ESI-MS: [M+H]: 450.

Step 6: Synthesis of 38

A solution of crude compound 38F (0.4 g, 0.9 mmol, 1.0 eq) in 90% aq TFA (3 mL) and Et₃SiH (3 mL) was stirred overnight at 30° C. The solvent was removed in vacuo, and the residue was dissolved in H₂O/MeCN. The resulting solution was adjusted to pH=12 with 1N NaOH and purified by prep-HPLC (18, neutral) to give 38 (37 mg, 30%) as white solid.

ESI-MS: [M+H]: 194.

¹H NMR (CD₃OD, 400 MHz): δ 7.475-7.473 (d, 1H), 7.001 (d, 1H), 2.535-2.435 (t, J=20, 2H), 0.289-0.253 (t, J=7.2, 2H)

EXAMPLE 39

2-Hydroxy-7-methylsulfonyl-3,4-dihydro-1,2-benzo-xaborinine-8-carboxylic acid

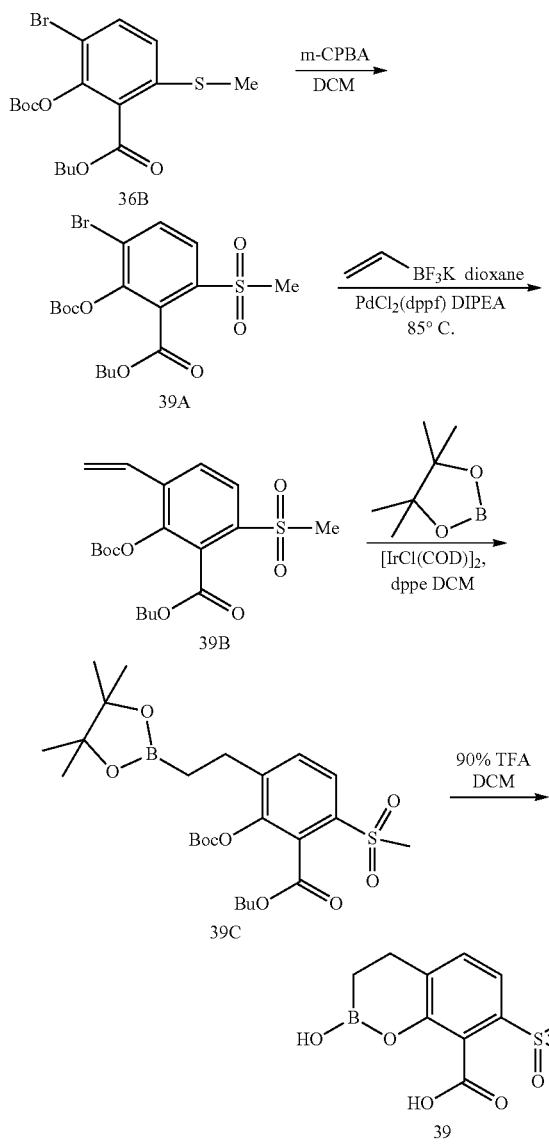

Step 1: Synthesis of 39A

To a solution of 36B (1.4 g, 3.35 mmol, 1.0 eq) in DCM (40 mL) was added m-CPBA (1.73 g, 10 mmol, 3.0 eq) slowly at 0° C. The mixture was slowly warmed up to room temperature in 3 hours. The reaction was monitored by TLC. The mixture was quenched with aqueous Na2S2O3 and washed with water. The organic layer was dried over Na$_2$SO$_4$ and then concentrated in vacuo to give crude 39A (1.31 g, 87%).

Step 2: Synthesis of 39B

A mixture of 39A (1.3 g, 2.88 mmol, 1.0 eq), CH$_2$CHBF$_3$K (0.77 g, 5.76 mmol, 2.0 eq), PdCl$_2$(dppf) (169 mg, 0.23 mmol, 0.08 eq) and DIPEA (1.83 g, 14.2 mmol, 3.0 eq) in dioxane (20 mL) was stirred at 85° C. for 16 hours under nitrogen atmosphere. The reaction was monitored by TLC. The mixture was filtered and concentrated in vacuo. The residue was purified by column chromatography to give 39B (870 mg, 76%).

ESI-MS: [M+H]$^+$: 399.

Step 3: Synthesis of 39C

To a solution of 39B (770 mg, 1.93 mmol, 1.0 eq) in DCM (7 mL) was added 4,4,5,5-tetramethyl-1,3,2-dioxaborolane (495 mg, 3.87 mmol, 2.0 eq), [IrCl(COD)]$_2$ (26 mg, 0.039 mmol, 0.02 eq) and dppe (31 mg, 0.077 mmol, 0.04 eq). The mixture was stirred at room temperature for 20 hours under nitrogen atmosphere. The reaction was monitored by TLC. The mixture was concentrated in vacuo, the residue was purified by prep-TLC to give 39C (120 mg, 12%).

ESI-MS: [M+H]$^+$: 527.

Step 4: Synthesis of 39

The solution of 39C (110 mg, 0.21 mmol, 1.0 eq) in 90% THF (1 mL) and DCM (4 mL) was stirred at room temperature for 2 hours. The reaction mixture was concentrated and the residue was dissolved in MeCN/water. The resulting solution was purified by prep-HPLC to give 39 (17 mg, 30%).

ESI-MS: [M−H2O+H]$^+$: 253.

$^1$H NMR (400 MHz, CD$_3$OD): δ 7.55 (d, J=7.6 Hz, 1H), 7.42-7.39 (m, 1H), 3.19 (s, 3H), 2.91-2.86 (m, 2H), 1.11-1.06 (m, 2H).

EXAMPLE 40

Disodium; 4,4-dihydroxy-8-methylsulfinyl-5-oxa-4-boranuidabicyclo[4.4.0]deca-1(6),7,9-triene-7-carboxylate

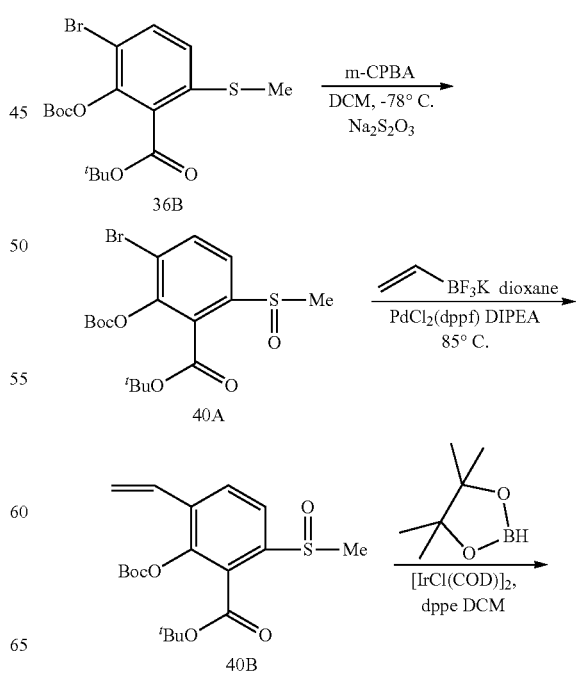

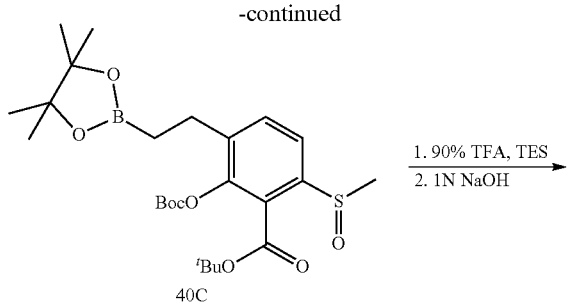

Step 1: Synthesis of 40A

To the solution of compound 36B (2.0 g, 4.79 mmol, 1.0 eq) in anhydrous DCM (10 mL) was added m-CPBA (0.827 g, 4.79 mmol, 1.0 eq) in DCM (2 mL) at −78° C. The reaction mixture was stirred at −78° C. for 2 hours before it was quenched with aqueous $Na_2S_2O_3$. The reaction mixture was partitioned in DCM and $H_2O$. After dried over $Na_2SO_4$ the organic layer was concentrated in vacuo. The residue was purified by column chromatography (PE/EA=5:1) to give compound 40A (2.02 g, 97%).

Step 2: Synthesis of 40B

A solution of compound 40A (2.02 g, 4.66 mmol, 1.0 eq), potassium vinyltrifluoroborate (1.56 g, 11.5 mmol, 2.5 eq), $Cs_2CO_3$ (4.46 g, 13.7 mmol, 3.0 eq) and $PdCl_2(dppf)$ (1.03 g, 1.4 mmol, 0.3 eq) in $THF/H_2O$ (30 ml, 9/1, v/v) was stirred at 85° C. overnight under $N_2$. The mixture was filtered and solvent was removed under reduced pressure. The residue was purified by column chromatography (PE/EA=5:1) to give compound 40B (1.56 g, 88%).

ESI-MS: [M+H]: 383.

Step 3: Synthesis of 40C

To a solution of 40B (500 mg, 1.31 mmol, 1.0 eq) in anhydrous DCM (7 mL) was added 4,4,5,5-tetramethyl-1,3,2-dioxaborolane (336 mg, 2.62 mmol, 2.0 eq), [IrCl(COD)]$_2$ (27 mg, 0.04 mmol, 0.03 eq) and dppe (32 mg, 0.08 mmol, 0.06 eq). The mixture was stirred at room temperature for 20 hours under nitrogen atmosphere. The reaction was monitored by TLC. The mixture was concentrated in vacuo, the residue was purified by column chromatography (PE/EA=5:1) to give compound 40C (0.59 g, 89%).

ESI-MS: [M+H]: 511.

Step 4: Synthesis of 40

A solution of compound 40C (300 mg, 0.59 mmol, 1.0 eq) in 90% TFA (2 mL) and DCM (2 mL) was stirred at room temperature for 3 h. The reaction mixture was concentrated and the residue was dissolved in MeCN/water. The resulting solution was adjusted to pH=10 with 1N NaOH and purified by prep-HPLC (18, neutral) to give 40 (50 mg, 33%) as white solid.

ESI-MS: [M+H]: 255.

$^1$H NMR (CD3OD, 400 MHz): δ 7.439-7.420 (m, 1H), 7.382-7.364 (m, 1H), 2.840 (s, 3H), 2.743-2.704 (t, J=8 Hz, 2H), 1.036-10.17 (t, J=7.6 Hz, 2H)

EXAMPLE 41

6-Chloro-2-hydroxy-7-methoxy-3,4-dihydro-1,2-benzoxaborinine-8-carboxylic acid

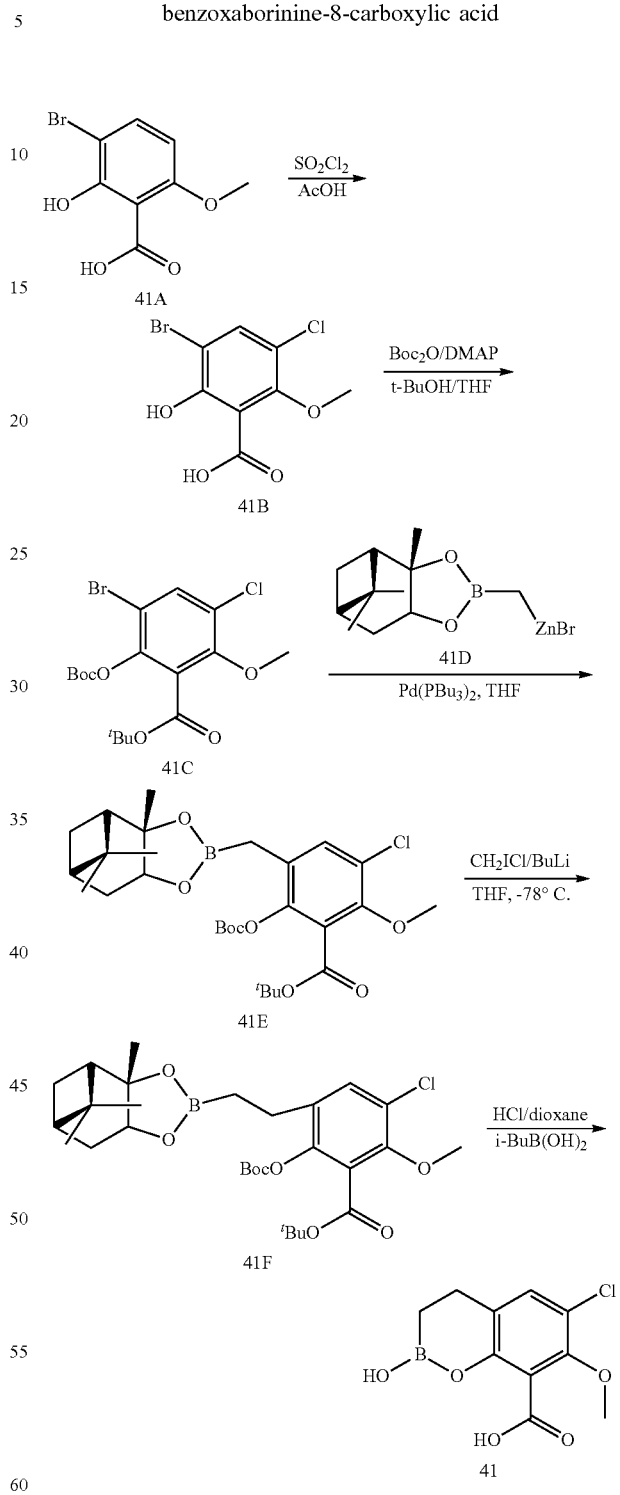

Step 1: Synthesis of 41B

To a solution of compound 41A (10.0 g, 40 mmol, 1.0 eq) in AcOH (100 mL) was added $SO_2Cl_2$ (11.0 g, 0.08 mol, 2.0 eq) dropwise over 5 min at room temperature. The reaction mixture was stirred at 40° C. overnight before it was concentrated in vacuo. The residue was purified by column chromatography (PE/EA=3:1) to give compound 41B (8.5 g, 80%).

Step 2: Synthesis of 41C

To a solution of compound 41B (8.5 g, 35.6 mmol, 1.0 eq) in t-BuOH/THF (200 mL, 1/1, v/v) was added (Boc)$_2$O (31 g, 142 mmol, 4.0 eq) and DMAP (427 mg, 3.5 mmol, 0.1 eq) over 20 minutes. The mixture was stirred at 65° C. overnight before it was concentrated in vacuo. The residue was purified by column chromatography (PE/EA=10:1) to give compound 41C (13 g, 75%).

Step 3: Synthesis of 41E

To a solution of compound 41C (13 g, 30 mmol, 1.0 eq) and Pd(PBu$_3$)$_2$ (1.5 g, 2.98 mmol, 0.1 eq) in anhydrous THF (400 mL) was added a solution of 41D (WO 15179308) (freshly made, about 40 mmol in THF, 1.3 eq) dropwise over 10 min under N$_2$. The mixture was stirred at room temperature overnight before it was concentrated in vacuo. The residue was purified by column chromatography (PE/EA=10:1) to give compound 41E (8.8 g, 60%).

ESI-MS: [M+H]: 551.

Step 4: Synthesis of 41F

To a solution of compound 41E (500 mg, 0.91 mmol, 1.0 eq) and CH$_2$ICl (319 mg, 1.82 mmol, 2.0 eq) in anhydrous THF (15 mL) was slowly added n-BuLi (0.54 mL, 2.5 M in hexanes, 1.36 mmol, 1.5 eq) over 10 minutes at −78° C. The mixture was slowly warmed up to room temperature overnight. The reaction solution was concentrated in vacuo and the residue was purified by column chromatography (PE/EA=10:1) to give compound 41F (0.46 g, 80%).

ESI-MS: [M+H]: 565.

Step 5: Synthesis of 41

To a solution of compound 41F (0.46 g, 0.816 mmol, 1.0 eq) in dioxane (4 mL) and concentrated HCl (4 mL) was added i-BuB(OH)$_2$ (166 mg, 1.63 mmol, 2.0 eq). The mixture was stirred at room temperature for 1 hours. The reaction mixture was concentrated under reduced pressure and the mixture was purified by prep-HPLC (18) to give 41 (21 mg, 15%) as white solid.

ESI-MS: [M+H]$^+$: 257.

$^1$H NMR (CD$_3$OD, 400 MHz): δ 7.260 (s, 1H), 3.858 (s, 3H), 2.723-2.684 (t, J=8.0, J=7.6, 2H), 1.080-1.041 (t, J=7.6, J=8.0, 2H)

EXAMPLE 42

Disodium; 4,4,8-trihydroxy-5-oxa-4-boranuidabicyclo[4.4.0]deca-1(6),7,9-triene-7-carboxylate

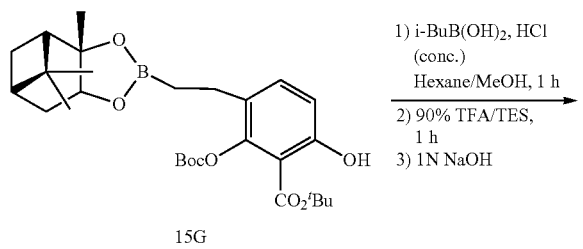

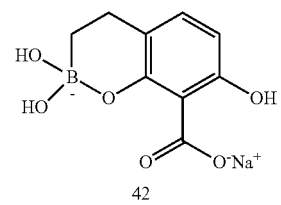

To the mixture of compound 15G (500 mg, 0.97 mmol, 1.0 eq), i-BuB(OH)$_2$ (148 mg, 1.45 mmol, 1.5 eq) in hexane (9 mL) and methanol (9 mL) was added about 10 drops of concentrated HCl at 0° C. The reaction mixture was stirred at room temperature overnight. The methanol layer was separated and washed with hexanes (2×). The methanol layer was then concentrated and the residue was added 90% aqueous TFA (6 mL) and TES (2 mL). The mixture was stirred at room temperature for 1 hours before it was concentrated under reduced pressure. The residue was dissolved in MeCN/water and adjusted to pH=12 with 0.1 N NaOH. The resulting solution was purified by prep-HPLC (18, neutral) to give 42 (6 mg, 10%) as yellow solid.

ESI-MS: [2M−H]$^-$: 415.

$^1$H NMR (CD$_3$OD, 400 MHz): δ 6.950 (d, 1H), 6.169-6.148 (d, J=8.4, 1H), 2.573-2.535 (t, J=8.0, J=7.2, 2H), 0.896-0.878 (t, 2H)

EXAMPLE 43

Disodium; 8-(2-fluoroethoxy)-4,4-dihydroxy-5-oxa-4-boranuidabicyclo[4.4.0]deca-1(6),7,9-triene-7-carboxylate

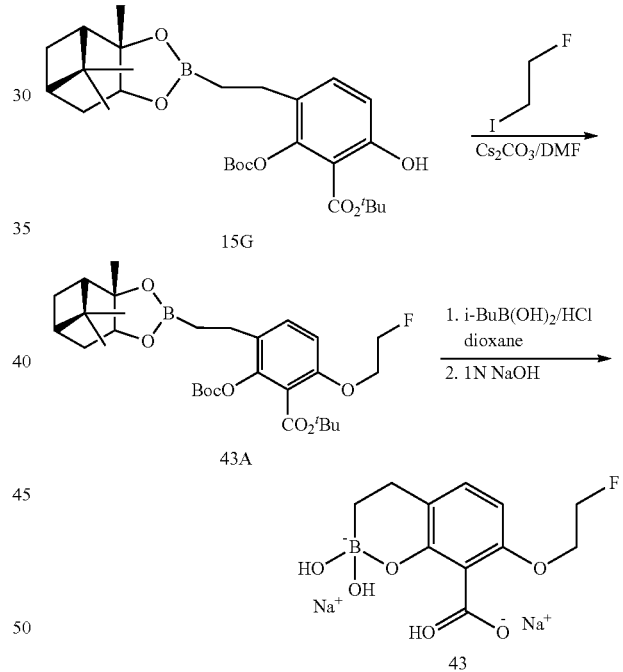

Step 1: Synthesis of 43A

The mixture of compound 15G (500 mg, 0.97 mmol, 1.0 eq), 1-fluoro-2-iodoethane (340 mg, 1.94 mmol, 2.0 eq) and Cs$_2$CO$_3$ (947 mg, 2.9 mmol, 3.0 eq) in anhydrous DMF (15 mL) was stirred at room temperature overnight. The solvent was removed under reduced pressure and the residue was purified by column chromatography (PE/EA=10:1) to give compound 43A (300 mg, 70%).

ESI-MS: [M+H]$^+$: 563.

Step 2: Synthesis of 43

To a solution of compound 43A (200 mg, 0.36 mmol, 1.0 eq) in dioxane (3 mL) and concentrated HCl (3 mL) was added i-BuB(OH)$_2$ (73 mg, 0.71 mmol, 2.0 eq). The mixture was stirred at rt for 1 hour. The reaction mixture was concentrated in vacuo, and the residue was dissolved in H₂O/MeCN. The resulting solution was adjusted to pH=12 with 1N NaOH and purified by prep-HPLC (18, neutral) to give 43 (62 mg, 50%) as white solid.

ESI-MS: [M+H]⁺: 255.

¹H NMR (CD₃OD, 400 MHz): δ 6.787-6.766 (d, J=8.4, 1H), 6.255-6.235 (d, J=8.0, 1H), 4.736-4.715 (t, J=4.0, J=4.4, 1H), 4.616-4.596 (t, 1H), 4.197-4.176 (t, 1H), 4.126-4.104 (t, 1H), 2.591-2.556 (t, 2H), 0.507-0.473 (t, J=6.8, 2H)

EXAMPLE 44

2-hydroxy-7-[2-hydroxy-1-(hydroxymethyl)ethoxy]-3,4-dihydro-1,2-benzoxaborinine-8-carboxylic acid

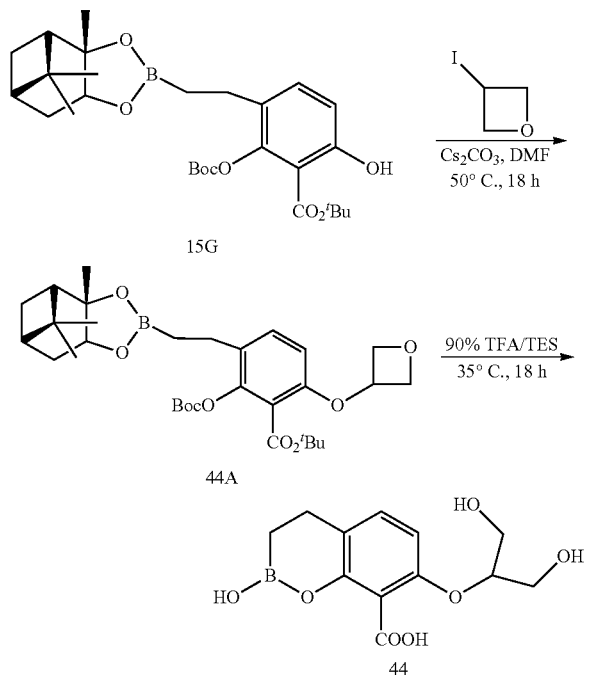

Step 1: Synthesis of 44A

To a solution of compound 15G (800 mg, 1.55 mmol, 1.0 eq) and 3-iodooxetane (485 mg, 2.63 mmol, 1.7 eq) in anhydrous DMF (15 mL) was added Cs₂CO₃. The mixture was stirred at 50° C. overnight before it was concentrated under reduced pressure. The residue was purified by column chromatography (PE/EA=20:1 to 5:1) to give compound 44A (200 mg, 30%).

ESI-MS: [M+H]⁺: 573.

Step 2: Synthesis of 44

The solution of compound 44A (200 mg) in 90% aqueous TFA (6 mL) and TES (2 mL) was stirred at 35° C. overnight before it was concentrated under reduced pressure. The mixture was purified by prep-HPLC to give 44 (26 mg, 20%) as white solid.

ESI-MS: [M−H2O+H]⁺: 265.

¹H NMR (CD₃OD, 400 MHz): δ 7.293-7.273 (d, J=8.0, 1H), 6.694-6.674 (d, J=8.0, 1H), 4.387-4.330 (t, J=10, 2H), 3.764-3.734 (t, J=6.4, J=5.6, 2H), 3.687-3.675 (d, J=5.2, 1H), 2.731 (s, 2H), 1.040 (s, 2H)

EXAMPLE 45

Disodium; 8-(cyclopropylmethoxy)-4,4-dihydroxy-5-oxa-4-boranuidabicyclo[4.4.0]deca-1(6),7,9-triene-7-carboxylate

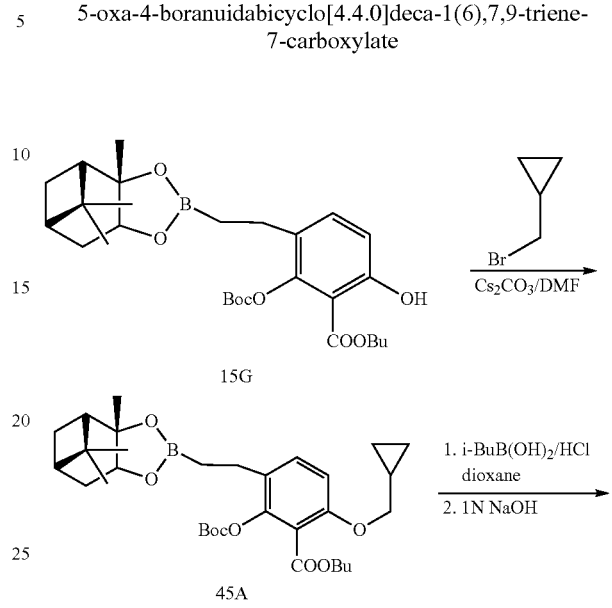

Step 1: Synthesis of 45A

To a solution of compound 15G (0.5 g, 0.97 mmol, 1.0 eq) and Cs₂CO₃ (0.947 g, 2.9 mmol, 3.0 eq) in anhydrous DMF (8 ml) was added (bromomethyl)cyclopropane (196 mg, 1.45 mmol, 1.5 eq) dropwise over 5 minutes. After 2.5 hours at room temperature, the reaction mixture was concentrated under reduced pressure and the residue was purified by prep-TLC (PE/EA=10:1) to give compound 45A (180 mg, 33%).

ESI-MS: [MH]⁺: 571.

Step 2: Synthesis of 45

To a solution of compound 45A (180 mg) in dioxane (2 mL) and concentrated HCl (0.2 mL) was added i-BuB(OH)₂ (65 mg, 0.64 mmol, 2 eq). The mixture was stirred at room temperature for 18 hours. The reaction mixture was concentrated in vacuo, and the residue was dissolved in H₂O/MeCN. The resulting solution was adjusted to pH=12 with 1N NaOH and purified by prep-HPLC (18, neutral) to give 45 (31 mg, 38%) as white solid.

ESI-MS: [M+H]⁺: 263.

¹H NMR (CD₃OD, 400 MHz): δ 6.696-6.675 (d, J=8.4, 1H), 6.180-6.159 (d, J=8.4, 1H), 3.774-3.757 (d, J=6.8, 2H), 2.576-2.542 (t, J=6.8, 2H), 1.318-1.228 (t, J=18, 1H), 0.507-0.485 (d, J=8.8, 2H), 0.402-0.368 (t, J=6.8, 2H), 0.311-0.299 (d, J=4.8, 2H).

EXAMPLE 46

7-(2-Amino-2-oxo-ethoxy)-2-hydroxy-3,4-dihydro-1,2-benzoxaborinine-8-carboxylic acid

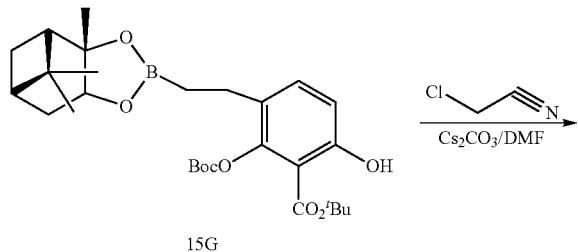

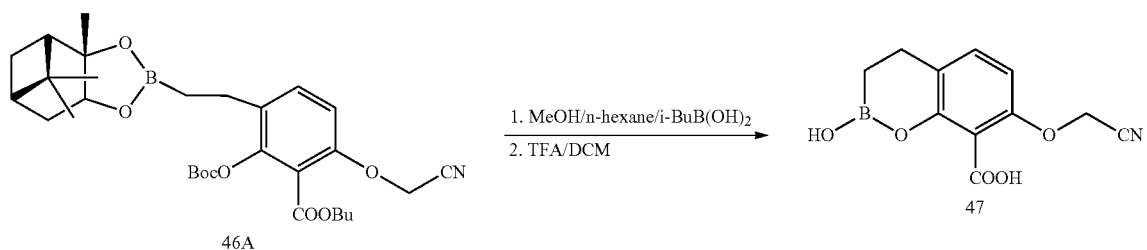

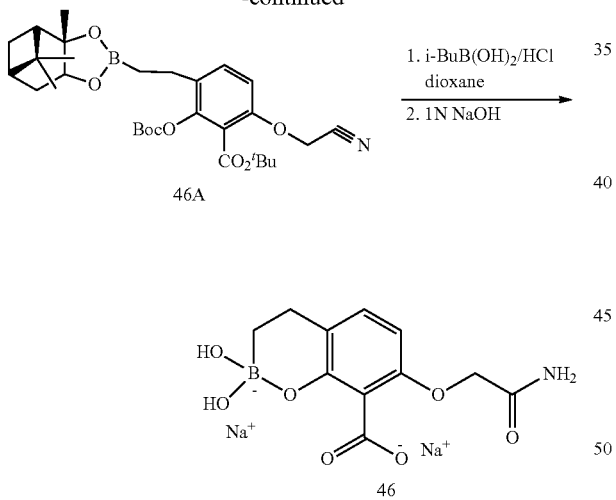

Step 1: Synthesis of 46A

To a solution of compound 15G (0.5 g, 0.97 mmol, 1.0 eq) and $Cs_2CO_3$ (0.947 g, 2.9 mmol, 3.0 eq) in anhydrous DMF (8 mL) was added of chloroacetonitrile (147 mg, 1.94 mmol, 2.0 eq) over 5 minutes. The mixture was stirred at room temperature for 1.5 hours before it was concentrated under reduced pressure. The residue was purified by column chromatography (PE/EA=5:1) to give compound 46A (0.30 g, 55.7%).

ESI-MS: $[M+H]^+$: 556.

Step 2: Synthesis of 46

To a solution of compound 46A (0.30 g) in dioxane (3 mL) and concentrated HCl (0.3 mL) was added i-BuB(OH)$_2$ (112 mg, 1.1 mmol, 2 eq). The mixture was stirred at room temperature for 18 hours. The reaction mixture was concentrated in vacuo, and the residue was dissolved in $H_2O$/MeCN. The resulting solution was adjusted to pH=12 with 1N NaOH and purified by prep-HPLC (18, neutral) to give 46 (41 mg, 28%) as white solid.

ESI-MS: $[M-H2O+H]^+$: 266.

$^1$H NMR (CD$_3$OD, 400 MHz): δ 6.749-6.728 (d, J=8.4, 1H), 6.148-6.127 (d, J=8.4, 1H), 4.463 (s, 2H), 3.703-3.678 (t, J=9.6, 1H), 3.593-3.570 (t, J=9.2, 1H), 2.537-2.503 (t, J=6.8, 2H), 0.419-0.392 (t, J=9.4, 2H).

EXAMPLE 47

7-(Cyanomethoxy)-2-hydroxy-3,4-dihydro-1,2-benzoxaborinine-8-carboxylic acid

To a solution of compound 46A (0.32 g, 0.58 mmol, 1.0 eq) and i-BuB(OH)$_2$ (0.836 g, 0.83 mmol, 1.5 eq) in MeOH/n-hexane (2.5 mL/2.5 mL) was added concentrated HCl (5 drops) dropwise. The reaction mixture was stirred at 30° C. for 3 hours. The methanol layer was separated and washed with hexanes (2×). The methanol layer was then concentrated and the residue was added DCM (2 mL) and then TFA (2.5 mL). The reaction solution was stirred at room temperature for 2.5 hours before it was concentrated under reduced pressure. The residue was purified by prep-HPLC (18) to give 46 (11 mg, 8%) as white solid.

ESI-MS: $[M+H]^+$: 248.

$^1$H NMR (CD$_3$OD, 400 MHz): δ 7.239-7.219 (d, J=0.8, 1H), 6.700 (d, 1H), 4.974 (s, 2H), 2.736-2.398 (t, J=6.4, 2H), 1.094-1.053 (t, J=8.0, 2H),

EXAMPLE 48

Disodium; 8-[2-(dimethylamino)ethoxy]-4,4-dihydroxy-5-oxa-4-boranuidabicyclo[4.4.0]deca-1(6),7,9-triene-7-carboxylate

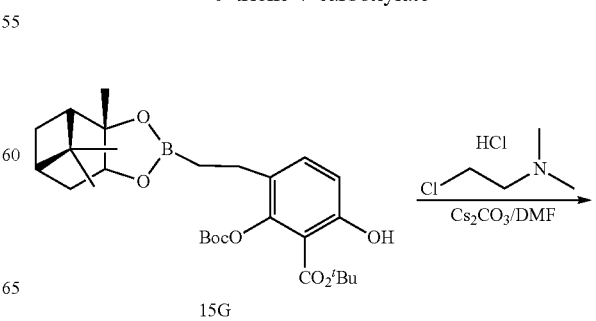

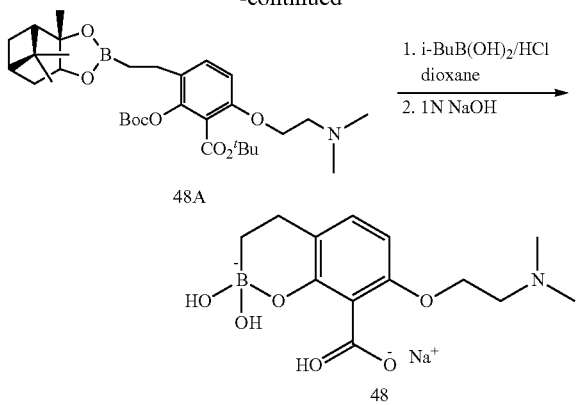

Step 1: Synthesis of 48A

A solution of compound 15G (0.8 g, 1.55 mmol, 1.0 eq), N,N-dimethyl-2-chloroethylamine HCl salt (0.67 g, 4.65 mmol, 3.0 eq) and Cs₂CO₃ (2.53 g, 7.75 mmol, 5.0 eq) in anhydrous DMF (15 mL) was stirred at 50° C. for 18 hours. The reaction mixture was concentrated under reduced pressure and the residue was partitioned in EA and 0.2 N HCl. The organic phase was concentrated to give crude 48A which was directly used for next step.

ESI-MS: [M+H]⁺: 588.

Step 2: Synthesis of 48

To a solution of crude compound 48A (0.8 g, 1.36 mmol, 1.0 eq) in dioxane (6 mL) and concentrated (6 mL) was added i-BuB(OH)₂ (0.275 g, 2.72 mmol, 2.0 eq). The mixture was stirred at room temperature for 18 hours. The reaction mixture was concentrated in vacuo, and the residue was dissolved in H₂O/MeCN. The resulting solution was adjusted to pH=12 with 1N NaOH and purified by prep-HPLC (18, neutral) to give 48 (61 mg, 16%) as white solid.

ESI-MS: [M+H]⁺: 280.

¹H NMR (CD3OD, 400 MHz): δ 6.788-6.766 (d, J=8.8, 1H), 6.276-6.255 (d, J=8.4, 1H), 4.193-40165 (t, J=11.2, 2H), 2.953 (t, 2H), 2.585-2.550 (t, J=14, 2H), 2.513 (s, 6H), 0.478-0.445 (t, J=13.2, 2H).

EXAMPLE 49

Disodium; 4,4-dihydroxy-8-(hydroxymethyl)-5-oxa-4-boranuidabicyclo[4.4.0]deca-1(6),7,9-triene-7-carboxylate

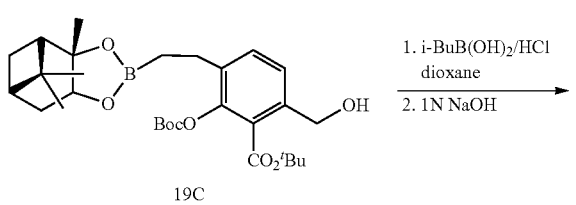

To a solution of 19C (150 mg, 0.28 mmol, 1.0 eq) in dioxane (2 mL) was added i-BuB(OH)₂ (58 mg, 0.57 mmol, 2.0 eq) and conc.HCl (2 mL). The reaction mixture was stirred at rt for 3 hours. The reaction mixture was concentrated in vacuo, and the residue was dissolved in H₂O/MeCN. The resulting solution was adjusted to pH=12 and purified by prep-HPLC (18, neutral) to give 49 (28 mg, 40%) as white solid.

ESI-MS: [M+H]⁺: 223.

¹H NMR (400 MHz, CD₃OD/H₂O): δ 7.15-7.12 (m, 1H), 6.76 (d, J=6.8 Hz, 1H), 4.77 (s, 2H), 3.30 (s, 1H), 2.66-2.60 (m, 2H), 1.30-1.26 (m, 2H).

EXAMPLE 50

Disodium; 8-(difluoromethyl)-4,4-dihydroxy-5-oxa-4-boranuidabicyclo[4.4.0]deca-1(6),7,9-triene-7-carboxylate

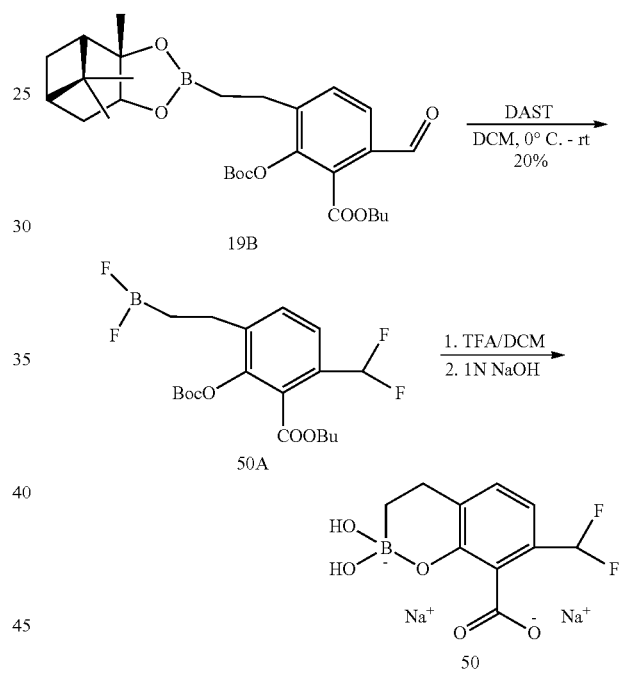

Step 1: Synthesis of 50A

To the solution of 19B (280 mg, 0.53 mmol, 1.0 eq) in DCM (8 mL) was added DAST (427 mg, 2.65 mmol, 5.0 eq) slowly at 0° C. The reaction mixture was stirred at room temperature for 16 hours. The mixture was diluted with DCM and washed with water. After concentration, the residue was purified by prep-TLC to give 50A (83 mg, 20%).

ESI-MS: [M+H]⁺: 421.

Step 2: Synthesis of 50

To the solution of 50A (60 mg, 0.143 mmol, 1.0 eq) in DCM (0.5 mL) was added TFA (0.2 mL). The resulting solution was stirred at room temperature for 1 hour before it was concentrated. The residue was dissolved in H₂O/MeCN. The resulting solution was adjusted to pH=12 and purified by prep-HPLC (18, neutral) to give 50 (18 mg, 60%).

ESI-MS: [2M–H]⁻: 483.

¹H NMR (400 MHz, CD₃OD): δ 7.65 (dt, 1H), 7.21 (d, J=7.6 Hz, 1H), 7.05 (d, J=8.0 Hz, 1H), 2.72-2.66 (t, 2H), 0.96-0.91 (t, 2H).

EXAMPLE 51

Disodium; 4,4-dihydroxy-8-(methanesulfonamido)-5-oxa-4-boranuidabicyclo[4.4.0]deca-1(6),7,9-triene-7-carboxylate

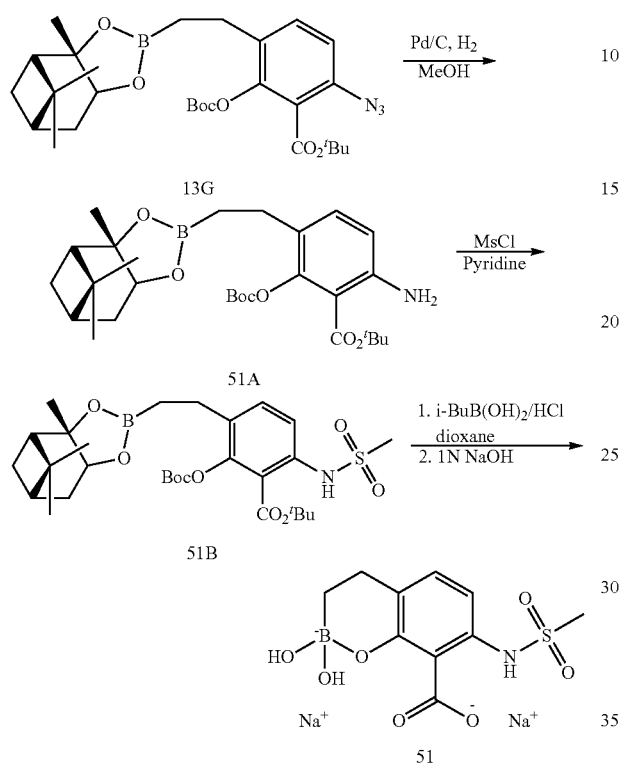

Step 1: Synthesis of 51A

A mixture of 13G (700 mg, 1.29 mmol, 1.0 eq) and Pd/C (150 mg, 10%) in MeOH (7 mL) was stirred under 1 atm hydrogen atmosphere at room temperature for 3 hours. The mixture was filtered and the filtrate was concentrated in vacuo. The residue was purified by flash chromatography on silica (PE/EA) to give 51A (320 mg, 48%).

ESI-MS: [M+H]⁺: 516.

Step 2: Synthesis of 51B

To a mixture of 51A (200 mg, 0.388 mmol, 1.0 eq) in Pyridine/DCM (3 mL/1 mL) was added MsCl (106 mg, 0.931 mmol, 2.4 eq) dropwise at 0° C. The mixture was stirred at room temperature for 3 hours before it was concentrated in vacuo. The residue was purified by prep-TLC to give 51B (110 mg, 48%).

ESI-MS: [M+H]⁺: 594.

Step 3: Synthesis of 51

To a solution of 51B (100 mg, 0.169 mmol, 1.0 eq) in dioxane (2 mL) was added i-BuB(OH)$_2$ (34.2 mg, 0.338 mmol, 2.0 eq) and concentrated HCl (2 mL). The reaction mixture was stirred at room temperature for 1 hour. The reaction mixture was concentrated in vacuo, and the residue was dissolved in H$_2$O/MeCN. The resulting solution was adjusted to pH=12 and purified by prep-HPLC (18, neutral) to give 51 (22 mg, 46%) as white solid.

ESI-MS: [2M−H]⁻: 569.

$^1$H NMR (400 MHz, CD$_3$OD): δ 6.80 (d, J=8.0 Hz, 1H), 6.68 (d, J=8.0 Hz, 1H), 2.84 (s, 3H), 2.62-2.58 (m, 2H), 0.48-0.43 (m, 2H).

EXAMPLE 52

Disodium; 4,4-dihydroxy-8-(sulfamoylamino)-5-oxa-4-boranuidabicyclo[4.4.0]deca-1(6),7,9-triene-7-carboxylate

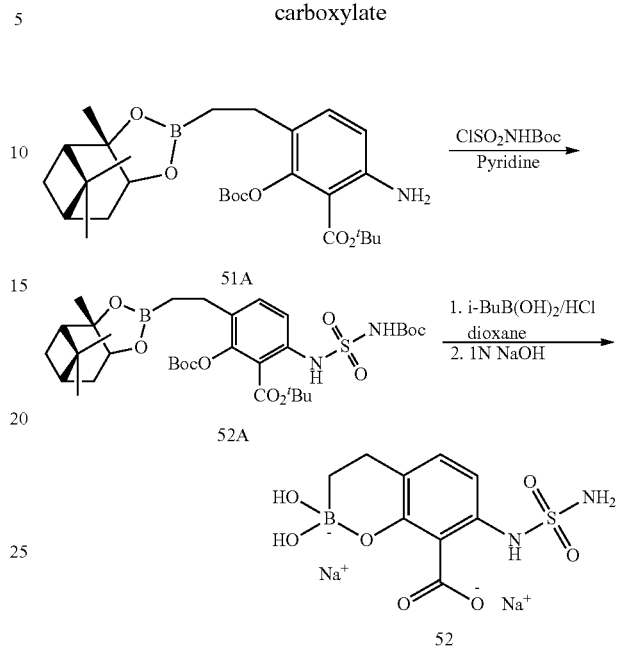

Step 1: Synthesis of 52A

To a mixture of 51A (130 mg, 0.252 mmol, 1.0 eq) in pyridine (3 mL) was added ClSO$_2$NHBoc (81.3 mg, 0.378 mmol, 1.5 eq) at 0° C., The mixture was stirred at room temperature for 1 hour before it was concentrated in vacuo. The residue was purified by prep-TLC to give 52A (100 mg, 57%).

ESI-MS: [M+H]⁺: 695.

Step 2: Synthesis of 52

To a solution of 52A (80 mg, 0.115 mmol, 1.0 eq) in dioxane (2 mL) was added i-BuB(OH)$_2$ (23.3 mg, 0.23 mmol, 2.0 eq) and concentrated HCl (1 mL). The reaction mixture was stirred at rt for 1 hour. The reaction mixture was concentrated in vacuo, and the residue was dissolved in H$_2$O/MeCN. The resulting solution was adjusted to pH=12 and purified by prep-HPLC (18, neutral) to give 52 (10 mg, 30%).

ESI-MS: [2M−H]⁻: 571.

$^1$H NMR (400 MHz, CD$_3$OD): δ 6.75 (d, J=7.6 Hz, 1H), 2.59-2.55 (m, 2H), 2.04-2.03 (m, 2H), 0.48-0.44 (m, 2H).

EXAMPLE 53

Trisodium; 4,4-dihydroxy-5-oxa-4-boranuidabicyclo[4.4.0]deca-1(6),7,9-triene-7,8-dicarboxylate

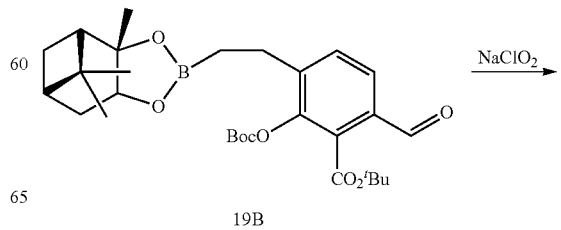

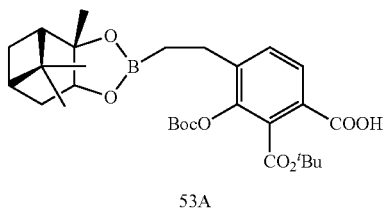

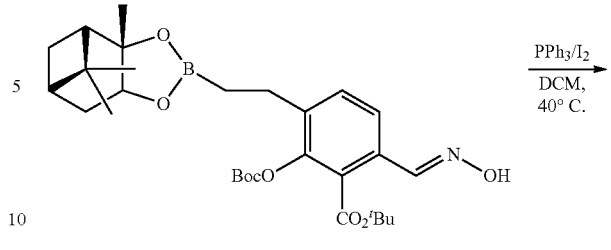

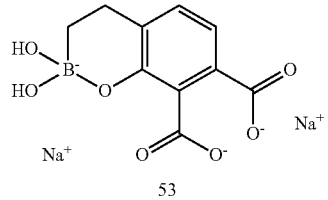

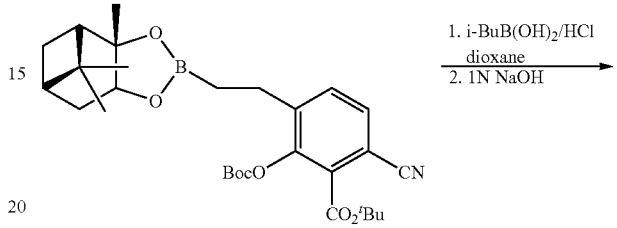

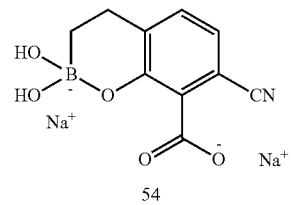

Step 1: Synthesis of 53A

A solution of compound 19B (330 mg, 0.624 mmol, 1.0 eq), NaClO$_2$ (113 mg, 1.25 mmol, 2 eq) and NH$_2$SO$_3$H (122 mg, 1.25 mmol, 2 eq) in dioxane/H$_2$O (9 mL/3 mL) was stirred at 0° C. for 2 hours. The reaction solution was concentrated under reduced pressure and the residue was purified by column chromatography (PE/EA=1:1) to give compound 53A (200 mg, 63%).

ESI-MS: [M+H]$^+$: 545.

Step 2: Synthesis of 53

To a solution of compound 53A (200 mg) and i-BuB(OH)$_2$ (75 mg, 0.73 mmol, 2 eq) in dioxane (3 mL) was added concentrated HCl (3 mL) at room temperature. The reaction mixture was stirred at rt for 1 hour. The reaction mixture was concentrated in vacuo, and the residue was dissolved in H$_2$O/MeCN. The resulting solution was adjusted to pH=12 and purified by prep-HPLC (18, neutral) to give 53 (11 mg, 10%) as white solid.

ESI-MS: [M+H]$^+$: 237.

$^1$H NMR (CD$_3$OD, 400 MHz): δ 7.021-7.003 (d, J=7.2, 1H), 6.810-6.791 (d, J=7.6, 1H), 2.647-2.614 (t, J=6.6, 2H), 0.524-0.491 (t, J=7.0, 2H)

EXAMPLE 54

Disodium; 8-cyano-4,4-dihydroxy-5-oxa-4-boranuidabicyclo[4.4.0]deca-1(6),7,9-triene-7-carboxylate

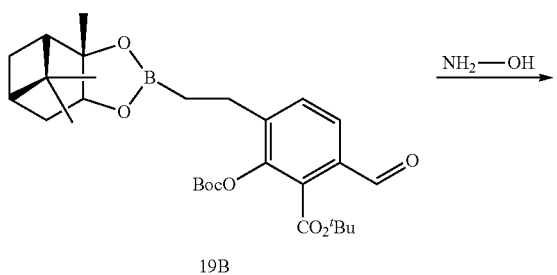

Step 1: Synthesis of 54A

To a solution of compound 19B (1.0 g, 1.89 mmol, 1.0 eq) in ethanol (15 mL) was added hydroxylamine (160 mg, 2.84 mmol, 1.5 eq). The mixture was stirred at room temperature for 2 hours before it was concentrated under reduced pressure. The crude product 54A (1.01 g) was used directly for next step.

ESI-MS: [M+H]$^+$: 544.

Step 2: Synthesis of 54B

To a solution of compound 54A (1.01 g, 1.86 mmol, 1.0 eq) and PPh$_3$ (1.07 g, 4.1 mmol, 2.2 eq) in DCM (20 mL) was added 12 (1.04 g, 4.1 mmol, 2.2 eq) at room temperature. The mixture was stirred at 40° C. overnight before it was concentrated under reduced pressure. The residue was purified by column chromatography (PE/EA=30:1 to 7:1) to give compound 54B (55 mg, 7%).

ESI-MS: [M+H]$^+$: 526.

Step 3: Synthesis of 54

To a solution of the compound 54B (55 mg) in dioxane (2 mL) and concentrated HCl (2 mL) was added i-BuB(OH)$_2$ (22 mg, 0.21 mmol, 2.0 eq). The reaction mixture was stirred at rt for 1 hour. The reaction mixture was concentrated in vacuo, and the residue was dissolved in H$_2$O/MeCN. The resulting solution was adjusted to pH=12 and purified by prep-HPLC (18, neutral) to give 54 (7 mg, 20%) as white solid.

ESI-MS: [M+H]$^+$: 218.

$^1$H NMR (CD$_3$OD, 400 MHz): δ 7.281-7.263 (d, J=7.2, 1H), 6.992-6.975 (d, J=6.8, 1H), 2.724-2.706 (t, 2H), 2.220-2.183 (t, 2H), 2.015-1.998 (t, 2H), 0.897-0.863 (t, 2H), 0.510-0.486 (t, 2H).

EXAMPLE 55

Disodium; 4,4-dihydroxy-8-(methoxyiminomethyl)-5-oxa-4-boranuidabicyclo[4.4.0]deca-1(6),7,9-triene-7-carboxylate

EXAMPLE 56

Disodium; 8-(difluoromethoxy)-4,4-dihydroxy-5-oxa-4-boranuidabicyclo[4.4.0]deca-1(6),7,9-triene-7-carboxylate

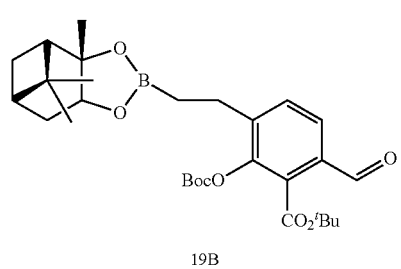
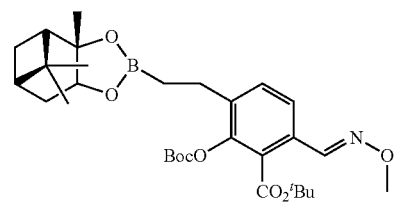
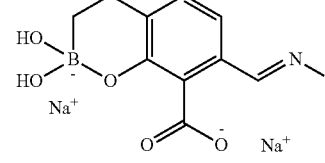
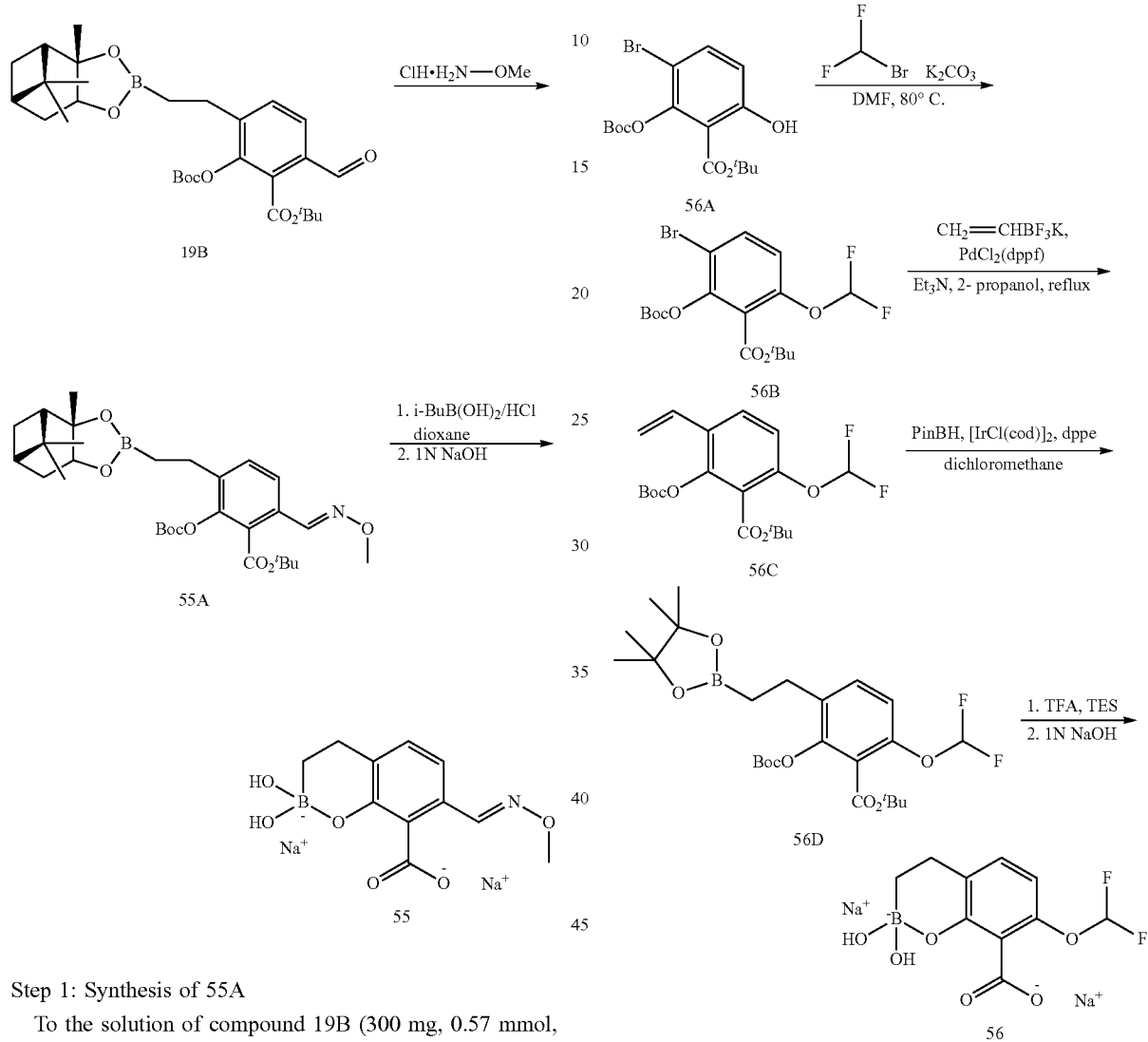

Step 1: Synthesis of 55A

To the solution of compound 19B (300 mg, 0.57 mmol, 1.0 eq) in ethanol (10 mL) was added methoxyamine hydrochloride salt. After 2 hours at room temperature, the reaction mixture was concentrated under reduced pressure. The crude intermediate 55A (300 mg) was used directly for next step without purification.

ESI-MS: [M+H]$^+$: 558.

Step 2: Synthesis of 55

To a solution of the crude 55A (300 mg) in dioxane (5 mL) and concentrated HCl (1 mL) was added i-BuB(OH)$_2$ (82 mg, 0.81 mmol, 1.5 eq). The reaction mixture was stirred at rt for 1 hour. The reaction mixture was concentrated in vacuo, and the residue was dissolved in H$_2$O/MeCN. The resulting solution was adjusted to pH=12 and purified by prep-HPLC (18, neutral) to give 55 (15 mg, 20%) as white solid.

ESI-MS: [M+H]$^+$: 250.

Step 1: Synthesis of 56B

A solution of compound 56A (prepared from 15C using procedure as in step 6 of Example 15) (6.00 g, 15.4 mmol, 1.0 eq) and potassium carbonate (2.13 g, 15.4 mmol, 1.0 eq) in anhydrous DMF (15 mL) was cooled to −78° C. and bubbled with bromodifluoromethane (~6 g, ~3 eq). The reaction mixture was warmed up and then heated up to 80° C. After 2.5 hours, the mixture was cooled down and partitioned in ethyl acetate and 0.1 N aqueous HCl. The organic layer was washed with water (2×10 mL) and dried over Na$_2$SO$_4$. The solvent was removed under reduced pressure, and the residue was purified by column chromatography (hexanes/EtOAc=15:1) to give compound 56B (2.2 g, 32%) as slight yellow oil.

H NMR (CDCl$_3$, 300 MHz): δ7.60 (d, 1H), 7.01 (d, 1H), 6.49 (t, 1H), 1.56 (s, 18H).

Step 2: Synthesis of 56C

The mixture of compound 56B (600 mg, 1.37 mmol, 1.0 eq), potassium vinyltrifluoroborate (457 mg, 3.43 mmol, 2.5 eq), PdCl$_2$(dppf) (57 mg, 0.07 mmol, 0.05 eq) and triethylamine (0.27 mL, 2.06 mmol, 1.5 eq) in 2-propanol (25 mL) was degassed and filled with N$_2$ (3×), then was heated to reflux. After refluxing for 18 hours, the mixture was cooled down and filtered. The solution was concentrated under reduced pressure, and the residue was purified by column chromatography (hexanes/EtOAc=6:1) to give compound 56C (478 mg, 90%) as slight yellow solid.

H NMR (CDCl$_3$, 300 MHz): δ7.55 (d, 1H), 7.15 (d, 1H), 6.72 (dd, 1H), 6.50 (t, 1H), 5.75 (d, 1H), 5.39 (d, 1H), 1.56 (s, 18H).

Step 3: Synthesis of 56D

The catalyst [IrCl(cod)]2 (16 mg, 0.025 mmol, 0.02 eq) and ligand dppe (20 mg, 0.049 mmol, 0.04 eq) were dissolved in dichloromethane (4 mL) under N$_2$ atmosphere and stirred at room temperature. After 5 minutes, pinBH (0.23 mL, 1.49 mmol, 1.2 eq) and the solution of compound 56C (478 mg, 1.24 mmol, 1.0 eq) were added under N$_2$ atmosphere. After stirring at room temperature for 18 hours, the reaction mixture was concentrated under reduced pressure, and the residue was purified by column chromatography (hexanes/EtOAc=10:1) to give compound 56D (315 mg, 49%) as slight yellow solid.

ESI-MS: [M+H]$^+$: 515.

Step 4: Synthesis of 56

To the mixture of compound 56D (315 mg, 0.612 mmol, 1.0 eq) and triethylsilane (712 mg, 6.12 mmol, 10 eq) was added TFA (5 mL) at room temperature. After 3 hours, the mixture was concentrated and re-dissolved in MeCN/H$_2$O (5 mL, 1/1, v/v) and adjusted to PH=9 with 1 N NaOH solution. The solution was stirred at room temperature for 20 hours and then purified by prep-HPLC (18, neutral) to give 56 Na salt (43 mg) as white solid.

H NMR (D$_2$O, 300 MHz): δ6.83 (d, J=8.4 Hz, 1H), 6.50 (t, J=74.7 Hz, 1H), 6.36 (d, J=8.4 Hz, 1H), 2.47 (t, J=7.5 Hz, 2H), 0.37 (t, J=7.2 Hz, 2H).

ESI-MS: [2M−H]$^-$: 515.

EXAMPLE 57

Disodium; 8-ethoxy-4,4-dihydroxy-5-oxa-4-boranuidabicyclo[4.4.0]deca-1(6),7,9-triene-7-carboxylate

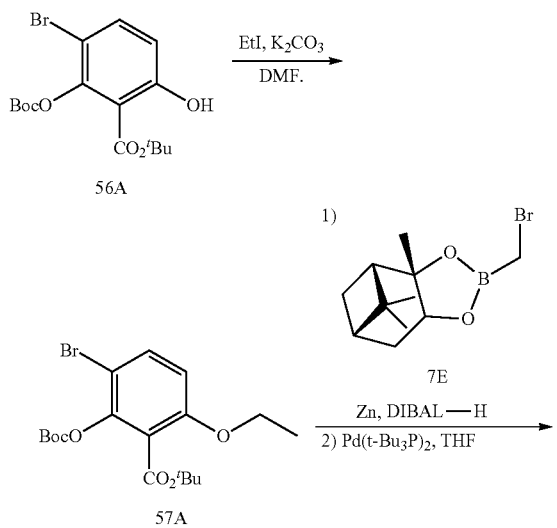

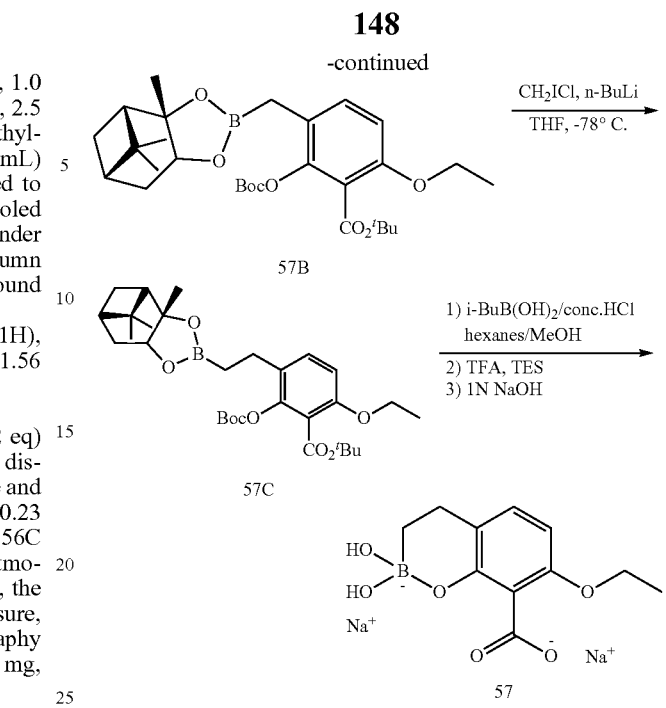

Step 1: Synthesis of 57A

To the solution of compound 56A (1.0 g, 2.6 mmol, 1.0 eq) and potassium carbonate (524 mg, 3.8 mmol, 1.5 eq) in anhydrous DMF (15 mL) was added iodoethane (2.1 mL, 26 mmol, 10 eq). After 18 hours at room temperature, the reaction mixture was partitioned in ethyl acetate and 0.1 N aqueous HCl. The organic layer was washed with water (2×) and dried over Na$_2$SO$_4$. The solvent was removed under reduced pressure, and the residue was purified by column chromatography (hexanes/EtOAc=20:1 to 5/1) to give compound 57A (1.06 g, 98%) as slight yellow oil.

$^1$H NMR (CDCl$_3$, 300 MHz): δ7.48 (d, J=9.0 Hz, 1H), 6.68 (d, J=9.0 Hz, 1H), 4.03 (q, J=7.2 Hz, 2H), 1.56 (s, 18H), 1.38 (t, J=7.2 Hz, 3H).

Step 2: Synthesis of 57B

To the mixture of Zn powder (830 mg, 12.7 mmol, 5.0 eq) and 7E (55 mg, 0.2 mmol) in anhydrous THF (2.0 mL) was added DIBAL-H (0.26 mL, 0.26 mmol, 1.0 M in hexanes, 0.05 eq) at room temperature. The mixture was stirred at 30° C. for 5 min, then more (+)-pinanediolborate methylenebromide (1.38 g, 5.0 mmol, 2.0 eq) in anhydrous THF (3.0 mL) was added drop-wise into the mixture over 10 minutes. The reaction mixture was stirred at 50° C. for 2 hours before it was cooled to room temperature and settled down. The top clear solution was transferred into a mixture of compound 57A (1.06 g, 2.5 mmol, 1.0 eq) and Pd(t-Bu3P)$_2$ (64 mg, 0.13 mmol, 0.05 eq) in THF (10 mL) under N$_2$ atmosphere. The mixture was stirred at room temperature for 2.5 hours before it was concentrated in vacuo. The obtained residue was purified by column chromatography (hexanes/EtOAc=10:1 to 5/1) to give compound 57B (1.25 g, 97%) as slight yellow oil.

ESI-MS: [M+H]$^+$: 531.

Step 3: Synthesis of 57C

To the solution of compound 57B (320 mg, 0.61 mmol, 1.0 eq) and chloroiodomethane (0.09 mL, 1.2 mmol, 2.0 eq) in THF (2.0 mL) was added n-BuLi (0.36 mL, 2.5 M in hexanes, 0.9 mmol, 1.5 eq) slowly at −78° C. under N$_2$ atmosphere. The resulting solution was slowly warmed up to room temperature in 18 hours before it was concentrated under reduced pressure. The obtained residue was purified by column chromatography (hexanes/EtOAc=10:1) to give compound 57C (250 mg, 76%) as slight yellow oil.

ESI-MS: [M+H]$^+$: 545.

Step 4: Synthesis of 57

To the mixture of compound 57C (75 mg, 0.14 mmol, 1.0 eq) and i-BuB(OH)$_2$ (42 mg, 0.42 mmol, 3.0 eq) in hexanes (3.0 mL) and MeOH (3.0 mL) was added concentrated HCl (2 drops) at room temperature. After 20 hours, the two layers were separated and the MeOH layer was washed with hexanes (2×). The MeOH layer was concentrated and was added triethylsilane (162 mg, 1.4 mmol, 10 eq) and TFA (3 mL) at room temperature. After 3 hours, the reaction mixture was concentrated and re-dissolved in MeCN/H$_2$O (5 mL, 1/1, v/v) and adjusted to PH=10 with 1 N NaOH solution. The solution was stirred at room temperature for 20 hours and then purified by prep-HPLC (18, neutral) to give 57 Na salt (31 mg) as white solid.

$^1$H NMR (D$_2$O, 300 MHz): δ6.67 (d, J=8.1 Hz, 1H), 6.15 (d, J=8.4 Hz, 1H), 3.98 (q, 2H), 2.55 (t, 2H), 1.31 (t, 3H), 0.42 (t, 2H).

ESI-MS: [M−H$_2$O+H]$^+$: 219.

EXAMPLE 58

8-Fluoro-2-hydroxy-3,5-dihydro-1,4,2-benzodioxaborepine-9-carboxylic acid

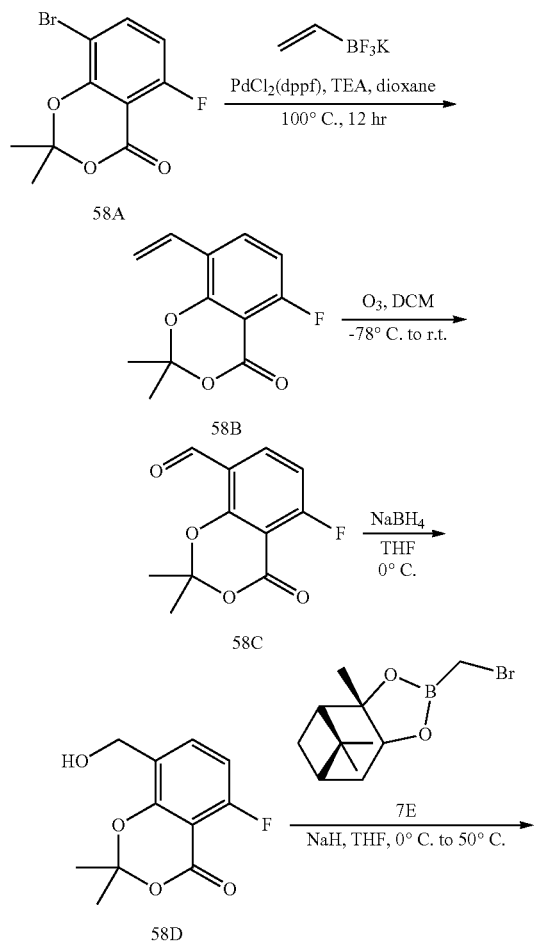

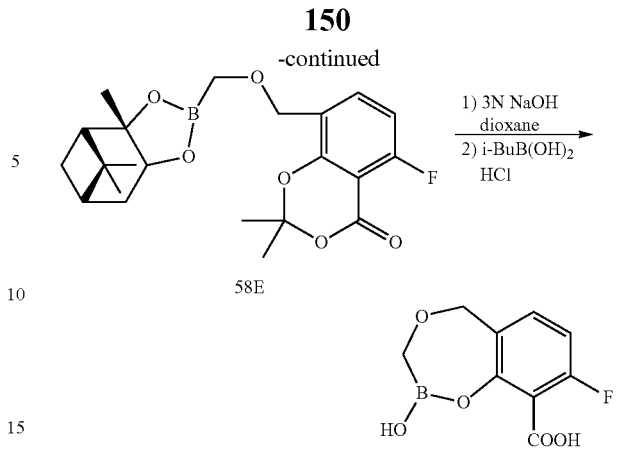

Step 1: Synthesis of 58B

The mixture of compound 58A (prepared from of 36A (WO 15179308) via hydrolysis as in synthesis of 36D and acetonide formation as in 7J) (4.4 g, 16 mmol, 1.0 eq), potassium vinyltrifluoroborate (3.2 g, 24 mol, 1.5 eq), TEA (4.86 g, 48 mol, 3.0 eq) and PdCl$_2$(dppf) (653 mg, 0.8 mmol, 0.05 eq) in dioxane (30 mL) was stirred at 100° C. for 12 hours under N$_2$ atmosphere. The mixture was concentrated and purified by column chromatography (hexanes/EtOAc=5:1 to 1/1) to give compound 58B (1.6 g, 45% yield) as yellow solid.

Step 2: Synthesis of 58C

To a solution of compound 58B (1.6 g, 7.2 mmol, 1.0 eq) in DCM (30 mL) was bubbled with O3 at −78° C. until the solution turned to slightly blue. The nitrogen was bubbled in to remove the color. The colorless solution was added dimethylsulfide (3 mL) and slowly warmed up to room temperature in 6 hours. The solvent was removed under reduced pressure and the residue was purified by column chromatography (PE/EA=3:1) to give compound 58C (1.0 g, 62%) as yellow oil.

Step 3: Synthesis of 58D

To a solution of compound 58C (1.0 g, 4.46 mmol, 1.0 eq) in anhydrous THF (20 mL) was added NaBH$_4$ (254 mg, 6.7 mmol, 1.5 eq) at 0° C. The mixture was stirred at room temperature for 1 hour before it was quenched with water. The reaction mixture was concentrated under reduced pressure, and the residue was purified by column chromatography (PE/EA=1:1) to give compound 58D (650 mg, 64%) as yellow solid.

$^1$H NMR (CDCl$_3$, 400 MHz): δ7.62 (dd, 1H), 6.85 (dd, 1H), 4.66 (s, 2H), 1.76 (s, 6H).

Step 4: Synthesis of 58E

To the solution of compound 58D (192 mg, 0.85 mmol, 1.0 eq) in anhydrous THF (4 mL) was added a suspension of NaH (51 mg, 60% in mineral oil, 1.28 mmol, 1.5 eq) in THF (2 mL) dropwise at 0° C. under nitrogen atmosphere. After 10 minutes, a solution of (+)-pinanediolborate methylenebromide (464 mg, 1.7 mmol, 2.0 eq) in THF (4 mL) was added into above solution and the reaction mixture was slowly heated up to 50° C. After 3 hours, the reaction was quenched with saturated aqueous NH$_4$Cl and extracted with ethyl acetate. The organic layer was dried over Na$_2$SO$_4$. The solvent was removed under reduced pressure, and the residue was purified by column chromatography (hexanes/EtOAc=20:1 to 5/1) to give compound 58E (102 mg, 29%) as colorless oil.

ESI-MS: [M+H]: 419.

Step 2: Synthesis of 58

The mixture of compound 58E (85 mg, 0.20 mmol, 1.0 eq) in dioxane (0.5 mL) and 3N NaOH (0.5 mL) was stirred at room temperature for 2 hours, LCMS indicating the disappearance of starting material. To this mixture was then added 5N HCl (0.7 mL) and i-BuB(OH)$_2$ (61 mg, 0.6 mmol, 3.0 eq). After overnight at room temperature, the reaction mixture was concentrated in vacuo and the residue was purified by prep-HPLC (18, acetonitrile and water as mobile phases, 0.1% HCOOH) to give 58 (8.7 mg) as white solid.

$^1$H NMR (CD$_3$OD, 300 MHz): δ7.53 (dd, 1H), 6.64 (dd, 1H), 4.48 (s, 2H), 3.30 (s, 2H).

ESI-MS: [3M−2H$_2$O—H]$^−$: 641.

EXAMPLE 59

Disodium; 4,4-dihydroxy-5-oxa-9-aza-4-boranuid-abicyclo[4.4.0]deca-1(6),7,9-triene-7-carboxylate

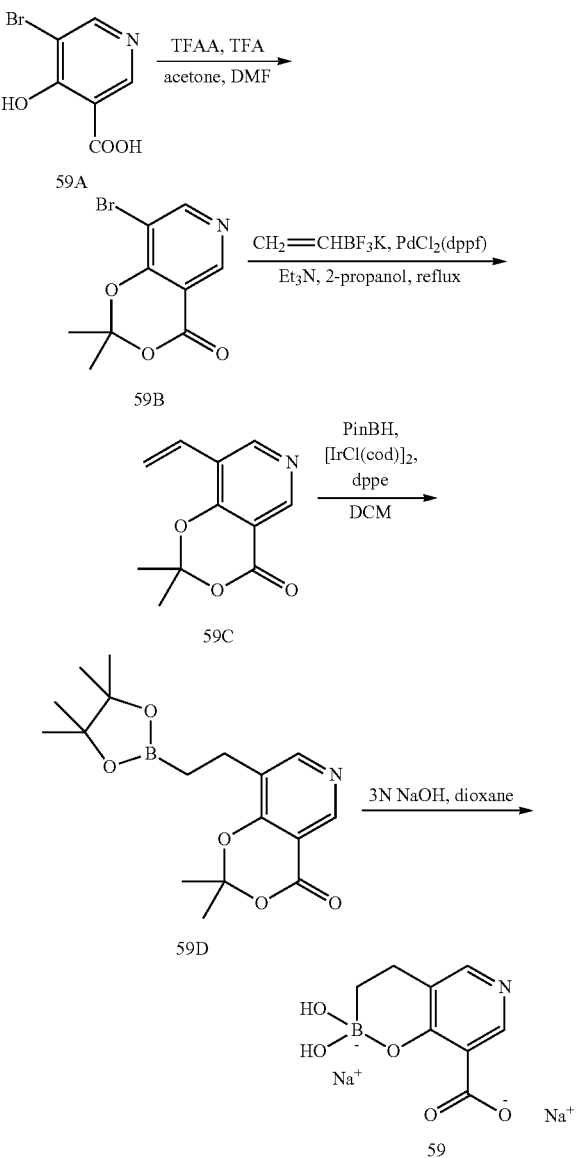

Step 1: Synthesis of 59B

To the solution of compound 59A (*J. Med. Chem.*, 2008, 51, 5330-41) (2.9 g, 13.3 mmol, 1.0 eq) in TFAA (6 mL) and TFA (12 mL) was added acetone (5 mL) dropwise at room temperature. After 1 hour, the reaction mixture was added DMF (15 mL) to give a clear brown solution, followed by more acetone (5 mL). After stirred at room temperature for 18 hours, the mixture was concentrated in vacuo and the residue was partitioned in EtOAc/hexanes (3/1, v/v) and saturated NaHCO$_3$. The organic layer was washed with water (2×) and dried over Na$_2$SO$_4$. The solvent was removed under reduced pressure, and the residue was purified by column chromatography (hexanes/EtOAc=3:1 to 0/1) to give compound 59B (2.1 g, 61%) as yellow solid.

$^1$H NMR (CDCl$_3$, 300 MHz): δ8.99 (s, 1H), 8.80 (s, 1H), 1.83 (s, 6H).

Step 2: Synthesis of 59C

The mixture of compound 59B (820 mg, 3.18 mmol, 1.0 eq), potassium vinyltrifluoroborate (554 mg, 4.13 mmol, 1.3 eq), PdCl$_2$(dppf) (130 mg, 0.16 mmol, 0.05 eq) and triethylamine (0.89 mL, 6.4 mmol, 2 eq) in 2-propanol (30 mL) was degassed and filled with N$_2$ (3×), then was heated to reflux. After refluxing for 20 hours, the mixture was cooled down and filtered. The solution was concentrated under reduced pressure, and the residue was purified by column chromatography (hexanes/EtOAc=3/1 to 1/1) to give compound 59C (517 mg, 79%) as slight yellow solid.

$^1$H NMR (CDCl$_3$, 300 MHz): δ8.97 (s, 1H), 8.74 (s, 1H), 6.76 (dd, 1H), 5.95 (d, J=18.0 Hz, 1H), 5.50 (d, J=11.4 Hz, 1H), 1.78 (s, 6H).

Step 3: Synthesis of 59D

The catalyst [IrCl(cod)]2 (24 mg, 0.036 mmol, 0.03 eq) and ligand dppe (29 mg, 0.073 mmol, 0.06 eq) were dissolved in dichloromethane (4 mL) under N$_2$ atmosphere and stirred at room temperature. After 5 minutes, pinBH (0.21 mL, 1.44 mmol, 1.2 eq) and compound 59C (246 mg, 1.2 mmol, 1.0 eq) were added, and the solution was flushed with N$_2$ again. After stirring at room temperature for 18 hours, the reaction mixture was concentrated under reduced pressure, and the residue was purified by column chromatography (hexanes/EtOAc=3/1 to 1/1) to give compound 59D (82 mg, 21%) as slight yellow solid.

ESI-MS: [M+H]$^+$: 334.

Step 4: Synthesis of 59

The mixture of compound 59D (82 mg, 0.24 mmol, 1.0 eq) in dioxane (0.5 mL) and 3N NaOH (0.5 mL) was stirred at room temperature for 2 hours, LCMS indicating the disappearance of starting material. The reaction mixture was concentrated in vacuo and the residue was purified by prep-HPLC (18, acetonitrile and water as mobile phases, neutral) to give 59 Na salt (8.0 mg) as off-white solid.

$^1$H NMR (D$_2$O, 300 MHz): δ8.05 (s, 1H), 7.86 (s, 1H), 2.59 (t, J=7.2 Hz, 2H), 0.41 (t, J=7.2 Hz, 2H).

ESI-MS: [M+H]$^+$: 194.

Example 60

Disodium; 3,3-dideuterio-4,4-dihydroxy-8-methoxy-5-oxa-4-boranuidabicyclo[4.4.0]deca-1(10),6,8-triene-7-carboxylate

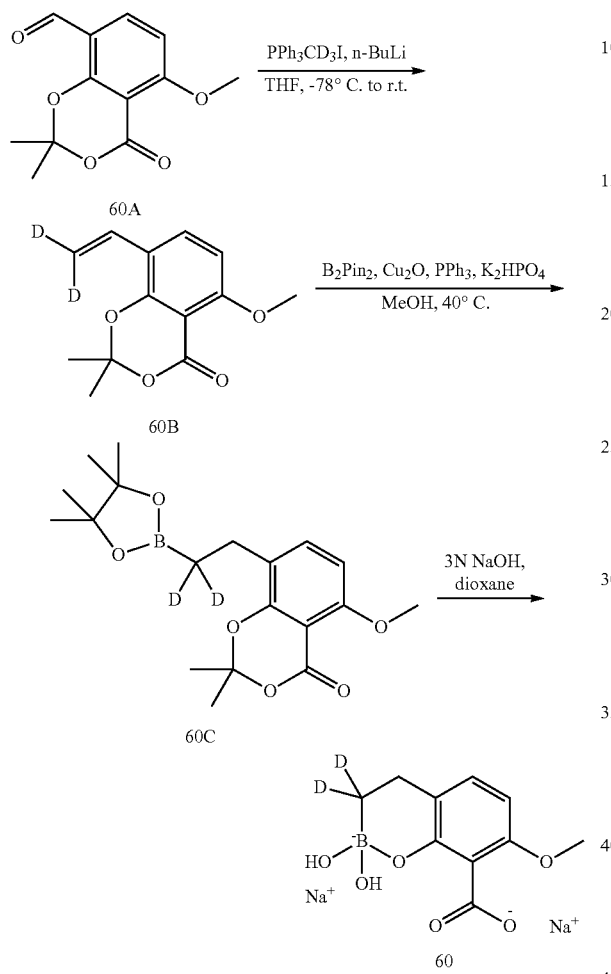

Step 1: Synthesis of 60B

To the solution of $PPh_3CD_3I$ (896 mg, 2.2 mmol, 1.1 eq) in THF (15 mL) was added n-BuLi (0.84 mL, 2.5 M in hexanes, 2.1 mmol, 1.05 eq) dropwise in 5 minutes at −78° C. After 1 hour, compound 60A (473 mg, 2.0 mmol, 1.0 eq) in THF (8 mL) was slowly added into above reaction mixture. The reaction mixture was slowly warmed up to room temperature and stirred for 1 hour. The mixture was quenched with saturated $NH_4Cl$ and extracted with EtOAc (2×). The organic layer was concentrated in vacuo and the residue was purified by column chromatography (hexanes/EtOAc=3:1 to 1/1) to give compound 60B (170 mg, 36%) as white solid.

$^1$H NMR ($CDCl_3$, 300 MHz): δ7.65 (d, J=9.0 Hz, 1H), 6.80 (s, 1H), 6.64 (d, J=9.0 Hz, 1H), 3.97 (s, 3H), 1.73 (s, 6H).

Step 2: Synthesis of 60C

The mixture of compound 60B (155 mg, 0.66 mmol, 1.0 eq), bis(pinacolato)diboron (192 mg, 0.76 mmol, 1.15 eq) and $PPh_3$ (19 mg, 0.07 mmol, 0.11 eq) in methanol (2 mL) was added $K_2HP_4$ (137 mg, 0.79 mmol, 1.2 eq), and then $Cu_2O$ (7.5 mg, 0.05 mmol, 0.08 eq). The resulting mixture was flushed with nitrogen and stirred at 40° C. for 6 hours before it was partitioned in EtOAc and 0.1 M $K_2HP_4$. The organic layer was washed with 0.1 M $K_2HP_4$ and dried over $Na_2SO_4$. The solution was concentrated under reduced pressure, and the residue was purified by column chromatography (hexanes/EtOAc=3/1 to 1/1) to give compound 60D (191 mg, 80%) as white crystal.

ESI-MS: $[M+H]^+$: 365.

Step 3: Synthesis of 60

The mixture of compound 60D (65 mg, 0.18 mmol, 1.0 eq) in dioxane (0.4 mL) and 3N NaOH (0.4 mL) was stirred at room temperature for 2 hours, LCMS indicating the disappearance of starting material. The reaction mixture was concentrated in vacuo and the residue was purified by prep-HPLC (18, acetonitrile and water as mobile phases, 0.1% HCOOH). The obtained solid was dissolved in MeCN/$H_2O$ and was adjusted to PH=8 with 0.1 N NaOH. Sodium salt of 60 was obtained as white solid (11 mg) after lyophilization.

$^1$H NMR ($D_2O$, 300 MHz): δ6.78 (d, J=8.4 Hz, 1H), 6.22 (d, J=8.4 Hz, 1H), 3.59 (s, 3H), 2.43 (s, 2H).

ESI-MS: $[M-H2O+H]^+$: 207.

EXAMPLE 61

Disodium; 8-carbamoyl-4,4-dihydroxy-5-oxa-4-boranuidabicyclo[4.4.0]deca-1(6),7,9-triene-7-carboxylate

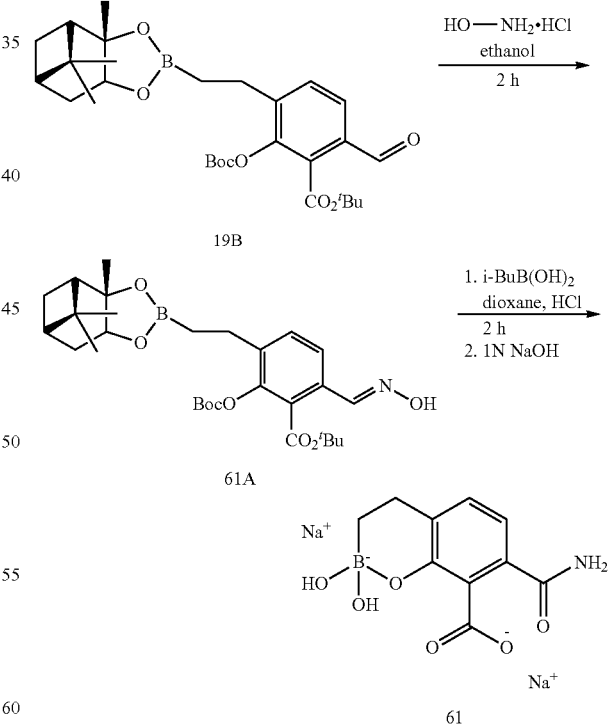

Step 1: Synthesis of 61A

To a solution of compound 19B (300 mg, 0.57 mmol, 1.0 eq) in ethanol (8.0 mL) was added hydroxyamine HCl salt (60 mg, 0.85 mmol, 1.5 eq). The mixture was stirred at room temperature for 2 hours before it was concentrated under reduced pressure. The residue was purified by prep-TLC to give compound 61A (200 mg, 65%).

ESI-MS: [M+H]⁺: 544.

Step 2: Synthesis of 61

To a solution of compound 61A (200 mg, 0.37 mmol, 1.0 eq) in dioxane (2 mL) was added i-BuB(OH)₂ (75 mg, 0.74 mmol, 2.0 eq) and concentrated HCl (2 mL). The reaction mixture was stirred at room temperature for 3 hours. The reaction mixture was concentrated in vacuo, and the residue was dissolved in H₂O/MeCN. The resulting solution was adjusted to pH=10 with 1N NaOH and purified by prep-HPLC (18, neutral) to give 61 Na salt (11 mg, 12%) as white solid.

ESI-MS: [M+H]⁺: 236.

$^1$H NMR (400 MHz, CD₃OD): δ 6.94 (d, J=7.6 Hz, 1H), 6.84 (d, J=7.6 Hz, 1H), 2.68-2.64 (m, 2H), 0.53-0.48 (m, 2H).

EXAMPLE 62

Disodium; 8-[4-(azetidin-1-yl)but-2-ynoxy]-4,4-dihydroxy-5-oxa-4-boranuidabicyclo[4.4.0]deca-1(6),7,9-triene-7-carboxylate

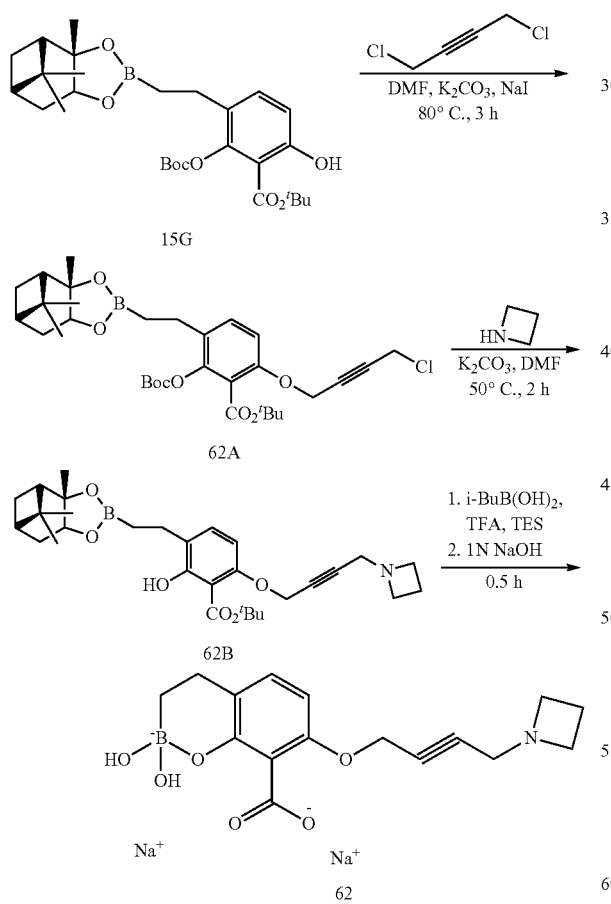

Step 1: Synthesis of 62A

To a solution of compound 15G (1.0 g, 1.9 mmol, 1.0 eq) in DMF (15 mL) was added 1,4-dichlorobut-2-yne (490 mg, 4.0 mmol, 2.0 eq), K₂CO₃ (800 mg, 5.8 mmol, 3.0 eq) and NaI (290 mg, 1.9 mmol, 1.0 eq). The mixture was stirred at 80° C. for 3 hours before it was concentrated under reduced pressure. The residue was purified by column chromatography (hexanes/EtOAc=10/1 to 5/1) to give compound 62A (900 mg, 77%).

ESI-MS: [M+H]⁺: 603.

Step 2: Synthesis of 62B

To a solution of compound 62A (500 mg, 0.83 mmol, 1.0 eq) in DMF (10 mL) was added azetidine (95 mg, 1.66 mmol, 2.0 eq) and K₂CO₃ (458 mg, 3.3 mmol, 4.0 eq). The mixture was stirred at 50° C. for 2 before it was concentrated under reduced pressure. The residue was purified by column chromatography (hexanes/EtOAc=10/1 to 3/1) to give compound 62B (220 mg, 43%).

ESI-MS: [M+H]⁺: 524.

Step 3: Synthesis of 62

The mixture of compound 62B (200 mg, 0.38 mmol, 1.0 eq), TES (0.5 mL) and i-BuB(OH)₂ (5 mg, 49 mmol, 2.0 eq) in 90% aqueous TFA (1 mL) was stirred at room temperature for half hour before it was concentrated in vacuo. The residue was dissolved in water/MeCN and adjusted to PH=12 with 1N NaOH. The solution was purified by prep-HPLC (18, neutral) to give 62 sodium salt (56 mg, 51%) as white solid.

ESI-MS: [M+H]⁺: 316.

$^1$H NMR (400 MHz, CD₃OD): δ 6.69 (d, J=8.4 Hz, 1H), 6.34 (d, J=8.4 Hz, 1H), 4.68 (s, 2H), 3.31-3.29 (m, 4H), 3.27-3.25 (m, 2H), 2.58-2.53 (m, 2H), 2.07-2.02 (m, 2H), 0.44-0.42 (m, 2H).

EXAMPLE 63

Disodium; 4,4-dihydroxy-8-methoxy-5-oxa-9-aza-4-boranuidabicyclo[4.4.0]deca-1(6),7,9-triene-7-carboxylate

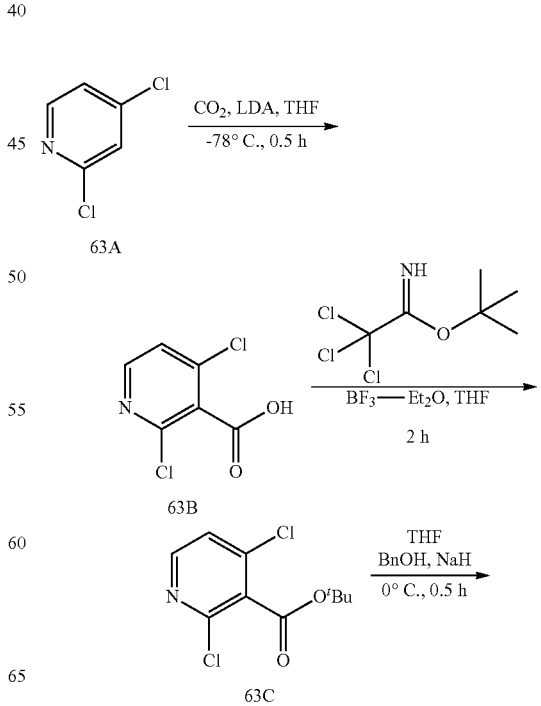

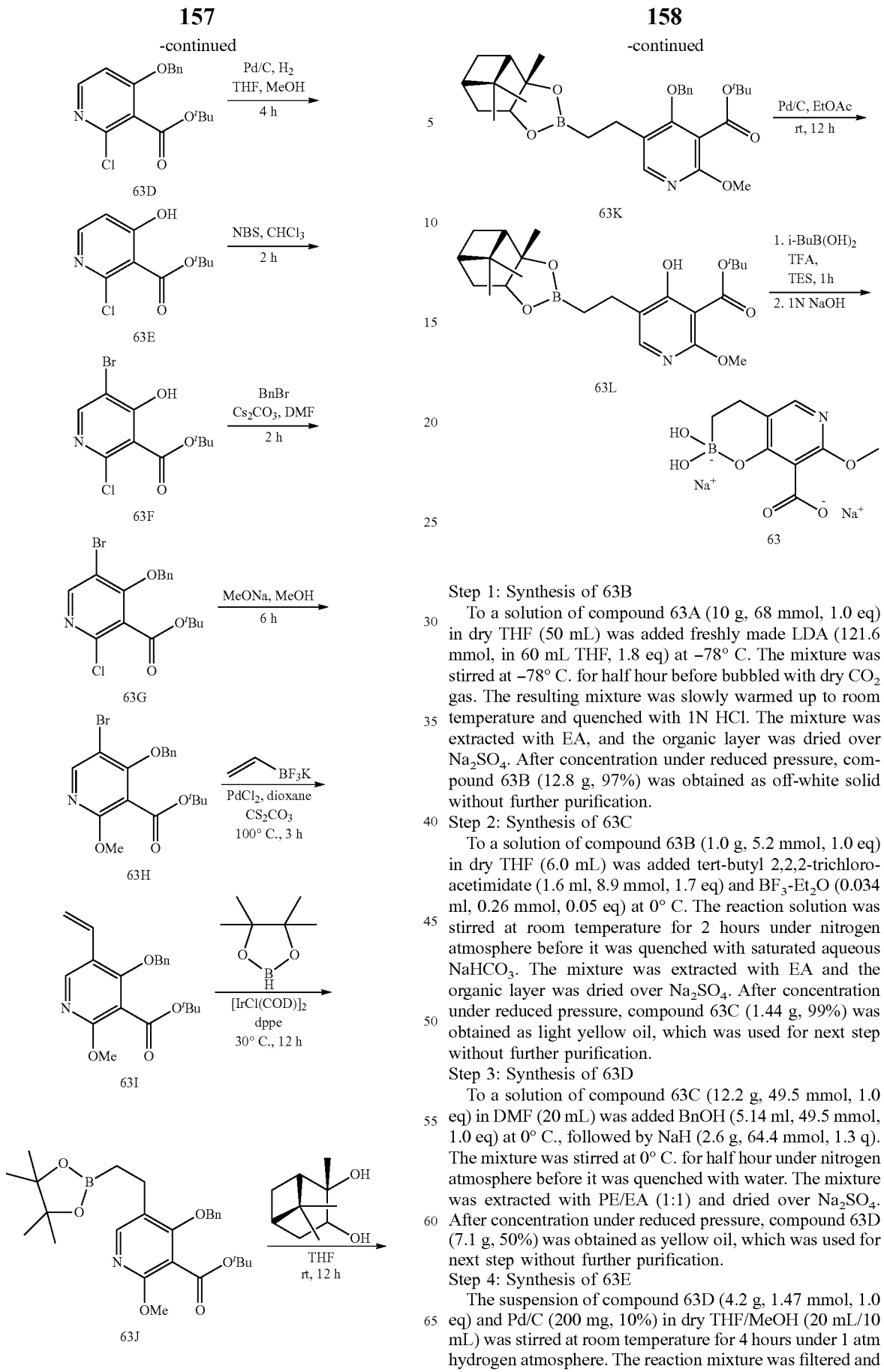

Step 1: Synthesis of 63B
To a solution of compound 63A (10 g, 68 mmol, 1.0 eq) in dry THF (50 mL) was added freshly made LDA (121.6 mmol, in 60 mL THF, 1.8 eq) at −78° C. The mixture was stirred at −78° C. for half hour before bubbled with dry CO₂ gas. The resulting mixture was slowly warmed up to room temperature and quenched with 1N HCl. The mixture was extracted with EA, and the organic layer was dried over Na₂SO₄. After concentration under reduced pressure, compound 63B (12.8 g, 97%) was obtained as off-white solid without further purification.

Step 2: Synthesis of 63C
To a solution of compound 63B (1.0 g, 5.2 mmol, 1.0 eq) in dry THF (6.0 mL) was added tert-butyl 2,2,2-trichloroacetimidate (1.6 ml, 8.9 mmol, 1.7 eq) and BF₃-Et₂O (0.034 ml, 0.26 mmol, 0.05 eq) at 0° C. The reaction solution was stirred at room temperature for 2 hours under nitrogen atmosphere before it was quenched with saturated aqueous NaHCO₃. The mixture was extracted with EA and the organic layer was dried over Na₂SO₄. After concentration under reduced pressure, compound 63C (1.44 g, 99%) was obtained as light yellow oil, which was used for next step without further purification.

Step 3: Synthesis of 63D
To a solution of compound 63C (12.2 g, 49.5 mmol, 1.0 eq) in DMF (20 mL) was added BnOH (5.14 ml, 49.5 mmol, 1.0 eq) at 0° C., followed by NaH (2.6 g, 64.4 mmol, 1.3 q). The mixture was stirred at 0° C. for half hour under nitrogen atmosphere before it was quenched with water. The mixture was extracted with PE/EA (1:1) and dried over Na₂SO₄. After concentration under reduced pressure, compound 63D (7.1 g, 50%) was obtained as yellow oil, which was used for next step without further purification.

Step 4: Synthesis of 63E
The suspension of compound 63D (4.2 g, 1.47 mmol, 1.0 eq) and Pd/C (200 mg, 10%) in dry THF/MeOH (20 mL/10 mL) was stirred at room temperature for 4 hours under 1 atm hydrogen atmosphere. The reaction mixture was filtered and the filtrate was concentrated and purified by column chromatography (PE/EA=5:1 to 1:1) to give compound 63E (3.3 g, 98%).

Step 5: Synthesis of 63F

To a solution of compound 63E (1.5 g, 6.22 mmol, 1.0 eq) in CHCl$_3$ (5 mL) at 0° C. was added NBS (1.22 g, 6.85 mmol, 1.1 eq). The mixture was stirred at room temperature for 2 hours before it was concentrated. The residue was triturated with PE/EA (20:1). After filtration, the filtrate was concentrated to give compound 63F (1.98 g, 98%), which was directly used for next step without further purification.

Step 6: Synthesis of 63G

To a solution of compound 63F (1.2 g, 2.93 mmol, 1.0 eq) in DMF (10 mL) was added Cs$_2$CO$_3$ (607 mg, 4.4 mmol, 1.5 eq) and BnBr (0.52 mL, 4.4 mmol, 1.5 eq). The mixture was stirred at room temperature for 2 hours before it was concentrated. The residue was purified by column chromatography (hexanes/EtOAc=20/1 to 5/1) to give compound 63G (1.0 g, 64%).

Step 7: Synthesis of 63H

To a solution of compound 63G (2.37 g, 5.97 mmol, 1.0 eq) in MeOH (20 mL) was added MeONa (645 mg, 11.9 mmol, 2.0 eq). The mixture was stirred at room temperature for 16 hours before it was concentrated. The residue was purified by column chromatography (hexanes/EtOAc=10/1) to give compound 63H (926 mg, 39%).

Step 8: Synthesis of 63I

To a solution of compound 63H (926 mg, 2.36 mmol, 1.0 eq) in dioxane/H$_2$O (12 mL/1.5 mL) was added potassium vinyltrifluoroborate (631 mg, 4.71 mmol, 2.0 eq), Cs$_2$CO$_3$ (2.3 g, 7.07 mmol, 3.0 eq) and PdCl$_2$(dppf) (154 mg, 0.18 mmol, 0.08 eq). The mixture was stirred at 100° C. for 3 hours under hydrogen atmosphere. The resulting mixture was filtered and the filtrate was concentrated in vacuo. The residue was purified by column chromatography (hexanes/EtOAc=4/1 to 2/1) to give compound 63I (408 mg, 50%).

Step 9: Synthesis of 63J

To a solution of compound 63I (100 mg, 0.3 mmol, 1.0 eq) in dichloromethane (10 mL) was added 4,4,5,5-tetramethyl-1,3,2-dioxaborolane (75 mg, 0.6 mmol, 2.0 eq), [IrCl(COD)]$_2$ (6 mg, 0.01 mmol, 0.03 eq) and dppe (7 mg, 0.02 mmol, 0.06 eq). The mixture was stirred at 30° C. for 12 hours under hydrogen atmosphere. The resulting mixture was concentrated under reduced pressure to give crude compound 63J (120 mg) which was used directly for the next step without further purification.

ESI-MS: [M+H]$^+$: 470.

Step 10: Synthesis of 63K

The solution of crude compound 63J (210 mg, 0.45 mmol, 1.0 eq) and (+)-pinanediol (114 mg, 0.67 mmol, 1.5 eq) in THF (5 mL) was stirred at room temperature for 12 hours. The resulting mixture was concentrated and the residue was purified by prep-TLC (hexanes/EtOAc=4/1) to give compound 63K (80 mg, 28%).

ESI-MS: [M+H]$^+$: 522.

Step 11: Synthesis of 63L

The suspension of compound 63K (75 mg, 0.14 mmol, 1.0 eq) and Pd/C (20 mg, 10%) in EtOAc (2 mL) was stirred at room temperature for 12 hours under 1 atm hydrogen atmosphere. The mixture was filtered and concentrated to give compound 63L (35 mg, 56%).

ESI-MS: [M+H]$^+$: 432.

Step 12: Synthesis of 63

To the mixture of compound 63L (35 mg, 0.08 mmol, 1.0 eq) and TES (1 mL) in TFA (90% aqueous, 3 mL) was added i-BuB(OH)$_2$ (17 mg, 0.16 mmol, 2 eq). The mixture was stirred at room temperature for 1 hour before it was concentrated to dryness. The residue was dissolved in H$_2$O/MeCN and was adjusted to PH=12 with 1N NaOH. The resulting solution was purified by prep-HPLC (18, neutral) to give 63 Na salt (8 mg, 44%) as white solid.

ESI-MS: [M+H]$^+$: 242.

$^1$H NMR (400 MHz, CD$_3$OD): δ 7.47 (s, 1H), 3.81 (s, 3H), 2.62-2.50 (m, 2H), 0.53-0.45 (m, 2H).

EXAMPLE 64

2-Hydroxy-7-[(1,3,4-thiadiazol-2-ylamino)methyl]-3,4-dihydro-1,2-benzoxaborinine-8-carboxylic acid

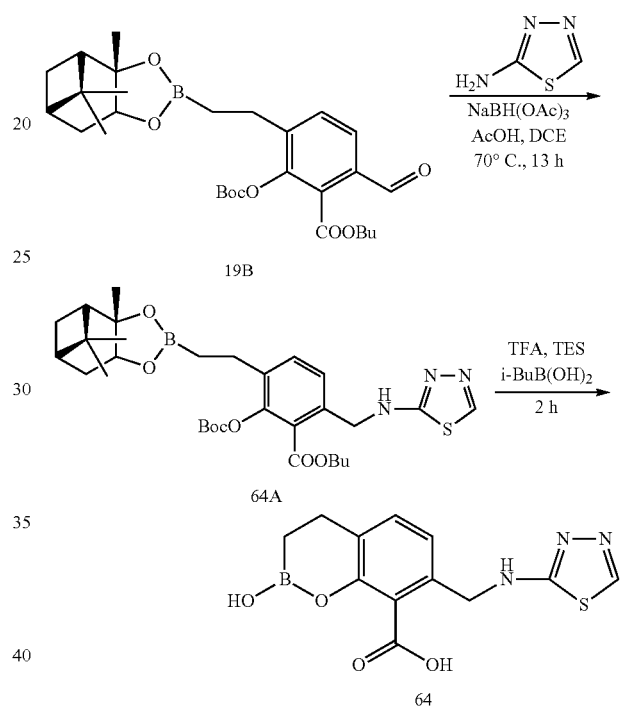

Step 1: Synthesis of 64A

The mixture of compound 19B (500 mg, 0.95 mmol, 1.0 eq), 4A molecular sieves (250 mg), AcOH (0.3 mL) and 1,3,4-thiadiazol-2-amine (240 mg, 2.4 mmol, 2.5 eq) in DCE (10 mL) was stirred at room temperature for 1 hour before NaBH(OAc)$_3$ (403 mg, 1.9 mmol, 2 eq) was added. The mixture was stirred at 70° C. for 12 hours before it was filtered and concentrated under reduced pressure. The residue was purified by column chromatography (hexanes/EtOAc=4/1 to 2/1) to give compound 64A (150 mg, 26%).

ESI-MS: [M+H]$^+$: 614.

Step 2: Synthesis of 64

To a solution of compound 64A (110 mg, 0.18 mmol, 1.0 eq) and TES (1 mL) in TFA (90% aqueous, 3 mL) was added i-BuB(OH)$_2$ (38 mg, 0.37 mmol, 2 eq). The mixture was stirred at room temperature for 2 hours before it was concentrated to dryness. The residue was purified by prep-HPLC (18, 0.1% HCOOH) to give 64 (13 mg, 24%) as white solid.

ESI-MS: [M+H]$^+$: 306.

$^1$H NMR (400 MHz, CD$_3$OD): δ 8.62 (d, J=14 Hz, 1H), 7.29-7.24 (m, 1H), 6.92-6.85 (m, 1H), 4.84-4.72 (m, 2H), 3.31-3.25 (m, 2H), 0.74-0.70 (m, 2H).

EXAMPLE 65

POTENTIATION OF AZTREONAM

The potency and spectrum of β-lactamase inhibitors (BLIs) was determined by assessing their aztreonam potentiation activity in a dose titration potentiation assay using strains of various bacteria that are resistant to aztreonam due to expression of various β-lactamases. Aztreonam is a monobactam antibiotic and is hydrolyzed by the majority of beta-lactamases that belong to class A or C (but not class B or D). The potentiation effect was observed as the ability of BLI compounds to inhibit growth in the presence of sub-inhibitory concentration of aztreonam. MICs of test strains varied from 64 μg/mL to >128 μg/mL. Aztreonam was present in the test medium at 4 μg/mL. Compounds were tested at concentrations up to 40 μg/mL. In this assay, potency of compounds was reported as the minimum concentration of BLI required to inhibit growth of bacteria in the presence of 4 μg/mL of aztreonam ($MPC_{@4}$). Table 1B summarizes the BLI potency of aztreonam potentiation ($MPC_{@4}$) for various strains overexpressing class A (ESBL and KPC), and class C beta-lactamases. Aztreonam MIC for each strain is also shown.

TABLE 1

Activity of BLIs to potentiate aztreonam against strains expressing class A and class C enzymes.

| | Aztreonam MIC (μg/mL) | | | | | | | |
|---|---|---|---|---|---|---|---|---|
| | >128 | >128 | >128 | 64 | 128 | >128 | | >128 |
| | AZT | AZT | AZT | AZT | AZT | AZT | 64 | AZT |
| | MPC4 | MPC4 | MPC4 | MPC4 | MPC4 | MPC4 | AZT | MPC4 |
| | CTX-M-14 | CTX-M-15 | SHV-5 | SHV-12 | TEM-10 | KPC-2 | MPC4 | CMY-6 |
| Compound | KP1005 | KP1009 | ec308 | KP1010 | ec302 | KP1004 | ECL1002 | EC1010 |
| 1 | X | X | X | X | X | X | Y | X |
| 2 | X | X | X | X | X | X | X | X |
| 3 | X | X | X | X | X | X | X | X |
| 4 | Z | Z | Z | Z | Z | Z | Z | Z |
| 5 | Z | Y | Z | Y | Z | X | Z | Y |
| 6 | X | X | Y | X | X | X | X | X |
| 7 | X | X | X | X | X | X | X | X |
| 8 | X | X | X | X | X | X | X | X |
| 9 | Z | Z | Y | Y | Z | X | Y | Y |
| 10 | Z | Z | Z | Y | Z | Y | Z | Z |
| 11 | Y | Y | Y | Y | Y | Y | Y | X |
| 12 | Z | Y | Y | Y | Z | Y | Y | Y |
| 13 | X | X | X | X | X | X | X | X |
| 14 | Y | Y | Y | X | Y | X | Z | Y |
| 15 | Y | X | X | X | X | X | X | X |
| 16 | X | X | Y | X | X | X | X | X |
| 17 | Z | Z | Z | Y | Z | X | Z | Y |
| 18 | Y | X | X | X | X | X | X | X |
| 19 | Y | X | X | X | Y | X | Y | X |
| 20 | Y | X | X | X | X | X | X | X |
| 21 | Y | Y | Y | X | Y | X | Y | X |
| 22 | Z | Y | Y | X | X | X | Y | X |
| 23 | Y | X | Y | X | X | X | X | X |
| 24 | X | X | X | X | X | X | X | X |
| 25 | Y | X | X | X | X | X | X | X |
| 26 | Y | Y | Y | X | Y | X | X | X |
| 27 | Z | Y | Y | X | Y | X | X | X |
| 28 | Z | Y | Y | X | X | X | Y | X |
| 29 | Y | Y | X | X | Y | X | X | X |
| 30 | Y | X | X | X | X | X | X | X |
| 31 | Y | Y | X | X | Y | X | X | X |
| 32 | Y | X | Y | X | X | X | X | X |
| 33 | Z | Z | Z | Z | Z | Z | Z | Y |
| 34 | X | X | X | X | X | X | X | X |
| 35 | X | X | X | X | X | X | X | X |
| 36 | Y | Y | X | X | X | X | X | X |
| 37 | Y | Y | Y | X | Y | X | Y | X |
| 38 | Z | Z | Z | Z | Z | Y | Z | Y |
| 39 | X | X | X | X | X | X | X | X |
| 40 | X | X | X | X | X | X | X | X |
| 41 | Y | X | X | X | X | X | X | X |
| 42 | Z | Z | Y | X | Y | Y | Z | Z |
| 43 | X | X | X | X | X | X | X | X |
| 44 | Y | Y | Y | X | Y | X | Y | X |
| 45 | Z | Z | Y | X | Y | X | Y | X |
| 46 | X | X | X | X | X | X | X | X |
| 47 | X | X | X | X | X | X | X | X |
| 48 | Z | Y | Y | X | Y | X | Y | X |
| 49 | X | X | X | X | X | X | X | X |
| 50 | X | X | X | X | X | X | X | X |
| 51 | Y | Y | X | X | X | Y | Z | Y |
| 52 | Z | Y | Y | X | Y | X | X | X |
| 53 | Y | Y | Y | X | Y | X | X | X |
| 54 | Z | Z | Z | Z | Z | Z | Z | Y |

TABLE 1-continued

Activity of BLIs to potentiate aztreonam against strains expressing class A and class C enzymes.

| | Aztreonam MIC (µg/mL) | | | | | | | |
|---|---|---|---|---|---|---|---|---|
| Compound | >128 AZT MPC4 CTX-M-14 KP1005 | >128 AZT MPC4 CTX-M-15 KP1009 | >128 AZT MPC4 SHV-5 ec308 | 64 AZT MPC4 SHV-12 KP1010 | 128 AZT MPC4 TEM-10 ec302 | >128 AZT MPC4 KPC-2 KP1004 | 64 AZT MPC4 ECL1002 | >128 AZT MPC4 CMY-6 EC1010 |
| 55 | Y | X | X | X | X | X | X | X |
| 56 | X | X | X | X | X | X | X | X |
| 57 | Y | X | X | X | X | X | X | X |
| 58 | Z | Z | Z | Y | Z | X | X | X |
| 59 | Y | Y | Y | X | X | X | Z | Y |
| 60 | X | X | X | X | X | X | X | X |
| 62 | X | X | X | X | X | X | X | X |
| 64 | Y | X | X | X | X | X | X | X |
| Tazobactam | Y | Y | Y | X | X | Z | Z | Y |
| Clavulanic Acid | X | X | X | X | X | Z | Z | Z |

X = $MPC_{@4} \leq 5$ µg/mL
Y = 5 µg/mL < $MPC_{@4} \leq 20$ µg/mL
Z = $MPC_{@4} > 20$ µg/mL

EXAMPLE 66

POTENTIATION OF TIGEMONAM

Selected β-lactamase inhibitors were also tested for their ability to potentiate the monobactam tigemonam. The potentiation effect was observed as the ability of BLI compounds to inhibit growth in the presence of sub-inhibitory concentration of tigemonam. MICs of test strains varied from 16 µg/mL to >64 µg/mL. Tigemonam was present in the test medium at 4 µg/mL. Compounds were tested at concentrations up to 40 µg/mL. In this assay potency of compounds was reported as the minimum concentration of BLI required to inhibit growth of bacteria in the presence of 4 µg/mL of aztreonam ($MPC_{@4}$). Table 2 summarizes the BLI potency of tigemonam potentiation ($MPC_{@4}$) for various strains overexpressing class A (ESBL) and class C beta-lactamases. Tigemonam MIC for each strain is also shown.

TABLE 2

Activity of BLIs to potentiate tigemonam against strains expressing class A and class C enzymes.

| | Tigemonam MIC (µg/mL) | | | | | | |
|---|---|---|---|---|---|---|---|
| Compound | >64 TIG MPC4 CTX-M-14 KP1005 | >64 TIG MPC4 CTX-M-15 KP1009 | >64 TIG MPC4 SHV-5 ec308 | >64 TIG MPC4 SHV-12 KP1010 | >64 TIG MPC4 TEM-10 ec302 | 32 TIG MPC4 ECL1002 | 16 TIG MPC4 CMY-6 EC1010 |
| 1 | X | X | X | X | Y | X | X |
| 2 | X | X | X | X | X | X | X |
| 3 | X | X | X | X | Y | X | X |
| 4 | Z | Z | Z | Z | Z | Y | X |
| 5 | Z | Z | Z | Y | Y | X | X |
| 6 | Y | X | X | X | Y | X | X |
| 7 | X | X | X | X | Y | X | X |
| 8 | X | X | X | X | X | X | X |
| 9 | Z | Z | Z | Y | Z | X | X |
| 10 | Z | Z | Z | Z | Z | Y | X |
| 11 | Z | Y | Y | X | Z | X | X |
| 12 | Z | Z | Z | Y | Z | X | X |
| 13 | X | X | X | X | X | X | X |
| 14 | Z | Y | Y | Y | Z | X | X |
| 15 | Z | Y | Y | X | Y | X | X |
| 16 | Y | Y | Y | X | Y | X | X |
| 17 | Z | Z | Z | Y | Z | Y | X |
| 18 | Z | Z | Z | X | X | X | X |
| 19 | Z | Y | Y | X | Z | X | X |
| 20 | Y | Y | Y | X | Y | X | X |
| 21 | Z | Y | Z | Y | Z | X | X |
| 22 | Z | Y | Y | X | Y | X | X |
| 23 | Z | Y | Y | X | Y | X | X |
| 24 | Z | X | X | X | X | X | X |
| 25 | Z | X | X | X | X | X | X |
| 26 | Z | Y | Y | X | Z | X | X |
| 27 | Z | Z | Z | Y | Z | X | X |
| 28 | Z | Z | X | X | Y | X | X |
| 29 | Y | Z | Y | Y | Z | X | X |

TABLE 2-continued

Activity of BLIs to potentiate tigemonam against strains expressing class A and class C enzymes.

| | Tigemonam MIC (µg/mL) | | | | | | |
|---|---|---|---|---|---|---|---|
| | >64 TIG MPC$_4$ CTX-M-14 | >64 TIG MPC$_4$ CTX-M-15 | >64 TIG MPC$_4$ SHV-5 | >64 TIG MPC$_4$ SHV-12 | >64 TIG MPC$_4$ TEM-10 | 32 TIG MPC$_4$ | 16 TIG MPC4 CMY-6 |
| Compound | KP1005 | KP1009 | ec308 | KP1010 | ec302 | ECL1002 | EC1010 |
| 30 | Y | Y | Y | X | Y | X | X |
| 31 | Y | Y | X | X | Y | X | X |
| 32 | Y | Y | Y | X | Z | X | X |
| 33 | Z | Z | Z | Z | Z | X | X |
| 34 | Z | X | X | X | X | X | X |
| 35 | Y | X | X | X | X | X | X |
| 36 | Y | Y | Y | X | Z | X | X |
| 37 | Z | Z | Z | Y | Z | X | X |
| 38 | Z | Z | Z | Z | Z | Y | X |
| 39 | Y | X | X | X | Y | X | X |
| 40 | X | X | X | X | X | X | X |
| 41 | Y | X | X | X | Y | X | X |
| 42 | Z | Z | Z | Y | Z | Y | X |
| 43 | X | X | X | X | Y | X | X |
| 44 | Z | Z | Z | Y | Z | X | X |
| 45 | Z | Z | Z | X | Z | X | X |
| 46 | Z | X | X | X | Y | X | X |
| 47 | X | X | X | X | X | X | X |
| 48 | Z | Z | Z | Y | Z | X | X |
| 49 | X | X | X | X | Y | X | X |
| 50 | X | X | X | X | X | X | X |
| 51 | Z | Z | Y | X | Y | X | X |
| 52 | Z | Z | Z | X | Z | X | X |
| 53 | Z | Z | Z | Y | Z | X | X |
| 54 | Z | Z | Z | Z | Z | Y | X |
| 55 | Z | Y | X | X | Y | X | X |
| 56 | X | X | X | X | X | X | X |
| 57 | Y | Y | Y | X | Y | X | X |
| 58 | Z | Z | Z | Z | Z | X | X |
| 59 | Z | Y | Z | Y | Y | Y | X |
| 60 | X | X | X | X | X | X | X |
| 62 | Y | Y | Y | X | Y | X | X |
| 64 | Y | Y | Y | X | X | X | X |
| Tazobactam | Y | Y | X | X | X | Y | X |
| Clavulanic Acid | X | X | X | X | X | Z | Z |

X = MPC$_{@4}$ ≤ 5 µg/mL
Y = 5 µg/mL < MPC$_{@4}$ ≤ 20 µg/mL
Z = MPC$_{@4}$ > 20 µg/mL

EXAMPLE 67

POTENTIATION OF BIAPENEM

β-lactamase inhibitors were also tested for their ability to potentiate the carbapenem biapenem against strains producing class A (KPC) and class D (OXA-48) carbapenemases. The potentiation effect was observed as the ability of BLI compounds to inhibit growth in the presence of a sub-inhibitory concentration of biapenem. Biapenem MIC of test strains were 16-32 µg/mL. Biapenem was present in the test medium at 1 µg/mL. Compounds were tested at concentrations up to 40 µg/mL. In this assay potency of compounds was reported as the minimum concentration of BLI required to inhibit growth of bacteria in the presence of 1 µg/mL of biapenem (MPC$_{@1}$). Table 3 summarizes the BLI potency of biapenem potentiation (MPC$_{@1}$) for two strains overexpressing class A (KPC) and class D (OXA-48) carbapenemases. Biapenem MIC for each strain is also shown.

TABLE 3

Activity of BLIs to potentiate biapenem against strains expressing class A (KPC) or class D (OXA-48) carbapenemases

| | Biapenem MIC (µg/mL) | |
|---|---|---|
| | 32 BPM MPC$_1$ KP1004 | 16 BPM MPC$_1$ OXA-48 |
| Compound | KPC-2 | KP1086 |
| 1 | X | Y |
| 2 | X | X |
| 3 | X | X |
| 4 | X | Z |
| 5 | X | X |
| 6 | X | X |
| 7 | X | X |
| 8 | X | X |
| 9 | X | X |
| 10 | X | Y |
| 11 | X | Y |
| 12 | X | Y |
| 13 | X | X |
| 14 | X | X |
| 15 | X | X |
| 16 | X | Y |

TABLE 3-continued

Activity of BLIs to potentiate biapenem against strains expressing class A (KPC) or class D (OXA-48) carbapenemases

| | Biapenem MIC (µg/mL) | |
|---|---|---|
| | 32 | 16 |
| | BPM MPC$_1$ KP1004 | BPM MPC$_1$ OXA-48 |
| Compound | KPC-2 | KP1086 |
| 17 | X | X |
| 18 | X | X |
| 19 | X | X |
| 20 | X | X |
| 21 | X | X |
| 22 | X | Y |
| 23 | X | X |
| 24 | X | X |
| 25 | X | X |
| 26 | X | X |
| 27 | X | Y |
| 28 | X | X |
| 29 | X | X |
| 30 | X | Y |
| 31 | X | X |
| 32 | X | X |
| 33 | X | X |
| 34 | X | X |
| 35 | X | X |
| 36 | X | X |
| 37 | X | X |
| 38 | X | Y |
| 39 | X | X |
| 40 | X | X |
| 41 | X | X |
| 42 | X | X |
| 43 | X | X |
| 44 | X | X |
| 45 | X | X |
| 46 | X | Y |
| 47 | X | X |
| 48 | X | X |
| 49 | X | X |
| 50 | X | X |
| 51 | X | X |
| 52 | X | X |
| 53 | X | X |
| 54 | X | Z |
| 55 | X | X |
| 56 | X | X |
| 57 | X | X |
| 58 | X | X |
| 59 | X | X |
| 60 | X | X |
| 62 | X | X |
| 64 | X | Y |
| Tazobactam | Z | Y |
| Clavulanic Acid | Y | Z |

X = MPC$_{@1}$ ≤ 5 µg/mL
Y = 5 µg/mL < MPC$_{@1}$ ≤ 20 µg/mL
Z = MPC$_{@1}$ > 20 µg/mL

EXAMPLE 68

POTENTIATION OF MEROPENEM

β-lactamase inhibitors were also tested for their ability to potentiate the carbapenem meropenem against strains of *Acinetobacter baumannii* producing class D (OXA-23 and OXA-72) carbapenemases. The potentiation effect was observed as the ability of BLI compounds to inhibit growth in the presence of a sub-inhibitory concentration of meropenem. Meropenem MIC of test strains were 32 to >64 µg/mL. Meropenem was present in the test medium at 8 µg/mL. Compounds were tested at concentrations up to 20 µg/mL. In this assay potency of compounds was reported as the minimum concentration of BLI required to inhibit growth of bacteria in the presence of 8 µg/mL of meropenem (MPC$_{@8}$). Table 4 summarizes the BLI potency of meropenem potentiation (MPC$_{@8}$) for two strains overexpressing OXA-72 and OXA-23 carbapenemases. Meropenem MIC for each strain is also shown.

TABLE 4

Activity of BLIs to potentiate meropenem against strains expressing class D carbapenemases from *Acinetobacter baumannii*

| | Meropenem MIC (µg/mL) | |
|---|---|---|
| | >64 | 32 |
| | MPM MPC$_8$ | MPM MPC$_8$ |
| Compound | AB1053 OXA-72 | AB1054 OXA-23 |
| 1 | ND | ND |
| 2 | ND | ND |
| 3 | Y | Z |
| 4 | ND | ND |
| 5 | Z | Y |
| 6 | X | X |
| 7 | X | X |
| 8 | X | X |
| 9 | Z | Z |
| 10 | Z | Z |
| 11 | X | Y |
| 12 | Y | Y |
| 13 | X | X |
| 14 | X | X |
| 15 | X | X |
| 16 | X | Y |
| 17 | X | X |
| 18 | X | X |
| 19 | X | X |
| 20 | Y | Y |
| 21 | X | X |
| 22 | Z | Y |
| 23 | X | X |
| 24 | X | X |
| 25 | X | X |
| 26 | X | Y |
| 27 | Y | Y |
| 28 | X | X |
| 29 | X | Y |
| 30 | X | X |
| 31 | X | X |
| 32 | X | X |
| 33 | Y | Y |
| 34 | X | X |
| 35 | X | X |
| 36 | Y | X |
| 37 | Z | Z |
| 38 | Z | Z |
| 39 | X | X |
| 40 | Z | Z |
| 41 | X | X |
| 42 | Z | Z |
| 43 | X | X |
| 44 | X | Y |
| 45 | X | X |
| 46 | X | Y |
| 47 | X | X |
| 48 | X | Y |
| 49 | Y | Y |
| 50 | Y | Y |
| 51 | Z | Z |
| 52 | Z | Z |
| 53 | X | X |
| 54 | Z | Z |
| 55 | Z | Z |
| 56 | X | X |
| 57 | X | X |
| 58 | Z | Z |
| 59 | Y | Z |
| 60 | X | X |

TABLE 4-continued

Activity of BLIs to potentiate meropenem against strains expressing class D carbapenemases from *Acinetobacter baumannii*

| | Meropenem MIC (µg/mL) | |
|---|---|---|
| | >64 MPM MPC$_8$ | 32 MPM MPC$_8$ |
| Compound | AB1053 OXA-72 | AB1054 OXA-23 |
| 62 | X | X |
| 64 | Y | Y |
| Tazobactam | ND | ND |
| Clavulanic Acid | ND | ND |

ND = Not determined.
X = MPC$_{@1}$ ≤ 5 µg/mL
Y = 5 µg/mL < MPC$_{@1}$ ≤ 20 µg/mL
Z = MPC$_{@1}$ > 20 µg/mL

EXAMPLE 69

INHIBITORY ACTIVITY $K_i$ values of inhibition of purified class A, C and D enzymes were determined spectrophotometrically using nitrocefin as reporter substrate. Purified enzymes were mixed with various concentrations of inhibitors in reaction buffer and incubated for 10 min at room temperature. Nitrocefin was added and substrate cleavage profiles were recorded at 490 nm every 10 sec for 10 min. The results of these experiments are presented in Table 5. These experiments confirmed that the described compounds are inhibitors with a broad-spectrum of activity towards various β-lactamases.

TABLE 5

Activity of BLIs (Ki, uM) to inhibit cleavage of nitrocefin by purified class A, C and D enzymes

| Compound | Ki (CTX-M-14, NCF), uM | Ki (SHV-12, NCF), uM | Ki (TEM-10, NCF), uM | Ki (KPC-2, NCF), uM | Ki (P99, NCF), uM | Ki (Pa-AmpC, NCF), uM | Ki (OXA-48, NCF), uM | Ki (OXA-23, NCF), uM |
|---|---|---|---|---|---|---|---|---|
| 1 | X | X | X | X | X | ND | X | ND |
| 2 | X | X | X | X | X | ND | X | ND |
| 3 | X | X | X | X | X | X | X | X |
| 4 | X | X | X | X | X | ND | X | ND |
| 5 | X | X | X | X | X | ND | X | Y |
| 6 | X | X | X | X | X | X | X | X |
| 7 | X | X | X | X | X | X | X | X |
| 8 | X | ND | X | X | X | X | X | X |
| 9 | X | Y | Y | X | X | X | X | Y |
| 10 | X | Y | Y | X | Y | X | X | Z |
| 11 | X | ND | X | X | X | X | X | X |
| 12 | X | ND | X | X | X | Y | X | Y |
| 13 | X | ND | X | X | X | X | X | X |
| 14 | X | ND | X | X | Y | Z | X | X |
| 15 | X | X | X | X | X | X | X | X |
| 16 | X | ND | X | X | X | X | X | X |
| 17 | X | Y | Y | X | Y | Y | X | X |
| 18 | X | X | X | X | X | X | X | X |
| 19 | X | ND | X | X | X | X | X | X |
| 20 | X | ND | X | X | X | X | X | X |
| 21 | X | ND | X | X | X | X | X | X |
| 22 | X | ND | X | X | X | X | X | X |
| 23 | X | X | X | X | X | X | X | X |
| 24 | X | X | X | X | X | X | X | X |
| 25 | X | X | X | X | X | X | X | X |
| 26 | ND | ND | X | X | X | X | X | X |
| 27 | X | ND | X | X | X | Y | X | X |
| 28 | X | ND | X | X | X | X | X | X |
| 29 | X | ND | X | X | X | X | X | X |
| 30 | ND | ND | X | X | X | X | X | X |
| 31 | ND | ND | X | X | X | X | X | X |
| 32 | ND | ND | X | X | X | X | X | X |
| 33 | X | ND | Z | Z | Y | Z | X | X |
| 34 | X | ND | X | X | X | X | X | X |
| 35 | X | ND | X | X | X | X | X | X |
| 36 | ND | ND | X | X | X | X | X | X |
| 37 | ND | ND | X | X | X | X | X | X |
| 38 | ND | ND | Y | Y | Z | Z | X | Z |
| 39 | X | ND | X | X | X | X | X | X |
| 40 | ND | ND | X | X | X | X | X | ND |
| 41 | X | ND | X | X | X | X | X | X |
| 42 | X | ND | X | X | Y | Y | X | Y |
| 43 | X | ND | X | X | X | X | X | X |
| 44 | ND | ND | X | X | X | X | X | X |
| 45 | X | ND | X | X | X | X | X | X |
| 46 | X | ND | X | X | X | X | X | X |
| 47 | ND | ND | X | X | X | X | X | X |
| 48 | X | ND | X | X | Y | Y | X | X |
| 49 | X | ND | X | X | X | X | X | X |
| 50 | X | ND | X | X | X | X | X | X |
| 51 | X | ND | X | X | X | X | X | X |

TABLE 5-continued

Activity of BLIs (Ki, uM) to inhibit cleavage of nitrocefin by purified class A, C and D enzymes

| Compound | Ki (CTX-M-14, NCF), uM | Ki (SHV-12, NCF), uM | Ki (TEM-10, NCF), uM | Ki (KPC-2, NCF), uM | Ki (P99, NCF), uM | Ki (Pa-AmpC, NCF), uM | Ki (OXA-48, NCF), uM | Ki (OXA-23, NCF), uM |
|---|---|---|---|---|---|---|---|---|
| 52 | X | ND | X | X | X | X | X | Y |
| 53 | X | ND | X | X | X | X | X | X |
| 54 | ND | ND | Z | Z | Y | Z | X | Y |
| 55 | X | ND | X | X | X | X | X | X |
| 56 | X | X | X | X | X | X | X | X |
| 57 | X | ND | X | X | X | X | X | X |
| 58 | X | ND | Y | X | X | X | X | Y |
| 59 | X | ND | X | X | Z | Y | X | Z |
| 60 | X | ND | X | X | X | X | X | X |
| 62 | X | ND | X | X | X | X | X | X |
| 64 | X | ND | X | X | X | X | X | X |
| Tazobactam | X | X | X | Z | Z | Y | Y | ND |
| Clavulanic Acid | X | X | X | Z | Z | ND | Z | ND |

$X = K_i \leq 0.1\ \mu M$
$Y = 0.1\ \mu M < K_i \leq 1\ \mu M$
$Z = K_i > 1\ \mu M$
ND = not determined

EXAMPLE 70

MEXAB-OPRM DEPENDENT EFFLUX OF BLIs

Efflux of BLIs from *Pseudomonas aeruginosa* by the MexAB-OprM efflux pump was also evaluated. The plasmid expressing the gene encoding KPC-2 was introduced into two strains of *P. aeruginosa*, PAM1032 and PAM 1154 that overexpressed or lacked MexAB-OprM, respectively. Due to expression of KPC-2 both strains became resistant to biapenem. Biapenem is not affected by efflux in *P. aeruginosa* and both strains had the same biapenem MIC of 32 μg/ml. Potency of BLIs to potentiate biapenem in these strains was determined. Potency was defined as the ability of BLI to decrease MIC of biapenem 64-fold, from 32 μg/ml to 0.5 μg/ml, or $MPC_{64}$. The ratio of $MPC_{64}$ values for each BLI in PAM1032/KPC-2 (efflux proficient) and PAM1154/KPC-2 (efflux deficient) was determined to generate the Efflux Index (EI).

TABLE 6

MexAB-OprM Dependent Efflux of BLIs from *P. aeruginosa*

| Compound | PAM1032/ KPC-2 Biapenem MPC64 | PAM1154/ KPC-2 Biapenem MPC64 | EI |
|---|---|---|---|
| 1 | 40 | 2.5 | 16 |
| 2 | 20 | 1.25 | 16 |
| 3 | 20 | 2.5 | 8 |
| 4 | >80 | 5 | >16 |
| 5 | 20 | 0.3 | 64 |
| 6 | 5 | 0.3 | 16 |
| 7 | 2.5 | 0.6 | 4 |
| 8 | 5 | 0.6 | 8 |

Although the invention has been described with reference to embodiments and examples, it should be understood that numerous and various modifications can be made without departing from the spirit of the invention. Accordingly, the invention is limited only by the following claims.

What is claimed is:
1. A compound of formula (III-2):

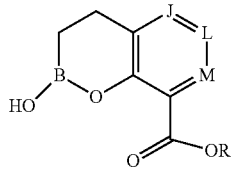

(III-2)

or a pharmaceutically acceptable salt thereof,
wherein:
J is $CR^5$;
L is $CR^5$;
M is $CR^5$;
each $R^5$ is independently selected from the group consisting of H, halogen, CN, $C_1$-$C_6$ alkyl, $C_1$-$C_6$ heteroalkyl, —$(CH_2)_p$—$Y^3$—$(CH_2)_q$M', $C_2$-$C_6$ alkenyl, $C_2$-$C_6$ alkynyl, —C(=$NR^1$)$R^2$, —C(O)$NR^1R^2$, —C(O)$NR^1OR^2$, —C(O)$OR^1$, —$NR^1CR^2$(=$NR^3$), —$NR^1$C(=$NR^2$)$NR^3R^4$, —$NR^1$C(O)$R^2$, —$NR^1$C(O)$NR^2R^3$, —$NR^1$C(O)$OR^2$, —$NR^1$S(O)$_2R^2$, —$NR^1$S(O)$_2NR^2R^3$, —$NR^1$S(O)$_2NR^1OR^3$, OH, O-aryl, SH, —S(O)($CH_2$)$_{1-3}R^4$, —S(O)$_2NR^1R^2$, —S(O)$_2NR^1OR^3$, $C_3$-$C_7$ carbocyclyl, $C_6$-$C_{10}$ aryl, 5-10 membered heterocyclyl, and 5-10 membered heteroaryl;
M' is selected from the group consisting of halogen, CN, $C_1$-$C_4$ alkyl, $C_2$-$C_4$ alkenyl, $C_2$-$C_4$ alkynyl, —C(=$NR^1$)$R^2$, —C(=$NR^1$)$NR^2R^3$, —C(O)$NR^1R^2$, —C(O)$NR^1OR^2$, —$NR^1CR^2$(=$NR^3$), —$NR^1$C(=$NR^2$)$NR^3R^4$, —$NR^1$C(O)$R^2$, —$NR^1$C(O)$NR^2R^3$, —$NR^1$C(O)$OR^2$, —$NR^1$S(O)$_2R^2$, —$NR^1$S(O)$_2NR^2R^3$, OH, —S(O)$_2R^1$, S(O)$_2NR^1R^2$, —S(O)$_2NR^1OR^3$, $C_3$-$C_7$ carbocyclyl, $C_6$-$C_{10}$ aryl, 3-10 membered heterocyclyl, and 5-10 membered heteroaryl;
$Y^3$ is selected from the group consisting of —$CR^1R^2$—, —$NR^1$—, —O—, —S—, —S(O)—, and —S(O)$_2$—;
$R^1$ is selected from the group consisting of H, halogen, $C_1$-$C_4$ alkyl, $OC_1$-$C_4$alkyl, $C_3$-$C_7$ carbocyclyl, $C_6$-$C_{10}$ aryl, 4-10 membered heterocyclyl, and 5-10 membered heteroaryl;

$R^2$ is selected from the group consisting of H, halogen, $C_1$-$C_4$ alkyl, $OC_1$-$C_4$alkyl, $C_3$-$C_7$ carbocyclyl, $C_6$-$C_{10}$ aryl, 4-10 membered heterocyclyl, and 5-10 membered heteroaryl;

$R^3$ is selected from the group consisting of H, halogen, $C_1$-$C_4$ alkyl, $OC_1$-$C_4$alkyl, $C_3$-$C_7$ carbocyclyl, $C_6$-$C_{10}$ aryl, 4-10 membered heterocyclyl, and 5-10 membered heteroaryl;

$R^4$ is selected from the group consisting of H, halogen, $C_1$-$C_4$ alkyl, $OC_1$-$C_4$alkyl, $C_3$-$C_7$ carbocyclyl, $C_6$-$C_{10}$ aryl, 4-10 membered heterocyclyl, and 5-10 membered heteroaryl;

R is selected from the group consisting of H, alkali metal cation, $NH_4^+$, $C_1$-$C_9$ alkyl, —$CR^{10}R^{11}OC(O)$$C_1$-$C_9$ alkyl, —$CR^{10}R^{11}OC(O)NR^{10}C_1$-$C_9$ alkyl, —$CR^{10}R^{11}OC(O)NR^{10}C_6$-$C_{10}$ aryl, —$CR^{10}R^{11}OC(O)OC_1$-$C_9$ alkyl, —$CR^{10}R^{11}OC(O)OC_6$-$C_{10}$ aryl, and —$CR^{10}R^{11}OC(O)C_6$-$C_{10}$ aryl; or R is

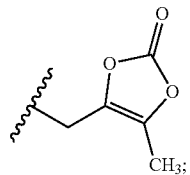 [SMILES: *Cc1oc(=O)oc1C]

$R^{10}$ is selected from the group consisting of H, $C_1$-$C_4$ alkyl, $C_3$-$C_7$ carbocyclyl, $C_6$-$C_{10}$ aryl, 5-10 membered heterocyclyl, and 5-10 membered heteroaryl;

$R^{11}$ is selected from the group consisting of H, $C_1$-$C_4$ alkyl, $C_3$-$C_7$ carbocyclyl, $C_6$-$C_{10}$ aryl, 5-10 membered heterocyclyl, and 5-10 membered heteroaryl;

p is 0, 1, or 2; and q is 0, 1, or 2;

wherein the $C_1$-$C_4$ alkyl of M' is optionally substituted with 1 or 2 substituents independently selected from the group consisting of halogen, CN, —$C(O)NR^1R^2$, —$NR^1R^2$, —$NR^1C(O)R^2$, $OR^1$, and heterocyclyl; and wherein the $C_2$-$C_4$ alkenyl, $C_2$-$C_4$ alkynyl, $C_3$-$C_7$ carbocyclyl, $C_6$-$C_{10}$ aryl, 3-10 membered heterocyclyl, and 5-10 membered heteroaryl of M' are each optionally substituted with 1 or 2 substituents independently selected from the group consisting of halogen, $C_1$-$C_4$ alkyl, —$C(O)NR^1R^2$, —$NR^1C(O)R^2$, —$(CH_2)_{0-4}CN$, —$(CH_2)_{0-4}NR^1R^2$, —$(CH_2)_{0-4}OR^1$, and —$(CH_2)_{0-4}$heterocyclyl.

2. The compound of claim 1, or a pharmaceutically acceptable salt thereof, wherein:

each $R^5$ is independently selected from the group consisting of H, halogen, CN, $C_1$-$C_6$ alkyl, $C_1$-$C_6$ heteroalkyl, —$(CH_2)_p$—$Y^3$—$(CH_2)_q$M', $C_2$-$C_6$ alkenyl, $C_2$-$C_6$ alkynyl, OH, O-aryl, SH, $C_3$-$C_7$ carbocyclyl, $C_6$-$C_{10}$ aryl, 5-10 membered heterocyclyl, and 5-10 membered heteroaryl;

M' is selected from the group consisting of $C_1$-$C_4$ alkyl, $C_2$-$C_4$ alkenyl, $C_2$-$C_4$ alkynyl, —$C(=NR^1)R^2$, —$C(=NR^1)NR^2R^3$, —$C(O)NR^1R^2$, —$C(O)NR^1OR^2$, —$NR^1CR^2(=NR^3)$, —$NR^1C(=NR^2)NR^3R^4$, —$NR^1C(O)R^2$, —$NR^1C(O)NR^2R^3$, —$NR^1C(O)OR^2$, —$NR^1S(O)_2R^2$, —$NR^1S(O)_2NR^2R^3$, —$S(O)_2R^1$, —$S(O)_2NR^1R^2$, —$S(O)_2NR^1OR^3$, $C_3$-$C_7$ carbocyclyl, $C_6$-$C_{10}$ aryl, 3-10 membered heterocyclyl, and 5-10 membered heteroaryl;

$Y^3$ is selected from the group consisting of —$CH_2$—, —$NR^1$—, —O—, —S—, —S(O)—, and —$S(O)_2$—;

$R^1$ is selected from the group consisting of H, $C_1$-$C_4$ alkyl, $C_3$-$C_7$ carbocyclyl, $C_6$-$C_{10}$ aryl, 4-10 membered heterocyclyl, and 5-10 membered heteroaryl;

$R^2$ is selected from the group consisting of H, $C_1$-$C_4$ alkyl, $C_3$-$C_7$ carbocyclyl, $C_6$-$C_{10}$ aryl, 4-10 membered heterocyclyl, and 5-10 membered heteroaryl;

$R^3$ is selected from the group consisting of H, $C_1$-$C_4$ alkyl, $C_3$-$C_7$ carbocyclyl, $C_6$-$C_{10}$ aryl, 4-10 membered heterocyclyl, and 5-10 membered heteroaryl;

$R^4$ is selected from the group consisting of H, $C_1$-$C_4$ alkyl, $C_3$-$C_7$ carbocyclyl, $C_6$-$C_{10}$ aryl, 4-10 membered heterocyclyl, and 5-10 membered heteroaryl;

R is selected from the group consisting of H, alkali metal cation, $NH_4^+$, $C_1$-$C_9$ alkyl, —$CR^{10}R^{11}OC(O)C_1$-$C_9$ alkyl, —$CR^{10}R^{11}OC(O)OC_1$-$C_9$ alkyl, —$CR^{10}R^{11}OC(O)OC_6$-$C_{10}$ aryl, and —$CR^{10}R^{11}OC(O)C_6$-$C_{10}$ aryl; or R is

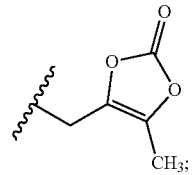 [SMILES: *Cc1oc(=O)oc1C]

p is 0 or 1; and q is 0 or 1;

wherein the $C_1$-$C_4$ alkyl of M' is optionally substituted with 1 or 2 substituents independently selected from the group consisting of halogen, —$C(O)NR^1R^2$, —$NR^1R^2$, —$NR^1C(O)R^2$, and $OR^1$; and wherein the $C_3$-$C_7$ carbocyclyl, $C_6$-$C_{10}$ aryl, 3-10 membered heterocyclyl, and 5-10 membered heteroaryl of M' are each optionally substituted with 1 or 2 substituents independently selected from the group consisting of halogen, $C_1$-$C_4$ alkyl, —$C(O)NR^1R^2$, —$NR^1C(O)R^2$, —$NR^1R^2$, and $OR^1$.

3. The compound of claim 1, or a pharmaceutically acceptable salt thereof, wherein at least one $R^5$ is independently selected from the group consisting of halogen, CN, $C_1$-$C_6$ heteroalkyl, —$(CH_2)_p$—$Y^3$—$(CH_2)_q$M', $C_2$-$C_6$ alkenyl, $C_2$-$C_6$ alkynyl, OH, $C_3$-$C_7$ carbocyclyl, $C_6$-$C_{10}$ aryl, 5-10 membered heterocyclyl, and 5-10 membered heteroaryl.

4. The compound of claim 1, or a pharmaceutically acceptable salt thereof, wherein at least one $R^5$ is independently selected from the group consisting of F, CN, $CHF_2$, $CF_3$, —C≡CH, —$C(O)NH_2$, OH, $OCH_3$, $OCH_2CH_3$, $SCH_3$, and —$S(O)_2CH_3$.

5. The compound of claim 1, or a pharmaceutically acceptable salt thereof, wherein at least one $R^5$ is independently selected from the group consisting of halogen, —$C(=NR^1)R^2$, —$C(O)NR^1R^2$, —S(O)-M', and —$S(O)_2$-M'.

6. The compound of claim 1, or a pharmaceutically acceptable salt thereof, wherein at least one $R^5$ is independently selected from the group consisting of $C_2$-$C_4$ alkynyl, diazolyl, and triazolyl.

7. The compound of claim 6, or a pharmaceutically acceptable salt thereof, wherein $R^5$ is selected from the group consisting of

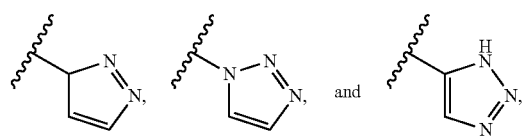 [SMILES: *C1C=CN=N1 ; *n1ccnn1 ; *c1cnn[nH]1]

8. The compound of claim 1, or a pharmaceutically acceptable salt thereof, wherein:
J is CH; and
at least one $R^5$ is independently selected from the group consisting of halogen, CN, $C_1$-$C_6$ alkyl, $C_1$-$C_6$ heteroalkyl, —$(CH_2)_p$—$Y^3$—$(CH_2)_q$M', $C_2$-$C_6$ alkenyl, $C_2$-$C_6$ alkynyl, —C(=$NR^1$)$R^2$, —C(O)$NR^1R^2$, —C(O)NR'$OR^2$, —C(O)OR', —$NR^1CR^2$(=$NR^3$), —$NR^1$C(=$NR^2$)$NR^3R^4$, —$NR^1$C(O)$R^2$, —$NR^1$C(O)$NR^2R^3$, —NR'C(O)$OR^2$, —$NR^1$S(O)$_2R^2$, —$NR^1$S(O)$_2$$NR^2R^3$, —$NR^1$S(O)$_2NR^1OR^3$, OH, O-aryl, SH, —S(O)$(CH_2)_{1-3}R^4$, —S(O)$_2NR^1R^2$, —S(O)$_2$NR'$OR^3$, $C_3$-$C_7$ carbocyclyl, $C_6$-$C_{10}$ aryl, 5-10 membered heterocyclyl, and 5-10 membered heteroaryl.

9. The compound of claim 1, or a pharmaceutically acceptable salt thereof, wherein at least two $R^5$ are independently selected from the group consisting of halogen and OM'.

10. The compound of claim 9, or a pharmaceutically acceptable salt thereof, wherein at least two $R^5$ are independently selected from the group consisting of (a) F and $OCH_3$, or (b) $C_1$ and $OCH_3$.

11. The compound of claim 1, or a pharmaceutically acceptable salt thereof, wherein:
at least one $R^5$ is independently —$(CH_2)_p$—$Y^3$—$(CH_2)_q$M'; and
$Y^3$ is selected from the group consisting of —NH—, —O—, —S—, —S(O)—, and —S(O)$_2$—.

12. The compound of claim 11, or a pharmaceutically acceptable salt thereof, wherein at least one M' is independently selected from the group consisting of CN, —$CH_2$F, —$CHF_2$, —$CF_3$, —CH($CH_2$OH)$_2$, —$(CH_2)_3NH_2$, —$CH_2$N$(CH_3)_2$, —C≡CH, —C≡C—$CH_2$OH, —C≡C—$CH_2OCH_3$, —C≡C—$CH_2NH_2$, —C≡C—$CH_2$-azetidin-1-yl, —C(O)$NH_2$, OH, —S(O)$_2CH_3$, and —S(O)$_2NH_2$.

13. The compound of claim 11, or a pharmaceutically acceptable salt thereof, wherein at least one M' is independently selected from the group consisting of cyclopropyl, azetidinyl, dioxolanyl, morpholinyl, thiadiazolyl, triazolyl, and pyridinyl, each optionally and independently substituted.

14. The compound of claim 11, or a pharmaceutically acceptable salt thereof, wherein at least one M' is independently selected from the group consisting of cyclopropyl, azetidin-1-yl, azetidin-3-yl, dioxolanyl, morpholinyl, thiadiazolyl, triazolyl, and pyridinyl, each optionally and independently substituted.

15. The compound of claim 11, or a pharmaceutically acceptable salt thereof, wherein at least one M' is independently selected from the group consisting of CN, $C_2$-$C_4$ alkenyl, and $C_2$-$C_4$ alkynyl, wherein the $C_2$-$C_4$ alkenyl and $C_2$-$C_4$ alkynyl are each optionally and independently substituted.

16. The compound of claim 1, or a pharmaceutically acceptable salt thereof, wherein the pharmaceutically acceptable salt is an alkali metal cation salt or an ammonium salt.

17. A pharmaceutical composition comprising a pharmaceutically acceptable excipient and a therapeutically effective amount of a compound of claim 1, or a pharmaceutically acceptable salt thereof.

18. The pharmaceutical composition of claim 7, wherein the pharmaceutical composition further comprises an additional medicament selected from the group consisting of an antibacterial agent, an antifungal agent, an antiviral agent, an anti-inflammatory agent, and an anti-allergic agent.

19. The pharmaceutical composition of claim 18, wherein the additional medicament is a beta-lactam antibacterial agent selected from the group consisting of Aztreonam, Biapenem, Carumonam, Ceftazidime, Ceftibuten, Doripenem, Ertapenem, Imipenem, Meropenem, Panipenem, Tebipenem, Tigemonam,

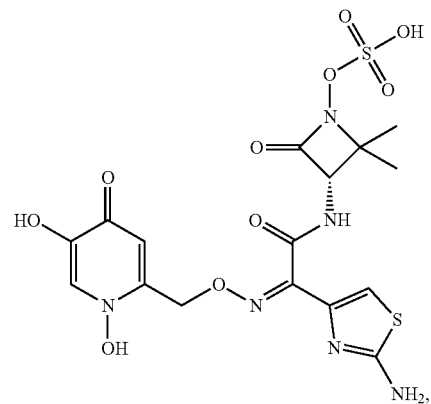

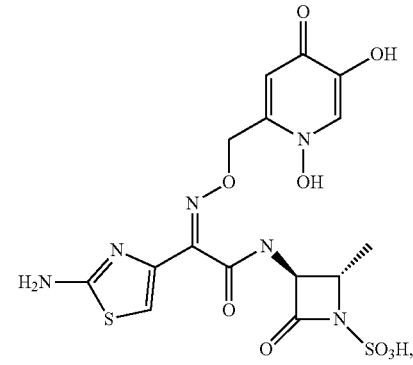

20. A method for treating a bacterial infection in a subject, comprising administering to a subject in need thereof a therapeutically effective amount of a compound of claim 1, or a pharmaceutically acceptable salt thereof.

21. The method of claim 20, wherein the method further comprises administering to the subject an additional medicament selected from the group consisting of an antibacterial agent, an antifungal agent, an antiviral agent, an anti-inflammatory agent, and an anti-allergic agent.

22. The method of claim 21, wherein the additional medicament is a beta-lactam antibacterial agent selected from the group consisting of Aztreonam, Biapenem, Carumonam, Ceftazidime, Ceftibuten, Doripenem, Ertapenem, Imipenem, Meropenem, Panipenem, Tebipenem, Tigemonam,

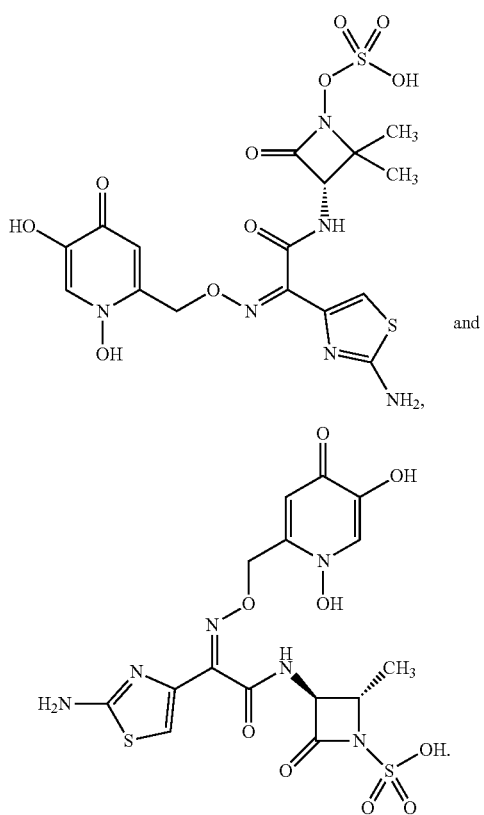
23. A compound selected from the group consisting of:
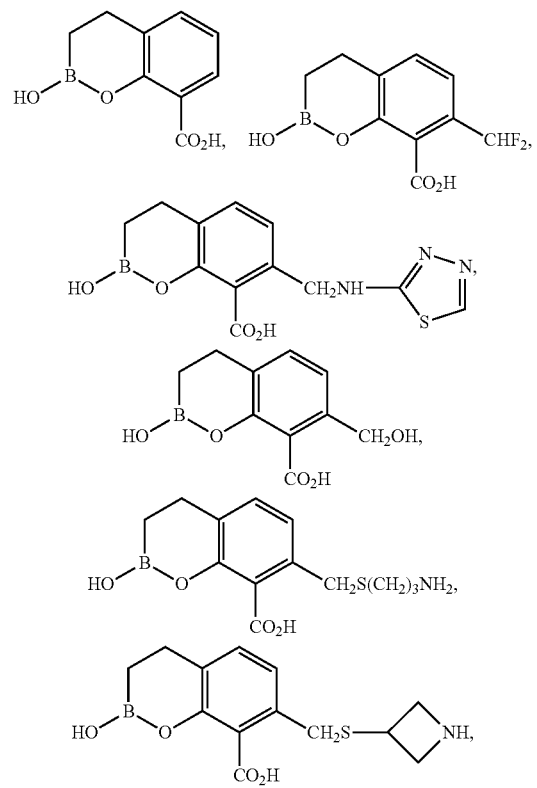
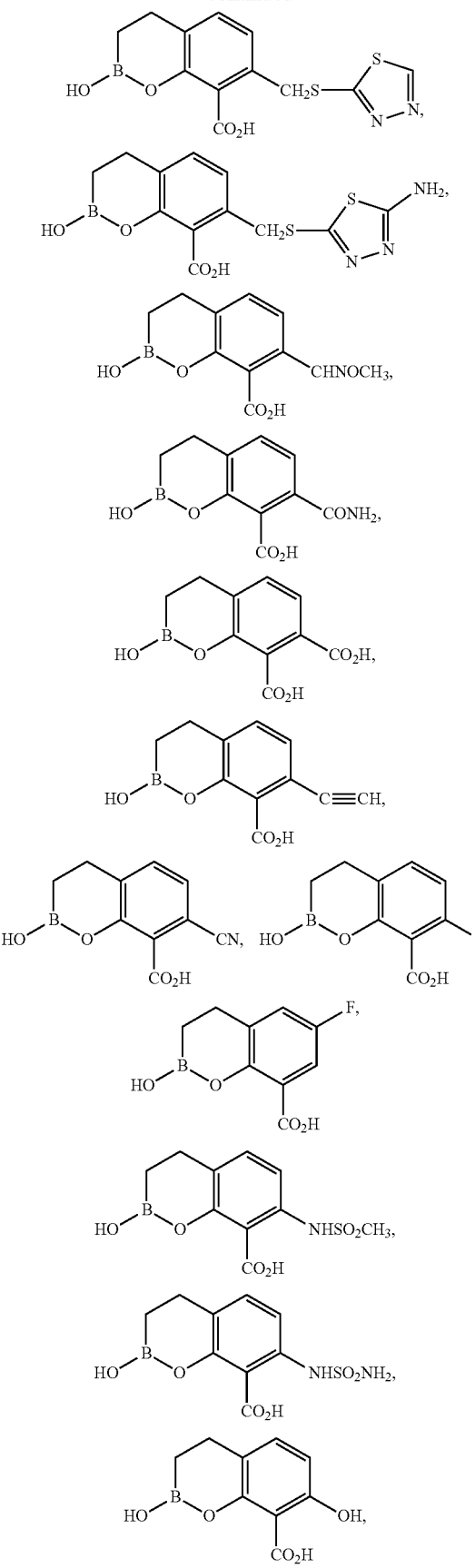

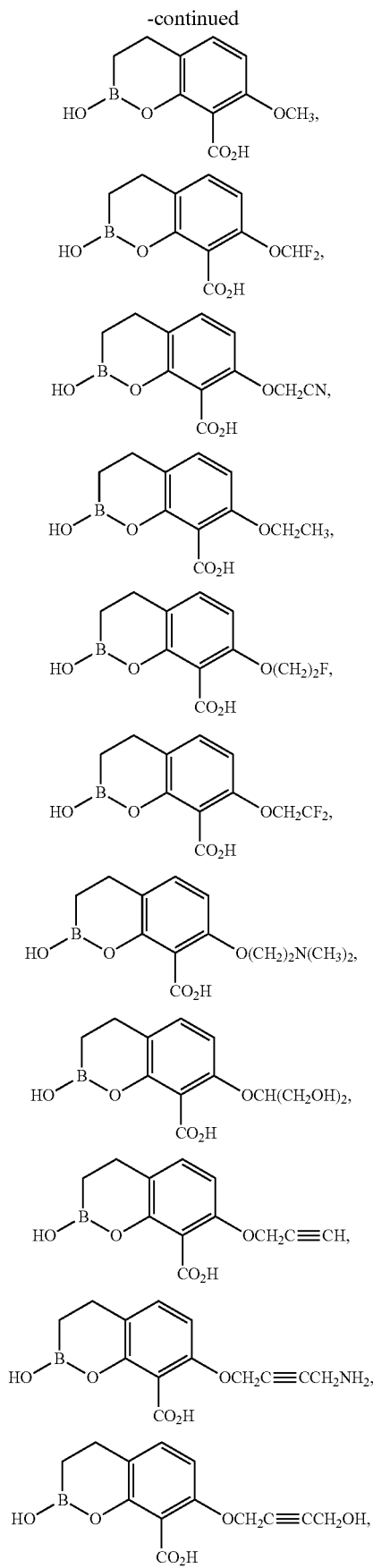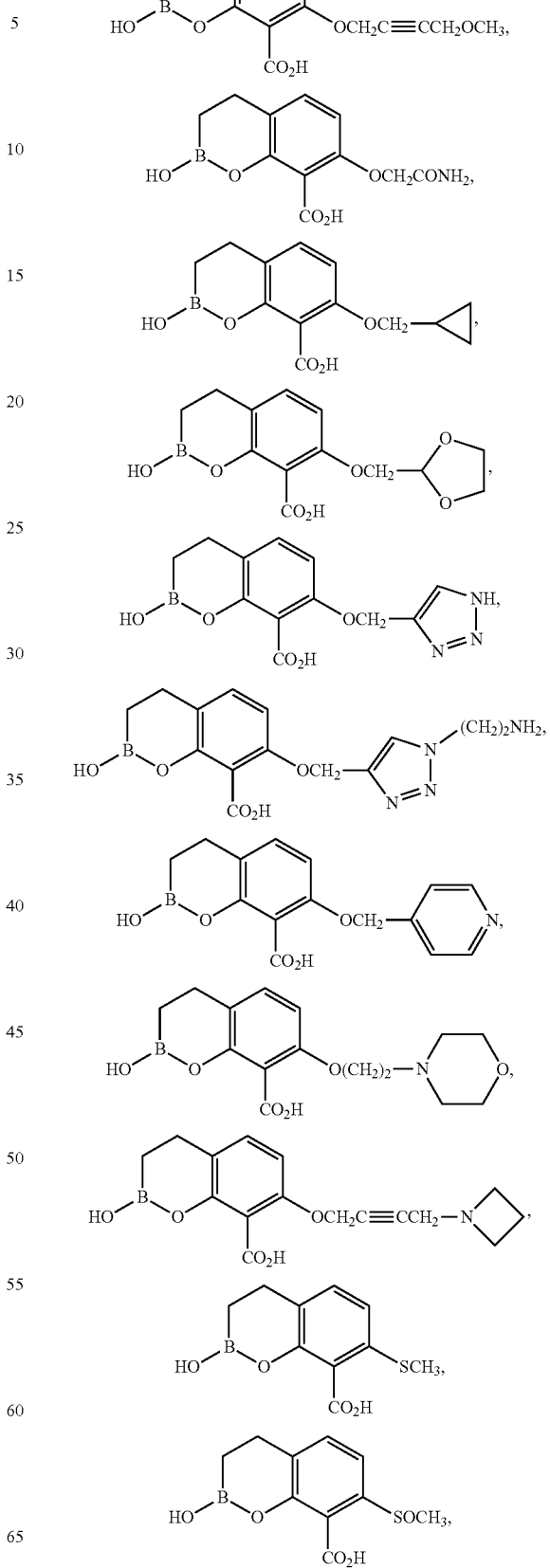

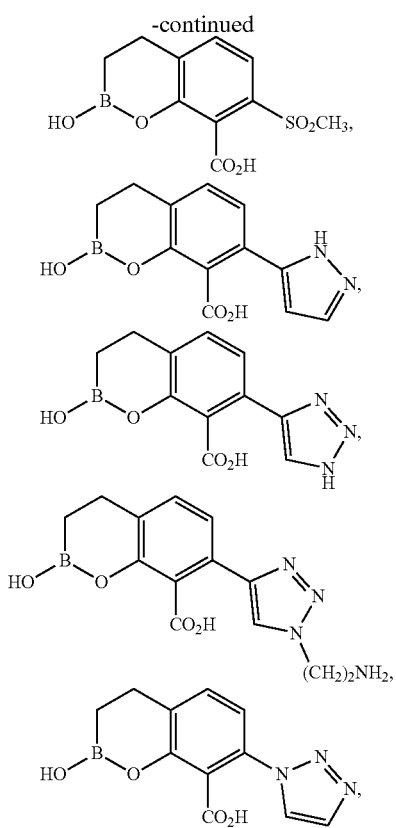
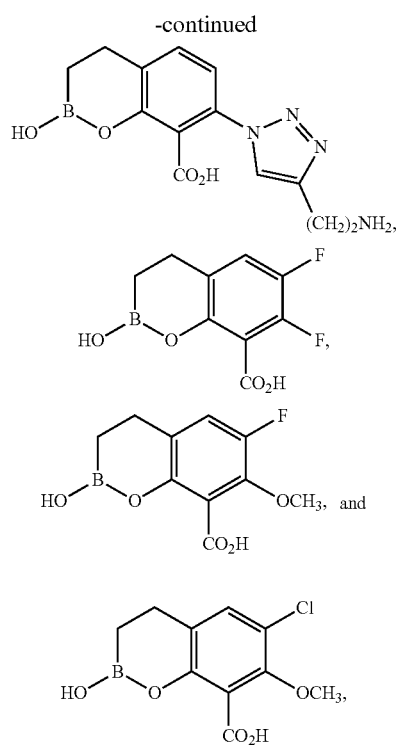
or a pharmaceutically acceptable salt thereof.
* * * * *

UNITED STATES PATENT AND TRADEMARK OFFICE
CERTIFICATE OF CORRECTION

PATENT NO. : 10,618,918 B2
APPLICATION NO. : 16/353693
DATED : April 14, 2020
INVENTOR(S) : Scott Hecker It is certified that error appears in the above-identified patent and that said Letters Patent is hereby corrected as shown below:

On the Title Page

On page 2, in Column 2, item (56), Other Publications, Line 26, delete "IPL-926"," and insert -- IPI-926", --.

On page 2, in Column 2, item (56), Other Publications, Line 42, delete "(PK_PD)" and insert -- (PK-PD) --.

On page 2, in Column 2, item (56), Other Publications, Line 44, after "changes." delete "abstr".

On page 3, in Column 2, item (56), Other Publications, Line 13, delete "Infecations" and insert -- Infections --.

On page 3, in Column 2, item (56), Other Publications, Line 20, delete "Carbamolylation" and insert -- Carbamoylation --.

On page 4, in Column 1, item (56), Other Publications, Line 43, delete "Sumposium" and insert -- Symposium --.

On page 4, in Column 2, item (56), Other Publications, Line 18, delete "bornonated" and insert -- boronated --.

On page 4, in Column 2, item (56), Other Publications, Line 41, delete "stereoselctive" and insert -- stereoselective --.

On page 4, in Column 2, item (56), Other Publications, Line 50, delete "Acitve" and insert -- Active --.

On page 5, in Column 2, item (56), Other Publications, Line 6, delete "Baronic" and insert -- Boronic --.

Signed and Sealed this
Twenty-third Day of July, 2024

Katherine Kelly Vidal
*Director of the United States Patent and Trademark Office*

CERTIFICATE OF CORRECTION (continued)
U.S. Pat. No. 10,618,918 B2

On page 5, in Column 2, item (56), Other Publications, Line 10, delete "Oranometallics" and insert -- Organometallics --.

On page 5, in Column 2, item (56), Other Publications, Line 63, delete "20752080" and insert -- 2075-2080 --.

On page 6, in Column 1, item (56), Other Publications, Line 14, delete "Anti Infect" and insert -- Anti-Infect --.

In the Specification

In Column 1, Line 61, delete "Anti Infect." and insert -- Anti-Infect. --.

In Column 3, Line 20, delete "C(O)(CH$_2$)$_{0-3}$SR$^3$," and insert -- —C(O)(CH$_2$)$_{0-3}$SR$^3$, --.

In Column 3, Lines 34-35, delete "C$_1$.6alkyl," and insert -- C$_{1-6}$alkyl, --.

In Column 3, Line 50, delete "indecently" and insert -- independently --.

In Column 4, Line 17, delete "cycano," and insert -- cyano, --.

In Column 4, Lines 66-67, delete "—CR$^{10}$R$^{11}$OC(O) NR$^{10}$C$_{6-10}$aryl," and insert -- —CR$^{10}$R$^{11}$OC(O)NR$^{10}$C$_{6-10}$aryl, --.

In Column 5, Line 40, delete "C(O)(CH$_2$)$_{1-3}$R$^4$," and insert -- —C(O)(CH$_2$)$_{1-3}$R$^4$, --.

In Column 5, Line 42, delete "NR$^1$C(O)NR$^1$R$^2$," and insert -- —NR$^1$C(O)NR$^1$R$^2$, --.

In Column 5, Line 43, delete "C(=NR$^1$)NR$^1$R$^2$," and insert -- —C(=NR$^1$)NR$^1$R$^2$, --.

In Column 7, Line 5, delete "I'" and insert -- III' --.

In Column 8, Line 30, delete "—(CH$_2$)$_{0-4}$-heterocyclyl" and insert -- —(CH$_2$)$_{0-4}$-heterocyclyl, --.

In Column 8, Lines 49-50, delete "—CR$^{10}$R$^{11}$OC(O) NR$^{10}$C$_{6-10}$aryl," and insert -- —CR$^{10}$R$^{11}$OC(O)NR$^{10}$C$_{6-10}$aryl, --.

In Column 10, Line 10, delete "—S—C$_{1-4}$ alkyl," and insert -- —S—C$_{1-6}$ alkyl, --.

In Column 10, Line 12, delete "—S(O)—C$_6$ alkyl," and insert -- —S(O)—C$_{1-6}$ alkyl, --.

In Column 11, Line 6 (approx.), delete "agents" and insert -- agents. --.

In Column 13, Line 18 (approx.), delete "(III)" and insert -- (II) --.

In Column 14, Line 3, delete "(IIb)" and insert -- (Ib), --.

CERTIFICATE OF CORRECTION (continued)
U.S. Pat. No. 10,618,918 B2

In Column 15, Line 19, delete "cycano," and insert -- cyano, --.

In Column 15, Line 49, delete "(I')," and insert -- (II'), --.

In Column 15, Line 49, delete "(I)," and insert -- (II), --.

In Column 16, Line 1, delete "(I')," and insert -- (II'), --.

In Column 17, Line 18, delete "(I')," and insert -- (II'), --.

In Column 23, Line 13, delete "from from" and insert -- from --.

In Column 25, Lines 21-27 (approx.), delete " 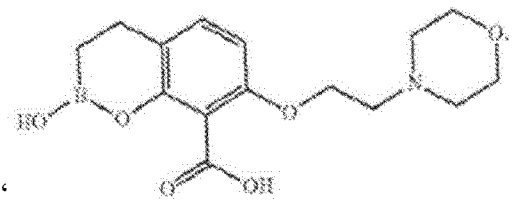 " and insert -- 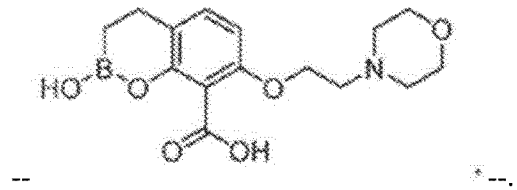 --.

In Column 29, Line 11, before "pharmaceutically" insert -- and --.

In Column 31, Lines 24-30 (approx.), delete " 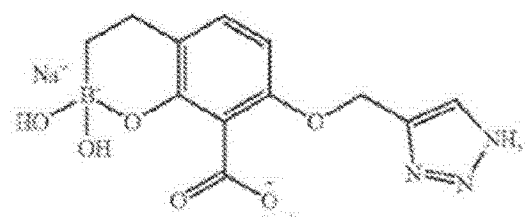 " and insert -- 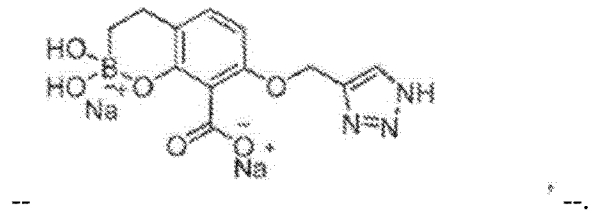 --.

In Column 33, Lines 1-8 (approx.), delete " 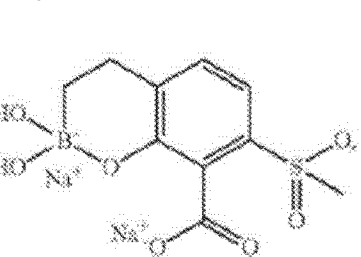 " and insert

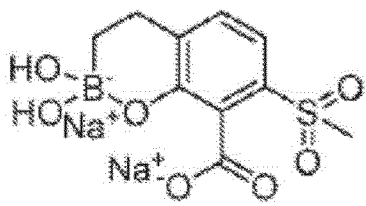

In Column 39, Line 15 (approx.), delete "pivoyloxymethyl," and insert -- pivaloyloxymethyl, --.

In Column 40, Line 2, delete "(IIc-salt)" and insert -- (IIIc-salt) --.

In Column 40, Line 26 (approx.), delete "(Ivb-salt):" and insert -- (IVb-salt): --.

In Column 43, Line 7, delete "isoquinlinyl," and insert -- isoquinolinyl, --.

In Column 43, Line 14, delete "isoxazollylalkyl," and insert -- isoxazolylalkyl, --.

In Column 44, Line 61, delete "R$_b$" and insert -- R$_B$ --.

In Column 45, Line 43, delete "substitutents" and insert -- substituents --.

In Column 47, Lines 15-20 (approx.), delete " 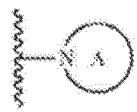 " and insert --  --.

In Column 47, Line 41 (approx.), delete "carbocylyl," and insert -- carbocyclyl, --.

In Column 47, Line 53 (approx.), delete "carbocylyl" and insert -- carbocyclyl --.

In Column 48, Line 17, delete "κ-7" and insert -- 5-7 --.

In Column 50, Line 65, delete "sterodirecting" and insert -- stereodirecting --.

In Column 51, Line 32, delete "1859-1885)," and insert -- (1859-1885), --.

In Column 51, Line 39, delete "sterodirecting" and insert -- stereodirecting --.

In Column 52, Line 42, delete "P. G. M." and insert -- (P. G. M. --.

In Column 53, Line 16 (approx.), delete "Y2=—NR2-" and insert -- Y$^2$=—NR$^2$- --.

In Column 54, Line 64, delete "enatiomerically" and insert -- enantiomerically --.

In Column 61, Line 29, delete "Ic" and insert -- IIIc --.

CERTIFICATE OF CORRECTION (continued)
U.S. Pat. No. 10,618,918 B2

In Column 61, Line 37 (approx.), delete "$CR^1R^2OR^1$," and insert -- $CR^1R^2OR'$, --.

In Column 62, Line 64, delete "intrapulmonarilly" and insert -- intrapulmonarily --.

In Column 63, Line 57, delete "form" and insert -- form, --.

In Column 67, Line 21, delete "embodiment" and insert -- embodiment, --.

In Column 68, Line 39, delete "Nisseria," and insert -- Neisseria, --.

In Column 68, Lines 39-40, delete "Baccillus" and insert -- Bacillus, --.

In Column 69, Line 3, delete "ovalus," and insert -- ovatus, --.

In Column 76, Line 13, delete "(18," and insert -- (C18, --.

In Column 76, Line 21, delete "2H). NMR:" and insert -- 2H). --.

In Column 77, Line 23 (approx.), delete "(18," and insert -- (C18, --.

In Column 77, Line 35, delete "[1.2]" and insert -- [1,2] --.

In Column 78, Line 28, delete "(18," and insert -- (C18, --.

In Column 80, Line 55 (approx.), delete "0.2.02-2.08" and insert -- 2.02-2.08 --.

In Column 81, Line 19 (approx.), delete "[IrCl(COD)]2," and insert -- [IrCl(COD)]$_2$, --.

In Column 81, Line 44 (approx.), delete "[IrCl(cod)]2" and insert -- [IrCl(COD)]$_2$ --.

In Column 81, Line 46 (approx.), delete "N2" and insert -- $N_2$ --.

In Column 82, Line 33 (approx.), delete "[IrCl(COD)]2" and insert -- [IrCl(COD)]$_2$ --.

In Column 83, Line 25, delete "vinyltrifluroborate" and insert -- vinyltrifluoroborate --.

In Column 83, Line 36, delete "[IrCl(COD)]2" and insert -- [IrCl(COD)]$_2$ --.

In Column 83, Line 45, delete "9H)." and insert -- 9H), --.

In Column 83, Line 65, delete "Cis" and insert -- C18 --.

In Column 85, Line 33, delete "Pd(t-Bu3P)2" and insert -- Pd(t-Bu$_3$P)$_2$ --.

In Column 87, Line 24, delete "methy" and insert -- methyl --.

CERTIFICATE OF CORRECTION (continued)
U.S. Pat. No. 10,618,918 B2

In Column 88, Line 8, delete "(18," and insert -- (C18, --.

In Column 89, Line 3, delete "(18," and insert -- (C18, --.

In Column 89, Line 65, delete "(18," and insert -- (C18, --.

In Column 91, Line 1, delete "12" and insert -- 12A --.

In Column 91, Line 38, delete "(18," and insert -- (C18, --.

In Column 94, Line 15 (approx.), delete "(18," and insert -- (C18, --.

In Column 94, Line 17 (approx.), delete "[M+H]:" and insert -- [M+H]$^+$: --.

In Column 95, Line 9 (approx.), delete "(18," and insert -- (C18, --.

In Column 97, Line 52, delete "[M+H]:" and insert -- [M+H]$^+$: --.

In Column 97, Line 53, delete "151" and insert -- 15I --.

In Column 97, Line 66, delete "151" and insert -- 15I --.

In Column 97, Line 67, delete "[M+H]:" and insert -- [M+H]$^+$: --.

In Column 98, Line 9 (approx.), delete "(18," and insert -- (C18, --.

In Column 99, Line 65, delete "(18," and insert -- (C18, --.

In Column 99, Line 67, delete "[M+H]:" and insert -- [M+H]$^+$: --.

In Column 100, Line 60 (approx.), delete "(18," and insert -- (C18, --.

In Column 101, Line 34 (approx.), delete "(18," and insert -- (C18, --.

In Column 102, Line 54, delete "03" and insert -- $O_3$ --.

In Column 103, Line 23, delete "(18," and insert -- (C18, --.

In Column 104, Line 20, delete "2- mercapitothiadiazole" and insert -- 2-mercaptothiadiazole --.

In Column 104, Line 34, delete "(18," and insert -- (C18, --.

In Column 105, Line 27, delete "(18," and insert -- (C18, --.

In Column 106, Line 33 (approx.), delete "(18," and insert -- (C18, --.

In Column 108, Line 60 (approx.), delete "(18," and insert -- (C18, --.

In Column 109, Line 61, delete "(18," and insert -- (C18, --.

In Column 110, Line 34 (approx.), delete "(18," and insert -- (C18, --.

In Column 112, Line 16 (approx.), delete "(18," and insert -- (C18, --.

In Column 113, Line 11 (approx.), delete "(18," and insert -- (C18, --.

In Column 114, Line 4, delete "(18," and insert -- (C18, --.

In Column 114, Line 6, delete "[M+H]:" and insert -- $[M+H]^+$: --.

In Column 114, Line 65, delete "(18," and insert -- (C18, --.

In Column 116, Line 23, delete "(18," and insert -- (C18, --.

In Column 116, Line 25, delete "[M+H]:" and insert -- $[M+H]^+$: --.

In Column 117, Line 14, delete "(18," and insert -- (C18, --.

In Column 119, Line 13 (approx.), delete "[IrCl(COD)]2" and insert -- $[IrCl(COD)]_2$ --.

In Column 119, Line 26 (approx.), delete "(18)" and insert -- (C18) --.

In Column 121, Line 46, delete "(18," and insert -- (C18, --.

In Column 123, Line 46, delete "(18)" and insert -- (C18) --.

In Column 124, Line 61 (approx.), delete "[IrCl(COD)]2" and insert -- $[IrCl(COD)]_2$ --.

In Column 125, Line 7 (approx.), delete "(18," and insert -- (C18, --.

In Column 126, Line 47, delete "[IrCl(COD)]2" and insert -- $[IrCl(COD)]_2$ --.

In Column 126, Line 60 (approx.), delete "(18)." and insert -- (C18). --.

In Column 128, Line 33 (approx.), delete "[M+H]:" and insert -- $[M+H]^+$: --.

In Column 128, Line 43 (approx.), delete "[M+H]:" and insert -- $[M+H]^+$: --.

In Column 128, Line 53 (approx.), delete "[M+H]:" and insert -- $[M+H]^+$: --.

In Column 128, Line 61 (approx.), delete "(18," and insert -- (C18, --.

In Column 128, Line 63 (approx.), delete "[M+H]:" and insert -- [M+H]+: --.

In Column 129, Lines 23-27 (approx.), delete " " and insert -- 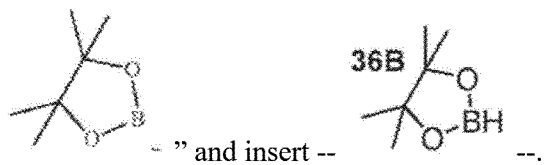 --.

In Column 129, Line 58, delete "Na2S2O3" and insert -- $Na_2S_2O_3$ --.

In Column 131, Line 42 (approx.), delete "[M+H]:" and insert -- $[M+H]^+$: --.

In Column 131, Line 54 (approx.), delete "[M+H]:" and insert -- $[M+H]^+$: --.

In Column 131, Line 62 (approx.), delete "(18," and insert -- (C18, --.

In Column 131, Line 64, delete "[M+H]:" and insert -- $[M+H]^+$: --.

In Column 131, Line 65, delete "(CD3OD," and insert -- ($CD_3OD$, --.

In Column 133, Line 6 (approx.), delete "(Boc)20" and insert -- $(Boc)_2O$ --.

In Column 133, Line 20, delete "[M+H]:" and insert -- $[M+H]^+$: --.

In Column 133, Line 30, delete "[M+H]:" and insert -- $[M+H]^+$: --.

In Column 133, Line 36 (approx.), delete "(18)" and insert -- (C18) --.

In Column 134, Line 13, delete "(18," and insert -- (C18, --.

In Column 135, Line 3, delete "(18," and insert -- (C18, --.

In Column 135, Lines 58-66, delete " 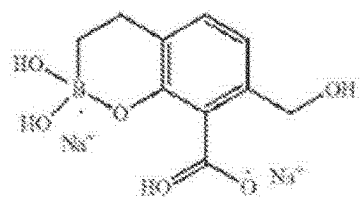 " and insert -- 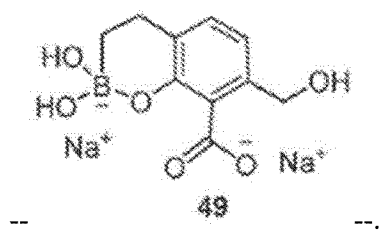 --.

CERTIFICATE OF CORRECTION (continued)
U.S. Pat. No. 10,618,918 B2

In Column 136, Line 50, delete "[MH]+:" and insert -- [M+H]$^+$: --.

In Column 136, Line 59, delete "(18," and insert -- (C18, --.

In Column 138, Line 5, delete "(18," and insert -- (C18, --.

In Column 138, Line 43, delete "(18)" and insert -- (C18) --.

In Column 139, Line 36 (approx.), delete "(18," and insert -- (C18, --.

In Column 139, Line 38 (approx.), delete "(CD3OD," and insert -- (CD$_3$OD, --.

In Column 140, Line 7, delete "(18," and insert -- (C18, --.

In Column 140, Line 63, delete "(18," and insert -- (C18, --.

In Column 141, Line 62, delete "(18," and insert -- (C18, --.

In Column 142, Line 34, delete "0° C.," and insert -- 0° C. --.

In Column 142, Line 46 (approx.), delete "(18," and insert -- (C18, --.

In Column 143, Lines 13-20 (approx.), delete " 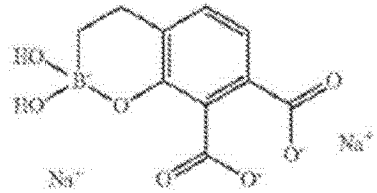 " and insert

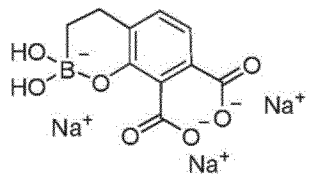

-- 53 --.

In Column 143, Line 41 (approx.), delete "(18," and insert -- (C18, --.

In Column 144, Line 60, delete "(18," and insert -- (C18, --.

In Column 145, Line 65, delete "(18," and insert -- (C18, --.

In Column 147, Line 15 (approx.), delete "[IrCl(cod)]2" and insert -- [IrCl(COD)]$_2$ --.

In Column 147, Line 33, delete "(18," and insert -- (C18, --.

In Column 148, Line 53, delete "Pd(t-Bu3P)₂" and insert -- Pd(t-Bu₃P)₂ --.

In Column 149, Line 18 (approx.), delete "(18," and insert -- (C18, --.

In Column 150, Line 67, delete "[M+H]:" and insert -- [M+H]⁺: --.

In Column 151, Line 9, delete "(18," and insert --(C18, --.

In Column 152, Line 42, delete "[IrCl(cod)]2" and insert -- [IrCl(COD)]₂ --.

In Column 152, Line 63 (approx.), delete "(18," and insert -- (C18, --.

In Column 154, Line 17 (approx.), delete "(18," and insert -- (C18, --.

In Column 155, Line 12 (approx.), delete "(18," and insert -- (C18, --.

In Column 156, Line 25 (approx.), delete "(18," and insert -- (C18, --.

In Column 160, Line 3, delete "(18," and insert -- (C18, --.

In Column 160, Line 62, delete "(18," and insert -- (C18, --.

In Column 171, Line 32 (approx.), delete "PAM 1154" and insert -- PAM1154 --.

In Column 171, Line 52, table 6, delete "MPC64" and insert -- MPC₆₄ --.

In Column 171, Line 52, table 6, delete "MPC64" and insert -- MPC₆₄ --.

In the Claims

In Column 172, Line 57, Claim 1, delete "S(O)₂NR¹R²," and insert -- —S(O)₂NR¹R², --.

In Column 173, Lines 16-17, Claim 1, delete "—CR¹⁰R¹¹OC (O)OC₁-C₉ alkyl," and insert -- —CR¹⁰R¹¹OC(O)OC₁-C₉ alkyl, --.

In Column 175, Lines 1-6, Claim 7, delete " " and insert -- --. 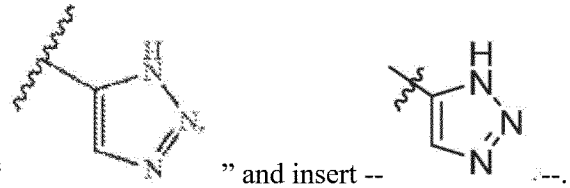

In Column 175, Line 15 (approx.), Claim 8, delete "—C(O)NR'OR²," and insert -- —C(O)NR¹OR², --.

In Column 175, Line 15 (approx.), Claim 8, delete "—C(O)OR'," and insert -- —C(O)OR¹, --.

CERTIFICATE OF CORRECTION (continued)
U.S. Pat. No. 10,618,918 B2

In Column 175, Line 18, Claim 8, delete "—NR'C(O)OR²," and insert -- —NR¹C(O)OR², --.

In Column 175, Line 20, Claim 8, delete "—S(O)₂NR'OR³," and insert -- —S(O)₂NR¹OR³, --.

In Column 175, Line 30, Claim 10, delete "C₁" and insert -- Cl --.

In Column 176, Line 18-49 (approx.), Claim 19, delete " 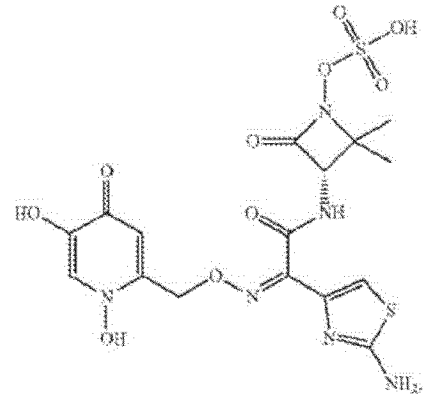 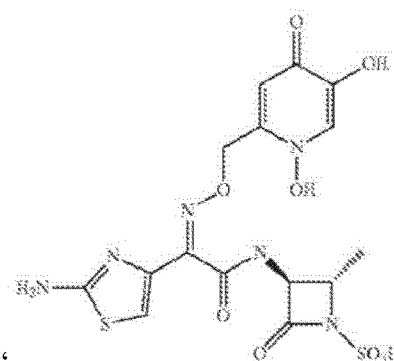 " and insert -- 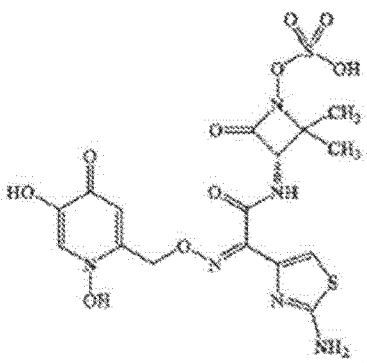 , and 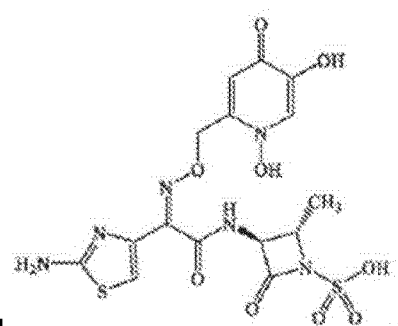 --.